(12) United States Patent
Rappuoli

(10) Patent No.: US 9,169,301 B2
(45) Date of Patent: Oct. 27, 2015

(54) CONSERVED NEISSERIAL ANTIGENS

(75) Inventor: Rino Rappuoli, Siena (IT)

(73) Assignee: GlaxoSmithKline Biologicals SA, Rixensart (BG)

( * ) Notice: Subject to any disclaimer, the term of this patent is extended or adjusted under 35 U.S.C. 154(b) by 7 days.

(21) Appl. No.: 12/589,218

(22) Filed: Oct. 19, 2009

(65) Prior Publication Data

US 2010/0041868 A1 Feb. 18, 2010

Related U.S. Application Data

(62) Division of application No. 11/800,090, filed on May 2, 2007, now Pat. No. 7,604,810, which is a division of application No. 09/980,602, filed as application No. PCT/IB00/00642 on Apr. 28, 2000, now Pat. No. 7,368,261.

(30) Foreign Application Priority Data

Apr. 30, 1999 (GB) .................................. 9910168.5
Mar. 9, 2000 (GB) .................................. 0005728.1

(51) Int. Cl.
*A61K 39/095* (2006.01)
*C07K 14/22* (2006.01)
*A61K 39/00* (2006.01)

(52) U.S. Cl.
CPC .............. *C07K 14/22* (2013.01); *A61K 39/095* (2013.01); *A61K 39/00* (2013.01)

(58) Field of Classification Search
CPC .............. A61K 39/095; A61K 39/102; A61K 2039/545; A61K 2039/55555; A61K 39/05; A61K 39/08; A61K 39/092; C07K 14/22; C07K 2319/00

USPC .......... 424/249.1, 185.1, 190.1, 203.1, 250.1; 435/7.1, 7.2, 7.32

See application file for complete search history.

(56) References Cited

U.S. PATENT DOCUMENTS

| 4,239,749 | A | 12/1980 | Buchanan |
| 5,547,670 | A | 8/1996 | Goldstein et al. |
| 6,013,267 | A | 1/2000 | Blake et al. |
| 6,028,049 | A | 2/2000 | Jacobs et al. |
| 6,197,312 | B1 | 3/2001 | Peak et al. |
| 6,248,329 | B1 | 6/2001 | Chandrashekar et al. |
| 6,709,660 | B1 | 3/2004 | Scarlato et al. |
| 6,914,131 | B1 | 7/2005 | Scarlato et al. |

(Continued)

FOREIGN PATENT DOCUMENTS

| EP | 0273116 | 7/1988 |
| EP | 0467714 | 1/1992 |

(Continued)

OTHER PUBLICATIONS

Accession No. Q9JQW0.*

(Continued)

*Primary Examiner* — Padma V Baskar
(74) *Attorney, Agent, or Firm* — Morrison & Foerster LLP

(57) ABSTRACT

To ensure maximum cross-strain recognition and reactivity, regions of proteins that are conserved between different Neisserial species, serogroups and strains can be used. The invention provides proteins which comprise stretches of amino acid sequence that are shared across the majority of *Neisseria*, particularly *N. meningitidis* and *N. gonorrhoeae*.

5 Claims, 97 Drawing Sheets

(56) References Cited

U.S. PATENT DOCUMENTS

| | | | |
|---|---|---|---|
| 7,348,006 B2 | 3/2008 | Contorni et al. | |
| 7,368,261 B1 | 5/2008 | Rappuoli | |
| 7,504,111 B2 | 3/2009 | Fontana et al. | |
| 7,517,684 B2* | 4/2009 | Rubenfield et al. | 435/325 |
| 7,576,176 B1* | 8/2009 | Fraser et al. | 530/350 |
| 7,604,810 B2 | 10/2009 | Rappuoli et al. | |
| 7,612,192 B2 | 11/2009 | Fraser et al. | |
| 7,862,827 B2 | 1/2011 | Giuliani et al. | |
| 8,114,960 B2 | 2/2012 | Arico et al. | |
| 8,703,914 B2 | 4/2014 | Arico et al. | |
| 2002/0160016 A1 | 10/2002 | Peak et al. | |
| 2004/0092711 A1 | 5/2004 | Arico et al. | |
| 2004/0110670 A1 | 6/2004 | Arico et al. | |
| 2005/0222385 A1 | 10/2005 | Pizza | |
| 2006/0051840 A1 | 3/2006 | Arico et al. | |
| 2006/0171957 A1 | 8/2006 | Pizza | |
| 2006/0240045 A1 | 10/2006 | Berthet et al. | |
| 2007/0082014 A1 | 4/2007 | Costantino | |
| 2008/0241180 A1 | 10/2008 | Contorni | |
| 2009/0232820 A1 | 9/2009 | Fraser et al. | |
| 2010/0267931 A1 | 10/2010 | Arico et al. | |
| 2013/0236489 A1 | 9/2013 | Serruto et al. | |

FOREIGN PATENT DOCUMENTS

| | | |
|---|---|---|
| EP | 1790660 | 5/2007 |
| FR | 2720408 | 12/1995 |
| JP | 2003525050 | 8/2003 |
| NL | 8901612 | 7/1990 |
| WO | WO-9006696 | 6/1990 |
| WO | WO-9216643 | 10/1992 |
| WO | WO-9503413 | 2/1995 |
| WO | WO-9533049 | 12/1995 |
| WO | WO-9629412 | 9/1996 |
| WO | WO-9710844 | 3/1997 |
| WO | WO-9713860 | 4/1997 |
| WO | WO-9728273 | 8/1997 |
| WO | WO-9924578 | 5/1999 |
| WO | WO-9936544 | 7/1999 |
| WO | WO-9957280 | 11/1999 |
| WO | WO-0022430 | 4/2000 |
| WO | WO-0050075 | 8/2000 |
| WO | WO-0066741 | 11/2000 |
| WO | WO-0066791 | 11/2000 |
| WO | WO-0071574 | 11/2000 |
| WO | WO-0071725 | 11/2000 |
| WO | WO-0131019 | 5/2001 |
| WO | WO-0152885 | 7/2001 |
| WO | WO-0164920 | 9/2001 |
| WO | WO-0164922 | 9/2001 |
| WO | WO-03009869 | 2/2003 |
| WO | WO-03010194 | 2/2003 |
| WO | WO-03020756 | 3/2003 |
| WO | WO-2004032958 | 4/2004 |
| WO | WO-2004048404 | 6/2004 |
| WO | WO-2004067030 | 8/2004 |
| WO | WO-2004112832 | 12/2004 |
| WO | WO-2005032583 | 4/2005 |
| WO | WO-2005033148 | 4/2005 |
| WO | WO-2005102384 | 11/2005 |
| WO | WO-2005106009 | 11/2005 |
| WO | WO-2008001224 | 1/2008 |

OTHER PUBLICATIONS

Accession: E81003.*
Accession: JC4817 ((sequence file Oct. 15, 1996).*
Devos et al., (Proteins: Structure, Function and Genetics, 2000, vol. 41: 98-107).*
Whisstock et al., (Quarterly Reviews of Biophysics 2003, vol. 36 (3): 307-340 ).*
Gomez et al. Vaccine 14: 1340-1346, 1996.*
Malorny et al. J. Bacteriol. 180: 1323-1330, 1998.*
Teerlink et al. J. Exp. Med. 166: 63-76, 1987.*
Forest et al. Gene 192: 165-169, 1997.*
Ala'Aldeen et al. Vaccine 12: 535-541, 1994.*
Abad et al. (2008). "PorB2/3 Protein Hybrid in *Neisseria meningitidis*," Emerging Infectious Diseases, 14(4):688-689.
Ala'Aldeen et al. (1996). "The Meningococcal Transferrin-binding Proteins 1 and 2 are Both Surface Exposed and Generate Bactericidal Antibodies Capable of Killing Homologous and Heterologous Strains," Vaccine 14(1):49-53.
Bartsevich et al. (Mar. 7, 1997). "Molecular Identification of a Novel Protein That Regulates Biogenesis of Photosystem I, a Membrane Protein Complex," The Journal of Biological Chemistry 272(10):6382-6387.
Bethell et al. (2002). "Meningococcal vaccines," Expert Review of Vaccines 1(1):75-84.
Blythe et al. (2005). "Benchmarking B cell epitope prediction: underperformance of existing methods," Protein Sci. 14:246-248.
Boslego et al. (1991). "Gonorrhea Vaccines" Chapter 17 in Vaccines and Immunotherapy, S. Cryz (Ed.). pp. 211-223.
Bowie, J. et al. (1990). "Deciphering the Message in Protein Sequences: Tolerance to Amino Acid Substitutions," Science 247: 1306-1310.
Bygraves et al. (1992). "Analysis of the Clonal Relationships Between Strains of *Neisseria meningitidis* by Pulsed Field Gel Electrophoresis," J. Gen Microbiol. 138:523-531.
Cann et al. (1989). "Detection of Antibodies to Common Antigens of Pathogenic and Commensal *Neisseria* Species," Journal of Medical Microbiology 30:23-30.
Caugant et al. (1987). "Genetic Structure of *Neisseria meningitidis* Populations in Relation to Serogroup, Serotype, and Outer Membrane Protein Pattern," J. Bacteriol. 69:2781-2792.
Christodoulides et al. (1994). "Immunization with a Multiple Antigen Peptide Containing Defined B- and T-Cell Epitopes: Production of Bacterial Antibodies Group B *Neisseria meningitidis*," Microbiology 140:2951-2960.
Cooney et al. (1993). "Three Contiguous Lipoprotein Genes in *Pasteurella haemolytica* A1 which are Homologous to a Lipoprotein Gene in Haemophilus Influenza Type B," Infection and Immunity 61 (11):4682-4688.
Cruse et al. *Illustrated Dict. of Immunology*, 2nd ed., CRC Press, 2003. pp. 46, 166, and 382.
Dempsey et al. (1991). "Physical Map of the Chromosome of *Neisseria gonorrhoeae* FA1090 with Locations of Genetic Markers, including Opa and Pil Genes," J. Bacteriol. 173:5476-5486.
Devries et al. (Aug. 1996). "Invasion of Primary Nasopharyngeal Epithelial Cells by *Neisseria meningitidis* is Controlled by Phase Variation of Multiple Surface Antigens," Infection and Immunity 64(8):2998-3006.
Ellis (1988). "New Technologies for Making Vaccines" in *Vaccines*. Plotkin et al. (Eds.) pp. 568-575.
Feng et al. (1996). "P55, an Immunogenic but Nonprotective 55-Kilodalton *Borrelia burgdorferi* Protein in Murine Lyme Disease," Infection and Immunity. 64(1):363-365.
Gervais et al. (1992). "Putative Lipoprotein YaeC Precursor," Database Swissport Acc No. p28635.
Greenspan et al. (1999). "Defining Epitopes: Its Not as Easy as It Seems," Nature Biotechnology 7:936-937.
Grifantini, R. et al. (2002). "Previously Unrecognized Vaccine Candidates against Group B Meningococcus Identified by DNA Microarrays," Nature Biotechnology 20(9): 914-921.
Guillen et al. (1996). "Expression in *Escherichia coli* and Immunological Characterization of a Hybrid Class I-P64K Protein from *Neisseria meningitidis*," Biotecnologia Aplicada13(4):271-275.
Herbert et al. (1995). *The Dictionary of Immunology*.Academic Press: London 4th edition, 3 pages.
Herbert, W. et al. (1985). *The Dictionary of Immunology*. Academic Press: London 3rd edition, pp. 58-59.
Holmes, E. (2001). "PSMA Specific Antibodies and their Diagnostic and Therapeutic Use," Expert Opinion on Investigational Drugs 10(3): 511-519.
Jacobsson et al. (2009). "Prevalence and sequence variations of the genes encoding the five antigens included in the novel 5CVMB vaccine covering group B meningococcal disease," Vaccine. 27:1579-1584.

(56) References Cited

OTHER PUBLICATIONS

Jolley et al. (2007). "Molecular typing of meningococci: recommendations for target choice and nomenclature," FEMS Microbiol. Rev. 31:89-96.
Legrain et al. (1995). "Production of Lipidated Meningococcal Transferrin Binding Protein 2 in *Escherichia coli*," Protein Expression and Purification 6:570-578.
Maiden et al. (1998). "Multilocus Sequence Typing: a Portable Approach to the Identification of Clones within Populations of Pathogenic Microorganisms," Proc. Natl. Acad. Sci. USA 95:3140-3145.
McGuiness et al. (1993). "Class 1 outer membrane protein of *Neisseria meningitidis*: epitope analysis of the antigenic diversity between strains, implications for subtype definition and molecular epidemiology," Mol Microbiol. 7:505-514.
Morley et al. (2002). "Vaccine prevention of meningococcal disease, coming soon?" Vaccine 20:666-687.
Moudallal et al. (1982). "Monoclonal anti bodies as probes of the antigenic structure of tobacco mosaic virus," EMBO Journal 1:1005-1010.
Ni et al. (1992). "Phylogenetic and Epidemiological Analysis of *Neisseria meningitidis* Using DNA Probes," Epidemiol. Infect. 109:227-239.
Perkins et al. (1998). "Immunogenicity of two efficacious outer membrane protein-based serogroup B meningococcal vaccines among young adults in Iceland," The Journal of Infectious Disease 177:683-691.
Perrett et al. (2005). "Towards an improved serogroup B *Neisseria meningitidis* vaccine," Expert Opinion on Biological Therapy 5(12):1611-1625.
Pettersson et al. (1999). "Sequence Variability of the Meningococcal Lactoferrin-binding Protein LbpB," Gene 231:105-110.
Pizza et al. (Mar. 10, 2000). "Identification of Vaccine Candidates Against Serogroup B Meningococcus by Whole-Genome Sequencing," Science 287(5459):1816-1820.
Poolman et al. (1985). "Colony Variants of *Neisseria meningitidis* Strain 2996 (B:2b:P1.2): Influence of Class-5 Out Membrane Proteins and Lipolysaccharides," J. Med. Microbiol 19:203-209.
Poolman et al. (1988). "Outer membrane protein sero-subtyping of *Neisseria meningitidis*," European Journal of Clinical Microbiology and Infectious Diseases 7:291-292.
Poolman. (1995). "Development of a Meningococcal Vaccine," Infect. Agents Dis. 4:13-28.
Renauld-Mongenie et al. (1997). "Identification of Human Transferrin-Binding Sites Within Meningococcal Transferrin-Binding Protein B," J. Bacteriology 197(20):6400-6407.
Roitt, I. et al. (1993). Immunology. Mosby: St. Louis, 4$^{th}$ edition, pp. 7,7-7,8.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Seiler et al. (1996). "Allelic Polymorphism and Site-specific Recombination in the Opc Locus of *Neisseria meningitidis*," Mol. Microbiol. 19(4):841-856.
Telford (Jun. 2008). "Bacterial Genome Variability and Its Impact on Vaccine Design," Cell Host & Microbe 3(6):408-416.
Tettelin et al. (2006). "Towards a universal group B *Streptococcus* vaccine using multistrain genome analysis," Expert Rev Vaccines 25:687-694.
Tettelin et al. (2000). "Complete Genome Sequence of *Neisseria meningitidis* Serogroup B Strain MC58," Science 287:1809-1815.
Thompson et al. (1994). "Clustal W: Improving the Sensitivity of Progressive Multiple Sequence Alignment through Sequence Weighting, Position-specific Gap Penalties and Weight Matrix Choice," Nucleic Acids Res. 22:4673-4680.
Thompson et al. (1998). "Multiple Sequence Alignment with Clustal X," Trends Biochem. Sci. 23:403-405.
Van Der Lay et al. (1992). "Construction of a Multivalent Meningococcal Vaccine Strain Based on the Class I Outer Membrane Protein," Infection and Immunity 60(8): 3516-3161.
Van Der Lay et al. (1995). "Construction of *Neisseria meningitidis* Strains Carrying Multiple Chromosomal Copies of the PorA Gene for Use in Production of a Multivalent Outer Membrane Vesicle Vaccine," Vaccine 13(4): 401-107.
Virji et al. (1992). "Variations in the Expression of Pili: the Effect on Adherence of *Neisseria meningitidis* to Human Epithelial and Endothelial Cells," Mol. Microbiol. 6:1271-1279.
Wolff et al. (1992). "Phylogeny and Nucleotide Sequence of a 23S rRNA Gene from *Neisseria gonorrhea* and *Neisseria meningitidis*," Nucleic Acids Res. 20:4657.
Parkhill et al. (Mar. 2000) "Complete DNA sequence of a serogroup A strain of *Neisseria meningitides* Z2491" 404: 502-505.
Donnelly et al. (2010). "Qualitative and quantitative assessment of meningococcal antigens to evaluate the potential strain coverage of protein-based vaccines," Proc Natl Acad Sci USA, 107(45):19490-5.
Experimental data: expression of NspA, fHBP and GNA2132 in N. meningitidis, filed in opposition against EP1534326, dated Aug. 4, 2010. 2 pages.
Giuliani et al. (2010). "Measuring antigen-specific bactericidial responses to a multicomponent vaccine against serogroup B meningococcus," Vaccine 28:5023-5030.
Lucidarme et al. (Sep. 16, 2009) "Characterization of fHbp, nhba (gna2132), nadA, porA, sequence type (ST), and genomic presence of IS1301 in group B meningococcal ST269 clonal complex isolates from England and Wales," Journal of Clinical Microbiology, 47(11):3577-85.
Lucidarme et al. (2010). "Characterization of fHbp, nhba (gna2132), nadA, porA, and sequence type in group B meningococcal case isolates collected in England and Wales during Jan. 2008 and potential coverage of an investigational group B meningococcal vaccine," Clinical and Vaccine Immunology 17(6):919-929.
Martin et al. (1998). "New Zealand epidemic of meningococcal disease identified by a strain with phenotype B:4:P1.4," JID 177:497-500.
Novartis (Jun. 9, 2011). "Novartis candidate vaccine Bexsero® shows significant potential in providing broad coverage against meningococcal serogroup B infections," Media Release, 6 pages.
Plikaytis et al. (2012). "Interlaboratory standardization of the sandwich enzyme-linked immunosorbent assay designed for MATS, a rapid, reproducible method for estimating the strain coverage of investigational vaccines," Clin Vaccine Immunol, (10):1609-17.
Seib et al. (2010). "Influence of serogroup B meningococcal vaccine antigens on growth and survival of the mengococcus in vitro and in ex vivo and in vivo models of infection," Vaccine 28(12):2416-2427.
Serruto et al. (2010). "Neisseria meningitidis GNA2132, a heparin-binding protein that induces protective immunity in humans," PNAS 107(8):3770-3775.
Voulhoux and Tommassen (2002). "Transport of lipoproteins to the cell surface in Neisseria meningitidis," 13th International Pathogenic Neisseria Conference 2002, p. 31.
Welsch et al. (2002). "Genome-derived antigen (GNA) 2132 elicits protective serum antibodies to groups B and C Neisseria meningitidis strains," 13th International Pathogenic Neisseria Conference 2002, p. 25.
Welsch et al. (2003). "Antibody to genome-derived neisserial antigen 2132, a Neisseria meningitidis candidate vaccine, confers protection against bacteremia in the absence of complement-mediated bactericidal activity," Journal of Infectious Diseases 188 (11):1730-1740.

\* cited by examiner

| | | | | | |
|---|---|---|---|---|---|
| zn07_1 | 349 | TFASGK | GTTATVSKDDDQGNITVK | YDVNVGDALNVNQLQNSGWNLDSKAVAGSSGKVISGN |
| zn20_1 | 349 | TFASGK | GTTATVSKDDDQGNITVK | YDVNVGDALNVNQLQNSGWNLDSKAVAGSSGKVISGN |
| zn21_1 | 349 | TFASGK | GTTATVSKDDDQGNITVK | YDVNVGDALNVNQLQNSGWNLDSKAVAGSSGKVISGN |
| zn06_1 | 349 | TFASGK | GTTATVSKDDDQGNITVK | YDVNVGDALNVNQLQNSGWNLDSKAVAGSSGKVISGN |
| zn19_1 | 349 | TFASGK | GTTATVSKDDDQGNITVM | YDVNVGDALNVNQLQNSGWNLDSKAVAGSSGKVISGN |
| zn03_1 | 351 | TFASGN | GTTATVSKDDDQGNITVK | YDVNVGDALNVNQLQNSGWNLDSKAVAGSSGKVISGN |
| zn18_1 | 351 | TFASGN | GTTATVSKDDDQGNITVK | YDVNVGDALNVNHLQNSGWNLDSKAVAGSSGKVISGN |
| zn11_ass | 351 | TFASGN | GTTATVSKDDDQGNITVK | YDVNVGDALNVNQLQNSGWDLDSKAVAGSSGKVISGN |
| zn02_1 | 351 | TFASGK | GTTATVSKDDDQGNITVK | YDVNVGDALNVNQLQNSGWNLDSKAVAGSSGKVISGN |
| zn04_1 | 355 | TFASGK | GTTATVSKDDDQGNITVK | YDVNVGDALNVNQLQNSGWNLDSKAVAGSSGKVISGN |
| zn16_1 | 355 | TFASGN | GTTATVSKDDDQGNITVK | YDVNVGDALNVNQLQNSGWNLDSKAVAGSSGKVISGN |
| zn14_1 | 356 | TFASGK | GTTATVSKDDDQGNITVK | YDVNVGDALNVNQLQNSGWNLDSKAVAGSSGKVISGN |
| zn249_1 | 349 | TFASGK | GTTATVSKDDDQGNITVK | YDVNVGDALNVNQLQNSGWNLDSKAVAGSSGKVISGN |
| zn10_1 | 349 | TFASGK | GTTATVSKDDDQGNITVK | YDVNVGDALNVNQLQNSGWNLDSKAVAGSSGKVISGN |
| zn22_1 | 349 | TFASGK | GTTATVSKDDDQGNITVK | YDVNVGDALNVNQLQNSGWNLDSKAVAGSSGKVISGN |
| zn23_1 | 349 | TFASGK | GTTATVSKDDDQGNITVK | YDVNVGDALNVNQLQNSGWNLDSKAVAGSSGKVISGN |
| zn28_ass | 346 | TFASGN | GTTATVSKDDDQGNITVK | YDVNVGDALNVNQLQNSGWNLDSKAVAGSSGKVISGN |
| zn24_1 | 346 | TFASGN | GTTATVSKDDDQGNITVK | YDVNVGDALNVNQLQNSGWNLDSKAVAGSSGKVISGN |
| zn25_ass | 352 | TFASGN | GTTATVSKDDDQGNITVK | YDVNVGDALNVNQLQNSGWNLDSKAVAGSSGKVISGN |
| zn08_1 | 357 | TFASGN | GTTATVSKDDDQGNITVK | YDVNVGDALNVNQLQNSGWNLDSKAVAGSSGKVISGN |
| zn29_ass | | TFASGN | GTTATVSKDDDQGNITVK | YDVNVGDALNVNQLQNSGWNLDSKAVAGSSGKVISGN |

| | | |
|---|---|---|
| zn07_1 | 588 | GYQW * |
| zn20_1 | 588 | GYQW * |
| zn21_1 | 588 | GYQW * |
| zn06_1 | 588 | GYQW * |
| zn19_1 | 588 | GYQW * |
| zn03_1 | 591 | GYQW * |
| zn18_1 | 591 | GYQW * |
| zn11_ass | 591 | GYQW * |
| zn02_1 | 591 | GYQW * |
| zn04_1 | 591 | GYQW * |
| zn16_1 | 595 | GYQW * |
| zn14_1 | 596 | GYQW * |
| z2491 | 589 | GYQW * |
| zn10_1 | 589 | GYQW * |
| zn22_1 | 589 | GYQW * |
| zn23_1 | 589 | GYQW * |
| zn28_ass | 586 | GYQW * |
| zn24_1 | 586 | GYQW * |
| zn25_ass | 586 | GYQW * |
| zn08_1 | 592 | GYQW * |
| zn29_ass | 597 | GYQW * |

```
zv11_4     60  EQIQVELEKKGYTVKLVEFTDYVRPNLALAEGELDINVFQHKPYLDDFKKKEHIN
zv29_4     60  EQIQVELEKKGYTVKLVEFTDYVRPNLALAEGELDINVFQHKPYLDDFKKKEHIN
zv22_4     60  EQIQPELEKKGYTVELVEFTDYVRPNLALGEGELDINVFQHKPYLDDFKKKEHIN
zv12_4ass  60  EQIQAELEKKGYTVKLVEFTDYVRPNLALAEGELDINVFQHKPYLDDFKKKEHIN
zv24_4ass  60  EHIQPELEKKGYTVELVEFTDDVRPNLALGEGELDITVFQHKPYLDDFKKKEQIN
```

| | | |
|---|---|---|
| fa1090_4 | 181 | KADIAENLKNIKIVELEAAQLPRSRADVDFAVVNGNYAISSGMKLTEALFQEP |
| zv32_4 | 181 | KADIAENLKNIKIVELEAAQLPRSRADVDFAVVNGNYAISSGMKLTEALFQEP |
| zv33_4 | 181 | KADIAENLKNIKIVELEAAQLPRSRADVDFAVVNGNYAISSGMKLTEALFQEP |
| zv02_4 | 180 | KADIAENLKNIKIVELEAAQLPRSRADVDFAVVNGNYAISSGMKLTEALFQEP |
| zv15_4 | 180 | KADIAENLKNIKIVELEAAQLPRSRADVDFAVVNGNYAISSGMKLTEALFQEP |
| zv03_4ass | 180 | KADIAENLKNIKIVELEAAQLPRSRADVDFAVVNGNYAISSGMKLTEALFQEP |
| zv04_4 | 180 | KADIAENLKNIKIVELEAAQLPRSRADVDFAVVNGNYAISSGMKLTEALFQEP |
| zv05_4 | 180 | KADIAENLKNIKIVELEAAQLPRSRADVDFAVVNGNYAISSGMKLTEALFQEP |
| zv09_4 | 180 | KADIAENLKNIKIVELEAAQLPRSRADVDFAVVNGNYAISSGMKLTEALFQEP |
| zv16_4 | 180 | KADIAENLKNIKIVELEAAQLPRSRADVDFAVVNGNYAISSGMKLTEALFQEP |
| zv18_4 | 180 | KADIAENLKNIKIVELEAAQLPRSRADVDFAVVNGNYAISSGMKLTEALFQEP |
| zv26_4 | 180 | KADIAENLKNIKIVELEAAQLPRSRADVDFAVVNGNYAISSGMKLTEALFQEP |
| zv28_4 | 180 | KADIAENLKNIKIVELEAAQLPRSRADVDFAVVNGNYAISSGMKLTEALFQEP |
| zv08_4 | 180 | KADIAENLKNIKIVELEAAQLPRSRADVDFAVVNGNYAISSGMKLTEALFQEP |
| zv10_4 | 180 | KADIAENLKNIKIVELEAAQLPRSRADVDFAVVNGNYAISSGMKLTEALFQEP |
| zv25_4 | 180 | KADIAENLKNIKIVELEAAQLPRSRADVDFAVVNGNYAISSGMKLTEALFQEP |
| zv17_4 | 180 | KADIAENLKNIKIVELEAAQLPRSRADVDFAVVNGNYAISSGMKLTEALFQEP |
| zv96_4 | 180 | KADIAENLKNIKIVELEAAQLPRSRADVDFAVVNGNYAISSGMKLTEALFQEP |
| zv06_4 | 180 | KADIAENLKNIKIVELEAAQLPRSRADVDFAVVNGNYAISSGMKLTEALFQEP |
| zv19_4 | 180 | KADIAENLKNIKIVELEAAQLPRSRADVDFAVVNGNYAISSGMKLTEALFQEP |
| zv20_4 | 180 | KADIAENLKNIKIVELEAAQLPRSRADVDFAVVNGNYAISSGMKLTEALFQEP |
| z2491_4 | 180 | KADIAENLKNIKIVELEAAQLPRSRADVDFAVVNGNYAISSGMKLTEALFQEP |

| | | |
|---|---|---|
| zv13_4 | 180 | KADIAENLKNIKIVELEAAQLPRSRADVDFAVVNGNYAISSGMKLTEALFQEP |
| zv27_4 | 180 | KADIAENLKNIKIVELEAAQLPRSRADVDFAVVNGNYAISSGMKLTEALFQEP |
| zv01_4 | 180 | KADIAENLKNIKIVELEAAQLPRSRADVDFAVVNGNYAISSGMKLTEALFQEP |
| zv07_4 | 180 | KADIAENLKNIKIVELEAAQLPRSRADVDFAVVNGNYAISSGMKLTEALFQEP |
| zv21_4 | 180 | KADIAENLKNIKIVELEAAQLPRSRADVDFAVVNGNYAISSGMKLTEALFQEP |
| zv11_4 | 180 | KADIAENLKNIKIVELEAAQLPRSRADVDFAVVNGNYAISSGMKLTEALFQEP |
| zv29_4 | 180 | KADIAENLKNIKIVELEAAQLPRSRADVDFAVVNGNYAISSGMKLTEALFQEP |
| zv22_4 | 180 | KADIAENLKNIKIVELEAAQLPRSRADVDFAVVNGNYAISSGMKLTEALFQEP |
| zv12_4ass | 180 | KADIAENLKNIKIVELEAAQLPRSRADVDFAVVNGNYAISSGMKLTEALFQEP |
| zv24_4ass | 180 | KADIAENLKNIKIVELEAAQLPRSRADVDFAVVNGNYAISSGMKLTEALFQEP |

| | | |
|---|---|---|
| gnmzq09 | 61 | AEPLSEAGYYVFPAAVEETFKQNGLTNAADIHAVQPEKLHQIFGNDAVLYITITEYGTS |
| gnmzq31 | 61 | AEPLSEAGYYVFPAAVEETFKQNGLTNAADIHAVRPEKLHQIFGNDAVLYITITEYGTS |
| fal090 | 61 | AEPLSEAGYYVFPAAVEETFKENGLTNAADIHAVRPEKLHQIFGNDAVLYITVTEYGTS |
| gnmzq32 | 61 | AEPLSEAGYYVFPAAVEETFKENGLTNAADIHAVRPEKLHQIFGNDAVLYITVTEYGTS |
| gnmzq33 | 61 | AEPLSEAGYYVFPAAVEETFKENGLTNAADIHAVRPEKLHQIFGNDAVLYITVTEYGTS |
| gnmzq01 | 61 | AAPLSEAGYYVFPAAVEETFKQNGLTNAADIHAVRPEKLHQIFGNDAVLYITVTEYGTS |
| gnmzq05 | 61 | AAPLSEAGYYVFPAAVEETFKQNGLTNAADIHAVRPEKLHQIFGNDAVLYITVTEYGTS |
| gnmzq08 | 61 | AAPLSEAGYYVFPAAVEETFKQNGLTNAADIHAVRPEKLHQIFGNDAVLYITVTEYGTS |
| gnmzq02 | 61 | AAPLSEAGYYVFPAAVEETFKQNGLTNAADIHAVRPEKLHQIFGNDAVLYITVTEYGTS |
| gnmzq03 | 61 | AAPLSEAGYYVFPAAVEETFKQNGLTNAADIHAVRPEKLHQIFGNDAVLYITVTEYGTS |
| gnmzq04 | 61 | AAPLSEAGYYVFPAAVEETFKQNGLTNAADIHAVRPEKLHQIFGNDAVLYITVTEYGTS |
| gnmzq07 | 61 | AAPLSEAGYYVFPAAVEETFKQNGLTNAADIHAVRPEKLHQIFGNDAVLYITVTEYGTS |
| gnmzq10 | 61 | AAPLSEAGYYVFPAAVEETFKQNGLTNAADIHAVRPEKLHQIFGNDAVLYITVTEYGTS |
| gnmzq11 | 61 | AAPLSEAGYYVFPAAVEETFKQNGLTNAADIHAVRPEKLHQIFGNDAVLYITVTEYGTS |
| gnmzq13 | 61 | AAPLSEAGYYVFPAAVEETFKQNGLTNAADIHAVRPEKLHQIFGNDAVLYITVTEYGTS |
| gnmzq15 | 61 | AAPLSEAGYYVFPAAVEETFKQNGLTNAADIHAVRPEKLHQIFGNDAVLYITVTEYGTS |
| gnmzq16 | 61 | AAPLSEAGYYVFPAAVEETFKQNGLTNAADIHAVRPEKLHQIFGNDAVLYITVTEYGTS |
| gnmzq17 | 61 | AAPLSEAGYYVFPAAVEETFKQNGLTNAADIHAVRPEKLHQIFGNDAVLYITVTEYGTS |
| gnmzq19 | 61 | AAPLSEAGYYVFPAAVEETFKQNGLTNAADIHAVRPEKLHQIFGNDAVLYITVTEYGTS |
| gnmzq21 | 61 | AAPLSEAGYYVFPAAVEETFKQNGLTNAADIHAVRPEKLHQIFGNDAVLYITVTEYGTS |
| gnmzq22 | 61 | AAPLSEAGYYVFPAAVEETFKQNGLTNAADIHAVRPEKLHQIFGNDAVLYITVTEYGTS |
| gnmzq23 | 61 | AAPLSEAGYYVFPAAVEETFKQNGLTNAADIHAVRPEKLHQIFGNDAVLYITVTEYGTS |
| gnmzq24 | 61 | AAPLSEAGYYVFPAAVEETFKQNGLTNAADIHAVRPEKLHQIFGNDAVLYITVTEYGTS |
| gnmzq25 | 61 | AAPLSEAGYYVFPAAVEETFKQNGLTNAADIHAVRPEKLHQIFGNDAVLYITVTEYGTS |
| gnmzq27 | 61 | AAPLSEAGYYVFPAAVEETFKQNGLTNAADIHAVRPEKLHQIFGNDAVLYITVTEYGTS |
| gnmzq28 | 61 | AAPLSEAGYYVFPAAVEETFKQNGLTNAADIHAVRPEKLHQIFGNDAVLYITVTEYGTS |
| gnmzq29 | 61 | AAPLSEAGYYVFPAAVEETFKQNGLTNAADIHAVRPEKLHQIFGNDAVLYITVTEYGTS |
| z2491 | 61 | AAPLSEAGYYVFPAAVEETFKQNGLTNAADIHAVRPEKLHQIFGNDAVLYITVTEYGTS |
| gnmzq14 | 61 | AAPLSEAGYYVFPAAVEETFKQNGLTNAADIHAVRPEKLHQIFGNDAVLYITVTEYGTS |
| gnmzq18 | 61 | AAPLSEAGYYVFPAAVEETFKQNGLTNAADIHAVRPEKLHQIFGNDAVLYITVTEYGTS |
| gnmzq26 | 61 | AAPLSEAGYYVFPAAVEETFKQNGLTNAADIHAVRPEKLHQIFGNDAVLYITVTEYGTS |

| | | |
|---|---|---|
| zz491_519 | 241 | LVAEANAEAIRQIAAALQTQGGADAVNLKIAEQYVAAFNNLAKESNTLIMPANVADIGSL |
| zv26_519 | 241 | LVAEANAEAIRQIAAALQTQGGADAVNLKIAEQYVAAFNNLAKESNTLIMPANVADIGSL |
| zv22_519ass | 241 | LVAEANAEAIRQIAAALQTQGGADAVNLKIAEQYVAAFNNLAKESNTLIMPANVADIGSL |
| fa1090_519 | 241 | LVAEANAEAIRQIAAALQTQGGADAVNLKIAEQYVAAFNNLAKESNTLIMPANVADIGSL |
| zv32_519 | 241 | LVAEANAEAIRQIAAALQTQGGADAVNLKIAEQYVAAFNNLAKESNTLIMPANVADIGSL |
| zv11_519 | 241 | LVAEANAEAIRQIAAALQTQGGADAVNLKIAEQYVAAFNNLAKESNTLIMPANVADIGSL |
| zv28_519 | 241 | LVAEANAEAIRQIAAALQTQGGADAVNLKIAEQYVAAFNNLAKESNTLIMPANVADIGSL |
| zv96_519 | 241 | LVAEANAEAIRQIAAALQTQGGADAVNLKIAEQYVAAFNNLAKESNTLIMPANVADIGSL |
| zv02_519 | 241 | LVAEANAEAIRQIAAALQTQGGADAVNLKIAEQYVAAFNNLAKESNTLIMPANVADIGSL |
| zv03_519 | 241 | LVAEANAEAIRQIAAALQTQGGADAVNLKIAEQYVAAFNNLAKESNTLIMPANVADIGSL |
| zv04_519 | 241 | LVAEANAEAIRQIAAALQTQGGADAVNLKIAEQYVAAFNNLAKESNTLIMPANVADIGSL |
| zv05_519 | 241 | LVAEANAEAIRQIAAALQTQGGADAVNLKIAEQYVAAFNNLAKESNTLIMPANVADIGSL |
| zv01_519 | 241 | LVAEANAEAIRQIAAALQTQGGADAVNLKIAEQYVAAFNNLAKESNTLIMPANVADIGSL |
| zv07_519 | 241 | LVAEANAEAIRQIAAALQTQGGADAVNLKIAEQYVAAFNNLAKESNTLIMPANVADIGSL |
| zv12_519 | 241 | LVAEANAEAIRQIAAALQTQGGADAVNLKIAEQYVAAFNNLAKESNTLIMPANVADIGSL |
| zv18_519 | 241 | LVAEANAEAIRQIAAALQTQGGADAVNLKIAEQYVAAFNNLAKESNTLIMPANVADIGSL |
| zv19_519 | 241 | LVAEANAEAIRQIAAALQTQGGADAVNLKIAEQYVAAFNNLAKESNTLIMPANVADIGSL |
| zv21_519ass | 241 | LVAEANAEAIRQIAAALQTQGGADAVNLKIAEQYVAAFNNLAKESNTLIMPANVADIGSL |
| zv27_519 | 241 | LVAEANAEAIRQIAAALQTQGGADAVNLKIAEQYVAAFNNLAKESNTLIMPANVADIGSL |
| zv20_519ass | 241 | LVAEANAEAIRQIAAALQTQGGADAVNLKIAEQYVAAFNNLAKESNTLIMPANVADIGSL |
| zv06_519ass | 241 | LVAEANAEAIRQIAAALQTQGGADAVNLKIAEQYVAAFNNLAKESNTLIMPANVADIGSL |
| zv29_519ass | 241 | LVAEANAEAIRQIAAALQTQGGADAVNLKIAEQYVAAFNNLAKESNTLIMPANVADIGSL |

FIG.6B(CONTD.)

| | | |
|---|---|---|
| zz4491_519 | 301 | ISAGMKIIDSSKTAK* |
| zv26_519 | 301 | ISAGMKIIDSSKTAK* |
| zv22_519ass | 301 | ISAGMKIIDSSKTAK* |
| fa1090_519 | 301 | ISAGMKIIDSSKTAK* |
| zv32_519 | 301 | ISAGMKIIDSSKTAK* |
| zv11_519 | 301 | ISAGMKIIDSSKTAK* |
| zv28_519 | 301 | ISAGMKIIDSSKTAK* |
| zv96_519 | 301 | ISAGMKIIDSSKTAK* |
| zv02_519 | 301 | ISAGMKIIDSSKTAK* |
| zv03_519 | 301 | ISAGMKIIDSSKTAK* |
| zv04_519 | 301 | ISAGMKIIDSSKTAK* |
| zv05_519 | 301 | ISAGMKIIDSSKTAK* |
| zv01_519 | 301 | ISAGMKIIDSSKTAK* |
| zv07_519 | 301 | ISAGMKIIDSSKTAK* |
| zv12_519 | 301 | ISAGMKIIDSSKTAK* |
| zv18_519 | 301 | ISAGMKIIDSSKTAK* |
| zv19_519 | 301 | ISAGMKIIDSSKTAK* |
| zv21_519ass | 301 | ISAGMKIIDSSKTAK* |
| zv27_519 | 301 | ISAGMKIIDSSKTAK* |
| zv20_519ass | 301 | ISAGMKIIDSSKTAK* |
| zv06_519ass | 301 | ISAGMKIIDSSKTAK* |
| zv29_519 | 301 | ISAGMKIIDSNKTAK* |

ORF 40

```
bz169     539  SMMAIGGGTYRGEAGYAIGYSSISDGGNWIIKGTASGNSRGHFGASASVGYQW*
bz83      539  SMMAIGGGTYRGEAGYAIGYSSISDGGNWIIKGTASGNSRGHFGASASVGYQW*
44-76     539  SMMAIGGGTYRGEAGYAIGYSSISDGGNWIIKGTASGNSRGHFGASASVGYQW*
mc58      539  SMMAIGGGTYRGEAGYAIGYSSISDGGNWIIKGTASGNSRGHFGASASVGYQW*
bz147     539  SMMAIGGGTYRGEAGYAIGYSSISDGGNWIIKGTASGNSRGHFGASASVGYQW*
nge28     538  SMMAIGGGTYRGEAGYAIGYSSISDGGNWIIKGTASGNSRGHFGASASVGYQW*
ng6-88    474  SMMAIGGGTYRGEAGYAIGYSSISDGGNWIIKGTASGNSRGHFGASASVGYQW*
ngf26     478  SMMAIGGGTYRGEAGYAIGYSSISDGGNWIIKGTASGNSRGHFGASASVGYQW*
ngh38     547  SMMAIGGGTYRGEAGYAIGYSSISDGGNWIIKGTASGNSRGHFGASASVGYQW*
ng3-88    542  SMMAIGGGTYRGEAGYAIGYSSISDGGNWIIKGTASGNSRGHFGASASVGYQW*
bz232     542  SMMAIGGGTYRGEAGYAIGYSSISDGGNWIIKGTASGNSRGHFGASASVGYQW*
nge31     542  SMMAIGGGTYRGEAGYAIGYSSISDGGNWIIKGTASGNSRGHFGASASVGYQW*
ngh15     546  SMMAIGGGTYRGEAGYAIGYSSISDTGNWVIKGTASGNSRGHFGTSASVGYQW*
2996      546  SMMAIGGGTYRGEAGYAIGYSSISDTGNWVIKGTASGNSRGHFGTSASVGYQW*
bz198     542  SMMAIGGDTYRGEAGYAIGYSSISDGGNWIIKGTASGNSRGHFGASASVGYQW*
297-0     542  SMMAIGGDTYRGEAGYAIGYSSISDGGNWIIKGTASGNSRGHFGASASVGYQW*
ngh36     546  SMMAIGGGTYRGEAGYAIGYSSISDGGNWIIKGTASGNSRGHFGASASVGYQW*
e26       548  SMMAIGGGTYRGEAGYAIGYSSISDGGNWIIKGTASGNSRGHFGASASVGYQW*
bz133     540  SMMAIGGGTYRGEAGYAIGYSSISDGGNWIIKGTASGNSRGHFGASASVGYQW*
205900    540  SMMAIGGGTYRGEAGYAIGYSSISDGGNWIIKGTASGNSRGHFGASASVGYQW*
f6124     540  SMMAIGGGTYRGEAGYAIGYSSISDGGNWIIKGTASGNSRGHFGASASVGYQW*
z2491     540  SMMAIGGGTYRGEAGYAIGYSSISDGGNWIIKGTASGNSRGHFGASASVGYQW*
860800    540  SMMAIGGGTYRGEAGYAIGYSSISDGGNWIIKGTASGNSRGHFGASASVGYQW*
1000      543  SMMAIGGGTYRGEAGYAIGYSSISDGGNWIIKGTASGNSRGHFGASASVGYQW*
528       543  SMMAIGGGTYRGEAGYAIGYSSISDGGNWIIKGTASGNSRGHFGASASVGYQW*
ngp165    537  SMMAIGGGTYRGEAGYAIGYSSISDTGNWVIKGTASGNSRGHFGTSASVGYQW*
90-18311  537  SMMAIGGGTYRGEAGYAIGYSSISDTGNWVIKGTASGNSRGHFGTSASVGYQW*
93-4286   537  SMMAIGGGTYRGEAGYAIGYSSISDTGNWVIKGTASGNSRGHFGTSASVGYQW*
swz107    546  SMMAIGGGTYRGEAGYAIGYSSISDGGNWIIKGTASGNSRGHFGASASVGYQW*
a22       547  SMMAIGGGTYRGEAGYAIGYSSISDGGNWIIKGTASGNSRGHFGASASVGYQW*
e32       548  SMMAIGGGTYRGEAGYAIGYSSISDGGNWIIKGTASGNSRGHFGASASVGYQW*
```

ORF46

```
BZ133    1   LGISRKISLILSILAVCLPMHAHASDLANDSFIRQVLDRQHFEPDGKYHLFGSRGELAER
BZ232    1   ----RKISLILSILAVCLPMHAHASDLANDSFIRQVLDRQHFEPDGKYHLFGSRGELAER
1000     1   ----KISLILSILAVCLPMHAHASDLANDSFIRQVLDRQHFEPDGKYHLFGSRGELAER
NGH38    1   LGISRKISLILSILAVCLPMHAHASDLANDSFIRQVLDRQHFEPDGKYHLFGSRGELAER
2996     1   LGISRKISLILSILAVCLPMHAHASDLANDSFIRQVLDRQHFEPDGKYHLFGSRGELAER
MC58     1   LGISRKISLILSILAVCLPMHAHASDLANDSFIRQVLDRQHFEPDGKYHLFGSRGELAER

BZ133   61   SGHIGLGNIQSHQLGNLMIQQAAIKGNIGYIVRFSDHGHEVHSPFDNHASHSDSDEAGSP
BZ232   57   SGHIGLGKIQSHQLGNLMIQQAAIKGNIGYIVRFSDHGHEVHSPFDNHASHSDSDEAGSP
1000    56   SGHIGLGNIQSHQLGNLFIQQAAIKGNIGYIVRFSDHGHEVHSPFDNHASHSDSDEAGSP
NGH38   61   SGHIGLGNIQSHQLGNLMIQQAAIKGNIGYIVRFSDHGHEVHSPFDNHASHSDSDEAGSP
2996    61   SGHIGLGNIQSHQLGNLMIQQAAIKGNIGYIVRFSDHGHEVHSPFDNHASHSDSDEAGSP
MC58    61   SGHIGLGKIQSHQLGNLMIQQAAIKGNIGYIVRFSDHGHEVHSPFDNHASHSDSDEAGSP

BZ133  121   VDGFSLYRIHWDGYEHHPADGYDGPQGGGYPVPKGARDIYSYDIKGVAQNIRLNLTDNRS
BZ232  117   VDGFSLYRIHWDGYEHHPADGYDGPQGGGYPAPKGARDIYSYDIKGVAQNIRLNLTDNRS
1000   116   VDGFSLYRIHWDGYEHHPADGYDGPQGGGYPAPKGARDIYSYDIKGVAQNIRLNLTDNRS
NGH38  121   VDGFSLYRIHWDGYEHHPADGYDGPQGGGYPAPKGARDIYSYDIKGVAQNIRLNLTDNRS
2996   121   VDGFSLYRIHWDGYEHHPADGYDGPQGGGYPAPKGARDIYSYDIKGVAQNIRLNLTDNRS
MC58   121   VDGFSLYRIHWDGYEHHPADGYDGPQGGGYPAPKGARDIYSYDIKGVAQNIRLNLTDNRS
```

FIG. 12A(CONTD.)

```
BZ133  181  TGQRLADRFHNAGAMLTQGVGDGFKRATRYSPELDRSGNAAEAFNGTADIVKNIIGAAGE
BZ2232 177  TGQRLADRFHNAGAMLTQGVGDGFKRATRYSPELDRSGNAAEAFNGTADIVKNIIGAAGE
1000   176  TGQRLADRFHNAGAMLTQGVGDGFKRATRYSPELDRSGNAAEAFNGTADIVKNIIGAAGE
NGH38  181  TGQRLADRFHNAGAMLTQGVGDGFKRATRYSPELDRSGNAAEAFNGTADIVKNIIGAAGE
2996   181  TGQRLADRFHNAGSMLTQGVGDGFKRATRYSPELDRSGNAAEAFNGTADIVKNIIGAAGE
MC58   181  TGQRLADRFHNAGSMLTQGVGDGFKRATRYSPELDRSGNAAEAFNGTADIVKNIIGAAGE

BZ133  241  IVGAGDAVQGISEGSNIAVMHGLGLLSTENKMARINDLADMAQLKDYAAAAIRDWAVQNP
BZ2232 237  IVGAGDAVQGISEGSNIAVMHGLGLLSTENKMARINDLADMAQLKDYAAAAIRDWAVQNP
1000   236  IVGAGDAVQGISEGSNIAVMHGLGLLSTENKMARINDLADMAQLKDYAAAAIRDWAVQNP
NGH38  241  IVGAGDAVQGISEGSNIAVMHGLGLLSTENKMARINDLADMAQLKDYAAAAIRDWAVQNP
2996   241  IVGAGDAVQGISEGSNIAVMHGLGLLSTENKMARINDLADMAQLKDYAAAAIRDWAVQNP
MC58   241  IVGAGDAVQGISEGSNIAVMHGLGLLSTENKMARINDLADMAQLKDYAAAAIRDWAVQNP

BZ133  301  NAAQGIEAVSNIFTAVIPIKGIGAVRGKYGLGGITAHPMKRSQMGAIALPKGKSAVSNNF
BZ2232 297  NAAQGIEAVSNIFTAVIPIKGIGAVRGKYGLGGITAHPYKRSQMGAIALPKGKSAVSNNF
1000   296  NAAQGIEAVSNIFMAAIPIKGIGAVRGKYGLGGITAHPYKRSQMGAIALPKGKSAVSDNF
NGH38  301  NAAQGIEAVSNIFMAAIPIKGIGAVRGKYGLGGITAHPHKRSQMGAIALPKGKSAVSDNF
2996   301  NAAQGIEAVSNIFMAAIPIKGIGAVRGKYGLGGITAHPHKRSQMGAIALPKGKSAVSDNF
MC58   301  NAAQGIEAVSNIFMAAIPIKGIGAVRGKYGLGGITAHPHKRSQMGAIALPKGKSAVSDNF
```

FIG. 12A (CONTD.)

```
BZ133  361  ADAAYAKYPSPYHSRNIRSNLEQRYGKENITSSTVPPSNGKNVKLADQRHPKTGVPFDGK
BZ232  357  ADAAYAKYPSPYHSRNIRSNLEQRYGKENITSSTVPPSNGKNVKLADQRHPKTGVPFDGK
1000   356  ADAAYAKYPSPYHSRNIRSNLEQRYGKENITSSTVPPSNGKNVKLADQRHPKTGVPFDGK
NGH38  361  ADAAYAKYPSPYHSRNIRSNLEQRYGKENITSSTVPPSNGKNVKLADQRHPKTGVPFDGK
2996   361  ADAAYAKYPSPYHSRNIRSNLEQRYGKENITSSTVPPSNGKNVKLADQRHPKTGVPFDGK
MC58   361  ADAAYAKYPSPYHSRNIRSNLEQRYGKENITSSTVPPSNGKNVKLADQRHPKTGVPFDGK

BZ133  421  GFPNFEKHVKYDTKLDIQELSGGGIPKAKPVFDAKPRWEVDRKLNKLTTREQVEKNVQEI
BZ232  417  GFPNFEKHVKY-------------------------------------------------
1000   416  GFPNFEKH----------------------------------------------------
NGH38  421  GFPNFEKHVKYDTKLDIQELSGGGIPKAKPVSDAKPRWEVDRKLNKLTTREQVEKNVQEI
2996   421  GFPNFEKHVKYDTKLDIQELSGGGIPKAKPVSDAKPRWEVDRKLNKLTTREQVEKNVQEI
MC58   421  GFPNFEKHVKYDTKLDIQELSGGGIPKAKPVFDAKPRWEVDRKLNKLTTREQVEKNVQEI

BZ133  481  RNGNKNSNFSQHAQLEREINKLKSADEINFADGMGKFTDSMNDKAFSRLVKSVKENGFTN
BZ232  428  ------------------------------------------------------------
1000   424  ------------------------------------------------------------
NGH38  481  RNGNKNSNFNQHAQLEREINKLKSADEINFADGMGKFTDSMDDKAFSRLVKSVKENGFTN
2996   481  RNGNKNSNFSQHAQLEREINKLKSADEINFADGMGKFTDSMNDKAFSRLVKSVKENGFTN
MC58   481  RNGNINSNFSQHAQLEREINKLKSADEINFADGMGKFTDSMNDKAFSRLVKSVKENGFTN
```

FIG. 12B

```
BZ133  541  PVVEYVEINGKAYIVRGNNRVFAAEYLGRIHELKFKKVDFPVPNTSWKNPTDVLNESGNV
BZ232  428  ············································................
10000  424  ············································................
NGH38  541  PVVEYVEINGKAYIVRGNNRVFAAEYLGRIHELKFKKVDFPVPNTSWKNPTDVLNESGNV
2996   541  PVVEYVEINGKAYIVRGNNRVFAAEYLGRIHELKFKKVDFPVPNTSWKNPTDVLNESGNV
MC58   541  PVVEYVEINGKAYIVRGNNRVFAAEYLGRIHELKFKKVDFPVPNTSWKNPTDVLNESGNV

BZ133  601  KRPRYRSK
BZ232  428  ········
10000  424  ········
NGH38  601  KRPRYRSK
2996   601  KRPRYRSK
MC58   601  KRPRYRSK
```

| | | |
|---|---|---|
| Ng-F62 | 183 | IHAPRTGKNIEITSLSHKYWSGKYAFARRVKKNDPSRFLN* |
| FA1090 | 183 | IHAPRTGRNIEITSLSHKYWSGKYAFARRVKKNDPSRFLN* |
| 1000 | 212 | IHAPRTGRNIEITSLSHKYWSGKYAFARRVKKNDPSRFLN* |
| 528 | 212 | IHAPRTGRNIEITSLSHKYWSGKYAFARRVKKNDPSRFLN* |
| NGE31 | 241 | IHAPRTGRNIEITSLSHKYWSGKYAFARRVKKNDPSRFLN* |
| Z2491 | 241 | IHAPRTGRNIEITSLSHKYWSGKYAFARRVKKNDPSRFLN* |
| 44-76 | 241 | IHAPRTGRNIEITSLSHKYWSGKYAFARRVKKNDPSRFLN* |
| NG6-88 | 212 | IHAPRTGRNIEITSLSHKYWSGKYAFARRVKKNDPSRFLN* |
| NGP165 | 212 | IHAPRTGRNIEITSLSHKYWSGKYAFARRVKKNDPSRFLN* |
| NGF26 | 212 | IHAPRTGRNIEITSLSHKYWSGKYAFARRVKKNDPSRFLN* |
| 2996 | 212 | IHAPRTGRNIEITSLSHKYWSGKYAFARRVKKNDPSRFLN* |
| 205900 | 212 | IHAPRTGRNIEITSLSHKYWSGKYAFARRVKKNDPSRFLN* |
| F6124 | 212 | IHAPRTGRNIEITSLSHKYWSGKYAFARRVKKNDPSRFLN* |
| 90-18311 | 212 | IHAPRTGRNIEITSLSHKYWSGKYAFARRVKKNDPSRFLN* |
| 93-4286 | 212 | IHAPRTGRNIEITSLSHKYWSGKYAFARRVKKNDPSRFLN* |
| A22 | 212 | IHAPRTGRNIEITSLSHKYWSGKYAFARRVKKNDPSRFLN* |
| BZ198 | 212 | IHAPRTGRNIEITSLSHKYWSGKYAFARKVKKNDPSRFLN* |
| 297-0 | 212 | IHAPRTGRNIEITSLSHKYWSGKYAFARRVKKNDPSRFLN* |
| BZ147 | 212 | IHAPRTGRNIEITSLSHKYWSGKYAFARRVKKNDPSRFLN* |
| BZ169 | 212 | IHAPRTGRNIEITSLSHKYWSGKYAFARRVKKNDPSRFLN* |
| BZ133 | 212 | IHAPRTGRNIEITSLSHKYWSGKYAFARRVKKNDPSRFLN* |
| NGH38 | 212 | IHAPRTGRNIEITSLSHKYWSGKYAFARRVKKNDPSRFLN* |
| NGH15 | 212 | IHAPRTGRNIEITSLSHKYWSGKYAFARRVKKNDPSRFLN* |
| NGH36 | 212 | IHAPRTGRNIEITSLSHKYWSGKYAFARRVKKNDPSRFLN* |
| BZ232 | 212 | IHAPRTGRNIEITSLSHKYWSGKYAFARRVKKNDPSRFLN* |
| BZ83 | 212 | IHAPRTGRNIEITSLSHKYWSGKYAFARRVKKNDPSRFLN* |
| MC58 | 212 | IHAPRTGRNIEITSLSHKYWSGKYAFARRVKKNDPSRFLN* |
| E26 | 212 | IHAPRTGRNIEITSLSHKYWSGKYAFARRVKKNDPSRFLN* |
| 860800 | 212 | IHAPRTGRNIEITSLSHKYWSGKYAFARRVKKNDPSRFLN* |
| E32 | 212 | IHAPRTGRNIEITSLSHKYWSGKYAFARRVKKNDPSRFLN* |
| NGE28 | 212 | IHAPRTGRNIEITSLSHKYWSGKYAFARRVKKNDPSRFLN* |
| NG3-88 | 212 | IHAPRTGRNIEITSLSHKYWSGKYAFARRVKKNDPSRFLN* |
| SWZ107 | 183 | IHAPRTGRNIEITSLSHKYWSGKYAFARRVKKNDPSRFLN* |
| Ng-SN4 | 183 | IHAPRTGRNIEITSLSHKYWSGKYAFARRKKKNDPSRFLN* |

```
2996       402  AGKYSYRPTDAEKGGFGVFAGKKEQD
93-4286    402  AGKYSYRPTDAEKGGFGVFAGKKEQD
BZ133      402  AGKYSYRPTDAEKGGFGVFAGKKEQD
SWZ107     402  AGKYSYRPTDAEKGGFGVFAGKKEQD
A22        403  AGKYSYRPTDAEKGGFGVFAGKKEQD
E26        400  AGKYSYRPTDAEKGGFGVFAGKKEQD
1000       401  AGKYSYRPTDAEKGGFGVFAGKKEQD
528        401  AGKYSYRPTDAEKGGFGVFAGKKEQD
E32        401  AGKYSYRPTDAEKGGFGVFAGKKEQD
NG6-88     401  AGKYSYRPTDAEKGGFGVFAGKKEQD
NGE31      401  AGKYSYRPTDAEKGGFGVFAGKKEQD
NGF26      401  AGKYSYRPTDAEKGGFGVFAGKKEQD
860800     401  AGKYSYRPTDAEKGGFGVFAGKKEQD
NGH15      394  AGKYSYRPTDAEKGGFGVFAGKKEQD
C11        398  AGKYSYRPTDAEKGGFGVFAGKKEQD
BZ198      467  AGKYSYRPTDAEKGGFGVFAGKKEQD
NGH38      467  AGKYSYRPTDAEKGGFGVFAGKKEQD
BZ169      463  AGKYSYRPTDAEKGGFGVFAGKKEQD
BZ83       463  AGKYSYRPTDAEKGGFGVFAGKKEQD
H44-76     463  AGKYSYRPTDAEKGGFGVFAGKKEQD
MC58       463  AGKYSYRPTDAEKGGFGVFAGKKEQD
NG3-88     461  AGKYSYRPTDAEKGGFGVFAGKKEQD
NGH36      461  AGKYSYRPTDAEKGGFGVFAGKKEQD
BZ147      456  AGKYSYRPTDAEKGGFGVFAGKKEQD
NGE28      455  AGKYSYRPTDAEKGGFGVFAGKKEQD
FA1090     404  AGKYSYRPTDAEKGGFGVFAGKKDRD
NG-F62     404  AGKYSYRPTDAEKGGFGVFAGKKDRD
205900     472  AGKYSYRPTDAEKGGFGVFAGKKEQD
90-18311   472  AGKYSYRPTDAEKGGFGVFAGKKEQD
NGP165     472  AGKYSYRPTDAEKGGFGVFAGKKEQD
Z2491      472  AGKYSYRPTDAEKGGFGVFAGKKEQD
F6124      472  AGKYSYRPTDAEKGGFGVFAGKKEQD
297-0      463  AGKYSYRPTDAEKGGFGVFAGKKEQD
BZ232      471  AGKYSYRPTDAEKGGFGVFAGKKEQD
N_lactam   468  AGKYSYRPTDAEKGGFGVFAGKKEQD
```

```
1000    1  MTIYFKNGFYDDTLGGIPEGAVAVRAEEYAALLAGQAQGGQIAADSDGRPVLTPPRPSEY
F6124   1  MTIYFKNGFYDDTLGGIPEGAVAVRAEEYAALLAGQAQGGQIAADSDGRPVLTPPRPSEY
C11     1  MTIYFKNGFYDDTLGGIPEGAVAVRAEEYAALLAGQAQGGQIAADSDGRPVLTPPRPSFY
2996    1  ----NGFYDDTLGSIPEGAVAVRAEEYAALLAGQAQGGQIAADSDGRPVLTPPRPSDY
BZ133   1  MTIYFKNGFYDDTLGSIPEGAVAVRAEEYAALLAGQAQGGQIAADSDGRPVLTPPRPSDY
MC58    1  MTIYFKNGFYDDTLGSIPEGAVAVRAEEYAALLAGQAQGGQIAADSDGRPVLTPPRPSDY
NGH38   1  --ISKTGFYDDTLGSIPEGAVAVRAEEYAALLAGQTQGGQIAADSDGRPVLTPPRPSEY
BZ232   1  -ITYFKNGFYDDTLGSIPEGAVAVRAEEYAALLAGQTQGGQIAADSDGRPVLTPPRPSEY 1000   61  HEWDGKKWEIGEAAAAARFAEQKTATAFRLAAKADELKNSLLAGYPQVEIDSFYRQEKEA
F6124  61  HEWDGKKWEIGEAAAAARFAEQKTATAFRLAAKADELKNSLLAGYPQVEIDSFYRQEKEA
C11    61  HEWDGKKWEIGEAAAAARFAEQKTATAFRLAAKADELKNSLLAGYPQVEIDSFYRQEKEA
2996   55  HEWDGKKWEIGEAAAAARFAEQKTATAFRLAAKADELKNSLLAGYPQVEIDSFYRQEKEA
BZ133  61  HEWDGKKWKIGEAAAAARFAEQKTATAFRLAAKADELKNSLLAGYPQVEIDSFYRQEKEA
MC58   61  HEWDGKKWKIGEAAAAARFAEQKTAIAFRLAAKADELKNSLLAGYPQVEIDSFYRQEKEA
NGH38  58  HEWDGKKWEIGEAAAAARFAEQKTATAFRLAAKADELKNSLLAGYPQVEIDSFYRQEKEA
BZ232  59  HEWDGKKWEIGEAAAAARFAEQKTATAFRLAAKADELKNSLLAGYPQVEIDSFYRQEKEA
```

FIG. 17(CONTD.)

| | | |
|---|---|---|
| 1000 | 121 | LARQADNNAPTPMLAQIAATRGVELDVLIEKVIEKSARLAVAAGAIIGK | RQQLEDK |
| F6124 | 121 | LARQADNNAPTPMLAQIAATRGVELDVLIEKVIEKSARLAVAAGAIIGK | RQQLEDK |
| C11 | 121 | LARQADNNAPTPMLAQIAAARGVELDVLIEKVEKSARLAVAAGAIIGK | RQQLEDK |
| 2996 | 115 | LARQADNNAPTPMLAQIAAARGVELDVLIEKVEKSARLAVAAGAIIGK | RQQLEDK |
| BZ133 | 121 | LARQADNNAPTPMLAQIAAARGVELDVLIEKVEKSARLAVAAGAIIGK | RQQLEDK |
| MC58 | 121 | LARQADNNAPTPMLAQIAAARGVELDVLIEKVEKSARLAVAAGAIIGK | RQQLEDK |
| NGH38 | 118 | LARQADNNAPTPMLAQIAAARGVELDVLIEKVEKSARLAVAAGAIIGK | RQQLEDK |
| BZ232 | 119 | LARQADNNAPTPMLAQIAAARGVELDVLIEKVEKSARLAVAAGAIIGKPAAAR | RQEHH |

| | | |
|---|---|---|
| 1000 | 177 | LNTIETAPGLDALEKEIEEWTLNIG |
| F6124 | 177 | LNTIETAPGLDALEKEIEEWTLNIG |
| C11 | 177 | LNTIETAPGLDALEKEIEEWTLNIG |
| 2996 | 171 | LNAIETAPGLDALEKEIEEWTLNIG |
| BZ133 | 177 | LNTIETAPGLDALEKEIEEWTLNIG |
| MC58 | 177 | LNTIETAPGLDALEKEIEEWTLNIG |
| NGH38 | 174 | LNAIETAPGLDALEKEIE------ |
| BZ232 | 179 | RN...PRPGLDALEKEIEEWTA-- |

|  | | |
|---|---|---|
| 1000 | 1 | MKKIFAALAAAAVGTASAATYKVDEYHANARFAIDHFNTSTNVGGFYGLTGSVEFDQAK |
| C11 | 1 | MKKIFAALAAAAVGTASAATYKVDEYHANARFAIDHFNTSTNVGGFYGLTGSVEFDQAK |
| 2996 | 1 | MKKIFAALAAAAVGTASAATYKVDEYHANARFAIDHFNTSTNVGGFYGLTGSVEFDQAK |
| BZ133 | 1 | MKKIFAALAAAAVGTASAATYKVDEYHANARFAIDHFNTSTNVGGFYGLTGSVEFDQAK |
| BZ232 | 1 | MKKIFAALAAAAVGTASAATYKVDEYHANARFAIDHFNTSTNVGGFYGLTGSVEFDQAK |
| NGH38 | 1 | MKKIFAALAAAASTASAATYKVDEYHANARFAIDHFNTSTNVGGFYGLTGSVEFDQAK |
| MC58 | 1 | MKKIFAALAAAAVGTASAATYKVDEYHANARFSIDHFNTSTNVGGFYGLTGSVEFDQAK |
| F6124 | 1 | MKKIITALAAAAVGTASAATYKVDEYHANARFAIDHFNTSTNVGGFYGLTGSVEFDQAK |

| | | |
|---|---|---|
| 1000 | 61 | RDGKIDITIPVANLQSGSQHFTDHLKSADIFDAAQYPDIRFVSTKFNFNGKKLVSVDGNL |
| C11 | 61 | RDGKIDITIPVANLQSGSQHFTDHLKSADIFDAAQYPDIRFVSTKFNFNGKKLVSVDGNL |
| 2996 | 61 | RDGKIDITIPVANLQSGSQHFTDHLKSADIFDAAQYPDIRFVSTKFNFNGKKLVSVDGNL |
| BZ133 | 61 | RDGKIDITIPVANLQSGSQHFTDHLKSADIFDAAQYPDIRFVSTKFNFNGKKLVSVDGNL |
| BZ232 | 61 | RDGKIDITIPVANLQSGSQHFTDHLKSADIFDAAQYPDIRFVSTKFNFNGKKLVSVDGNL |
| NGH38 | 61 | RDGKIDITIPVANLQSGSQHFTDHLKSADIFDAAQYPDIRFVSTKFNFNGKKLVSVDGNL |
| MC58 | 61 | RDGKIDITIPANLQSGSQHFTDHLKSADIFDAAQYPDIRFVSTKFNFNGKKLVSVDGNL |
| F6124 | 61 | RDGKIDITIPVANLQSGSQHFTDHLKSADIFDAAQYPDIRFVSTKFNFNGKKLVSVDGNL |

FIG. 19(CONTD.)

| | | |
|---|---|---|
| 1000 | 121 | TMHGKTAPVKLKAEKFNCYQSPMEKTEVCGGDFSTTIDRTKWGVDYLVNVGMTKSVRIDI |
| C11 | 121 | TMHGKTAPVKLKAEKFNCYQSPMEKTEVCGGDFSTTIDRTKWGVDYLVNVGMTKSVRIDI |
| 2996 | 121 | TMHGKTAPVKLKAEKFNCYQSPMEKTEVCGGDFSTTIDRTKWGVDYLVNVGMTKSVRIDI |
| BZ133 | 121 | TMHGKTAPVKLKAEKFNCYQSPWAKTEVCGGDFSTTIDRTKWGVDYLVNVGMTKSVRIDI |
| BZ232 | 121 | TMHGKTAPVKLKAEKFNCYQSPMAKTEVCGGDFSTTIDRTKWGVDYLVNVGMTKSVRIDI |
| NGH38 | 121 | TMHGKTAPVKLKAEKFNCYQSPMEKTEVCGGDFSTTIDRTKWGVDYLVNVGMTKSVRIDI |
| MC58 | 121 | TMHGKTAPVKLKAEKFNCYQSPWEKTEVCGGDFSTTIDRTKWGMDYLVNVGMTKSVRIDI |
| F6124 | 121 | TMHGKTAPVKLKAEKFNCYQSPMLKTEVCGGDFSTTIDRTKWGMDYLVNVGMTKSVRIDI |

| | | |
|---|---|---|
| 1000 | 181 | QIEAAKQ |
| C11 | 181 | QIEAAKQ |
| 2996 | 181 | QIEAAKQ |
| BZ133 | 181 | QIEAAKQ |
| BZ232 | 181 | QIEAAKQ |
| NGH38 | 181 | QIEAAKQ |
| MC58 | 181 | QIEAAKQ* |
| F6124 | 181 | QIEAAKQ |

FIGURE 20A: Orf 4 (33 kD)
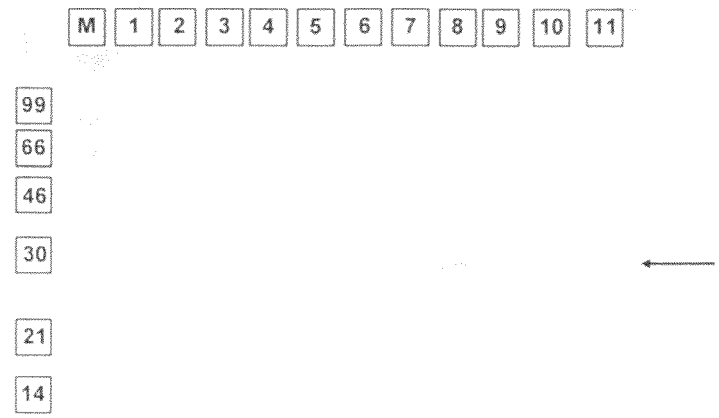
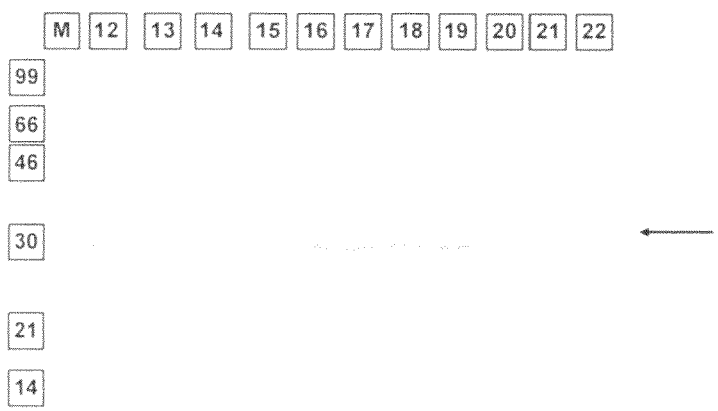
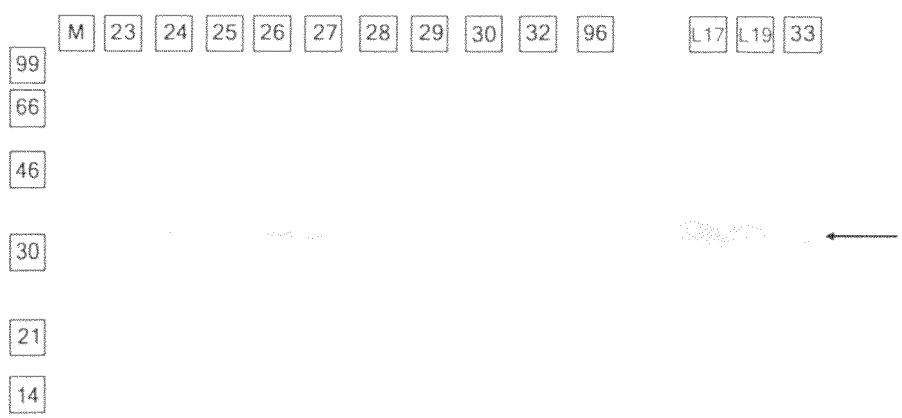

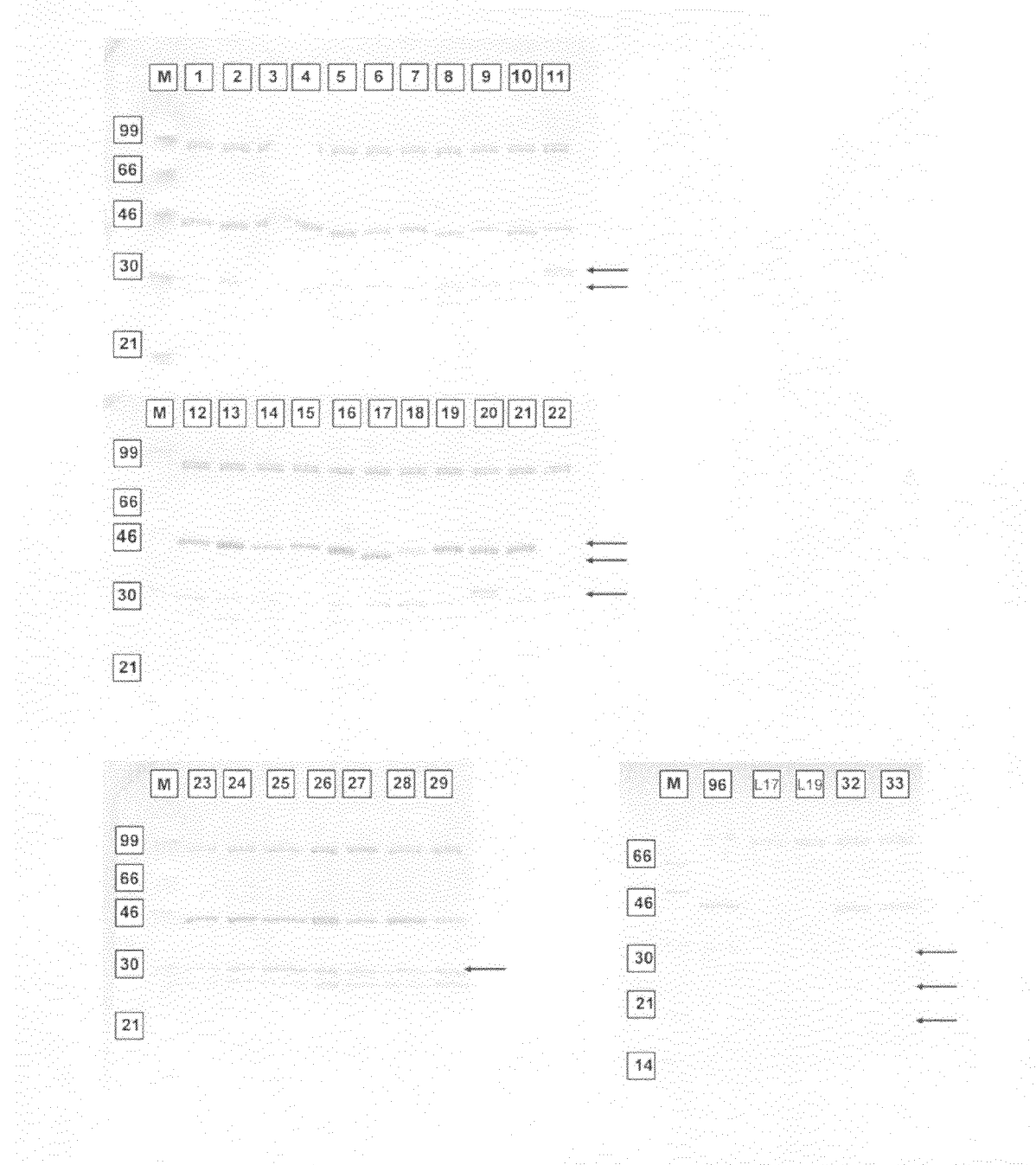
FIGURE 20B: 225 (27 kD) *

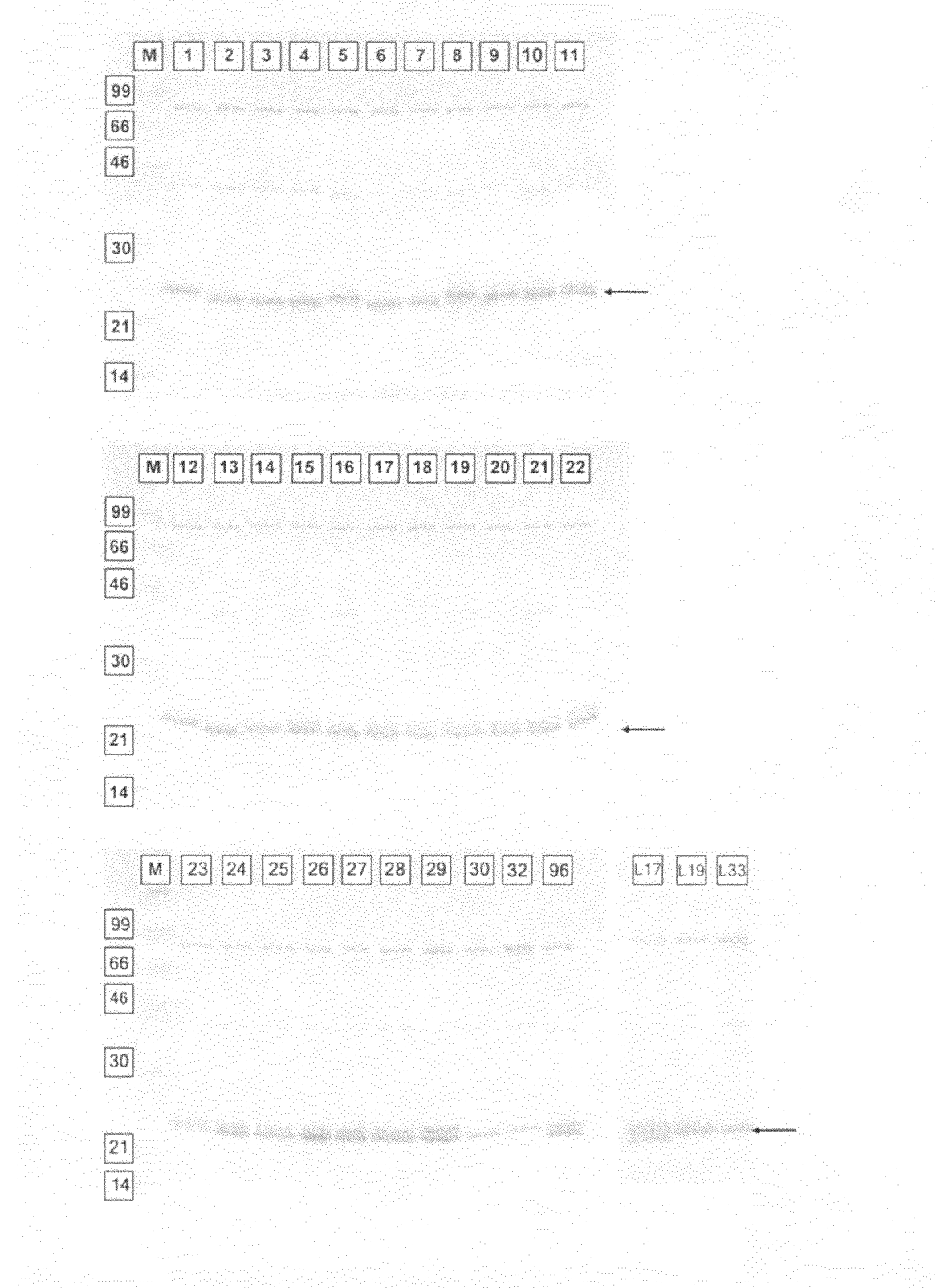

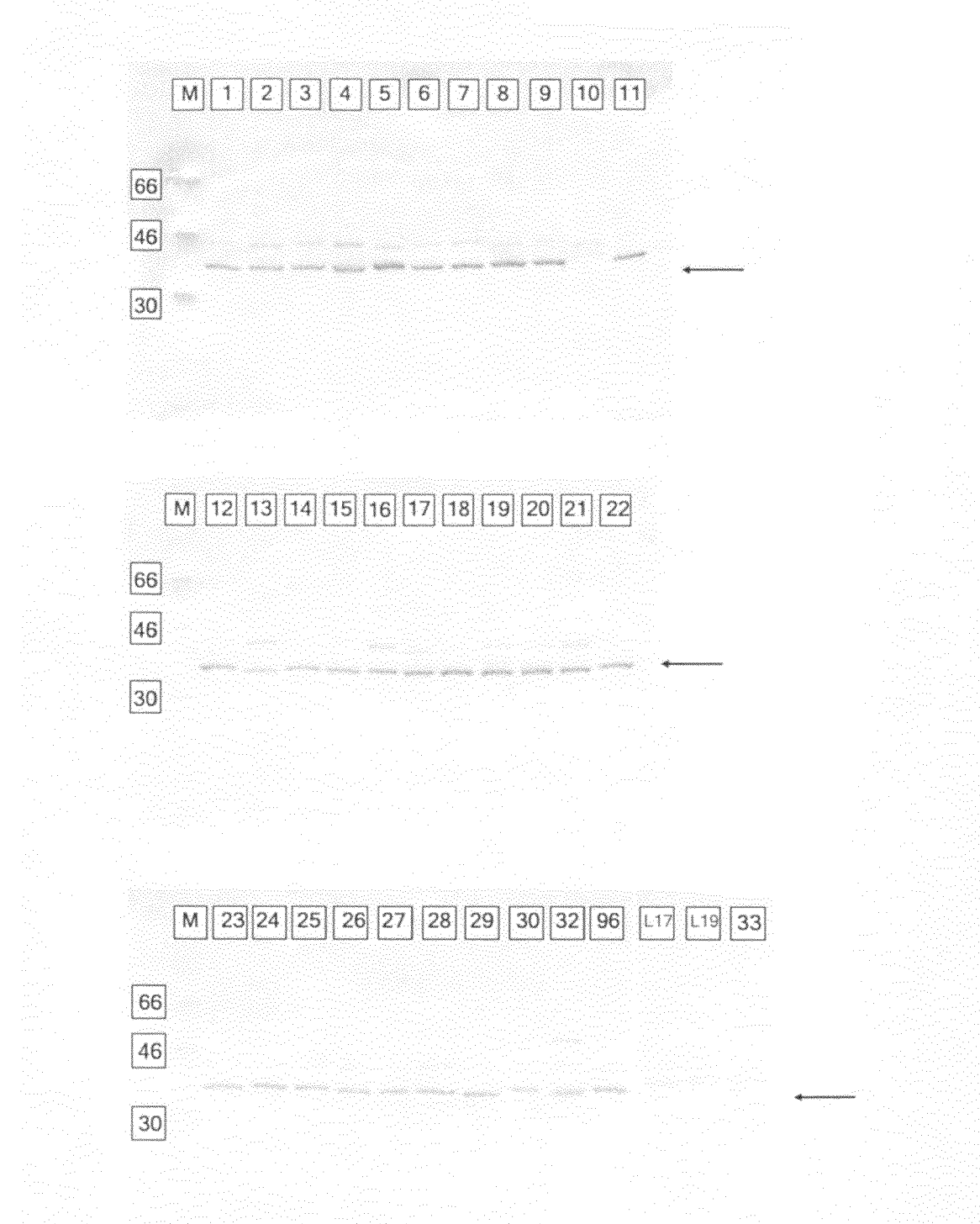
FIGURE 20D: 519 (35 kD)

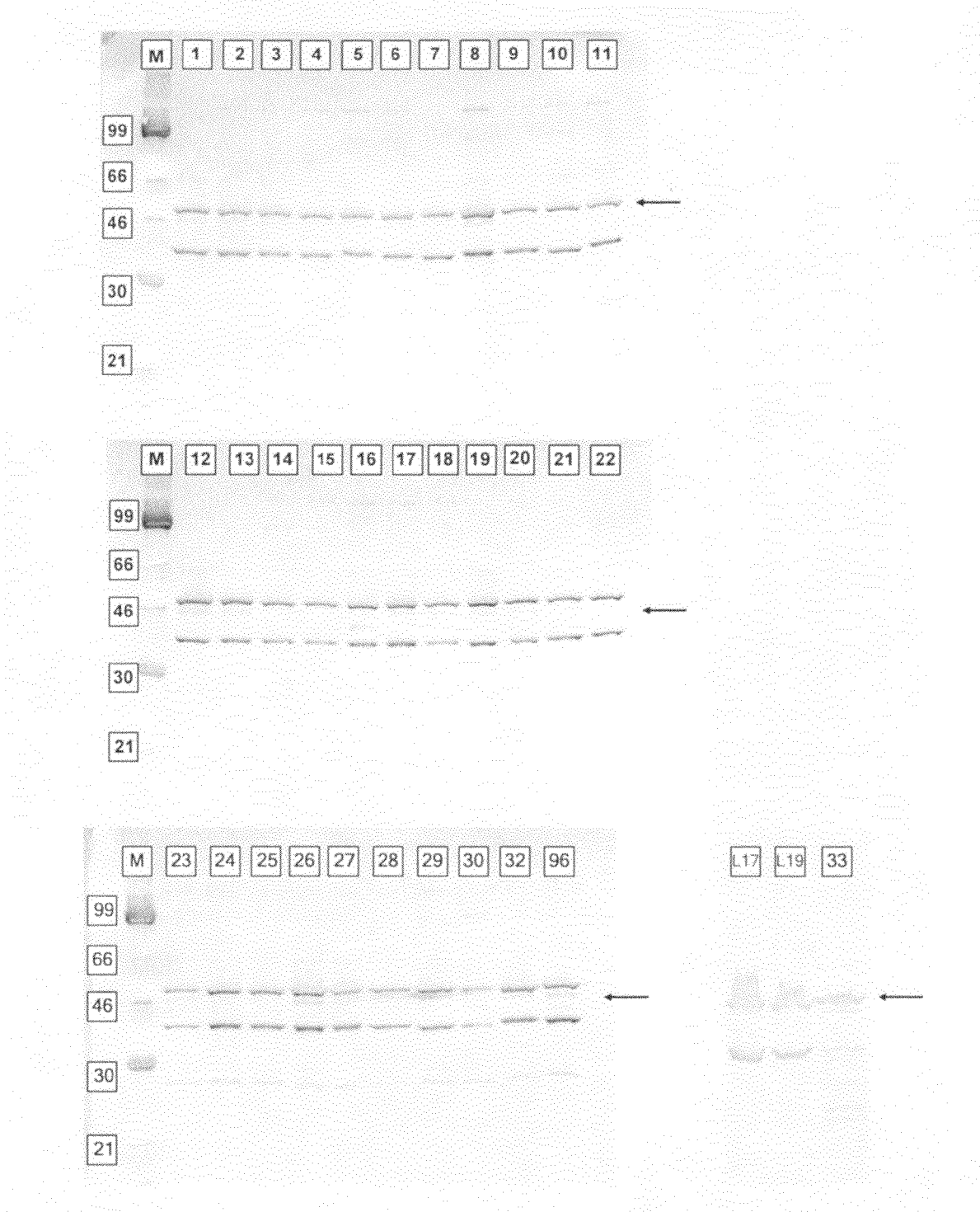

CONSERVED NEISSERIAL ANTIGENS

CROSS REFERENCE TO RELATED APPLICATIONS

This application is a Divisional of U.S. patent application Ser. No. 11/800,090, filed May 2, 2007 (now U.S. Pat. No. 7,604,810), which is a Divisional of U.S. patent application Ser. No. 09/980,602, filed on Sep. 20, 2002 (now U.S. Pat. No. 7,368,261), entitled CONSERVED NEISSERIAL ANTIGENS, which is the National Stage of International Application No. PCT/IB00/00642, filed Apr. 28, 2000, which claims the benefit of United Kingdom Application No. 0005728.1, titled CONSERVED NEISSERIAL ANTIGENS, filed Mar. 9, 2000; and the benefit of United Kingdom Application No. 9910168.5, titled CONSERVED NEISSERIAL ANTIGENS, filed Apr. 30, 1999; all of which are incorporated herein by reference in their entireties.

The contents of all documents cited herein are incorporated by reference in their entirety.

FIELD OF THE INVENTION

This invention relates to conserved antigens from the *Neisseria* bacteria.

SUBMISSION ON COMPACT DISC

The content of the following submission on compact discs is incorporated herein by reference in its entirety: A computer readable form (CRF) of the Sequence Listing on compact disc (file name: 223002099211SeqList.txt, date recorded: Oct. 19, 2009, size: 605 KB); a duplicate compact disc copy of the Sequence Listing (COPY 1) (file name: 223002099211SeqList.txt, date recorded: Oct. 19, 2009, size: 605 KB); and a duplicate compact disc copy of the Sequence Listing (COPY 2) (file name: 223002099211 SeqList.txt, date recorded: Oct. 19, 2009, size: 605 KB).

BACKGROUND ART

*Neisseria meningitidis* and *Neisseria gonorrhoeae* are non-motile, gram negative diplococci that are pathogenic in humans.

Based on the organism's capsular polysaccharide, 12 serogroups of *N. meningitidis* have been identified. Group A is the pathogen most often implicated in epidemic disease in sub-Saharan Africa. Serogroups B and C are responsible for the vast majority of cases in the United States and in most developed countries. Serogroups W135 and Y are responsible for the rest of the cases in the United States and developed countries.

The meningococcal vaccine currently in use is a tetravalent polysaccharide vaccine composed of serogroups A, C, Y and WI 35. This approach cannot be used for Meningococcus B, however, because the menB capsular polysaccharide is a polymer of α(2-8)-linked N-acetyl neuraminic acid that is also present in mammalian tissue. One approach to a menB vaccine uses mixtures of outer membrane proteins (OMPs) To overcome the antigenic variability, multivalent vaccines containing up to nine different porins have been constructed [eg. Poolman (1992) Development of a meningococcal vaccine. *Infect. Agents Dis.* 4:13-28]. Additional proteins to be used in outer membrane vaccines have been the opa and opc proteins, but none of these approaches have been able to overcome the antigenic variability [eg. Ala'Aldeen & Borriello (1996) The meningococcal transferrin-binding proteins 1 and 2 are both surface exposed and generate bactericidal antibodies capable of killing homologous and heterologous strains. *Vaccine* 14(1):49-53].

A large number of Neisserial protein and nucleotide sequences are disclosed in WO99/24578, WO99/36544, WO99/57280 and WO00/22430. The contents of these four applications are incorporated herein by reference. Comprehensive sequence data from strain MC58 is disclosed in Tettelin et al. [*Science* (2000) 287:1809-1815], the contents of which are also incorporated herein by reference.

DESCRIPTION OF THE INVENTION

To ensure maximum cross-strain recognition and reactivity, regions of proteins that are conserved between different Neisserial species, serogroups and strains can be used. The invention therefore provides proteins which comprise stretches of amino acid sequence that are shared across the majority of *Neisseria*, particularly *N. meningitidis* and *N. gonorrhoeae*.

The invention provides a protein comprising a fragment of a Neisserial protein, wherein said fragment consists of n consecutive conserved amino acids, with the proviso that the invention does not include within its scope full-length Neisserial proteins. Depending on the particular protein, n is 7 or more (eg. 8, 10, 12, 14, 16, 18, 20 or more). The fragment preferably comprises an antigenic or immunogenic region of the Neisserial protein.

A "conserved" amino acid is one that is present in a particular Neisserial protein in at least x % of *Neisseria*. The value of x may be 50% or more eg. 66%, 75%, 80%, 90%, 95% or even 100% (ie. the amino acid is found in the protein in question in all *Neisseria*).

In order to determine whether an amino acid is "conserved" in a particular Neisserial protein, it is necessary to compare that amino acid residue in the sequences of the protein in question from a plurality of different *Neisseria* (a "reference population"). The reference population may include a number of different *Neisseria* species (preferably *N. meningitidis* and *N. gonorrhoeae*) or may include a single species. The reference population may include a number of different serogroups of a particular species (such as the A, B, C, W135, X, Y, Z and 29E serogroups of *N. meningitidis*) or a single serogroup. The reference population may also include a number of different strains from a particular serogroup (such as the NG6/88, BZ198, NG3/88, 297-0, BZ147, BZ169, 528, BZ133, NGE31, NGH38, NGH15, BZ232, BZ83, and 44/76 strains of *N. meningitidis* B). A preferred reference population consists of the 5 most common strains of *N. meningitidis* and/or the 5 most common strains of *N. gonorrhoeae*.

The reference population preferably comprises k strains taken from k different branches of a suitable phylogenetic tree, such as those disclosed in (a) Ni et al. (1992) *Epidemiol Infect* 109:227-239 (b) Wolff et al. (1992) *Nucleic Acids Res* 20:4657 (c) Bygraves & Maiden (1992) *J. Gen. Microbiol.* 138:523-531 (d) Caugant et al. (1987) *J. Bacteriol.* 69:2781-2792. Another phylogenetic tree that can be used is shown in FIG. 8 herein, and another in FIG. 9b.

It will be appreciated that a particular species, serogroup or strain should only be included in the reference population if it encodes the protein in which the amino acid in question is located. In the case of amino acids within ORF40 described below, for instance, the reference population should not include *N. gonorrhoeae* because this species does not contain ORF40.

For proteins found in both *N. meningitidis* and *N. gonorrhoeae*, therefore, a preferred reference population comprises:

*N. meningitidis* A, strain Z249
*N. meningitidis* B, strains NG6/88
*N. meningitidis* W, strains A22
*N. gonorrhoeae*, strain Ng F62

These are described in (a) Seiler A. et al. (1996) *Mol. Microbiol.* 19(4):841-856 (b) Maiden et al. (1998) *Proc. Natl. Acad. Sci. USA* 95:3140-3145 (c) Virji et al. (1992) *Mol. Microbiol.* 6:1271-1279 (d) Dempsey et al. (1991) *J. Bacteriol.* 173:5476-5486.

For proteins found only in *N. meningitidis*, however, a preferred reference population comprises:

*N. meningitidis* A, strain Z2491
*N. meningitidis* B, strains NG6/88
*N. meningitidis* W, strains A22

Amino acid sequences of different *Neissieriae* can easily be compared using computers. This will typically involve the alignment of a number of sequences using an algorithm such as CLUSTAL [Thompson et al. (1994) *Nucleic Acids Res* 22:4673-4680; *Trends Biochem Sci* (1998) 23:403-405] or, preferably, PILEUP [part of the GCG Wisconsin package, preferably version 9.0].

Conserved amino acids are readily apparent in a multiple sequence alignment—at the amino acid position in question a majority of the aligned sequences will contain a particular amino acid. Conserved amino acids can be made more visually apparent by using a program such as BOXSHADE [available, for instance, at the NIH on-line], PRETTYBOX [GCG Wisconsin, version 10] or JALVIEW [available on-line at EBI].

The protein preferably comprises a fragment of one of the proteins disclosed in WO99/24578, WO99/36544, WO99/57280 or WO00/22430, or of one of the 2158 ORFs disclosed in Tettelin et al. [*Science* (2000) 287:1809-1815]. More particularly, it preferably comprises a fragment of one or more of ORF4, ORF40, ORF46, protein 225, protein 235, protein 287, protein 519, protein 726, protein 919 and protein 953 disclosed therein (see examples herein). Typically, the protein of the invention will not comprise a protein sequence explicitly disclosed in WO99/24578, WO99/36544, WO99/57280, WO00/22430, or Tettelin et al.

The invention also provides a protein comprising one of the sequences shown in the Figures.

The proteins of the invention can, of course, be prepared by various means (eg. recombinant expression, native expression, purification from cell culture, chemical synthesis etc.) and in various forms (eg. native, fusions etc.). They are preferably prepared in substantially pure form (ie. substantially free from other Neisserial or host cell proteins)

According to a further aspect, the invention provides antibodies which bind to these proteins. These may be polyclonal or monoclonal and may be produced by any suitable means.

According to a further aspect, the invention provides nucleic acid encoding the proteins of the invention. It should also be appreciated that the invention provides nucleic acid comprising sequences complementary to these (eg. for antisense or probing purposes).

Furthermore, the invention provides nucleic acid which can hybridise to the *N. meningitidis* nucleic acid disclosed in the examples, preferably under "high stringency" conditions (eg. 65° C. in a 0.1×SSC, 0.5% SDS solution).

Nucleic acid according to the invention can, of course, be prepared in many ways (eg. by chemical synthesis, from genomic or cDNA libraries, from the organism itself etc.) and can take various forms (eg. single stranded, double stranded, vectors, probes etc.).

In addition, the term "nucleic acid" includes DNA and RNA, and also their analogues, such as those containing modified backbones, and also peptide nucleic acids (PNA) etc.

According to a further aspect, the invention provides vectors comprising nucleotide sequences of the invention (eg. expression vectors) and host cells transformed with them.

According to a further aspect, the invention provides compositions comprising protein, antibody, and/or nucleic acid according to the invention. These compositions may be suitable as vaccines, for instance, or as diagnostic reagents, or as immunogenic compositions.

The invention also provides nucleic acid, protein, or antibody according to the invention for use as medicaments (eg. as vaccines) or as diagnostic reagents. It also provides the use of nucleic acid, protein, or antibody according to the invention in the manufacture of: (i) a medicament for treating or preventing infection due to Neisserial bacteria; (ii) a diagnostic reagent for detecting the presence of Neisserial bacteria or of antibodies raised against Neisserial bacteria; and/or (iii) a reagent which can raise antibodies against Neisserial bacteria. The use is preferably applicable to all species of *Neisseria*.

Where a Neisserial protein contains more than q % conserved amino acids, the invention provides the use of the Neisserial protein, or a fragment thereof, as a non-strain-specific protein that exhibits cross-reactivity between many species, serogroups and strains. The value of q may be 50%, 60%, 75%, 80%, 90%, 95% or even 100%.

The invention also provides a method of treating a patient, comprising administering to the patient a therapeutically effective amount of nucleic acid, protein, and/or antibody according to the invention.

According to further aspects, the invention provides various processes.

A process for producing proteins of the invention is provided, comprising the step of culturing a host cell according to the invention under conditions which induce protein expression.

A process for producing protein or nucleic acid of the invention is provided, wherein the protein or nucleic acid is synthesised in part or in whole using chemical means.

A process for detecting polynucleotides of the invention is provided, comprising the steps of: (a) contacting a nucleic probe according to the invention with a biological sample under hybridizing conditions to form duplexes; and (b) detecting said duplexes.

A process for detecting proteins of the invention is provided, comprising the steps of: (a) contacting an antibody according to the invention with a biological sample under conditions suitable for the formation of an antibody-antigen complexes; and (b) detecting said complexes.

A summary of standard techniques and procedures which may be employed in order to perform the invention (eg. to utilise the disclosed sequences for vaccination or diagnostic purposes) follows. This summary is not a limitation on the invention but, rather, gives examples that may be used, but are not required.

General

The practice of the present invention will employ, unless otherwise indicated, conventional techniques of molecular biology, microbiology, recombinant DNA, and immunology, which are within the skill of the art. Such techniques are explained fully in the literature eg. Sambrook *Molecular*

*Cloning; A Laboratory Manual, Second Edition* (1989); *DNA Cloning, Volumes I and ii* (D. N Glover ed. 1985); *Oligonucleotide Synthesis* (M. J. Gait ed, 1984); *Nucleic Acid Hybridization* (B. D. Hames & S. J. Higgins eds. 1984); *Transcription and Translation* (B. D. Hames & S. J. Higgins eds. 1984); *Animal Cell Culture* (R. I. Freshney ed. 1986); *Immobilized Cells and Enzymes* (IRL Press, 1986); B. Perbal, *A Practical Guide to Molecular Cloning* (1984); the *Methods in Enzymology* series (Academic Press, Inc.), especially volumes 154 & 155; *Gene Transfer Vectors for Mammalian Cells* (J. H. Miller and M. P. Calos eds. 1987, Cold Spring Harbor Laboratory); Mayer and Walker, eds. (1987), *Immunochemical Methods in Cell and Molecular Biology* (Academic Press, London); Scopes, (1987) *Protein Purification: Principles and Practice*, Second Edition (Springer-Verlag, N.Y.), and *Handbook of Experimental Immunology, Volumes I-IV* (D. M. Weir and C. C. Blackwell eds 1986).

Standard abbreviations for nucleotides and amino acids are used in this specification.

All publications, patents, and patent applications cited herein are incorporated in full by reference. In particular, the contents of international patent applications WO99/24578, WO99/36544, WO99/57280 and WO00/22430 are incorporated herein.

DEFINITIONS

A composition containing X is "substantially free of" Y when at least 85% by weight of the total X+Y in the composition is X. Preferably, X comprises at least about 90% by weight of the total of X+Y in the composition, more preferably at least about 95% or even 99% by weight.

The term "comprising" means "including" as well as "consisting" eg. a composition "comprising" X may consist exclusively of X or may include something additional to X, such as X+Y.

The term "heterologous" refers to two biological components that are not found together in nature. The components may be host cells, genes, or regulatory regions, such as promoters. Although the heterologous components are not found together in nature, they can function together, as when a promoter heterologous to a gene is operably linked to the gene. Another example is where a Neisserial sequence is heterologous to a mouse host cell. A further examples would be two epitopes from the same or different proteins which have been assembled in a single protein in an arrangement not found in nature.

An "origin of replication" is a polynucleotide sequence that initiates and regulates replication of polynucleotides, such as an expression vector. The origin of replication behaves as an autonomous unit of polynucleotide replication within a cell, capable of replication under its own control. An origin of replication may be needed for a vector to replicate in a particular host cell. With certain origins of replication, an expression vector can be reproduced at a high copy number in the presence of the appropriate proteins within the cell. Examples of origins are the autonomously replicating sequences, which are effective in yeast; and the viral T-antigen, effective in COS-7 cells.

A "mutant" sequence is defined as DNA, RNA or amino acid sequence differing from but having sequence identity with the native or disclosed sequence. Depending on the particular sequence, the degree of sequence identity between the native or disclosed sequence and the mutant sequence is preferably greater than 50% (eg. 60%, 70%, 80%, 90%, 95%, 99% or more, calculated using the Smith-Waterman algorithm as described above). As used herein, an "allelic variant" of a nucleic acid molecule, or region, for which nucleic acid sequence is provided herein is a nucleic acid molecule, or region, that occurs essentially at the same locus in the genome of another or second isolate, and that, due to natural variation caused by, for example, mutation or recombination, has a similar but not identical nucleic acid sequence. A coding region allelic variant typically encodes a protein having similar activity to that of the protein encoded by the gene to which it is being compared. An allelic variant can also comprise an alteration in the 5' or 3' untranslated regions of the gene, such as in regulatory control regions (eg. see U.S. Pat. No. 5,753,235).

Expression Systems

The Neisserial nucleotide sequences can be expressed in a variety of different expression systems; for example those used with mammalian cells, baculoviruses, plants, bacteria, and yeast.

i. Mammalian Systems

Mammalian expression systems are known in the art. A mammalian promoter is any DNA sequence capable of binding mammalian RNA polymerase and initiating the downstream (3') transcription of a coding sequence (eg. structural gene) into mRNA. A promoter will have a transcription initiating region, which is usually placed proximal to the 5' end of the coding sequence, and a TATA box, usually located 25-30 base pairs (bp) upstream of the transcription initiation site. The TATA box is thought to direct RNA polymerase II to begin RNA synthesis at the correct site. A mammalian promoter will also contain an upstream promoter element, usually located within 100 to 200 bp upstream of the TATA box. An upstream promoter element determines the rate at which transcription is initiated and can act in either orientation [Sambrook et al. (1989) "Expression of Cloned Genes in Mammalian Cells." In *Molecular Cloning: A Laboratory Manual, 2nd ed.*].

Mammalian viral genes are often highly expressed and have a broad host range; therefore sequences encoding mammalian viral genes provide particularly useful promoter sequences. Examples include the SV40 early promoter, mouse mammary tumor virus LTR promoter, adenovirus major late promoter (Ad MLP), and herpes simplex virus promoter. In addition, sequences derived from non-viral genes, such as the murine metallotheionein gene, also provide useful promoter sequences. Expression may be either constitutive or regulated (inducible), depending on the promoter can be induced with glucocorticoid in hormone-responsive cells.

The presence of an enhancer element (enhancer), combined with the promoter elements described above, will usually increase expression levels. An enhancer is a regulatory DNA sequence that can stimulate transcription up to 1000-fold when linked to homologous or heterologous promoters, with synthesis beginning at the normal RNA start site. Enhancers are also active when they are placed upstream or downstream from the transcription initiation site, in either normal or flipped orientation, or at a distance of more than 1000 nucleotides from the promoter [Maniatis et al. (1987) *Science* 236.1237; Alberts et al. (1989) *Molecular Biology of the Cell*, 2nd ed.]. Enhancer elements derived from viruses may be particularly useful, because they usually have a broader host range. Examples include the SV40 early gene enhancer [Dijkema et al (1985) *EMBO J.* 4:761] and the enhancer/promoters derived from the long terminal repeat (LTR) of the Rous Sarcoma Virus [Gorman et al. (1982b) *Proc. Natl. Acad. Sci.* 79:6777] and from human cytomegalovirus [Boshart et al. (1985) *Cell* 41:521]. Additionally, some enhancers are regulatable and become active only in the presence of an inducer, such as a hormone or metal ion [Sassone-Corsi and Borelli (1986) *Trends Genet.* 2:215; Maniatis et al. (1987) *Science* 236:1237].

A DNA molecule may be expressed intracellularly in mammalian cells. A promoter sequence may be directly linked with the DNA molecule, in which case the first amino acid at the N-terminus of the recombinant protein will always be a methionine, which is encoded by the ATG start codon. If desired, the N-terminus may be cleaved from the protein by in vitro incubation with cyanogen bromide.

Alternatively, foreign proteins can also be secreted from the cell into the growth media by creating chimeric DNA molecules that encode a fusion protein comprised of a leader sequence fragment that provides for secretion of the foreign protein in mammalian cells. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell. The adenovirus triparite leader is an example of a leader sequence that provides for secretion of a foreign protein in mammalian cells.

Usually, transcription termination and polyadenylation sequences recognized by mammalian cells are regulatory regions located 3' to the translation stop codon and thus, together with the promoter elements, flank the coding sequence. The 3' terminus of the mature mRNA is formed by site-specific post-transcriptional cleavage and polyadenylation [Birnstiel et al. (1985) *Cell* 41:349; Proudfoot and Whitelaw (1988) "Termination and 3' end processing of eukaryotic RNA. In *Transcription and splicing* (ed. B. D. Hames and D. M. Glover); Proudfoot (1989) *Trends Biochem. Sci.* 14:105]. These sequences direct the transcription of an mRNA which can be translated into the polypeptide encoded by the DNA. Examples of transcription terminator/polyadenylation signals include those derived from SV40 [Sambrook et al (1989) "Expression of cloned genes in cultured mammalian cells." In *Molecular Cloning: A Laboratory Manual*].

Usually, the above described components, comprising a promoter, polyadenylation signal, and transcription termination sequence are put together into expression constructs. Enhancers, introns with functional splice donor and acceptor sites, and leader sequences may also be included in an expression construct, if desired. Expression constructs are often maintained in a replicon, such as an extrachromosomal element (eg. plasmids) capable of stable maintenance in a host, such as mammalian cells or bacteria. Mammalian replication systems include those derived from animal viruses, which require trans-acting factors to replicate. For example, plasmids containing the replication systems of papovaviruses, such as SV40 [Gluzman (1981) *Cell* 23:175] or polyomavirus, replicate to extremely high copy number in the presence of the appropriate viral T antigen. Additional examples of mammalian replicons include those derived from bovine papillomavirus and Epstein-Barr virus. Additionally, the replicon may have two replication systems, thus allowing it to be maintained, for example, in mammalian cells for expression and in a prokaryotic host for cloning and amplification. Examples of such mammalian-bacteria shuttle vectors include pMT2 [Kaufman et al. (1989) *Mol. Cell. Biol.* 9:946] and pHEBO [Shimizu et al. (1986) *Mol. Cell. Biol.* 6:1074].

The transformation procedure used depends upon the host to be transformed. Methods for introduction of heterologous polynucleotides into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the art and include many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (eg. Hep G2), and a number of other cell lines.

ii. Baculovirus Systems

The polynucleotide encoding the protein can also be inserted into a suitable insect expression vector, and is operably linked to the control elements within that vector. Vector construction employs techniques which are known in the art. Generally, the components of the expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media.

After inserting the DNA sequence encoding the protein into the transfer vector, the vector and the wild type viral genome are transfected into an insect host cell where the vector and viral genome are allowed to recombine. The packaged recombinant virus is expressed and recombinant plaques are identified and purified. Materials and methods for baculovirus/insect cell expression systems are commercially available in kit form from, inter alia, Invitrogen, San Diego Calif. ("MaxBac" kit). These techniques are generally known to those skilled in the art and fully described in Summers and Smith, *Texas Agricultural Experiment Station Bulletin No. 1555* (1987) (hereinafter "Summers and Smith").

Prior to inserting the DNA sequence encoding the protein into the baculovirus genome, the above described components, comprising a promoter, leader (if desired), coding sequence of interest, and transcription termination sequence, are usually assembled into an intermediate transplacement construct (transfer vector). This construct may contain a single gene and operably linked regulatory elements; multiple genes, each with its owned set of operably linked regulatory elements; or multiple genes, regulated by the same set of regulatory elements. Intermediate transplacement constructs are often maintained in a replicon, such as an extrachromosomal element (eg. plasmids) capable of stable maintenance in a host, such as a bacterium. The replicon will have a replication system, thus allowing it to be maintained in a suitable host for cloning and amplification.

Currently, the most commonly used transfer vector for introducing foreign genes into AcNPV is pAc373. Many other vectors, known to those of skill in the art, have also been designed. These include, for example, pVL985 (which alters the polyhedrin start codon from ATG to ATT, and which introduces a BamHI cloning site 32 basepairs downstream from the ATT; see Luckow and Summers, *Virology* (1989) 17:31.

The plasmid usually also contains the polyhedrin polyadenylation signal (Miller et al. (1988) *Ann. Rev. Microbiol.*, 42:177) and a prokaryotic ampicillin-resistance (amp) gene and origin of replication for selection and propagation in *E. coli*.

Baculovirus transfer vectors usually contain a baculovirus promoter. A baculovirus promoter is any DNA sequence capable of binding a baculovirus RNA polymerase and initiating the downstream (5' to 3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A baculovirus transfer vector may also have a second domain called an enhancer, which, if present, is usually distal to the structural gene. Expression may be either regulated or constitutive.

Structural genes, abundantly transcribed at late times in a viral infection cycle, provide particularly useful promoter sequences. Examples include sequences derived from the gene encoding the viral polyhedron protein, Friesen et al., (1986) "The Regulation of Baculovirus Gene Expression," in: *The Molecular Biology of Baculoviruses* (ed. Walter Doerfler); EPO Publ. Nos. 127 839 and 155 476; and the gene encoding the p10 protein, Vlak et al., (1988), *J. Gen. Virol.* 69:765.

DNA encoding suitable signal sequences can be derived from genes for secreted insect or baculovirus proteins, such as the baculovirus polyhedrin gene (Carbonell et al. (1988) *Gene,* 73:409). Alternatively, since the signals for mammalian cell posttranslational modifications (such as signal peptide cleavage, proteolytic cleavage, and phosphorylation) appear to be recognized by insect cells, and the signals required for secretion and nuclear accumulation also appear to be conserved between the invertebrate cells and vertebrate cells, leaders of non-insect origin, such as those derived from genes encoding human α-interferon, Maeda et al., (1985), *Nature* 315:592; human gastrin-releasing peptide, Lebacq-Verheyden et al., (1988), *Molec. Cell. Biol.* 8:3129; human IL-2, Smith et al., (1985) *Proc. Nat'l Acad. Sci. USA,* 82:8404; mouse IL-3, (Miyajima et al., (1987) *Gene* 58:273; and human glucocerebrosidase, Martin et al. (1988) *DNA,* 7:99, can also be used to provide for secretion in insects.

A recombinant polypeptide or polyprotein may be expressed intracellularly or, if it is expressed with the proper regulatory sequences, it can be secreted. Good intracellular expression of nonfused foreign proteins usually requires heterologous genes that ideally have a short leader sequence containing suitable translation initiation signals preceding an ATG start signal. If desired, methionine at the N-terminus may be cleaved from the mature protein by in vitro incubation with cyanogen bromide.

Alternatively, recombinant polyproteins or proteins which are not naturally secreted can be secreted from the insect cell by creating chimeric DNA molecules that encode a fusion protein comprised of a leader sequence fragment that provides for secretion of the foreign protein in insects. The leader sequence fragment usually encodes a signal peptide comprised of hydrophobic amino acids which direct the translocation of the protein into the endoplasmic reticulum.

After insertion of the DNA sequence and/or the gene encoding the expression product precursor of the protein, an insect cell host is co-transformed with the heterologous DNA of the transfer vector and the genomic DNA of wild type baculovirus—usually by co-transfection. The promoter and transcription termination sequence of the construct will usually comprise a 2-5 kb section of the baculovirus genome. Methods for introducing heterologous DNA into the desired site in the baculovirus virus are known in the art. (See Summers and Smith supra; Ju et al. (1987); Smith et al., *Mol. Cell. Biol.* (1983) 3:2156; and Luckow and Summers (1989)). For example, the insertion can be into a gene such as the polyhedrin gene, by homologous double crossover recombination; insertion can also be into a restriction enzyme site engineered into the desired baculovirus gene. Miller et al., (1989), *Bioessays* 4:91. The DNA sequence, when cloned in place of the polyhedrin gene in the expression vector, is flanked both 5' and 3' by polyhedrin-specific sequences and is positioned downstream of the polyhedrin promoter.

The newly formed baculovirus expression vector is subsequently packaged into an infectious recombinant baculovirus. Homologous recombination occurs at low frequency (between about 1% and about 5%); thus, the majority of the virus produced after cotransfection is still wild-type virus. Therefore, a method is necessary to identify recombinant viruses. An advantage of the expression system is a visual screen allowing recombinant viruses to be distinguished. The polyhedrin protein, which is produced by the native virus, is produced at very high levels in the nuclei of infected cells at late times after viral infection. Accumulated polyhedrin protein forms occlusion bodies that also contain embedded particles. These occlusion bodies, up to 15 µm in size, are highly refractile, giving them a bright shiny appearance that is readily visualized under the light microscope. Cells infected with recombinant viruses lack occlusion bodies. To distinguish recombinant virus from wild-type virus, the transfection supernatant is plaqued onto a monolayer of insect cells by techniques known to those skilled in the art. Namely, the plaques are screened under the light microscope for the presence (indicative of wild-type virus) or absence (indicative of recombinant virus) of occlusion bodies. "Current Protocols in Microbiology" Vol. 2 (Ausubel et al. eds) at 16.8 (Supp. 10, 1990); Summers and Smith, supra; Miller et al. (1989).

Recombinant baculovirus expression vectors have been developed for infection into several insect cells. For example, recombinant baculoviruses have been developed for, inter alia: *Aedes aegypti, Autographa californica, Bombyx mori, Drosophila melanogaster, Spodoptera frugiperda,* and *Trichoplusia ni* (WO 89/046699; Carbonell et al., (1985) *J. Virol.* 56:153; Wright (1986) *Nature* 321:718; Smith et al., (1983) *Mol. Cell. Biol.* 3:2156; and see generally, Fraser, et al. (1989) *In Vitro Cell. Dev. Biol.* 25:225).

Cells and cell culture media are commercially available for both direct and fusion expression of heterologous polypeptides in a baculovirus/expression system, cell culture technology is generally known to those skilled in the art. See, eg. Summers and Smith supra.

The modified insect cells may then be grown in an appropriate nutrient medium, which allows for stable maintenance of the plasmid(s) present in the modified insect host. Where the expression product gene is under inducible control, the host may be grown to high density, and expression induced. Alternatively, where expression is constitutive, the product will be continuously expressed into the medium and the nutrient medium must be continuously circulated, while removing the product of interest and augmenting depleted nutrients. The product may be purified by such techniques as chromatography, eg. HPLC, affinity chromatography, ion exchange chromatography, etc.; electrophoresis; density gradient centrifugation; solvent extraction, or the like. As appropriate, the product may be further purified, as required, so as to remove substantially any insect proteins which are also secreted in the medium or result from lysis of insect cells, so as to provide a product which is at least substantially free of host debris, eg. proteins, lipids and polysaccharides.

In order to obtain protein expression, recombinant host cells derived from the transformants are incubated under conditions which allow expression of the recombinant protein encoding sequence. These conditions will vary, dependent upon the host cell selected. However, the conditions are readily ascertainable to those of ordinary skill in the art, based upon what is known in the art.

iii. Plant Systems

There are many plant cell culture and whole plant genetic expression systems known in the art. Exemplary plant cellular genetic expression systems include those described in patents, such as: U.S. Pat. No. 5,693,506; U.S. Pat. No. 5,659,122; and U.S. Pat. No. 5,608,143. Additional examples of genetic expression in plant cell culture has been described by Zenk, *Phytochemistry* 30:3861-3863 (1991). Descriptions of plant protein signal peptides may be found in addition to the references described above in Vaulcombe et al., *Mol. Gen. Genet.* 209:33-40 (1987); Chandler et al., *Plant Molecular Biology* 3:407-418 (1984); Rogers, *J. Biol. Chem.* 260:3731-3738 (1985); Rothstein et al., *Gene* 55:353-356 (1987); Whittier et al., Nucleic Acids Research 15:2515-2535 (1987); Wirsel et al., *Molecular Microbiology* 3:3-14 (1989); Yu et al., *Gene* 122:247-253 (1992). A description of the regulation of plant gene expression by the phytohormone, gibberellic acid and secreted enzymes induced by gibberellic acid can be found in R. L. Jones and J. MacMillin, Gibberellins: in: *Advanced Plant Physiology*. Malcolm B. Wilkins, ed., 1984 Pitman Publishing Limited, London, pp. 21-52. References that describe other metabolically-regulated genes: Sheen, *Plant Cell*, 2:1027-1038 (1990); Maas et al., *EMBO J.* 9:3447-3452 (1990); Benkel and Hickey, *Proc. Natl. Acad. Sci.* 84:1337-1339 (1987)

Typically, using techniques known in the art, a desired polynucleotide sequence is inserted into an expression cassette comprising genetic regulatory elements designed for operation in plants. The expression cassette is inserted into a desired expression vector with companion sequences upstream and downstream from the expression cassette suitable for expression in a plant host. The companion sequences will be of plasmid or viral origin and provide necessary characteristics to the vector to permit the vectors to move DNA from an original cloning host, such as bacteria, to the desired plant host. The basic bacterial/plant vector construct will preferably provide a broad host range prokaryote replication origin; a prokaryote selectable marker; and, for *Agrobacterium* transformations, T DNA sequences for *Agrobacterium*-mediated transfer to plant chromosomes. Where the heterologous gene is not readily amenable to detection, the construct will preferably also have a selectable marker gene suitable for determining if a plant cell has been transformed. A general review of suitable markers, for example for the members of the grass family, is found in Wilmink and Dons, 1993, *Plant Mol. Biol. Reptr,* 11(2):165-185.

Sequences suitable for permitting integration of the heterologous sequence into the plant genome are also recommended. These might include transposon sequences and the like for homologous recombination as well as Ti sequences which permit random insertion of a heterologous expression cassette into a plant genome. Suitable prokaryote selectable markers include resistance toward antibiotics such as ampicillin or tetracycline. Other DNA sequences encoding additional functions may also be present in the vector, as is known in the art.

The nucleic acid molecules of the subject invention may be included into an expression cassette for expression of the protein(s) of interest. Usually, there will be only one expression cassette, although two or more are feasible. The recombinant expression cassette will contain in addition to the heterologous protein encoding sequence the following elements, a promoter region, plant 5' untranslated sequences, initiation codon depending upon whether or not the structural gene comes equipped with one, and a transcription and translation termination sequence. Unique restriction enzyme sites at the 5' and 3' ends of the cassette allow for easy insertion into a pre-existing vector.

A heterologous coding sequence may be for any protein relating to the present invention. The sequence encoding the protein of interest will encode a signal peptide which allows processing and translocation of the protein, as appropriate, and will usually lack any sequence which might result in the binding of the desired protein of the invention to a membrane. Since, for the most part, the transcriptional initiation region will be for a gene which is expressed and translocated during germination, by employing the signal peptide which provides for translocation, one may also provide for translocation of the protein of interest. In this way, the protein(s) of interest will be translocated from the cells in which they are expressed and may be efficiently harvested. Typically secretion in seeds are across the aleurone or scutellar epithelium layer into the endosperm of the seed. While it is not required that the protein be secreted from the cells in which the protein is produced, this facilitates the isolation and purification of the recombinant protein.

Since the ultimate expression of the desired gene product will be in a eucaryotic cell it is desirable to determine whether any portion of the cloned gene contains sequences which will be processed out as introns by the host's splicosome machinery. If so, site-directed mutagenesis of the "intron" region may be conducted to prevent losing a portion of the genetic message as a false intron code, Reed and Maniatis, *Cell* 41:95-105, 1985.

The vector can be microinjected directly into plant cells by use of micropipettes to mechanically transfer the recombinant DNA. Crossway, *Mol. Gen. Genet,* 202:179-185, 1985. The genetic material may also be transferred into the plant cell by using polyethylene glycol, Krens, et al., *Nature,* 296, 72-74, 1982. Another method of introduction of nucleic acid segments is high velocity ballistic penetration by small particles with the nucleic acid either within the matrix of small beads or particles, or on the surface, Klein, et al., *Nature,* 327, 70-73, 1987 and Knudsen and Muller, 1991, *Planta,* 185:330-336 teaching particle bombardment of barley endosperm to create transgenic barley. Yet another method of introduction would be fusion of protoplasts with other entities, either minicells, cells, lysosomes or other fusible lipid-surfaced bodies, Fraley, et al., *Proc. Natl. Acad. Sci. USA,* 79, 1859-1863, 1982.

The vector may also be introduced into the plant cells by electroporation. (Fromm et al., *Proc. Natl Acad. Sci. USA* 82:5824, 1985). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

All plants from which protoplasts can be isolated and cultured to give whole regenerated plants can be transformed by the present invention so that whole plants are recovered which contain the transferred gene. It is known that practically all plants can be regenerated from cultured cells or tissues, including but not limited to all major species of sugarcane, sugar beet, cotton, fruit and other trees, legumes and vegetables. Some suitable plants include, for example, species from the genera *Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersion, Nicotiana, Solanum, Petunia, Digitalis, Majorana, Cichorium, Helianthus, Lactuca, Bromus, Asparagus, Antirrhinum, Her-* erocallis, Nemesia, Pelargonium, Panicuni, Pennisetum, Ranunculus, Senecio, Salpiglossis, Cucumis, Browaalia, Glycine, Loliun, Zea, Triticum, Sorghum, and Datura.

Means for regeneration vary from species to species of plants, but generally a suspension of transformed protoplasts containing copies of the heterologous gene is first provided. Callus tissue is formed and shoots may be induced from callus and subsequently rooted. Alternatively, embryo formation can be induced from the protoplast suspension. These embryos germinate as natural embryos to form plants. The culture media will generally contain various amino acids and hormones, such as auxin and cytokinins. It is also advantageous to add glutamic acid and proline to the medium, especially for such species as corn and alfalfa. Shoots and roots normally develop simultaneously. Efficient regeneration will depend on the medium, on the genotype, and on the history of the culture. If these three variables are controlled, then regeneration is fully reproducible and repeatable.

In some plant cell culture systems, the desired protein of the invention may be excreted or alternatively, the protein may be extracted from the whole plant. Where the desired protein of the invention is secreted into the medium, it may be collected. Alternatively, the embryos and embryoless-half seeds or other plant tissue may be mechanically disrupted to release any secreted protein between cells and tissues. The mixture may be suspended in a buffer solution to retrieve soluble proteins. Conventional protein isolation and purification methods will be then used to purify the recombinant protein. Parameters of time, temperature pH, oxygen, and volumes will be adjusted through routine methods to optimize expression and recovery of heterologous protein.

iv. Bacterial Systems

Bacterial expression techniques are known in the art. A bacterial promoter is any DNA sequence capable of binding bacterial RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site and a transcription initiation site. A bacterial promoter may also have a second domain called an operator, that may overlap an adjacent RNA polymerase binding site at which RNA synthesis begins. The operator permits negative regulated (inducible) transcription, as a gene repressor protein may bind the operator and thereby inhibit transcription of a specific gene. Constitutive expression may occur in the absence of negative regulatory elements, such as the operator. In addition, positive regulation may be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli (E. coli)* [Raibaud et al. (1984) *Annu. Rev. Genet.* 18:173]. Regulated expression may therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) [Chang et al. (1977) *Nature* 198:1056], and maltose. Additional examples include promoter sequences derived from biosynthetic enzymes such as tryptophan (trp) [Goeddel et al. (1980) *Nuc. Acids Res.* 8:4057; Yelverton et al. (1981) *Nucl. Acids Res.* 9:731; U.S. Pat. No. 4,738,921; EP-A-0036776 and EP-A-0121775]. The g-laotamase (bla) promoter system [Weissmann (1981) "The cloning of interferon and other mistakes." In *Interferon* 3 (ed. 1. Gresser)], bacteriophage lambda PL [Shimatake et al. (I 981) *Nature* 292:128] and T5 [U.S. Pat. No. 4,689,406] promoter systems also provide useful promoter sequences.

In addition, synthetic promoters which do not occur in nature also function as bacterial promoters. For example, transcription activation sequences of one bacterial or bacteriophage promoter may be joined with the operon sequences of another bacterial or bacteriophage promoter, creating a synthetic hybrid promoter [U.S. Pat. No. 4,551,433]. For example, the tac promoter is a hybrid trp-lac promoter comprised of both trp promoter and lac operon sequences that is regulated by the lac repressor [Amann et al. (1983) *Gene* 25:167; de Boer et al. (1983) *Proc. Natl. Acad. Sci.* 80:21]. Furthermore, a bacterial promoter can include naturally occurring promoters of non-bacterial origin that have the ability to bind bacterial RNA polymerase and initiate transcription. A naturally occurring promoter of non-bacterial origin can also be coupled with a compatible RNA polymerase to produce high levels of expression of some genes in prokaryotes. The bacteriophage T7 RNA polymerase/promoter system is an example of a coupled promoter system [Studier et al. (1986) *J. Mol. Biol.* 189:113; Tabor et al. (1985) *Proc Natl. Acad. Sci.* 82:1074]. In addition, a hybrid promoter can also be comprised of a bacteriophage promoter and an *E. coli* operator region (EPO-A-0 267 851).

In addition to a functioning promoter sequence, an efficient ribosome binding site is also useful for the expression of foreign genes in prokaryotes. In *E. coli*, the ribosome binding site is called the Shine-Dalgarno (SD) sequence and includes an initiation codon (ATG) and a sequence 3-9 nucleotides in length located 3-11 nucleotides upstream of the initiation codon [Shine et al. (1975) *Nature* 254:34]. The SD sequence is thought to promote binding of mRNA to the ribosome by the pairing of bases between the SD sequence and the 3' and of *E. coli* 16S rRNA [Steitz et al. (1979) "Genetic signals and nucleotide sequences in messenger RNA." In *Biological Regulation and Development: Gene Expression* (ed. R. F. Goldberger)]. To express eukaryotic genes and prokaryotic genes with weak ribosome-binding site [Sambrook et al. (1989) "Expression of cloned genes in *Escherichia coli*." In *Molecular Cloning: A Laboratory Manual*].

A DNA molecule may be expressed intracellularly. A promoter sequence may be directly linked with the DNA molecule, in which case the first amino acid at the N-terminus will always be a methionine, which is encoded by the ATG start codon. If desired, methionine at the N-terminus may be cleaved from the protein by in vitro incubation with cyanogen bromide or by either in vivo on in vitro incubation with a bacterial methionine N-terminal peptidase (EPO-A-0 219 237).

Fusion proteins provide an alternative to direct expression. Usually, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of a foreign gene and expressed in bacteria. The resulting fusion protein preferably retains a site for a processing enzyme (factor Xa) to cleave the bacteriophage protein from the foreign gene [Nagai et al. (1984) *Nature* 309:810]. Fusion proteins can also be made with sequences from the lacZ [Jia et al. (1987) *Gene* 60:197], trpE [Allen et al. (1987) J. Biotechnol. 5:93; Makoff et al. (1989) *J. Gen. Microbiol.* 135:11], and Chey [EP-A-0 324 647] genes. The DNA sequence at the junction of the two amino acid sequences may or may not encode a cleavable site.

Another example is a ubiquitin fusion protein. Such a fusion protein is made with the ubiquitin region that preferably retains a site for a processing enzyme (eg. ubiquitin specific processing-protease) to cleave the ubiquitin from the foreign protein. Through this method, native foreign protein can be isolated [Miller et al. (1989) *Bio/Technology* 7:698].

Alternatively, foreign proteins can also be secreted from the cell by creating chimeric DNA molecules that encode a fusion protein comprised of a signal peptide sequence fragment that provides for secretion of the foreign protein in bacteria [U.S. Pat. No. 4,336,336]. The signal sequence fragment usually encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the foreign gene.

DNA encoding suitable signal sequences can be derived from genes for secreted bacterial proteins, such as the *E. coli* outer membrane protein gene (ompA) [Masui et al. (1983), in: *Experimental Manipulation of Gene Expression*; Ghrayeb et al. (1984) *EMBO J.* 3:2437] and the *E. coli* alkaline phosphatase signal sequence (phoA) [Oka et al. (1985) *Proc. Natl. Acad. Sci.* 82:7212]. As an additional example, the signal sequence of the alpha-amylase gene from various *Bacillus* strains can be used to secrete heterologous proteins from *B. subtilis* [Palva et al. (1982) *Proc. Natl. Acad. Sci. USA* 79:5582; EP-A-0 244 042].

Usually, transcription termination sequences recognized by bacteria are regulatory regions located 3' to the translation stop codon, and thus together with the promoter flank the coding sequence. These sequences direct the transcription of an mRNA which can be translated into the polypeptide encoded by the DNA. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Usually, the above described components, comprising a promoter, signal sequence (if desired), coding sequence of interest, and transcription termination sequence, are put together into expression constructs. Expression constructs are often maintained in a replicon, such as an extrachromosomal element (eg. plasmids) capable of stable maintenance in a host, such as bacteria. The replicon will have a replication system, thus allowing it to be maintained in a prokaryotic host either for expression or for cloning and amplification. In addition, a replicon may be either a high or low copy number plasmid. A high copy number plasmid will generally have a copy number ranging from about 5 to about 200, and usually about 10 to about 150. A host containing a high copy number plasmid will preferably contain at least about 10, and more preferably at least about 20 plasmids. Either a high or low copy number vector may be selected, depending upon the effect of the vector and the foreign protein on the host.

Alternatively, the expression constructs can be integrated into the bacterial genome with an integrating vector. Integrating vectors usually contain at least one sequence homologous to the bacterial chromosome that allows the vector to integrate. Integrations appear to result from recombinations between homologous DNA in the vector and the bacterial chromosome. For example, integrating vectors constructed with DNA from various *Bacillus* strains integrate into the *Bacillus* chromosome (EP-A-0 127 328). Integrating vectors may also be comprised of bacteriophage or transposon sequences.

Usually, extrachromosomal and integrating expression constructs may contain selectable markers to allow for the selection of bacterial strains that have been transformed. Selectable markers can be expressed in the bacterial host and may include genes which render bacteria resistant to drugs such as ampicillin, chloramphenicol, erythromycin, kanamycin (neomycin), and tetracycline [Davies et al. (1978) *Annu. Rev. Microbiol.* 32:469]. Selectable markers may also include biosynthetic genes, such as those in the histidine, tryptophan, and leucine biosynthetic pathways.

Alternatively, some of the above described components can be put together in transformation vectors. Transformation vectors are usually comprised of a selectable market that is either maintained in a replicon or developed into an integrating vector, as described above.

Expression and transformation vectors, either extra-chromosomal replicons or integrating vectors, have been developed for transformation into many bacteria. For example, expression vectors have been developed for, inter alia, the following bacteria: *Bacillus subtilis* [Palva et al. (1982) *Proc. Natl. Acad. Sci. USA* 79:5582; EP-A-0 036 259 and EP-A-0 063 953; WO 84/04541], *Escherichia coli* [Shimatake et al. (1981) *Nature* 292:128; Amann et al. (1985) *Gene* 40:183; Studier et al. (1986) *J. Mol. Biol.* 189:113; EP-A-0 036 776, EP-A-0 136 829 and EP-A-0 136 907], *Streptococcus cremoris* [Powell et al. (1988) *Appl. Environ. Microbiol.* 54:655]; *Streptococcus lividans* [Powell et al. (1988) *Appl. Environ. Microbiol.* 54:655], *Streptomyces lividans* [U.S. Pat. No. 4,745,056].

Methods of introducing exogenous DNA into bacterial hosts are well-known in the art, and usually include either the transformation of bacteria treated with $CaCl_2$ or other agents, such as divalent cations and DMSO. DNA can also be introduced into bacterial cells by electroporation. Transformation procedures usually vary with the bacterial species to be transformed. See eg. [Masson et al. (1989) *FEMS Microbiol. Lett.* 60:273; Palva et al. (1982) *Proc. Natl. Acad. Sci. USA* 79:5582; EP-A-0 036 259 and EP-A-0 063 953; WO 84/04541, *Bacillus*], [Miller et al. (1988) *Proc. Natl. Acad. Sci.* 85:856; Wang et al. (1990) *J. Bacteriol.* 172:949, *Campylobacter*], [Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids. In *Genetic Engineering: Proceedings of the International Symposium on Genetic Engineering* (eds. H. W. Boyer and S, Nicosia); Mandel et al. (1970) *J. Mol. Biol.* 53:159; Taketo (1988) *Biochim. Biophys. Acta* 949:318; *Escherichia*], [Chassy et al. (1987) *FEMS Microbiol. Lett.* 44:173 *Lactobacillus*]; [Fiedler et al. (1988) *Anal. Biochem* 170:38, *Pseudomonas*]; [Augustin et al. (1990) *FEMS Microbiol. Lett.* 66:203, *Staphylococcus*], [Barany et al. (1980) *J. Bacteriol.* 144:698; Harlander (1987) "Transformation of *Streptococcus* lactis by electroporation, in: *Streptococcal Genetics* (ed. J. Ferretti and R. Curtiss III); Perry et al. (1981) *Infect. Immun.* 32:1295; Powell et al. (1988) *Appl. Environ. Microbiol.* 54:655; Somkuti et al. (1987) *Proc. 4th Evr. Cong. Biotechnology* 1:412, *Streptococcus*].

v. Yeast Expression

Yeast expression systems are also known to one of ordinary skill in the art. A yeast promoter is any DNA sequence capable of binding yeast RNA polymerase and initiating the downstream (3') transcription of a coding sequence (eg. structural gene) into mRNA. A promoter will have a transcription initiation region which is usually placed proximal to the 5' end of the coding sequence. This transcription initiation region usually includes an RNA polymerase binding site (the "TATA Box") and a transcription initiation site. A yeast promoter may also have a second domain called an upstream activator sequence (UAS), which, if present, is usually distal to the structural gene. The UAS permits regulated (inducible) expression. Constitutive expression occurs in the absence of a UAS. Regulated expression may be either positive or negative, thereby either enhancing or reducing transcription.

Yeast is a fermenting organism with an active metabolic pathway, therefore sequences encoding enzymes in the metabolic pathway provide particularly useful promoter sequences. Examples include alcohol dehydrogenase (ADH) (EP-A-0 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK) (EPO-A-0 329 203). The yeast PHO5 gene, encoding acid phosphatase, also provides useful promoter sequences [Myanohara et al. (1983) Proc. Natl. Acad. Sci. USA 80:1]J.

In addition, synthetic promoters which do not occur in nature also function as yeast promoters. For example, UAS sequences of one yeast promoter may be joined with the transcription activation region of another yeast promoter, creating a synthetic hybrid promoter. Examples of such hybrid promoters include the ADH regulatory sequence linked to the GAP transcription activation region (U.S. Pat. Nos. 4,876,197 and 4,880,734). Other examples of hybrid promoters include promoters which consist of the regulatory sequences of either the ADH2, GAL4, GAL10, OR PHO5 genes, combined with the transcriptional activation region of a glycolytic enzyme gene such as GAP or PyK (EP-A-0 164 556). Furthermore, a yeast promoter can include naturally occurring promoters of non-yeast origin that have the ability to bind yeast RNA polymerase and initiate transcription. Examples of such promoters include, inter alia, [Cohen et al. (1980) Proc. Natl. Acad. Sci. USA 77:1078; Henikoff et al. (1981) Nature 283:835; Hollenberg et al. (1981) Curr. Topics Microbiol. Immunol. 96:119; Hollenberg et al. (1979) "The Expression of Bacterial Antibiotic Resistance Genes in the Yeast Saccharomyces cerevisiae," in: Plasmids of Medical, Environmental and Commercial Importance (eds. K. N. Timmis and A. Puhler); Mercerau-Puigalon et al. (1980) Gene 11:163; Panthier et al. (1980) Curr. Genet. 2:109;].

A DNA molecule may be expressed intracellularly in yeast. A promoter sequence may be directly linked with the DNA molecule, in which case the first amino acid at the N-terminus of the recombinant protein will always be a methionine, which is encoded by the ATG start codon. If desired, methionine at the N-terminus may be cleaved from the protein by in vitro incubation with cyanogen bromide.

Fusion proteins provide an alternative for yeast expression systems, as well as in mammalian, baculovirus, and bacterial expression systems. Usually, a DNA sequence encoding the N-terminal portion of an endogenous yeast protein, or other stable protein, is fused to the 5' end of heterologous coding sequences. Upon expression, this construct will provide a fusion of the two amino acid sequences. For example, the yeast or human superoxide dismutase (SOD) gene, can be linked at the 5' terminus of a foreign gene and expressed in yeast. The DNA sequence at the junction of the two amino acid sequences may or may not encode a cleavable site. See eg. EP-A-0 196 056. Another example is a ubiquitin fusion protein. Such a fusion protein is made with the ubiquitin region that preferably retains a site for a processing enzyme (eg. ubiquitin-specific processing protease) to cleave the ubiquitin from the foreign protein. Through this method, therefore, native foreign protein can be isolated (eg. WO88/024066).

Alternatively, foreign proteins can also be secreted from the cell into the growth media by creating chimeric DNA molecules that encode a fusion protein comprised of a leader sequence fragment that provide for secretion in yeast of the foreign protein. Preferably, there are processing sites encoded between the leader fragment and the foreign gene that can be cleaved either in vivo or in vitro. The leader sequence fragment usually encodes a signal peptide comprised of hydrophobic amino acids which direct the secretion of the protein from the cell.

DNA encoding suitable signal sequences can be derived from genes for secreted yeast proteins, such as the yeast invertase gene (EP-A-0 012 873; JPO. 62,096,086) and the A-factor gene (U.S. Pat. No. 4,588,684). Alternatively, leaders of non-yeast origin, such as an interferon leader, exist that also provide for secretion in yeast (EP-A-0 060 057).

A preferred class of secretion leaders are those that employ a fragment of the yeast alpha-factor gene, which contains both a "pre" signal sequence, and a "pro" region. The types of alpha-factor fragments that can be employed include the full-length pre-pro alpha factor leader (about 83 amino acid residues) as well as truncated alpha-factor leaders (usually about 25 to about 50 amino acid residues) (U.S. Pat. Nos. 4,546,083 and 4,870,008; EP-A-0 324 274). Additional leaders employing an alpha-factor leader fragment that provides for secretion include hybrid alpha-factor leaders made with a presequence of a first yeast, but a pro-region from a second yeast alphafactor. (eg. see WO 89/02463.)

Usually, transcription termination sequences recognized by yeast are regulatory regions located 3' to the translation stop codon, and thus together with the promoter flank the coding sequence. These sequences direct the transcription of an mRNA which can be translated into the polypeptide encoded by the DNA. Examples of transcription terminator sequence and other yeast-recognized termination sequences, such as those coding for glycolytic enzymes.

Usually, the above described components, comprising a promoter, leader (if desired), coding sequence of interest, and transcription termination sequence, are put together into expression constructs. Expression constructs are often maintained in a replicon, such as an extrachromosomal element (eg. plasmids) capable of stable maintenance in a host, such as yeast or bacteria. The replicon may have two replication systems, thus allowing it to be maintained, for example, in yeast for expression and in a prokaryotic host for cloning and amplification. Examples of such yeast-bacteria shuttle vectors include YEp24 [Botstein et al. (1979) Gene 8:17-24], pCl/1 [Brake et al. (1984) Proc. Natl. Acad. Sci USA 81:4642-4646], and YRp17 [Stinchcomb et al. (1982) J. Mol. Biol. 158:157]. In addition, a replicon may be either a high or low copy number plasmid. A high copy number plasmid will generally have a copy number ranging from about 5 to about 200, and usually about 10 to about 150. A host containing a high copy number plasmid will preferably have at least about 10, and more preferably at least about 20. Enter a high or low copy number vector may be selected, depending upon the effect of the vector and the foreign protein on the host. See eg. Brake et al., supra.

Alternatively, the expression constructs can be integrated into the yeast genome with an integrating vector. Integrating vectors usually contain at least one sequence homologous to a yeast chromosome that allows the vector to integrate, and preferably contain two homologous sequences flanking the expression construct. Integrations appear to result from recombinations between homologous DNA in the vector and the yeast chromosome [Orr-Weaver et al. (1983) *Methods in Enzymol.* 101:228-245]. An integrating vector may be directed to a specific locus in yeast by selecting the appropriate homologous sequence for inclusion in the vector. See Orr-Weaver et al., supra. One or more expression construct may integrate, possibly affecting levels of recombinant protein produced [Rine et al. (1983) *Proc. Natl. Acad. Sci. USA* 80:6750]. The chromosomal sequences included in the vector can occur either as a single segment in the vector, which results in the integration of the entire vector, or two segments homologous to adjacent segments in the chromosome and flanking the expression construct in the vector, which can result in the stable integration of only the expression construct.

Usually, extrachromosomal and integrating expression constructs may contain selectable markers to allow for the selection of yeast strains that have been transformed. Selectable markers may include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker may also provide yeast with the ability to grow in the presence of toxic compounds, such as metal. For example, the presence of CUP1 allows yeast to grow in the presence of copper ions [Butt et al. (1987) *Microbiol, Rev.* 51:351].

Alternatively, some of the above described components can be put together into transformation vectors. Transformation vectors are usually comprised of a selectable marker that is either maintained in a replicon or developed into an integrating vector, as described above.

Expression and transformation vectors, either extrachromosomal replicons or integrating vectors, have been developed for transformation into many yeasts. For example, expression vectors have been developed for, inter alia, the following yeasts: *Candida albicans* [Kurtz, et al. (1986) *Mol. Cell. Biol.* 6:142], *Candida maltosa* [Kunze, et al. (1985) *J. Basic Microbiol.* 25:141]. *Hansenula polymorpha* [Gleeson, et al. (1986) *J. Gen. Microbiol.* 132:3459; Roggenkamp et al. (1986) *Mol. Gen. Genet.* 202:302], *Kluyveromyces fragilis* [Das, et al. (1984) *J. Bacteriol.* 158:1165], *Kluyveromyces lactis* [De Louvencourt et al. (1983) *J. Bacteriol.* 154:737; Van den Berg et al. (1990) *Bio/Technology* 8:135], *Pichia guillerimondii* [Kunze et al. (1985) *J. Basic Microbiol.* 25:141], *Pichia pastoris* [Cregg, et al. (1985) *Mol. Cell. Biol.* 5:3376; U.S. Pat. Nos. 4,837,148 and 4,929,555], *Saccharomyces cerevisiae* [Hinnen et al. (1978) *Proc. Natl. Acad. Sci. USA* 75:1929; Ito et al. (1983) *J. Bacteriol.* 153:163], *Schizosaccharomyces pombe* [Beach and Nurse (1981) *Nature* 300:706], and *Yarrowia lipolytica* [Davidow, et al. (1985) *Curr. Genet.* 10:380471 Gaillardin, et al. (1985) *Curr. Genet.* 10:49].

Methods of introducing exogenous DNA into yeast hosts are well-known in the art, and usually include either the transformation of spheroplasts or of intact yeast cells treated with alkali cations. Transformation procedures usually vary with the yeast species to be transformed. See eg. [Kurtz et al. (1986) *Mol. Cell. Biol.* 6:142; Kunze et al. (1985) *J. Basic Microbiol.* 25:141; *Candida*]; [Gleeson et al. (1986) *J. Gen. Microbiol.* 132:3459; Roggenkamp et al. (1986) *Mol. Gen. Genet.* 202:302; *Hansenula*]; [Das et al. (1984) *J. Bacteriol.* 158:1165; De Louvencourt et al. (1983) *J. Bacteriol.* 154: 1165; Van den Berg et al. (1990) *Bio/Technology* 8:135; *Kluyveromyces*]; [Cregg et al. (1985) *Mol. Cell. Biol.* 5:3376; Kunze et al. (1985) *J. Basic Microbiol.* 25:141; U.S. Pat. Nos. 4,837,148 and 4,929,555; *Pichia*]; [Hinnen et al. (1978) *Proc. Natl. Acad. Sci. USA* 75; 1929; Ito et al. (1983) *J. Bacteriol.* 153:163 *Saccharomyces*]; [Beach and Nurse (1981) *Nature* 300:706; *Schizosaccharomyces*]; [Davidow et al. (1985) *Curr. Genet.* 10:39; Gaillardin et al. (1985) *Curr. Genet.* 10:49; *Yarrowia*].

Antibodies

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

Antibodies against the proteins of the invention are useful for affinity chromatography, immunoassays, and distinguishing/identifying Neisserial proteins.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 µg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antisera is obtained by bleeding the immunized animal into a glass or plastic container, incubating the blood at 25° C. for one hour, followed by incubating at 4° C. for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256:495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (eg. hypoxanthine, aminopterin, thymidine medium, "HAT"). The resulting hybridomas are plated by limiting dilution, and are assayed for the production of antibodies which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $^{32}$P and $^{125}$I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}$I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with $^{125}$I, or with an anti-biotin MAb labeled with HRP. Other permutations and possibilities will be readily apparent to those of ordinary skill in the art, and are considered as equivalents within the scope of the instant invention.

Pharmaceutical Compositions

Pharmaceutical compositions can comprise either polypeptides, antibodies, or nucleic acid of the invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the compositions of the invention can be administered directly to the subject. The subjects to be treated can be animals; in particular, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Vaccines

Vaccines according to the invention may either be prophylactic (ie. to prevent infection) or therapeutic (ie. to treat disease after infection).

Such vaccines comprise immunising antigen(s), immunogen(s), polypeptide(s), protein(s) or nucleic acid, usually in combination with "pharmaceutically acceptable carriers," which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles. Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogens.

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59™ (WO 90/14837; Chapter 10 in *Vaccine design: the subunit and adjuvant approach*, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); (3) saponin adjuvants, such as Stimulon™ (Cambridge Bioscience. Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc; and (6) other substances that act as immunostimulating agents to enhance the effectiveness of the composition. Alum and MF59™ are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'-dipalmitoyl-sn-glycero-3-hydroxyphosphoryloxy)-ethylamine (MTP-PE), etc.

The immunogenic compositions (eg. the immunising antigen/immunogen/polypeptide/protein/nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies, the degree of protection desired, the formulation of the vaccine, the treating doctor's assessment of the medical situation, and other relevant factors. It is expected that the amount will fall in a relatively broad range that can be determined through routine trials.

The immunogenic compositions are conventionally administered parenterally, eg. by injection, either subcutaneously, intramuscularly, or transdermally/transcutaneously (eg. WO98/20734). Additional formulations suitable for other modes of administration include oral and pulmonary formulations, suppositories, and transdermal applications. Dosage treatment may be a single dose schedule or a multiple dose schedule. The vaccine may be administered in conjunction with other immunoregulatory agents.

As an alternative to protein-based vaccines, DNA vaccination may be employed [eg. Robinson & Torres (1997) Seminars in Immunology 9:271-283; Donnelly et al. (1997) Annu Rev Immunol 15:617-648; see later herein].

Gene Delivery Vehicles

Gene therapy vehicles for delivery of constructs including a coding sequence of a therapeutic of the invention, to be delivered to the mammal for expression in the mammal, can be administered either locally or systemically. These constructs can utilize viral or non-viral vector approaches in in vivo or ex vivo modality. Expression of such coding sequence can be induced using endogenous mammalian or heterologous promoters. Expression of the coding sequence in vivo can be either constitutive or regulated.

The invention includes gene delivery vehicles capable of expressing the contemplated nucleic acid sequences. The gene delivery vehicle is preferably a viral vector and, more preferably, a retroviral, adenoviral, adeno-associated viral (AAV), herpes viral, or alphavirus vector. The viral vector can also be an astrovirus, coronavirus, orthomyxovirus, papovavirus, paramyxovirus, parvovirus, picornavirus, poxvirus, or togavirus viral vector. See generally, Jolly (1994) Cancer Gene Therapy 1:51-64; Kimura (1994) Human Gene Therapy 5:845-852; Connelly (1995) Human Gene Therapy 6:185-193; and Kaplitt (1994) Nature Genetics 6:148-153.

Retroviral vectors are well known in the art and we contemplate that any retroviral gene therapy vector is employable in the invention, including B, C and D type retroviruses, xenotropic retroviruses (for example, NZB-X1, NZB-X2 and NZB9-1 (see O'Neill (1985) J. Virol. 53:160) polytropic retroviruses eg. MCF and MCF-MLV (see Kelly (1983) J. Virol. 45:291), spumaviruses and lentiviruses. See RNA Tumor Viruses, Second Edition, Cold Spring Harbor Laboratory, 1985.

Portions of the retroviral gene therapy vector may be derived from different retroviruses. For example, retrovector LTRs may be derived from a Murine Sarcoma Virus, a tRNA binding site from a Rous Sarcoma Virus, a packaging signal from a Murine Leukemia Virus, and an origin of second strand synthesis from an Avian Leukosis Virus.

These recombinant retroviral vectors may be used to generate transduction competent retroviral vector particles by introducing them into appropriate packaging cell lines (see U.S. Pat. No. 5,591,624). Retrovirus vectors can be constructed for site-specific integration into host cell DNA by incorporation of a chimeric integrase enzyme into the retroviral particle (see WO96/37626). It is preferable that the recombinant viral vector is a replication defective recombinant virus.

Packaging cell lines suitable for use with the above-described retrovirus vectors are well known in the art, are readily prepared (see WO95/30763 and WO92/05266), and can be used to create producer cell lines (also termed vector cell lines or "VCLs") for the production of recombinant vector particles. Preferably, the packaging cell lines are made from human parent cells (eg. HT1080 cells) or mink parent cell lines, which eliminates inactivation in human serum.

Preferred retroviruses for the construction of retroviral gene therapy vectors include Avian Leukosis Virus, Bovine Leukemia, Virus, Murine Leukemia Virus, Mink-Cell Focus-inducing Virus, Murine Sarcoma Virus, Reticuloendotheliosis Virus and Rous Sarcoma Virus. Particularly preferred Murine Leukemia Viruses include 4070A and 1504A (Hartley and Rowe (1976) J Virol 19:19-25), Abelson (ATCC No. VR-999), Friend (ATCC No. VR-245), Graffi, Gross (ATCC Nol VR-590), Kirsten, Harvey Sarcoma Virus and Rauscher (ATCC No. VR-998) and Moloney Murine Leukemia Virus (ATCC No. VR-190). Such retroviruses may be obtained from depositories or collections such as the American Type Culture Collection ("ATCC") in Rockville, Md. or isolated from known sources using commonly available techniques.

Exemplary known retroviral gene therapy vectors employable in this invention include those described in patent applications GB2200651, EP0415731, EP0345242, EP0334301, WO89/02468; WO89/05349, WO89/09271, WO90/02806, WO90/07936, WO94/03622, WO93/25698, WO93/25234, WO93/11230, WO93/10218, WO91/02805, WO91/02825. WO95/07994, U.S. Pat. No. 5,219,740, U.S. Pat. No. 4,405,712, U.S. Pat. No. 4,861,719, U.S. Pat. No. 4,980,289, U.S. Pat. No. 4,777,127, U.S. Pat. No. 5,591,624. See also Vile (1993) *Cancer Res* 53:3860-3864; Vile (1993) *Cancer Res* 53:962-967; Ram (1993) *Cancer Res* 53 (1993) 83-88; Takamiya (1992) *J Neurosci Res* 33:493-503; Baba (1993) *J Neurosurg* 79:729-735; Mann (1983) *Cell* 33:153; Cane (1984) *Proc Natl Acad Sci* 81:6349; and Miller (1990) *Human Gene Therapy* 1.

Human adenoviral gene therapy vectors are also known in the art and employable in this invention. See, for example, Berkner (1988) *Biotechniques* 6:616 and Rosenfeld (1991) *Science* 252:431, and WO93/07283, WO93/06223, and WO93/07282. Exemplary known adenoviral gene therapy vectors employable in this invention include those described in the above referenced documents and in WO94/12649, WO93/03769, WO93/19191, WO94/28938, WO95/11984, WO95/00655, WO95/27071, WO95/29993, WO95/34671, WO96/05320, WO94/08026, WO94/11506, WO93/06223, WO94/24299, WO95/14102, WO95/24297, WO95/02697, WO94/28152, WO94/24299, WO95/09241, WO95/25807, WO95/05835, WO94/18922 and WO95/09654. Alternatively, administration of DNA linked to killed adenovirus as described in Curiel (1992) *Hum. Gene Ther.* 3:147-154 may be employed. The gene delivery vehicles of the invention also include adenovirus associated virus (AAV) vectors. Leading and preferred examples of such vectors for use in this invention are the AAV-2 based vectors disclosed in Srivastava, WO93/09239. Most preferred AAV vectors comprise the two AAV inverted terminal repeats in which the native D-sequences are modified by substitution of nucleotides, such that at least 5 native nucleotides and up to 18 native nucleotides, preferably at least 10 native nucleotides up to 18 native nucleotides, most preferably 10 native nucleotides are retained and the remaining nucleotides of the D-sequence are deleted or replaced with non-native nucleotides. The native D-sequences of the AAV inverted terminal repeats are sequences of 20 consecutive nucleotides in each AAV inverted terminal repeat (ie. there is one sequence at each end) which are not involved in HP formation. The non-native replacement nucleotide may be any nucleotide other than the nucleotide found in the native D-sequence in the same position. Other employable exemplary AAV vectors are pWP-19, pWN-1, both of which are disclosed in Nahreini (1993) *Gene* 124:257-262. Another example of such an AAV vector is psub201 (see Samulski (1987) *J. Virol.* 61:3096). Another exemplary AAV vector is the Double-D ITR vector. Construction of the Double-D ITR vector is disclosed in U.S. Pat. No. 5,478,745. Still other vectors are those disclosed in Carter U.S. Pat. No. 4,797,368 and Muzyczka U.S. Pat. No. 5,139,941, Chartejee U.S. Pat. No. 5,474,935, and Kotin WO94/288157. Yet a further example of an AAV vector employable in this invention is SSV9AFABTKneo, which contains the AFP enhancer and albumin promoter and directs expression predominantly in the liver. Its structure and construction are disclosed in Su (1996) *Human Gene Therapy* 7:463-470. Additional AAV gene therapy vectors are described in U.S. Pat. No. 5,354,678, U.S. Pat. No. 5,173,414, U.S. Pat. No. 5,139,941, and U.S. Pat. No. 5,252,479.

The gene therapy vectors of the invention also include herpes vectors. Leading and preferred examples are herpes simplex virus vectors containing a sequence encoding a thymidine kinase polypeptide such as those disclosed in U.S. Pat. No. 5,288,641 and EP0176170 (Roizman). Additional exemplary herpes simplex virus vectors include HFEM/ICP6-LacZ disclosed in WO95/04139 (Wistar Institute), pHSVlac described in Geller (1988) *Science* 241:1667-1669 and in WO90/09441 and WO92/07945, HSV Us3::pgC-lacZ described in Fink (1992) *Human Gene Therapy* 3:11-19 and HSV 7134, 2 RH 105 and GAL4 described in EP 0453242 (Breakefield), and those deposited with the ATCC as accession numbers ATCC VR-977 and ATCC VR-260.

Also contemplated are alpha virus gene therapy vectors that can be employed in this invention. Preferred alpha virus vectors are Sindbis viruses vectors. Togaviruses, Semliki Forest virus (ATCC VR-67; ATCC VR-1247), Middleberg virus (ATCC VR-370), Ross River virus (ATCC VR-373; ATCC VR-1246), Venezuelan equine encephalitis virus (ATCC VR923; ATCC VR-1250; ATCC VR-1249; ATCC VR-532), and those described in U.S. Pat. Nos. 5,091,309, 5,217,879, and WO92/10578. More particularly, those alpha virus vectors described in U.S. Ser. No. 08/405,627, filed Mar. 15, 1995, WO94/21792, WO92/10578, WO95/07994, U.S. Pat. No. 5,091,309 and U.S. Pat. No. 5,217,879 are employable. Such alpha viruses may be obtained from depositories or collections such as the ATCC in Rockville, Md. or isolated from known sources using commonly available techniques. Preferably, alphavirus vectors with reduced cytotoxicity are used (see U.S. Ser. No. 08/679,640).

DNA vector systems such as eukaryotic layered expression systems are also useful for expressing the nucleic acids of the invention. See WO95/07994 for a detailed description of eukaryotic layered expression systems. Preferably, the eukaryotic layered expression systems of the invention are derived from alphavirus vectors and most preferably from Sindbis viral vectors.

Other viral vectors suitable for use in the present invention include those derived from poliovirus, for example ATCC VR-58 and those described in Evans, *Nature* 339 (1989) 385 and Sabin (1973) *J. Biol. Standardization* 1:115; rhinovirus, for example ATCC VR-1110 and those described in Arnold (1990) *J Cell Biochem* L401; pox viruses such as canary pox virus or vaccinia virus, for example ATCC VR-111 and ATCC VR-2010 and those described in Fisher-Hoch (1989) *Proc Natl Acad Sci* 86:317; Flexner (1989) *Ann NY Acad Sci* 569: 86, Flexner (1990) *Vaccine* 8:17; in U.S. Pat. No. 4,603,112 and U.S. Pat. No. 4,769,330 and WO89/01973; SV40 virus, for example ATCC VR-305 and those described in Mulligan (1979) *Nature* 277:108 and Madzak (1992) *J Gen Virol* 73:1533; influenza virus, for example ATCC VR-797 and recombinant influenza viruses made employing reverse genetics techniques as described in U.S. Pat. No. 5,166,057 and in Enami (1990) *Proc Natl Acad Sci* 87:3802-3805; Enami & Palese (1991) *J Virol* 65:2711-2713 and Luytjes (1989) *Cell* 59:110, (see also McMichael (1983) *NEJ Med* 309:13, and Yap (1978) *Nature* 273:238 and *Nature* (1979) 277:108); human immunodeficiency virus as described in EP-0386882 and in Buchschacher (1992) *J. Virol.* 66:2731; measles virus, for example ATCC VR-67 and VR-1247 and those described in EP-0440219; Aura virus, for example ATCC VR-368; Bebaru virus, for example ATCC VR-600 and ATCC VR-1240; Cabassou virus, for example ATCC VR-922; Chikungunya virus, for example ATCC VR-64 and ATCC VR-1241; Fort Morgan Virus, for example ATCC VR-924; Getah virus, for example ATCC VR-369 and ATCC VR-1243; Kyzylagach virus, for example ATCC VR-927; Mayaro virus, for example ATCC VR-66; Mucambo virus, for example ATCC VR-580 and ATCC VR-1244; Ndumu virus, for example ATCC VR-371; Pixuna virus, for example ATCC VR-372 and ATCC VR-1245; Tonate virus, for example ATCC VR-925; Triniti virus, for example ATCC VR-469; Una virus, for example ATCC VR-374; Whataroa virus, for example ATCC VR-926; Y-62-33 virus, for example ATCC VR-375; O'Nyong virus, Eastern encephalitis virus, for example ATCC VR-65 and ATCC VR-1242; Western encephalitis virus, for example ATCC VR-70, ATCC VR-1251, ATCC VR-622 and ATCC VR-1252; and coronavirus, for example ATCC VR-740 and those described in Hamre (1966) *Proc Soc Exp Biol Med* 121:190.

Delivery of the compositions of this invention into cells is not limited to the above mentioned viral vectors. Other delivery methods and media may be employed such as, for example, nucleic acid expression vectors, polycationic condensed DNA linked or unlinked to killed adenovirus alone, for example see U.S. Ser. No. 08/366,787, filed Dec. 30, 1994 and Curiel (1992) *Hum Gene Ther* 3:147-154 ligand linked DNA, for example see Wu (1989) *J Biol Chem* 264:16985-16987, eucaryotic cell delivery vehicles cells, for example see U.S. Ser. No. 08/240,030, filed May 9, 1994, and U.S. Ser. No. 08/404,796, deposition of photopolymerized hydrogel materials, hand-held gene transfer particle gun, as described in U.S. Pat. No. 5,149,655, ionizing radiation as described in U.S. Pat. No. 5,206,152 and in WO92/11033, nucleic charge neutralization or fusion with cell membranes. Additional approaches are described in Philip (1994) *Mol Cell Biol* 14:2411-2418 and in Woffendin (1994) *Proc Natl Acad Sci* 91:1581-1585.

Particle mediated gene transfer may be employed, for example see U.S. Ser. No. 60/023,867. Briefly, the sequence can be inserted into conventional vectors that contain conventional control sequences for high level expression, and then incubated with synthetic gene transfer molecules such as polymeric DNA-binding cations like polylysine, protamine, and albumin, linked to cell targeting ligands such as asialoorosomucoid, as described in Wu & Wu (1987) *J. Biol. Chem.* 262:4429-4432, insulin as described in Hucked (1990) *Biochem Pharmacol* 40:253-263, galactose as described in Plank (1992) *Bioconjugate Chem* 3:533-539, lactose or transferrin.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm.

Liposomes that can act as gene delivery vehicles are described in U.S. Pat. No. 5,422,120, WO95/13796, WO94/23697, WO91/14445 and EP-524,968. As described in U.S. Ser. No. 60/023,867, on non-viral delivery, the nucleic acid sequences encoding a polypeptide can be inserted into conventional vectors that contain conventional control sequences for high level expression, and then be incubated with synthetic gene transfer molecules such as polymeric DNA-binding cations like polylysine, protamine, and albumin, linked to cell targeting ligands such as asialoorosomucoid, insulin, galactose, lactose, or transferrin. Other delivery systems include the use of liposomes to encapsulate DNA comprising the gene under the control of a variety of tissue-specific or ubiquitously-active promoters. Further non-viral delivery suitable for use includes mechanical delivery systems such as the approach described in Woffendin et al (1994) *Proc. Natl. Acad. Sci. USA* 91(24):11581-11585. Moreover, the coding sequence and the product of expression of such can be delivered through deposition of photopolymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and WO92/11033

Exemplary liposome and polycationic gene delivery vehicles are those described in U.S. Pat. Nos. 5,422,120 and 4,762,915; in WO 95/13796; WO94/23697; and WO91/14445; in EP-0524968; and in Stryer, Biochemistry, pages 236-240 (1975) W.H. Freeman, San Francisco; Szoka (1980) *Biochem Biophys Acta* 600:1; Bayer (1979) *Biochem Biophys Acta* 550:464; Rivnay (1987) *Meth Enzymol* 149:119; Wang (1987) *Proc Natl Acad Sci* 84:7851; Plant (1989) *Anal Biochem* 176:420.

A polynucleotide composition can comprises therapeutically effective amount of a gene therapy vehicle, as the term is defined above. For purposes of the present invention, an effective dose will be from about 0.01 mg/kg to 50 mg/kg or 0.05 mg/kg to about 10 mg/kg of the DNA constructs in the individual to which it is administered.

Delivery Methods

Once formulated, the polynucleotide compositions of the invention can be administered (1) directly to the subject; (2) delivered ex vivo, to cells derived from the subject; or (3) in vitro for expression of recombinant proteins. The subjects to be treated can be mammals or birds. Also, human subjects can be treated.

Direct delivery of the compositions will generally be accomplished by injection, either subcutaneously, intraperitoneally, intravenously or intramuscularly or delivered to the interstitial space of a tissue. The compositions can also be administered into a lesion. Other modes of administration include oral and pulmonary administration, suppositories, and transdermal or transcutaneous applications (eg. see WO98/20734), needles, and gene guns or hyposprays. Dosage treatment may be a single dose schedule or a multiple dose schedule.

Methods for the ex vivo delivery and reimplantation of transformed cells into a subject are known in the art and described in eg. WO93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by the following procedures, for example, dextran-mediated transfection, calcium phosphate precipitation, polybrene mediated transfection, protoplast fusion, electroporation, encapsulation of the polynucleotide(s) in liposomes, and direct microinjection of the DNA into nuclei, all well known in the art.

Polynucleotide and Polypeptide Pharmaceutical Compositions

In addition to the pharmaceutically acceptable carriers and salts described above, the following additional agents can be used with polynucleotide and/or polypeptide compositions.

A. Polypeptides

One example are polypeptides which include, without limitation: asioloorosomucoid (ASOR); transferrin; asialoglycoproteins; antibodies; antibody fragments; ferritin; interleukins; interferons, granulocyte, macrophage colony stimulating factor (GM-CSF), granulocyte colony stimulating factor (G-CSF), macrophage colony stimulating factor (M-CSF), stem cell factor and erythropoietin. Viral antigens, such as envelope proteins, can also be used. Also, proteins from other invasive organisms, such as the 17 amino acid peptide from the circumsporozoite protein of *plasmodium falciparum* known as RII.

B. Hormones, Vitamins, Etc.

Other groups that can be included are, for example: hormones, steroids, androgens, estrogens, thyroid hormone, or vitamins, folic acid.

C. Polyalkylenes, Polysaccharides, Etc.

Also, polyalkylene glycol can be included with the desired polynucleotides/polypeptides. In a preferred embodiment, the polyalkylene glycol is polyethylene glycol. In addition, mono-, di-, or polysaccharides can be included. In a preferred embodiment of this aspect, the polysaccharide is dextran or DEAE-dextran. Also, chitosan and poly(lactide-co-glycolide)

D. Lipids, and Liposomes

The desired polynucleotide/polypeptide can also be encapsulated in lipids or packaged in liposomes prior to delivery to the subject or to cells derived therefrom.

Lipid encapsulation is generally accomplished using liposomes which are able to stably bind or entrap and retain nucleic acid. The ratio of condensed polynucleotide to lipid preparation can vary but will generally be around 1:1 (mg DNA:micromoles lipid), or more of lipid. For a review of the use of liposomes as carriers for delivery of nucleic acids, see, Hug and Sleight (1991) *Biochim. Biophys. Acta.* 1097:1-17; Straubinger (1983) *Meth. Enzymol.* 101:512-527.

Liposomal preparations for use in the present invention include cationic (positively charged), anionic (negatively charged) and neutral preparations. Cationic liposomes have been shown to mediate intracellular delivery of plasmid DNA (Felgner (1987) *Proc. Natl. Acad. Sci. USA* 84:7413-7416); mRNA (Malone (1989) *Proc. Natl. Acad. Sci. USA* 86:6077-6081); and purified transcription factors (Debs (1990) *J. Biol. Chem.* 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner supra). Other commercially available liposomes include transfectace (DDAB/DOPE) and DOTAP/DOPE (Boerhinger). Other cationic liposomes can be prepared from readily available materials using techniques well known in the art. See, eg. Szoka (1978) *Proc. Natl. Acad. Sci. USA* 75:4194-4198; WO90/11092 for a description of the synthesis of DOTAP (1,2-bis(oleoyloxy)-3-(trimethylammonio) propane) liposomes.

Similarly, anionic and neutral liposomes are readily available, such as from Avanti Polar Lipids (Birmingham, Ala.), or can be easily prepared using readily available materials. Such materials include phosphatidyl choline, cholesterol, phosphatidyl ethanolamine, dioleoylphosphatidyl choline (DOPC), dioleoylphosphatidyl glycerol (DOPG), dioleoylphosphatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See eg. Straubinger (1983) *Meth. Immunol.* 101:512-527; Szoka (1978) *Proc. Natl. Acad. Sci. USA* 75:4194-4198; Papahadjopoulos (1975) *Biochim. Biophys. Acta* 394:483; Wilson (1979) *Cell* 17:77); Deamer & Bangham (1976) *Biochim. Biophys. Acta* 443:629; Ostro (1977) *Biochem. Biophys. Res. Commun.* 76:836; Fraley (1979) *Proc. Natl. Acad. Sci. USA* 76:3348); Enoch & Strittmatter (1979) *Proc. Natl. Acad. Sci. USA* 76:145; Fraley (1980) *J. Biol. Chem.* (1980) 255:10431; Szoka & Papahadjopoulos (1978) *Proc. Natl. Acad. Sci. USA* 75:145; and Schaefer-Ridder (1982) *Science* 215:166.

E. Lipoproteins

In addition, lipoproteins can be included with the polynucleotide/polypeptide to be delivered. Examples of lipoproteins to be utilized include: chylomicrons, HDL, IDL, LDL, and VLDL. Mutants, fragments, or fusions of these proteins can also be used. Also, modifications of naturally occurring lipoproteins can be used, such as acetylated LDL. These lipoproteins can target the delivery of polynucleotides to cells expressing lipoprotein receptors. Preferably, if lipoproteins are including with the polynucleotide to be delivered, no other targeting ligand is included in the composition.

Naturally occurring lipoproteins comprise a lipid and a protein portion. The protein portion are known as apoproteins. At the present, apoproteins A, B, C, D, and E have been isolated and identified. At least two of these contain several proteins, designated by Roman numerals, AI, AII, AIV; CI, CII, CIII.

A lipoprotein can comprise more than one apoprotein. For example, naturally occurring chylomicrons comprises of A, B, C, and E, over time these lipoproteins lose A and acquire C and E apoproteins. VLDL comprises A, B, C, and E apoproteins, LDL comprises apoprotein B; and HDL comprises apoproteins A, C, and E.

The amino acid of these apoproteins are known and are described in, for example, Breslow (1985) *Annu Rev. Biochem* 54:699; Law (1986) *Adv. Exp Med. Biol.* 151:162; Chen (1986) *J Biol Chem* 261:12918; Kane (1980) *Proc Natl Acad Sci USA* 77:2465; and Utermann (1984) *Hum Genet* 65:232.

Lipoproteins contain a variety of lipids including, triglycerides, cholesterol (free and esters), and phospholipids. The composition of the lipids varies in naturally occurring lipoproteins. For example, chylomicrons comprise mainly triglycerides. A more detailed description of the lipid content of naturally occurring lipoproteins can be found, for example, in *Meth. Enzymol.* 128 (1986). The composition of the lipids are chosen to aid in conformation of the apoprotein for receptor binding activity. The composition of lipids can also be chosen to facilitate hydrophobic interaction and association with the polynucleotide binding molecule.

Naturally occurring lipoproteins can be isolated from serum by ultracentrifugation, for instance. Such methods are described in *Meth. Enzymol.* (supra); Pitas (1980) *J. Biochem.* 255:5454-5460 and Mahey (1979) *J Clin. Invest* 64:743-750. Lipoproteins can also be produced by in vitro or recombinant methods by expression of the apoprotein genes in a desired host cell. See, for example, Atkinson (1986) *Annu Rev Biophys Chem* 15:403 and Radding (1958) *Biochim Biophys Acta* 30: 443. Lipoproteins can also be purchased from commercial suppliers, such as Biomedical Technologies, Inc., Stoughton, Mass., USA. Further description of lipoproteins can be found in WO98/06437.

F. Polycationic Agents

Polycationic agents can be included, with or without lipoprotein, in a composition with the desired polynucleotide/polypeptide to be delivered.

Polycationic agents, typically, exhibit a net positive charge at physiological relevant pH and are capable of neutralizing the electrical charge of nucleic acids to facilitate delivery to a desired location. These agents have both in vitro, ex vivo, and in vivo applications. Polycationic agents can be used, to deliver nucleic acids to a living subject either intramuscularly, subcutaneously, etc.

The following are examples of useful polypeptides as polycationic agents: polylysine, polyarginine, polyornithine, and protamine. Other examples include histones, protamines, human serum albumin, DNA binding proteins, non-histone chromosomal proteins, coat proteins from DNA viruses, such as (X174, transcriptional factors also contain domains that bind DNA and therefore may be useful as nucleic aid condensing agents. Briefly, transcriptional factors such as C/CEBP, c-jun, c-fos, AP-1, AP-2, AP-3, CPF, Prot-1, Sp-1, Oct-1, Oct-2, CREP, and TFIID contain basic domains that bind DNA sequences.

Organic polycationic agents include: spermine, spermidine, and purtrescine.

The dimensions and of the physical properties of a polycationic agent can be extrapolated from the list above, to construct other polypeptide polycationic agents or to produce synthetic polycationic agents.

Synthetic polycationic agents which are useful include, for example, DEAE-dextran, polybrene. Lipofectin™, and lipofectAMINE™ are monomers that form polycationic complexes when combined with polynucleotides/polypeptides.

Immunodiagnostic Assays

Neisserial antigens of the invention can be used in immunoassays to detect antibody levels (or, conversely, anti-Neisserial antibodies can be used to detect antigen levels). Immunoassays based on well defined, recombinant antigens can be developed to replace invasive diagnostics methods. Antibodies to Neisserial proteins within biological samples, including for example, blood or serum samples, can be detected. Design of the immunoassays is subject to a great deal of variation, and a variety of these are known in the art. Protocols for the immunoassay may be based, for example, upon competition, or direct reaction, or sandwich type assays. Protocols may also, for example, use solid supports, or may be by immunoprecipitation. Most assays involve the use of labeled antibody or polypeptide; the labels may be, for example, fluorescent, chemiluminescent, radioactive, or dye molecules. Assays which amplify the signals from the probe are also known; examples of which are assays which utilize biotin and avidin, and enzyme-labeled and mediated immunoassays, such as ELISA assays.

Kits suitable for immunodiagnosis and containing the appropriate labeled reagents are constructed by packaging the appropriate materials, including the compositions of the invention, in suitable containers, along with the remaining reagents and materials (for example, suitable buffers, salt solutions, etc.) required for the conduct of the assay, as well as suitable set of assay instructions.

Nucleic Acid Hybridisation

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook et al. [supra] Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 120 to 200° C. below the calculated Tm of the hybrid under study. The temperature and salt conditions can often be determined empirically in preliminary experiments in which samples of genomic DNA immobilized on filters are hybridized to the sequence of interest and then washed under conditions of different stringencies. See Sambrook et al. at page 9.50.

Variables to consider when performing, for example, a Southern blot are (1) the complexity of the DNA being blotted and (2) the homology between the probe and the sequences being detected. The total amount of the fragment(s) to be studied can vary a magnitude of 10, from 0.1 to 1 µg for a plasmid or phage digest to $10^{-9}$ to $10^{-8}$ g for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4-8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm = 81 + 16.6(\log_{10} Ci) + 0.4[\%(G+C)] - 0.6(\% \text{ formamide}) - 600/n - 1.5(\% \text{ mismatch}).$$

where Ci is the salt concentration (monovalent ions) and n is the length of the hybrid in base pairs (slightly modified from Meinkoth & Wahl (1984) *Anal. Biochem.* 138: 267-284).

In designing a hybridization experiment, some factors affecting nucleic acid hybridization can be conveniently altered. The temperature of the hybridization and washes and the salt concentration during the washes are the simplest to adjust. As the temperature of the hybridization increases (ie. stringency), it becomes less likely for hybridization to occur between strands that are nonhomologous, and as a result, background decreases. If the radiolabeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology between the probe and the target fragment are not known, the simplest approach is to start with both hybridization and wash conditions which are nonstringent. If non-specific bands or high background are observed after autoradiography, the filter can be washed at high stringency and reexposed. If the time required for exposure makes

BRIEF DESCRIPTION OF THE DRAWINGS

Figure 1A:
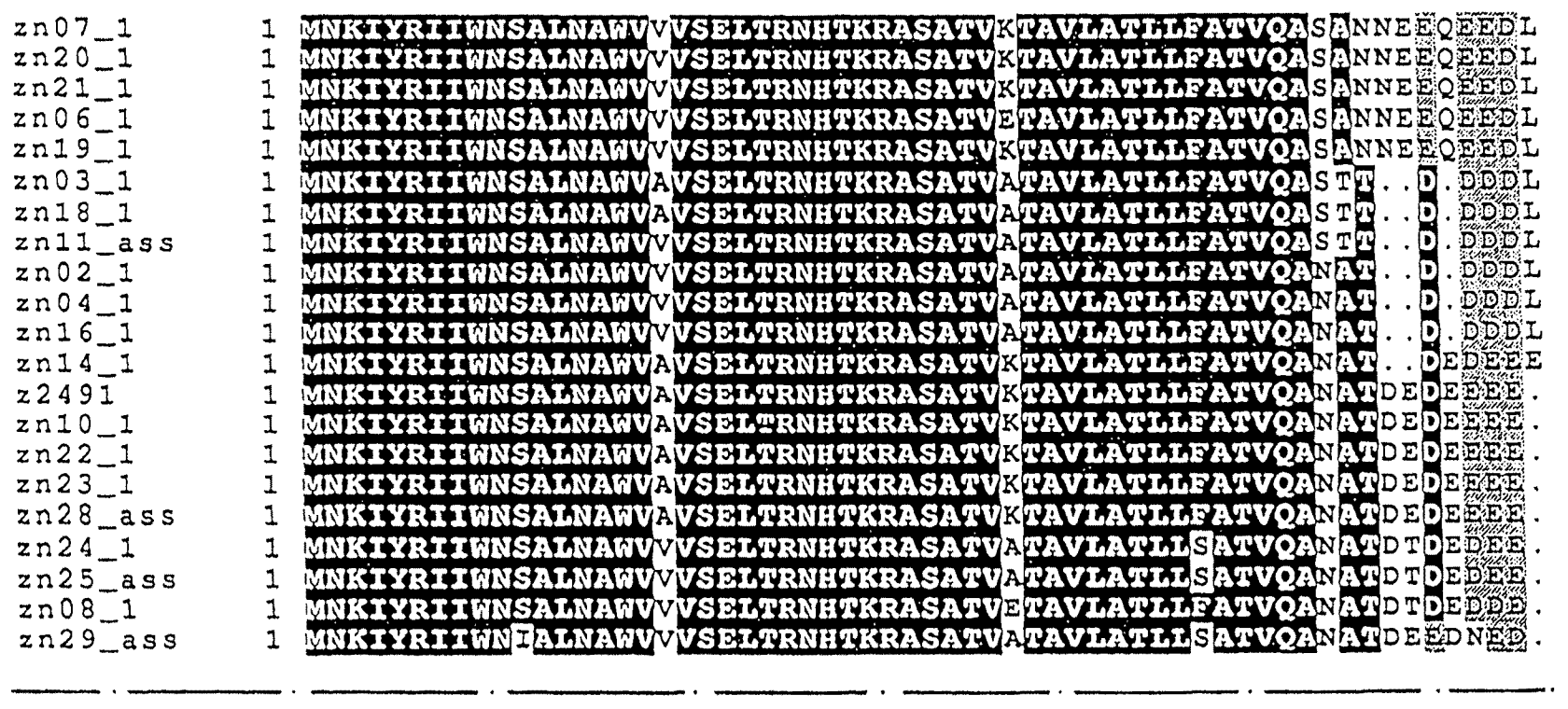
Figure 1A:
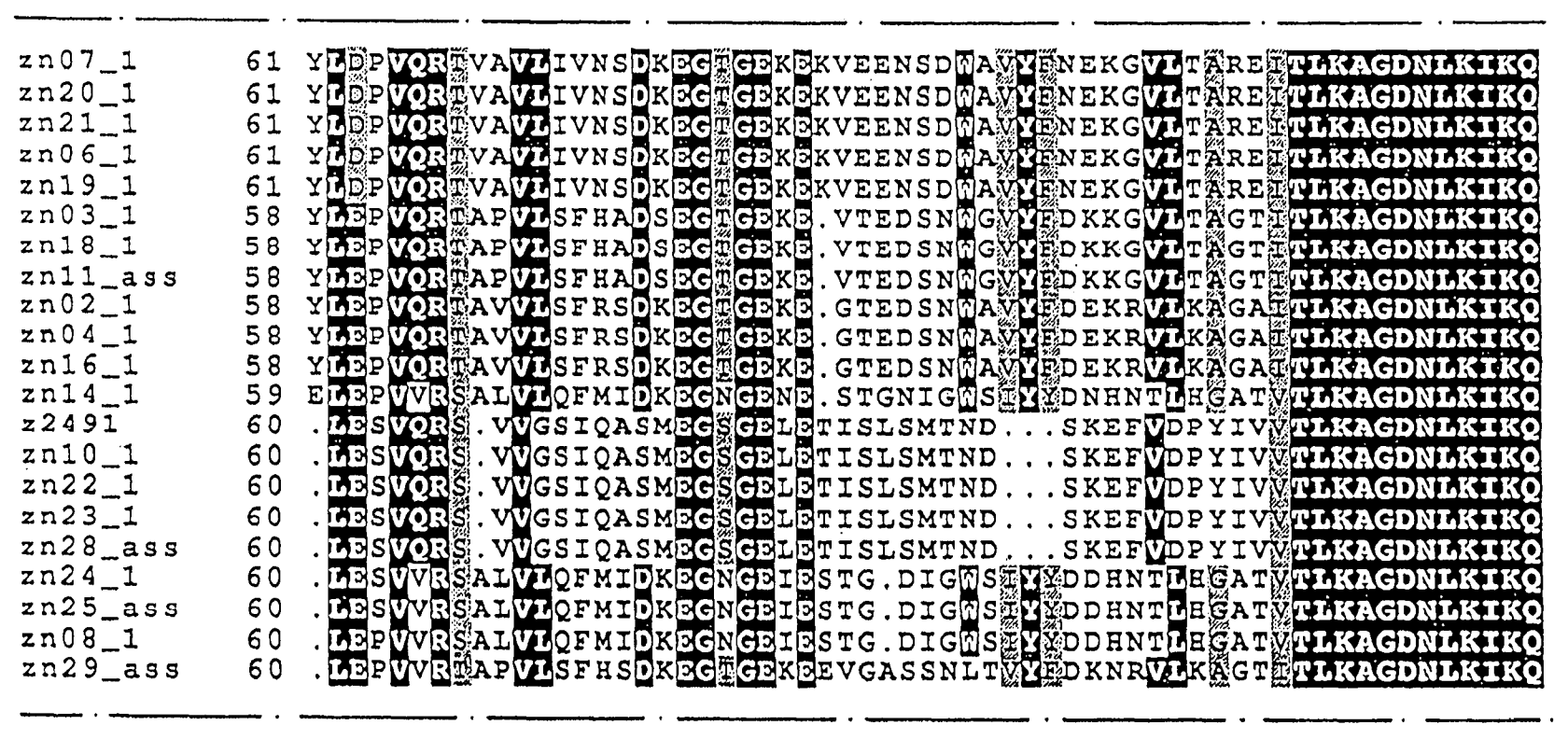
Figure 1A:
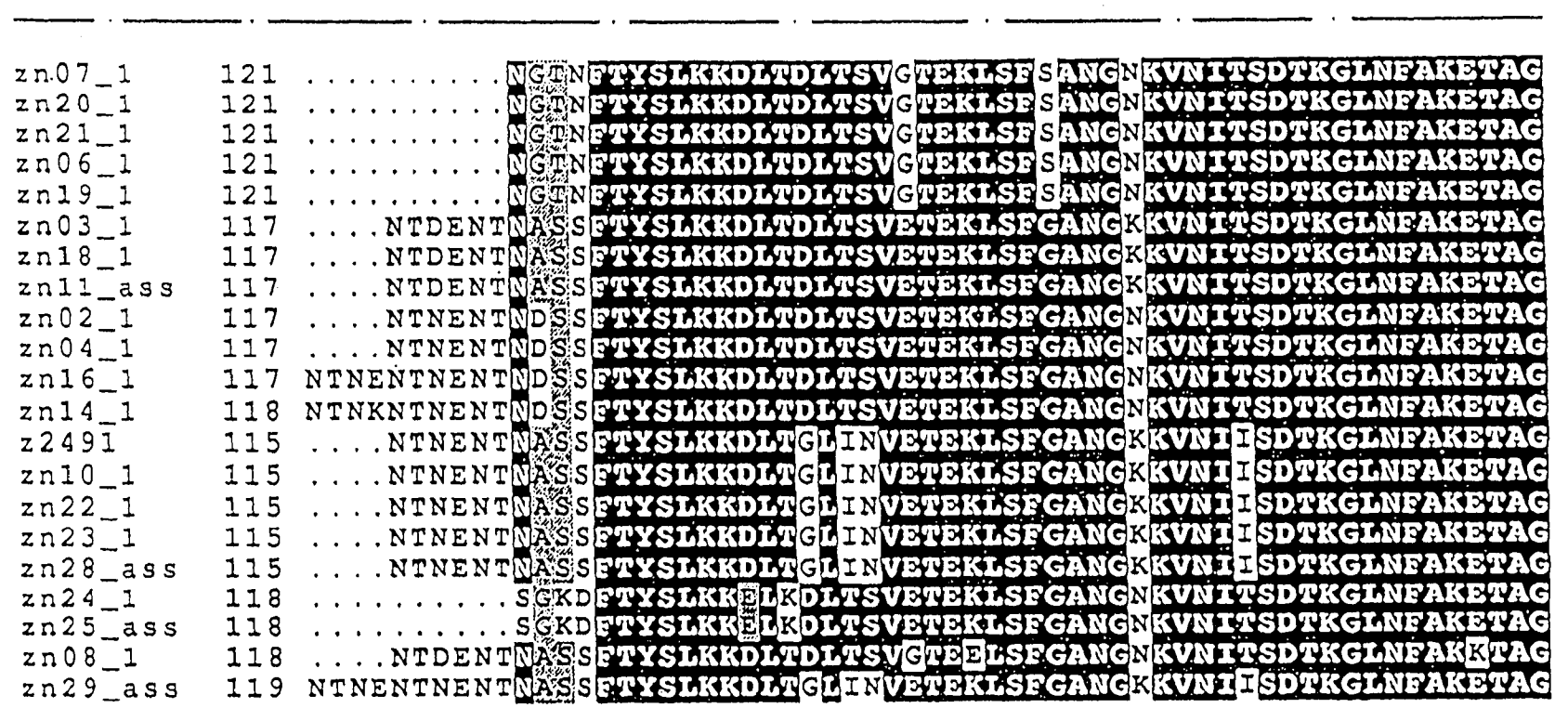
Figure 1B:
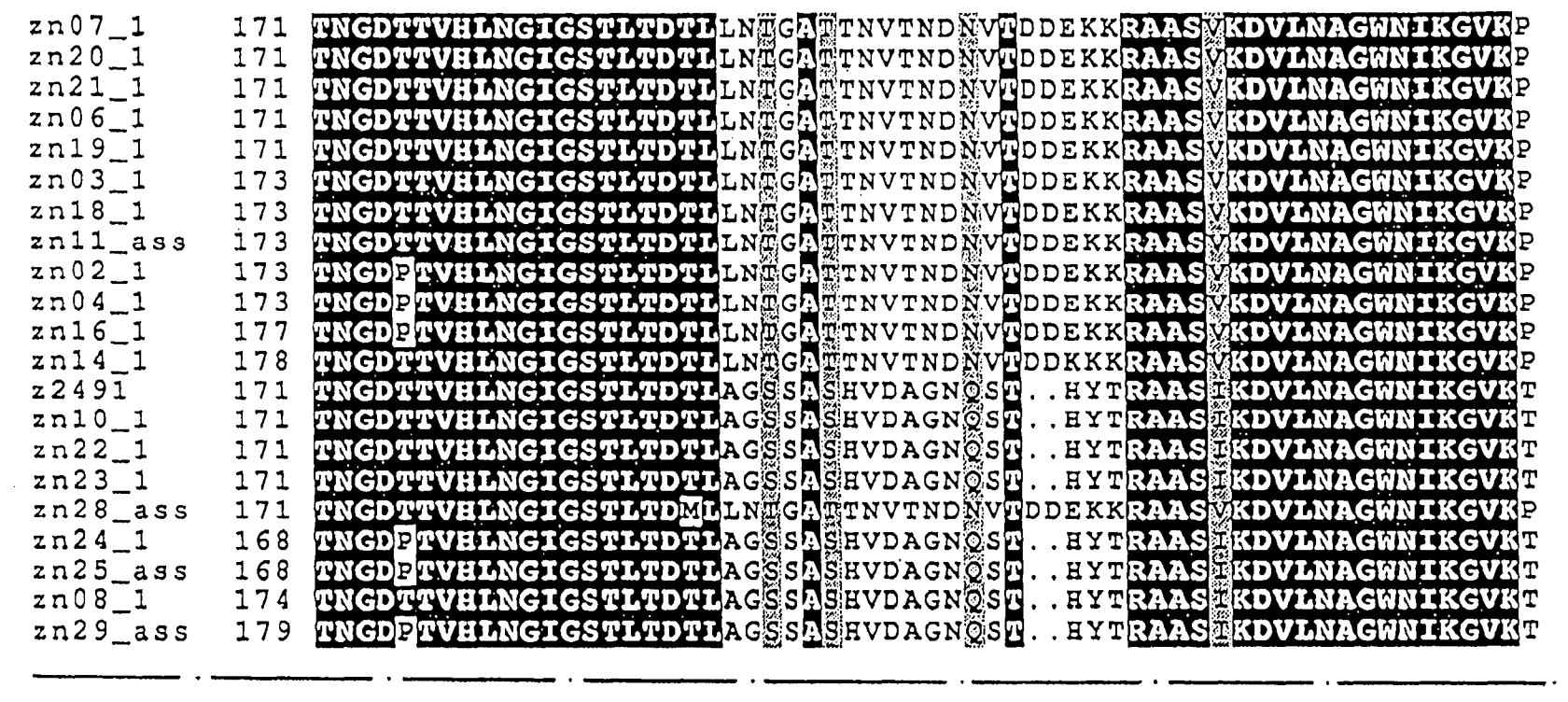
Figure 1B:
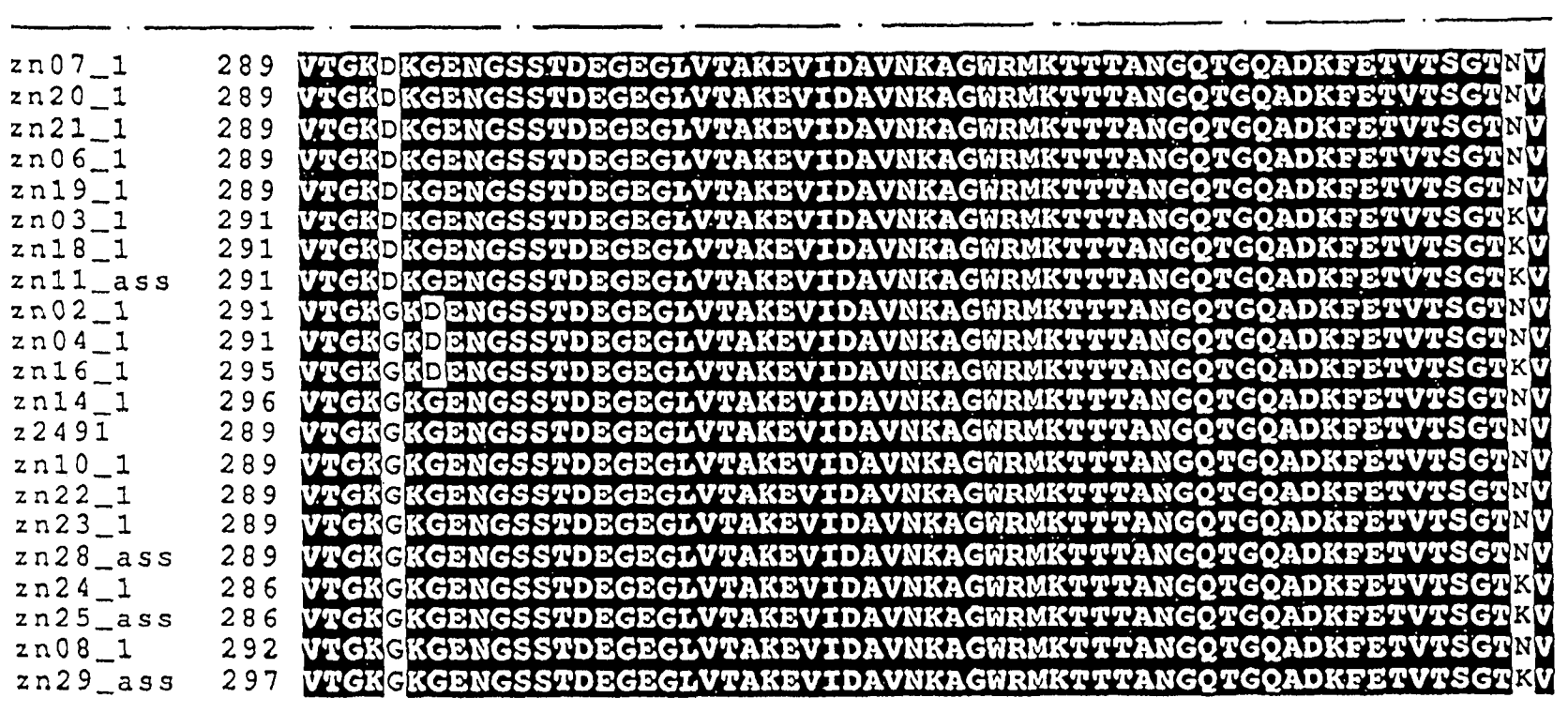
Figure 1C:
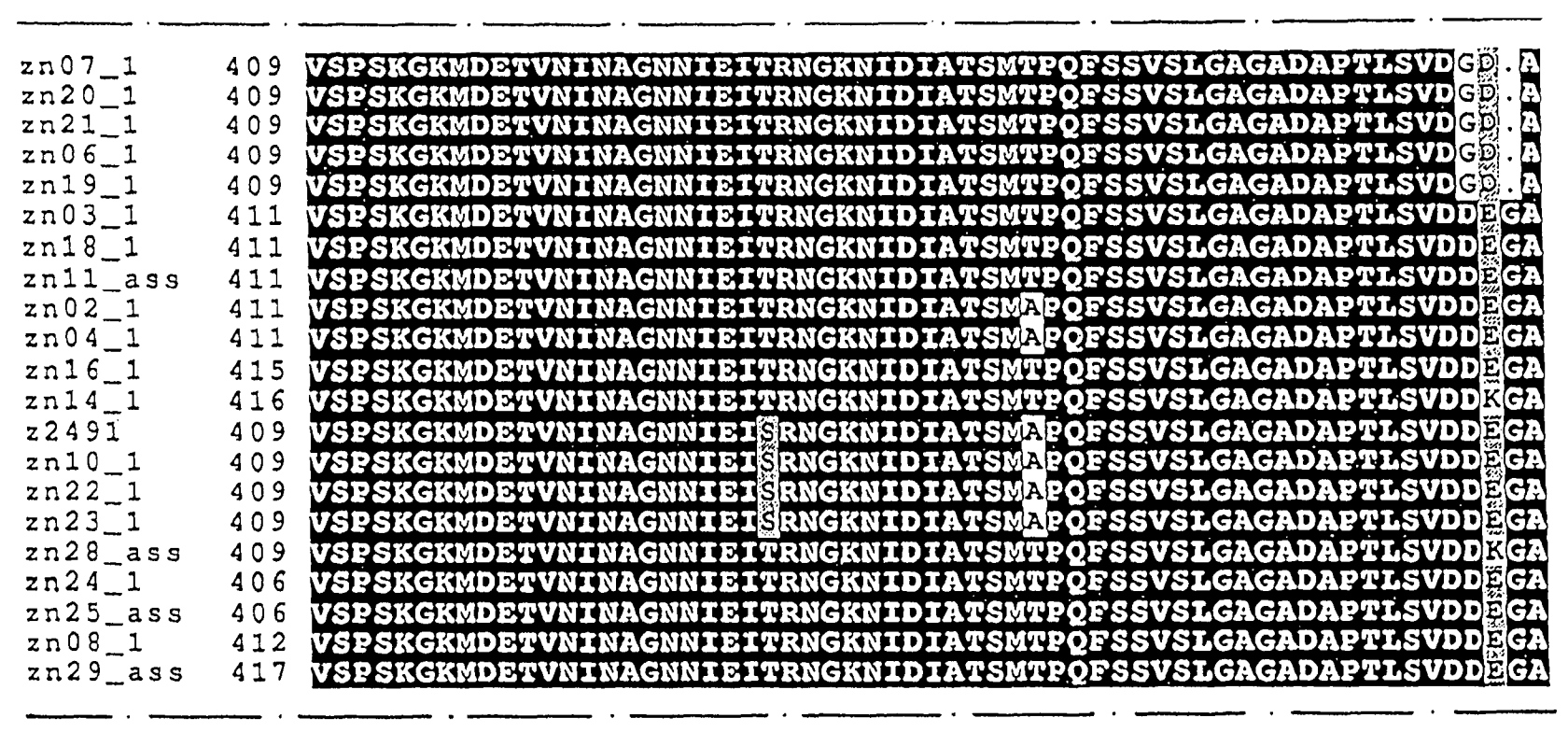
Figure 1C:
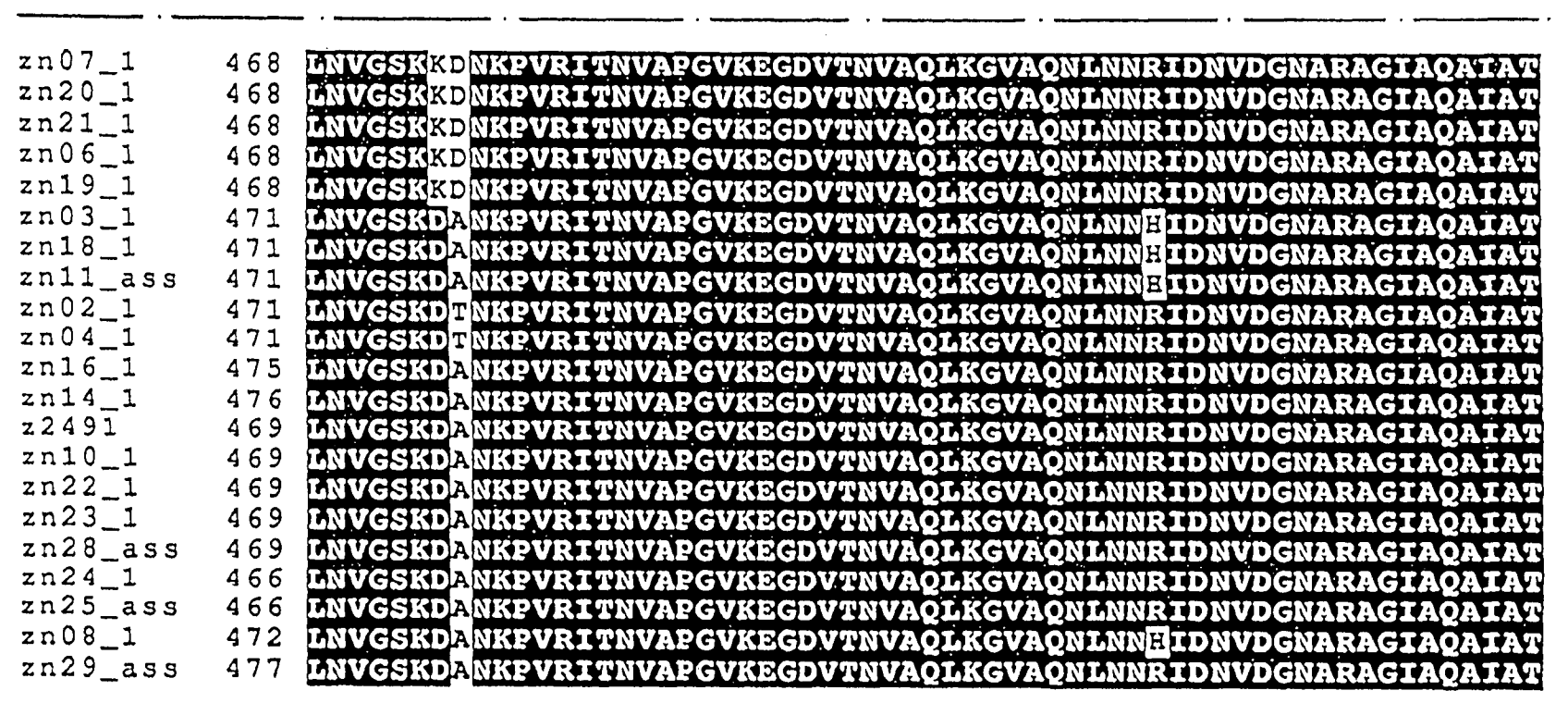
Figure 1D:
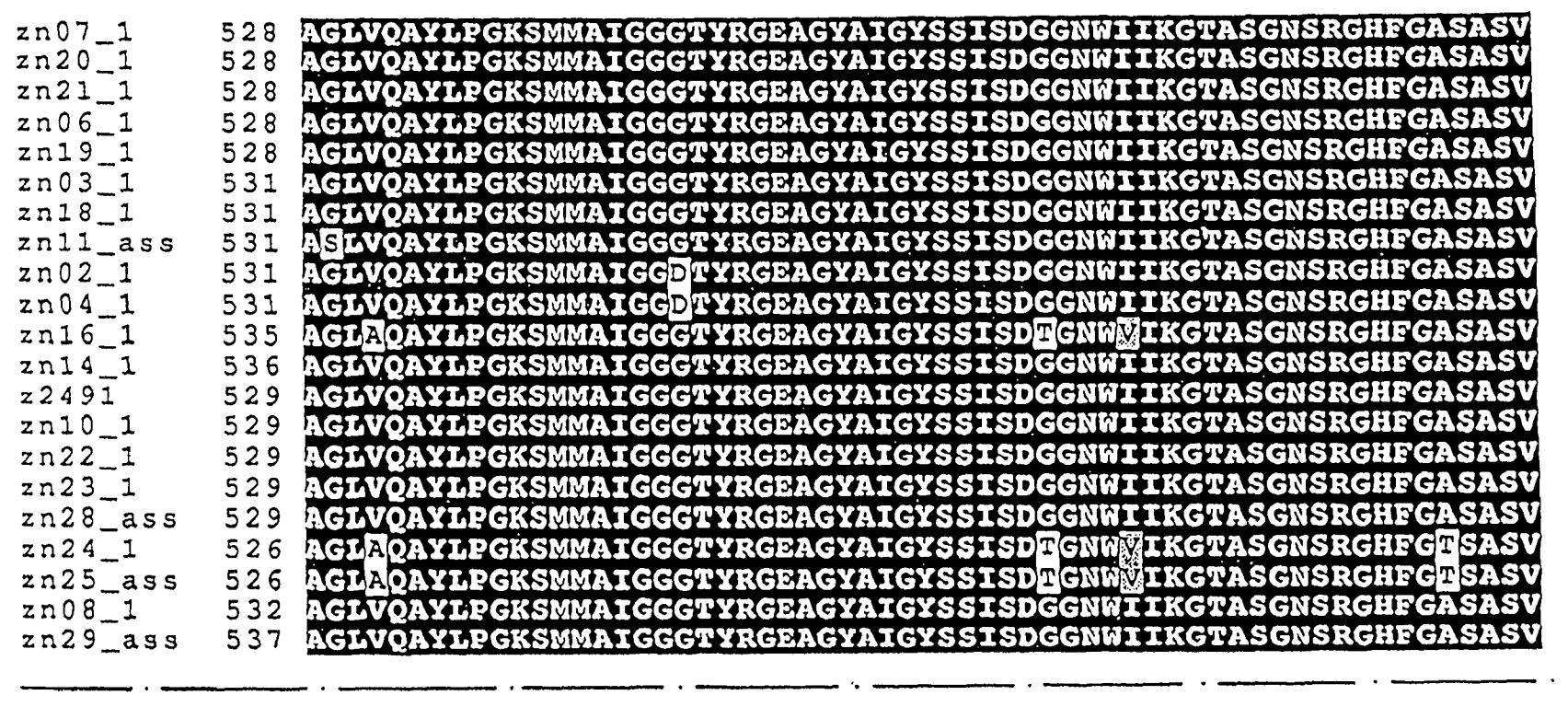
Figure 7A:
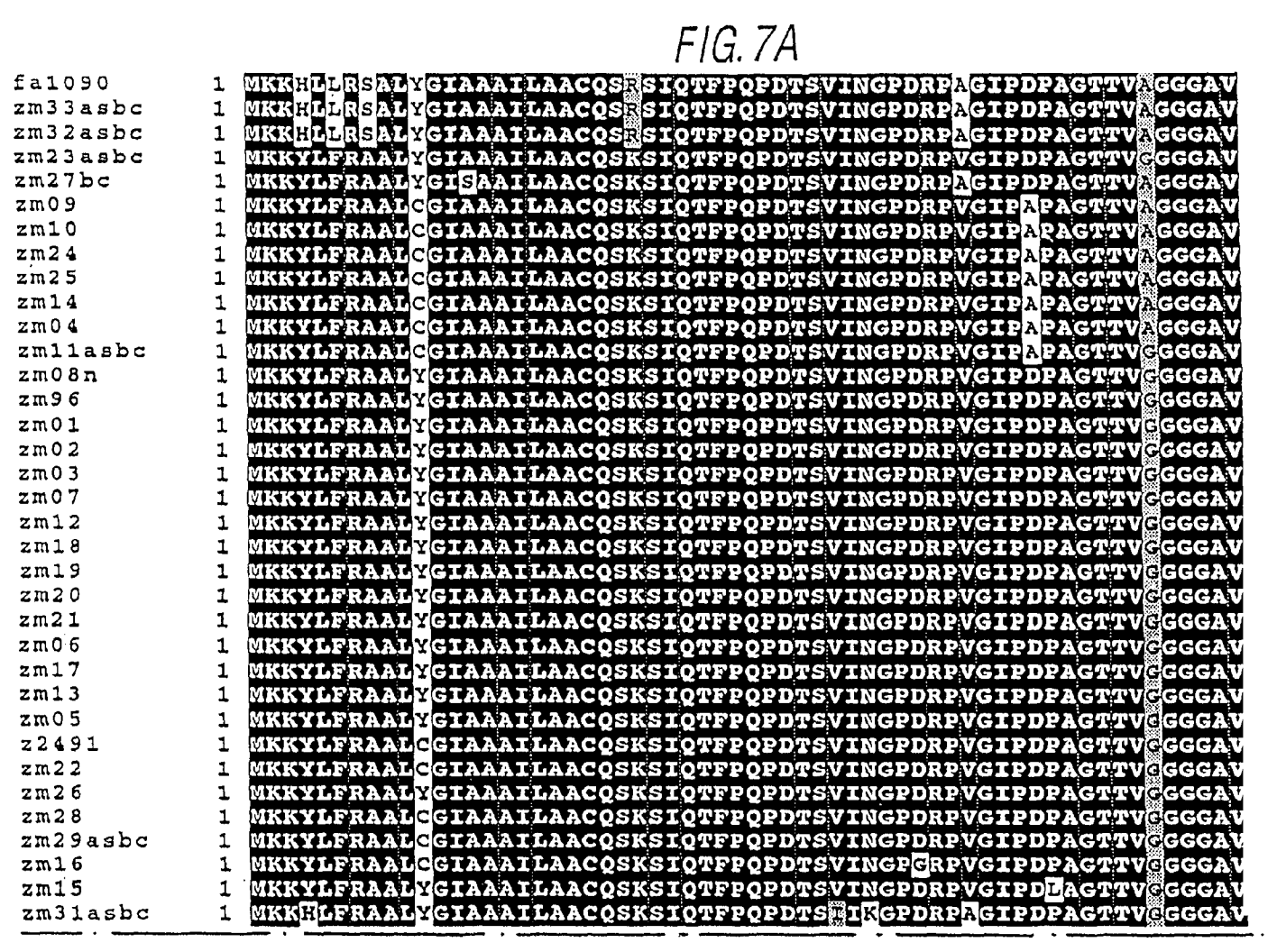
Figure 7A:
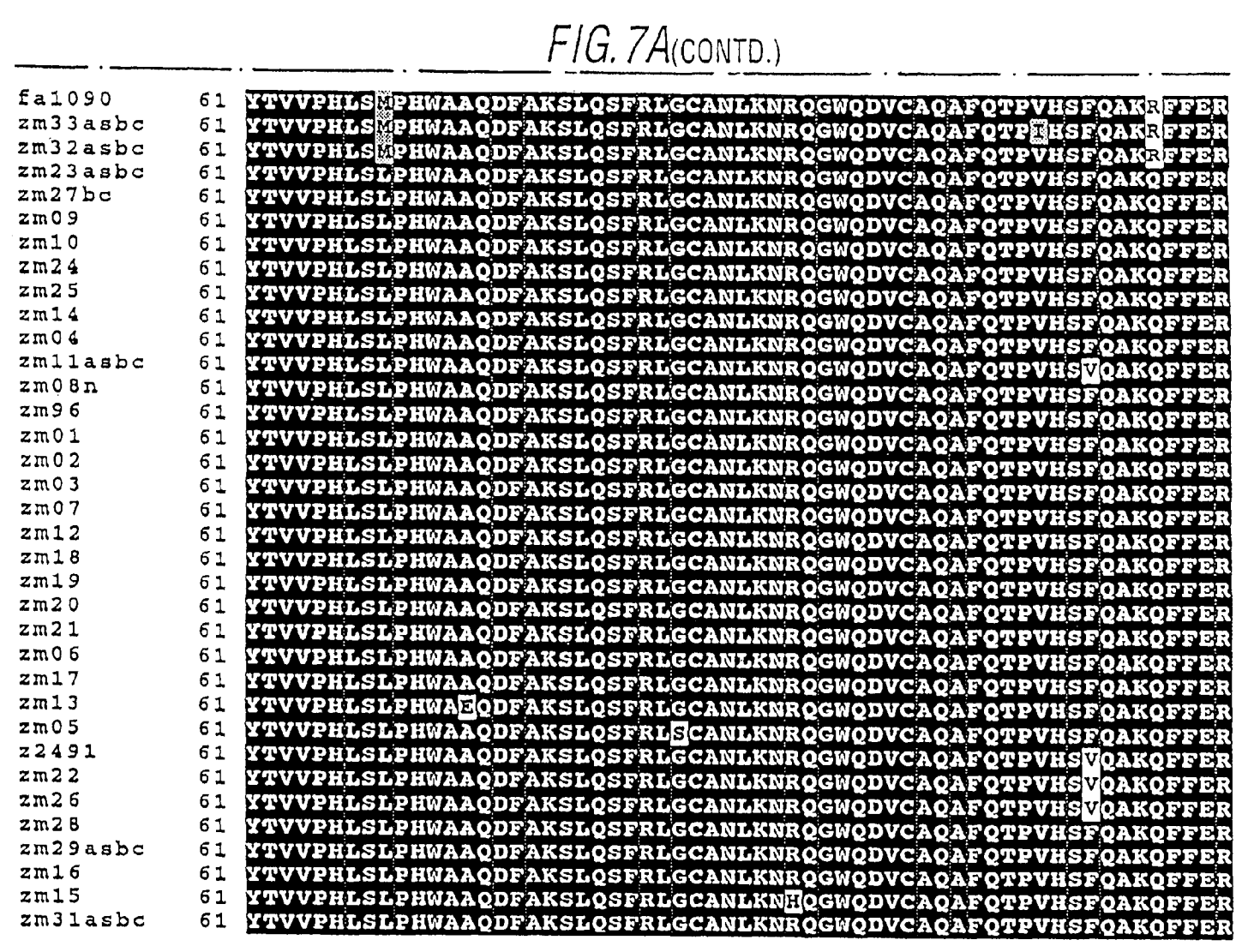
Figure 7B:
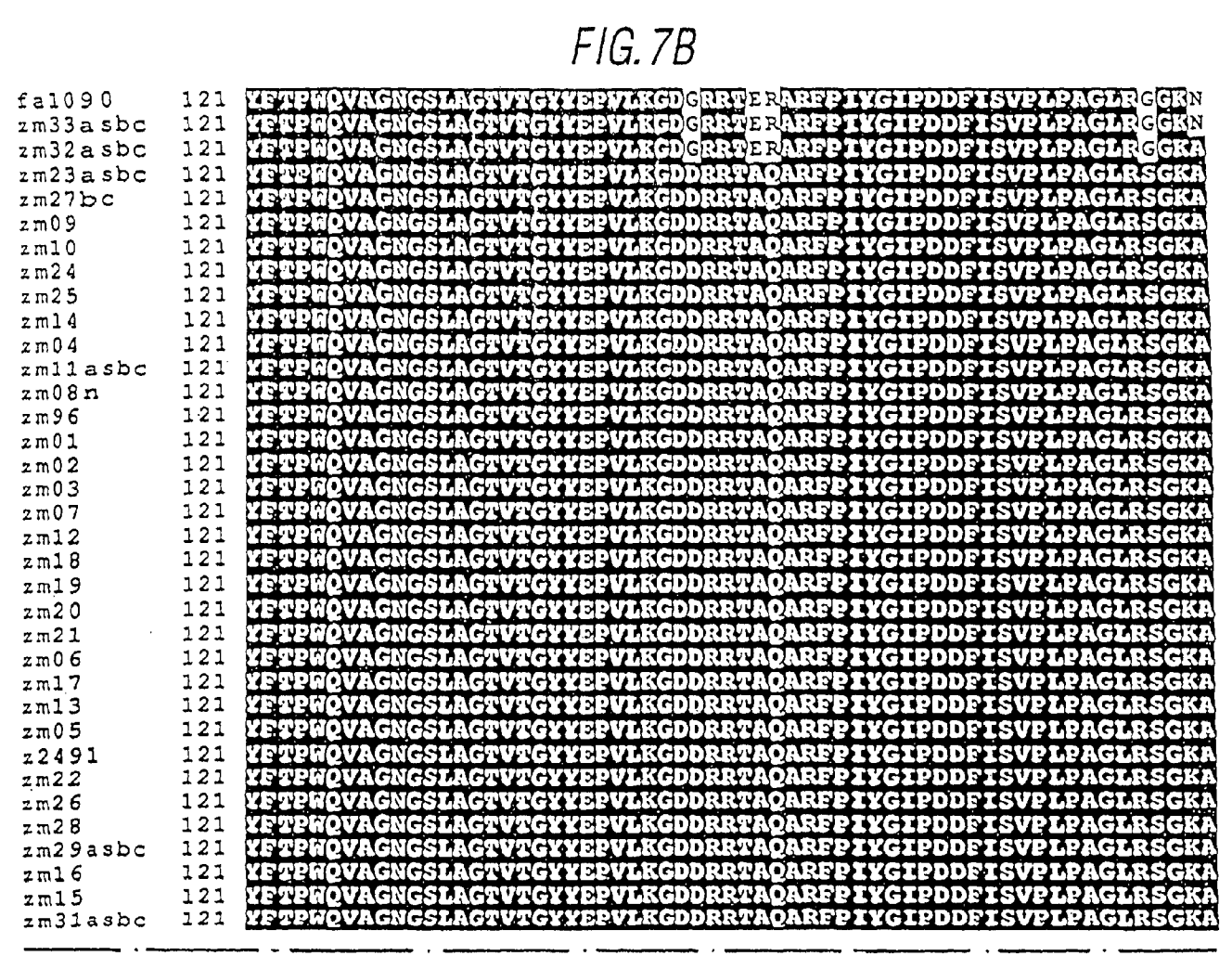
Figure 7B:
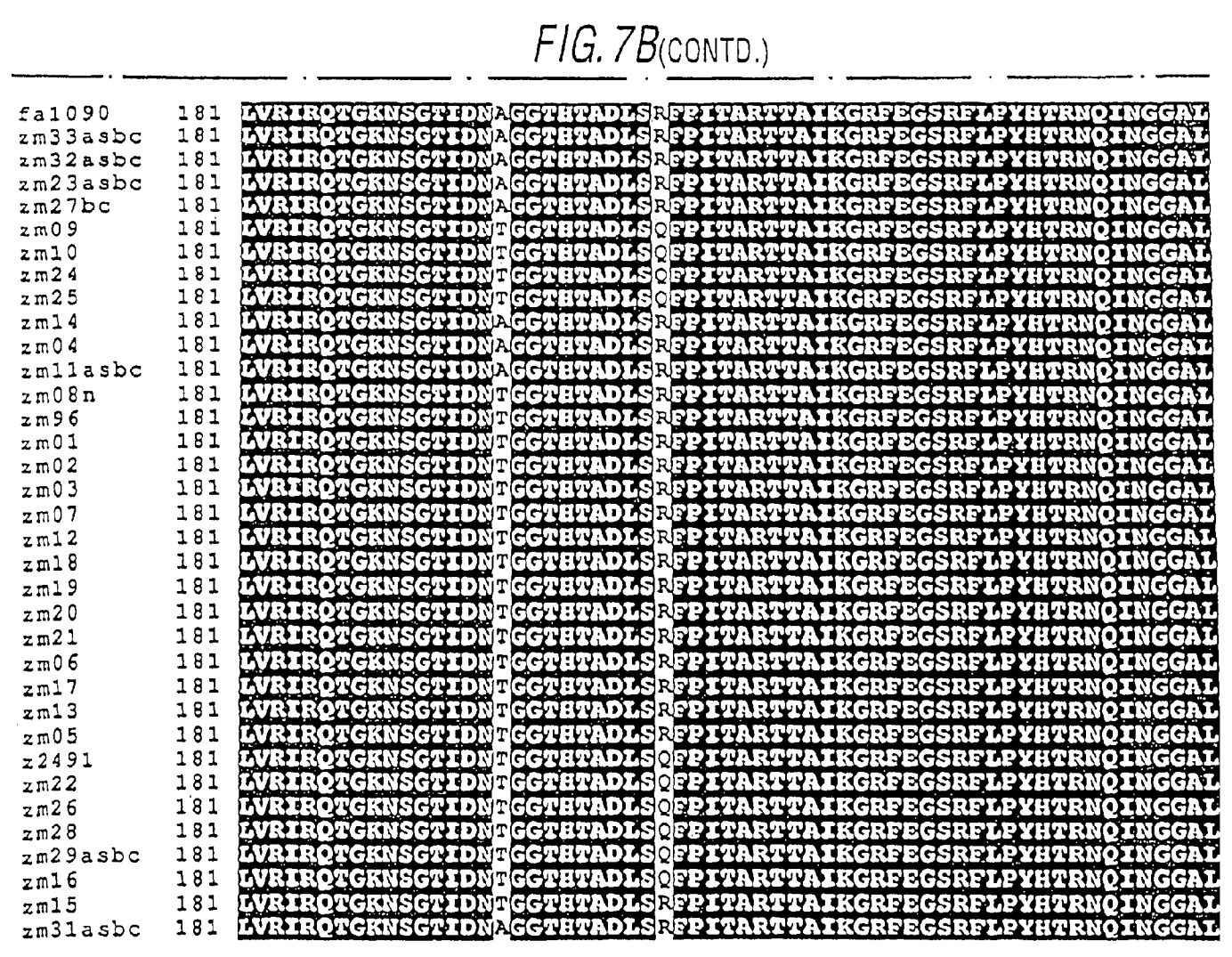
Figure 7C:
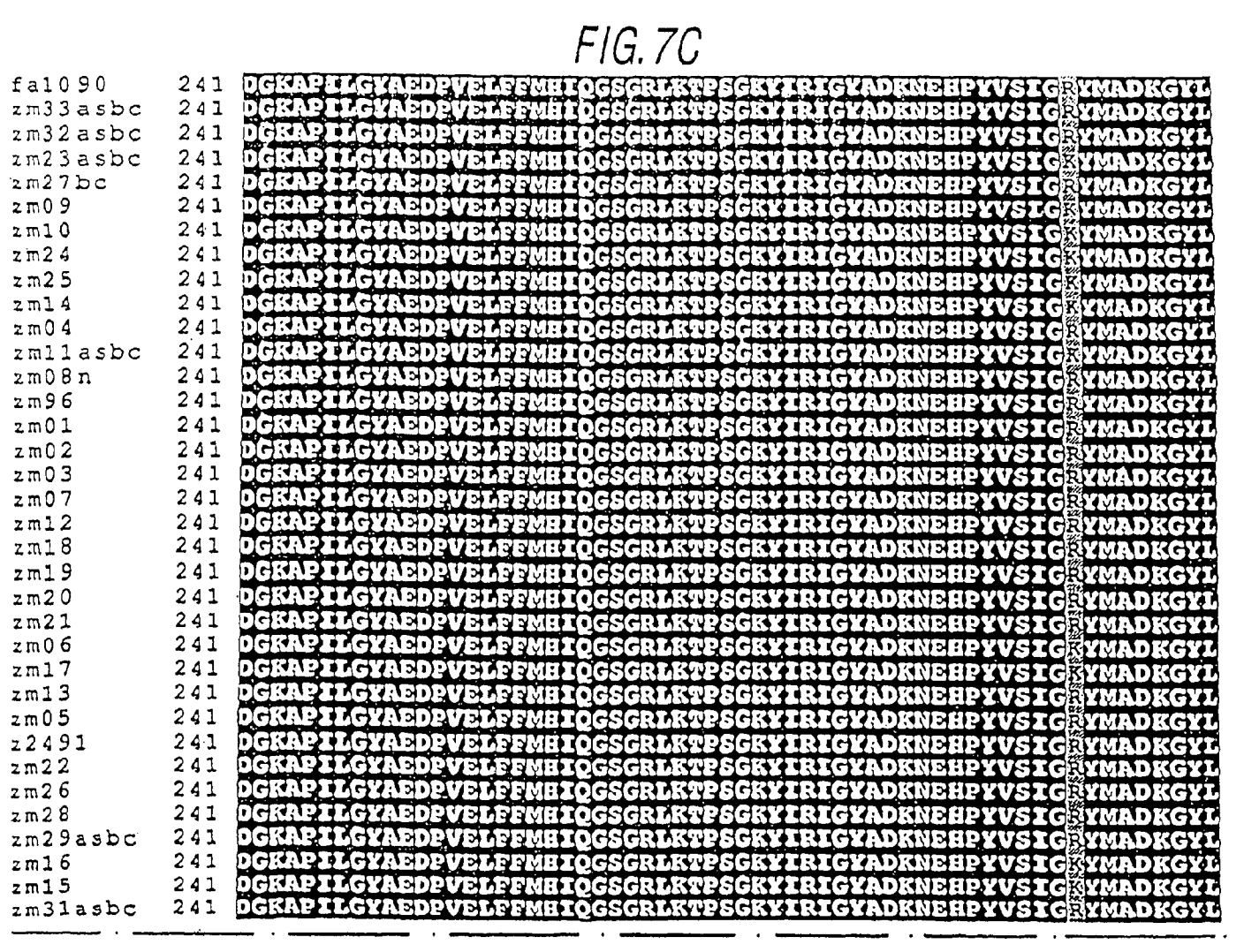
Figure 7C:
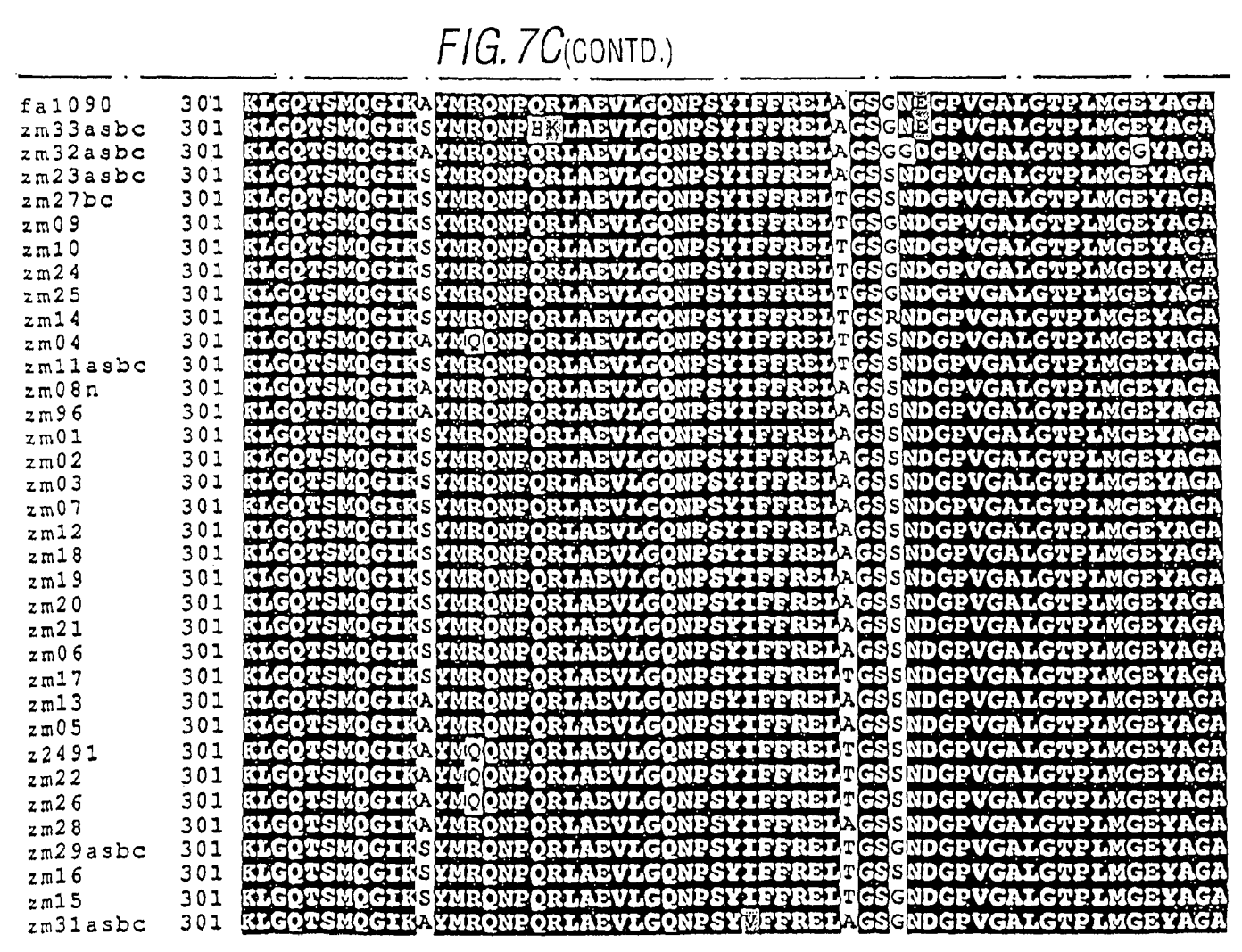
Figure 7D:
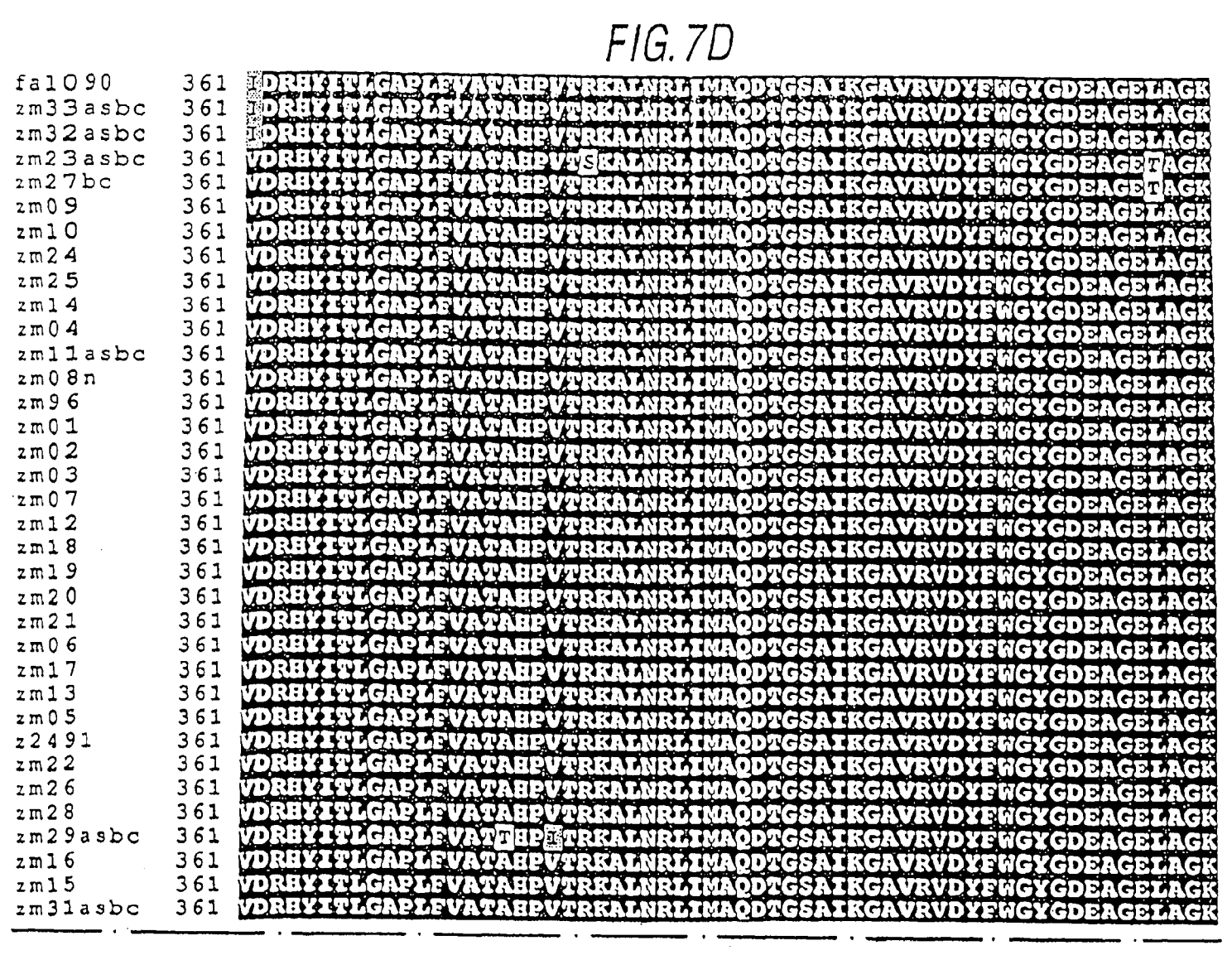
Figure 7D:
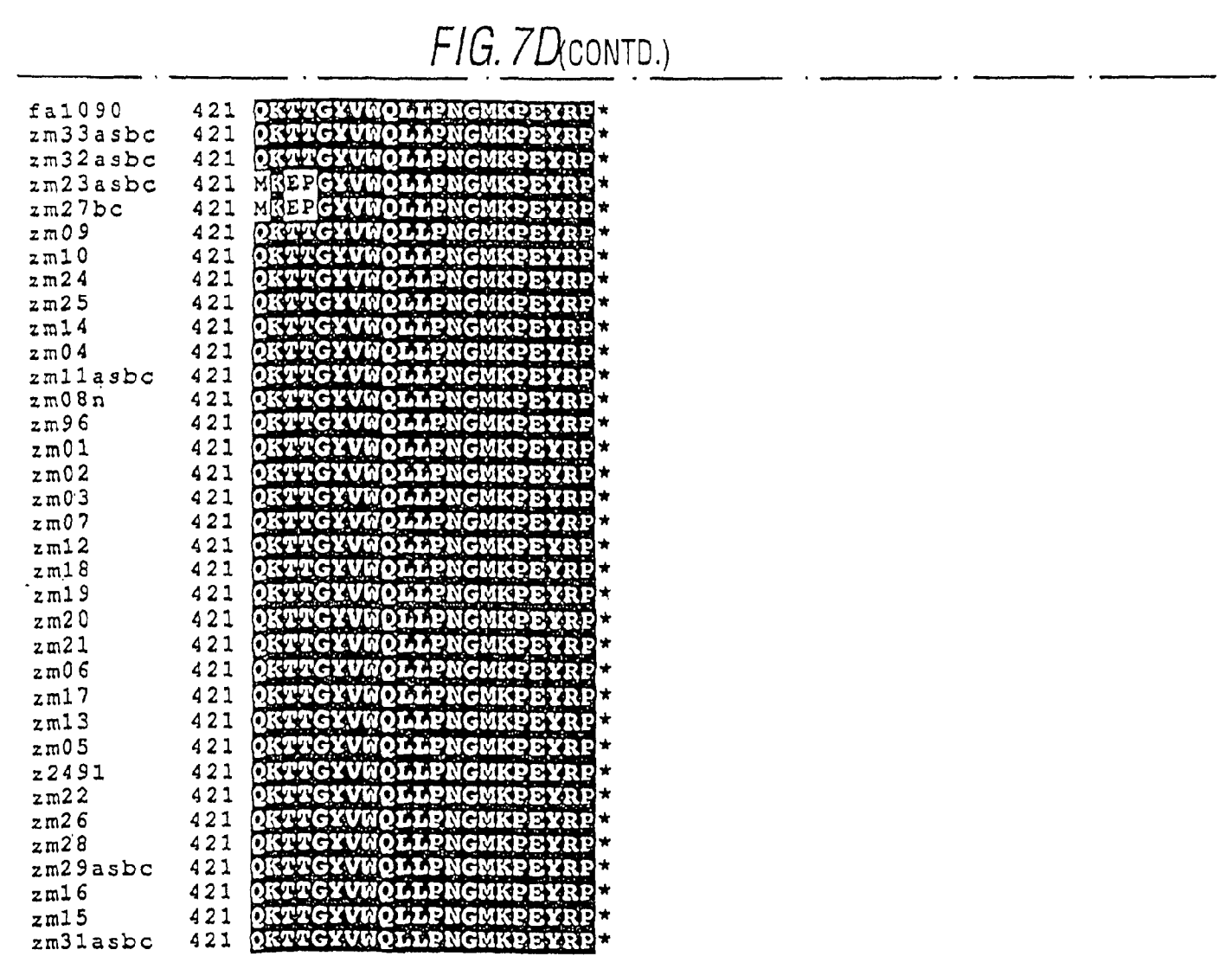

FIGS. 1A-1D to 7A-7D show BOXSHADE-rendered alignments of (1) ORF40 (SEQ ID NOS:1-21) (2) ORF4 (SEQ ID NOS:22-53) (3) 225 (SEQ ID NOS:54-87) (4) 235 (SEQ ID NOS:88-118) (5) 287 (SEQ ID NOS:119-124) (6) 519 (SEQ ID NOS:125-146) (7) 919 (SEQ ID NOS:147-181).

Conserved amino acids have a solid background.

Figure 8:
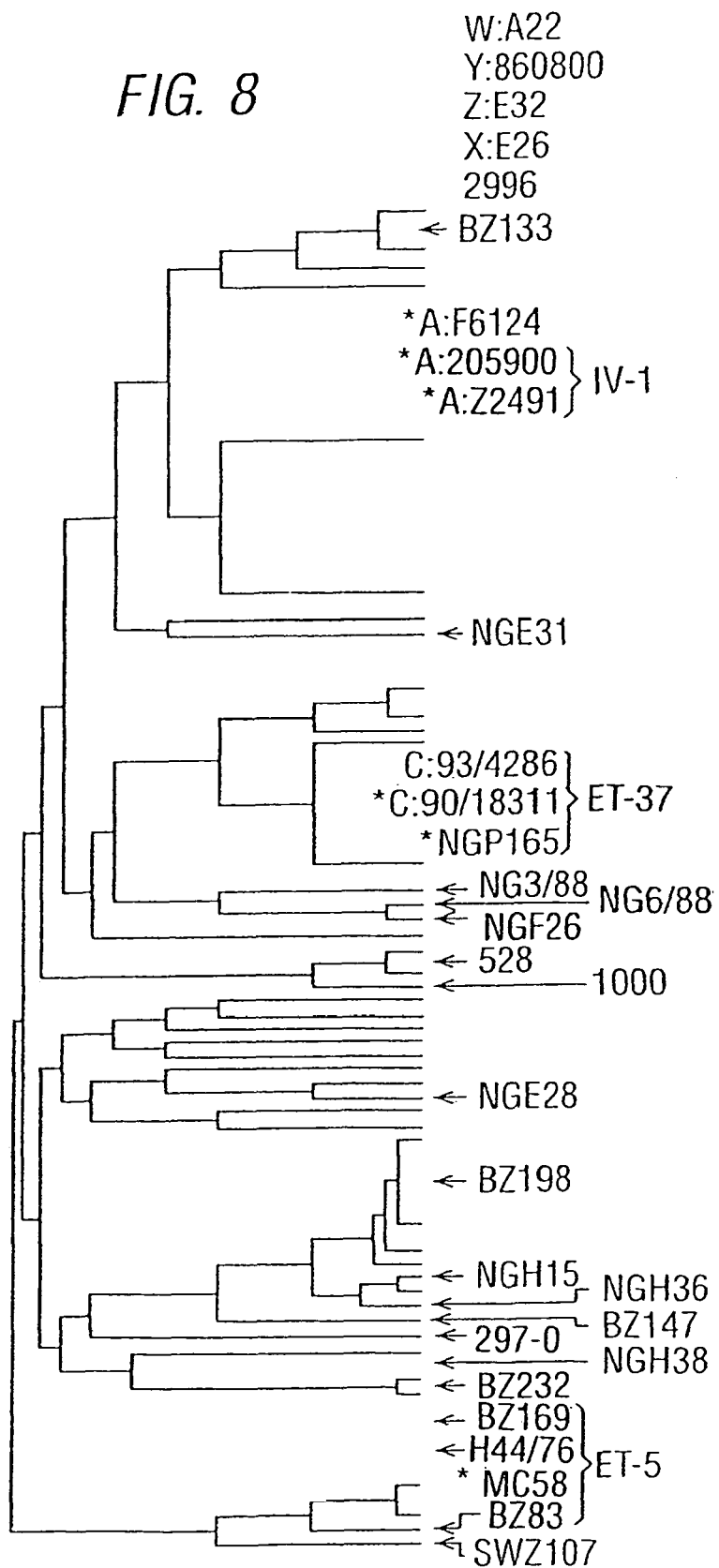

FIG. 8 shows a phylogenetic tree.

Figure 9A:
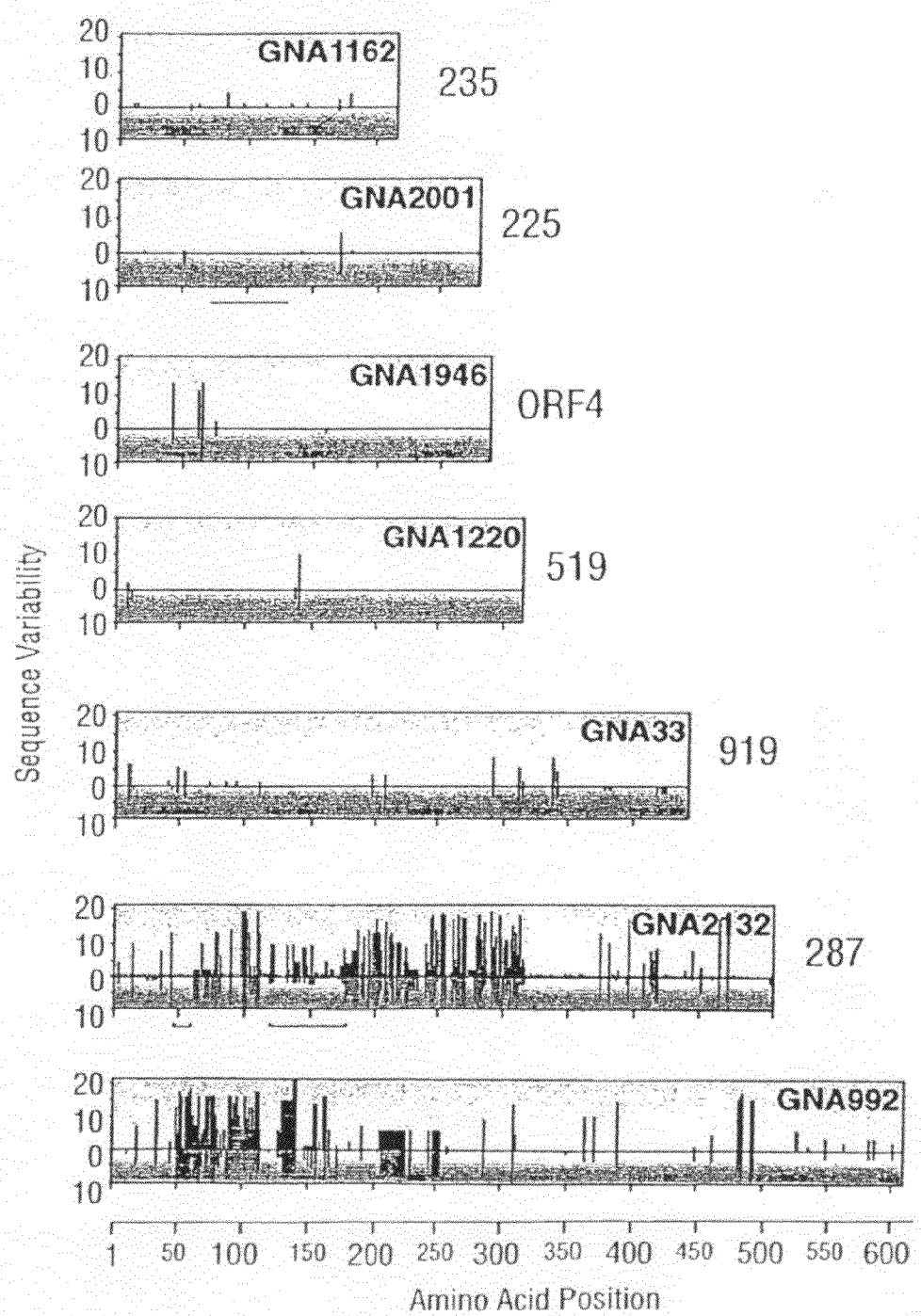
Figure 9B:
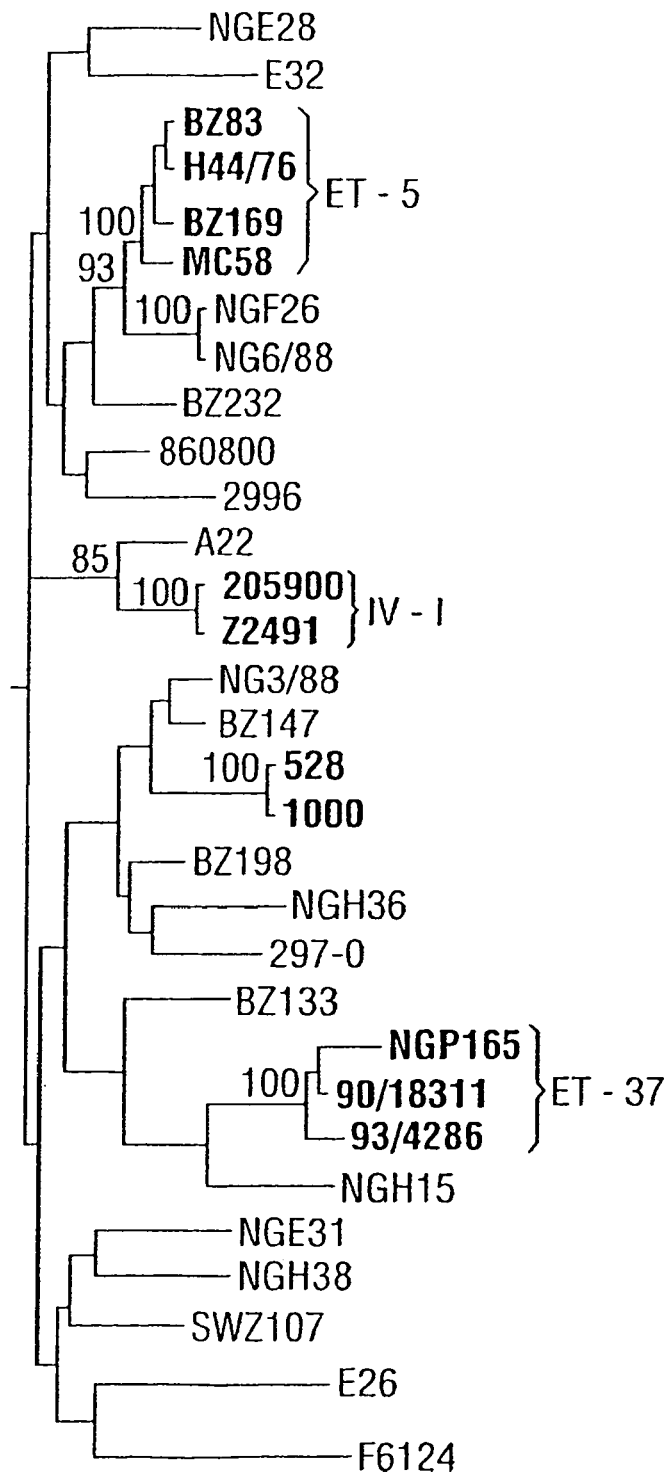

FIG. 9A illustrates amino acid sequence variability within *N. meningitidis* for ORF4, ORF40, 225, 235, 287, 519, and 919. These sequences were used to construct the phylogenetic tree shown in FIG. 9B.

Figure 10A:
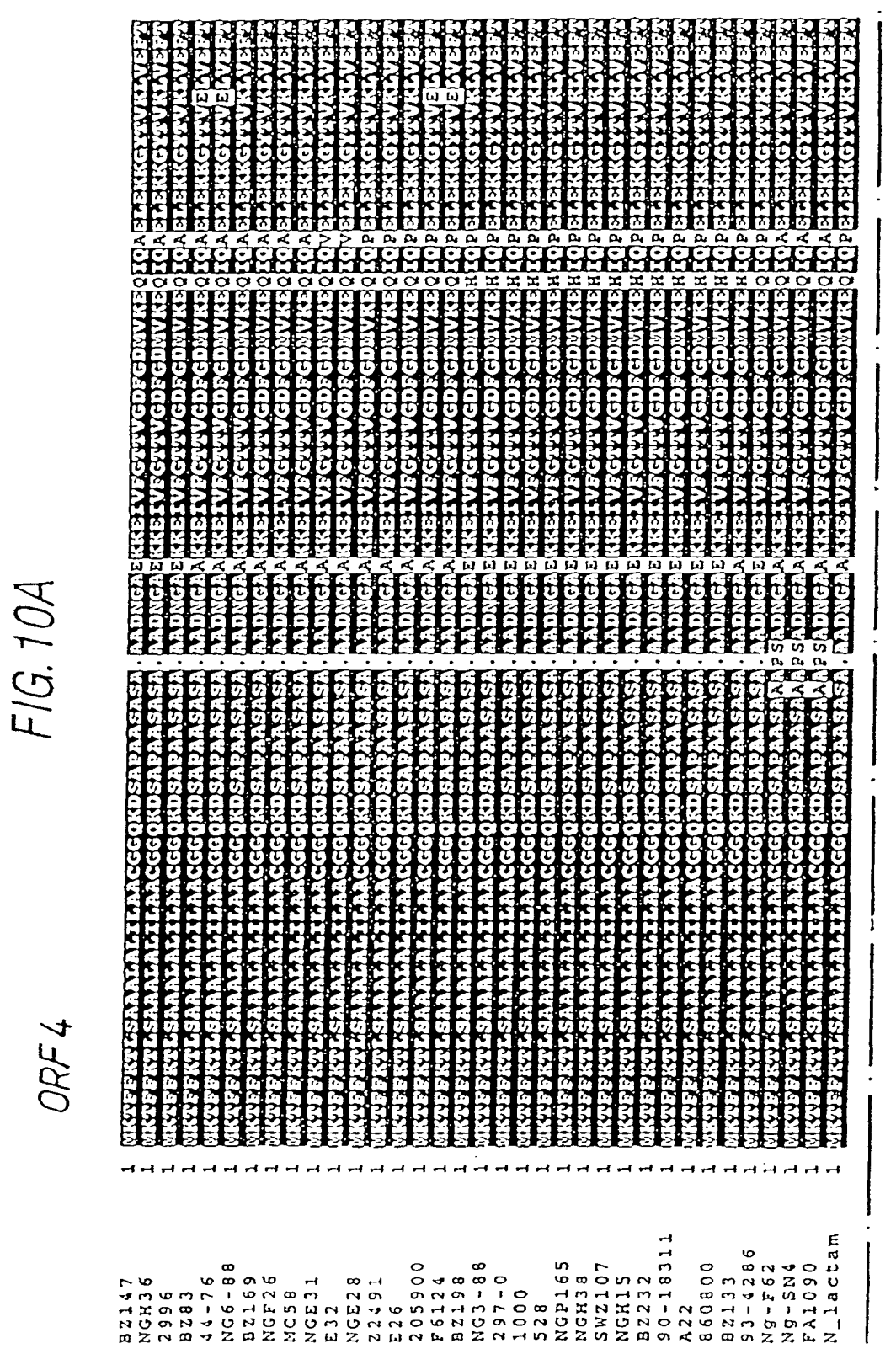
Figure 10A:
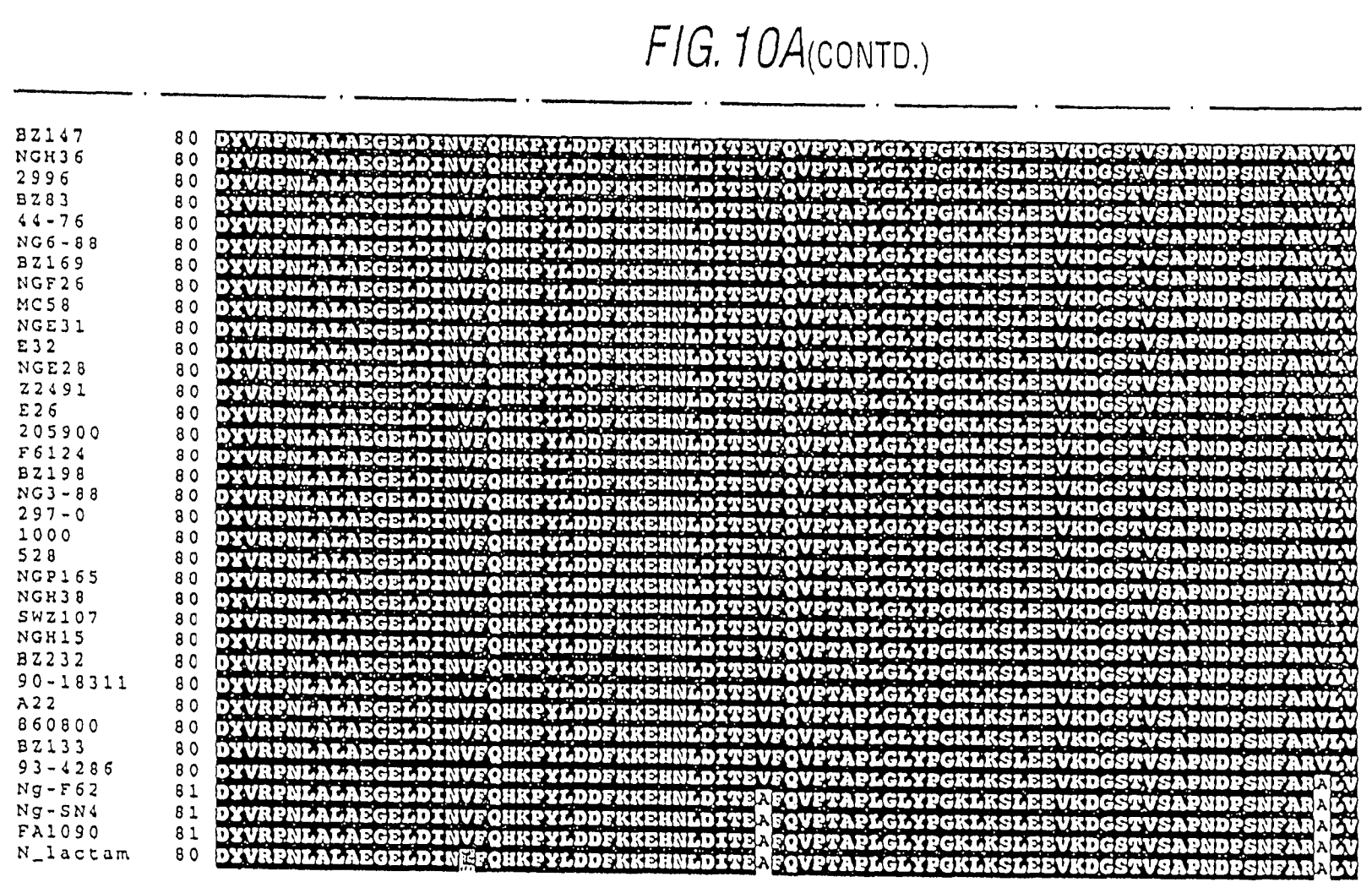
Figure 10B:
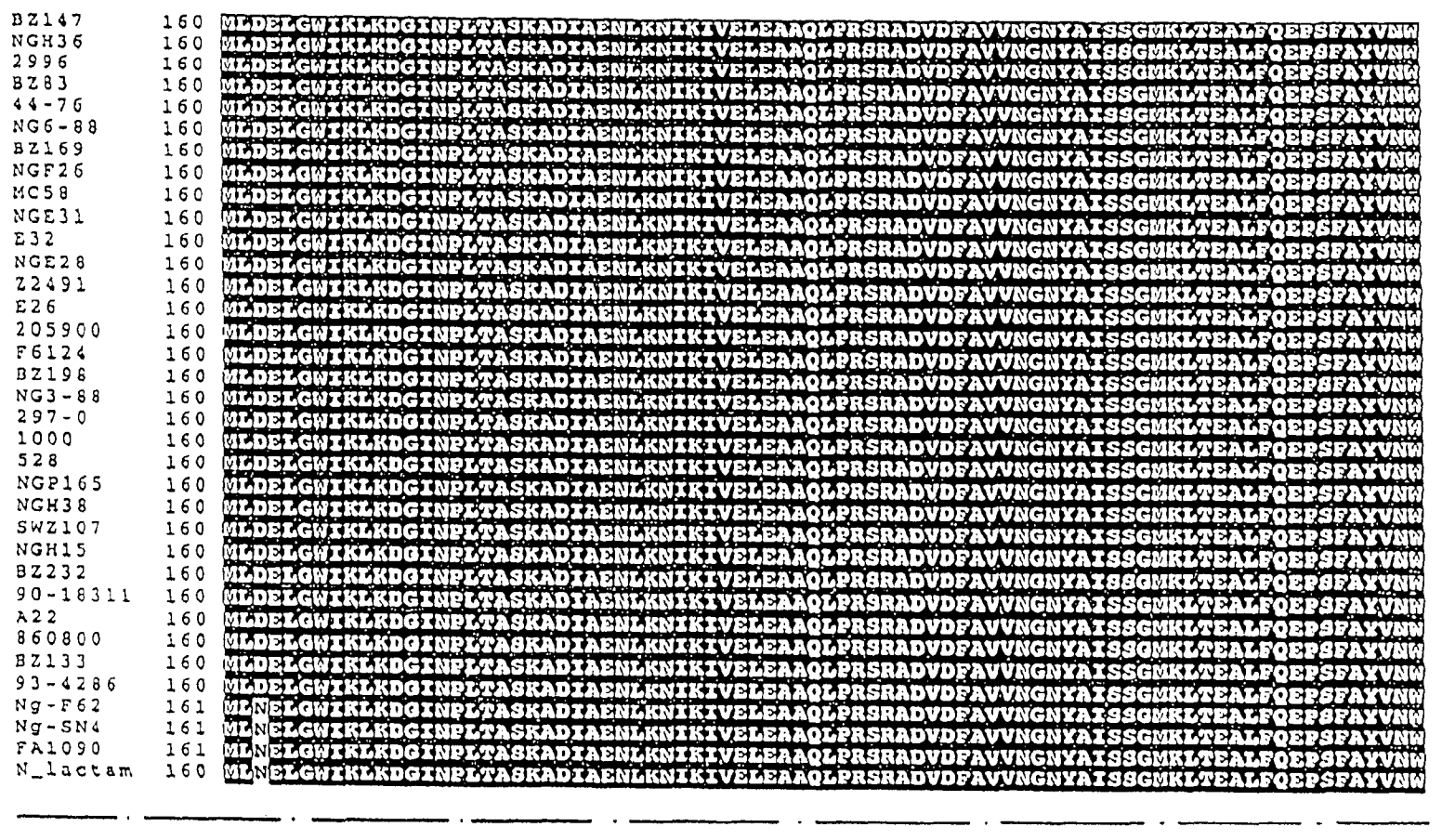
Figure 10B:
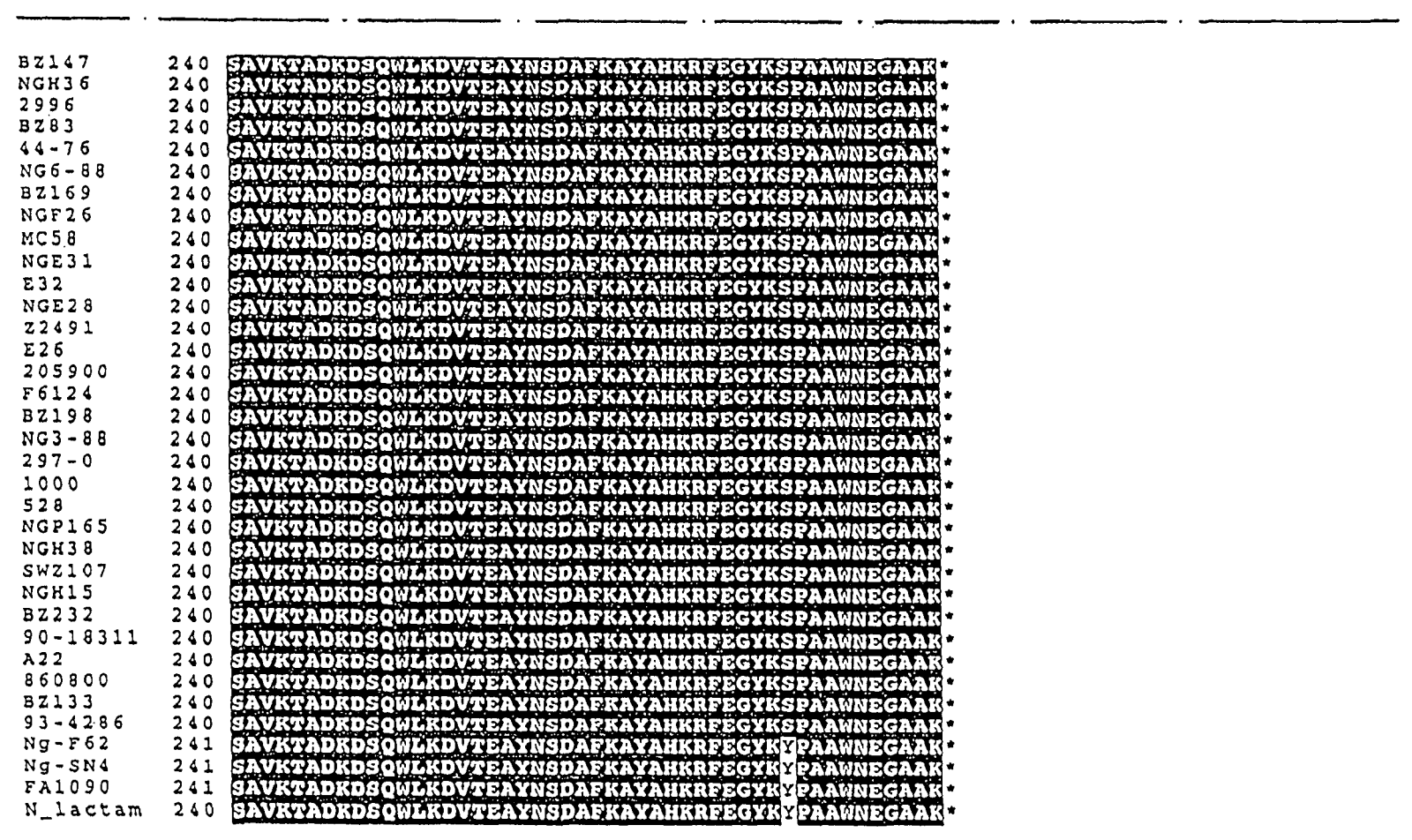

FIGS. 10A-10B to 19 show BOXSHADE-rendered alignments of (10) ORF4 (SEQ ID NOS:22-53) (11) ORF40 (SEQ ID NOS:1-21) (12) ORF46 (SEQ ID NOS:182-187) (13) 225 (SEQ ID NOS: 54-87) (14) 235 (SEQ ID NOS: 88-118) (15) 287 (SEQ ID NOS: 119-124) (16) 519 (SEQ ID NOS: 125-146) (17) 726 (SEQ ID NOS:188-195) (18) 919 (SEQ ID NOS: 147-181) (19) 953 (SEQ ID NOS:196-203).

FIGS. 20A-20E shows Western blots for ORF4, 225, 235, 519 and 919.

EXAMPLES

Example 1

Example 1 of WO99/36544 discloses the cloning and expression of a Neisserial protein referred to as "ORF40". Protein and DNA sequences from serogroup A and B *N. meningitidis* are disclosed, and the complete protein sequences show 83.7% identity over 601 aa overlap.

ORF40 was sequenced for a reference population of 21 strains of *N. meningitidis*:

| Identification number | Strain | Reference |
|---|---|---|
| Group B | | |
| zn02_1 | BZ198 | Seiler et al. (1996) |
| zn03_1 | NG3/88 | Seiler et al. (1996) |
| zn04_1 | 297-0 | Seiler et al. (1996) |
| zn06_1 | BZ147 | Seiler et al. (1996) |
| zn07_1 | BZ169 | Seiler et al. (1996) |
| zn08_1 | 528 | Seiler et al. (1996) |
| zn10_1 | BZ133 | Seiler et al. (1996) |
| zn11_1ass | NGE31 | Seiler et al. (1996) |
| zn14_1 | NGH38 | Seiler et al. (1996) |
| zn16_1 | NGH15 | Seiler et al. (1996) |
| zn18_1 | BZ232 | Seiler et al. (1996) |
| zn19_1 | BZ83 | Seiler et al. (1996) |
| zn20_1 | 44/76 | Seiler et al. (1996) |
| zn21_1 | MC58 | Virji et al. (1992) |
| Group A | | |
| zn22_1 | 205900 | Chiron SpA |
| zn23_1 | F6124 | Chiron SpA |
| z2491_1 | Z2491 | Maiden et al. (1998) |
| Group C | | |
| zn24_1 | 90/18311 | Chiron SpA |
| zn25_1ass | 93/4286 | Chiron SpA |
| Others | | |
| zn28_1ass | 860800 (group Y) | Maiden et al. (1998) |
| zn29_1ass | E32 (group Z) | Maiden et al. (1998) |

An alignment of these 21 sequences is shown in FIGS. 1A-1D. Stretches of conserved amino acids are evident. The first 17 amino acids, for instance, are conserved (MNKIYRIIWNSALNAWV SEQ ID NO:204), although the serine at residue 11 is not present in 100% of *Neisseria*. This is followed by an amino acid which is not conserved, which is in turn followed by a stretch of 16 conserved amino acids (VSELTRNHTKRASATV SEQ ID NO:205). The C-terminal of the protein consists of 116 conserved amino acids.

The conserved regions identified in this example confirm that fragments of the full-length ORF40 protein are suitable as multi-specific vaccines or diagnostic reagents.

ORF40 was re-sequenced for 31 strains in total, and the sequences were aligned. The results are shown in FIGS. 11A-11D.

Conserved regions of particular interest are:

```
                                       (SEQ ID NO: 204)
MNKIYRIIWNSALNAWV (SEQ ID NO: 205)
VSELTRNHTKRASATV (SEQ ID NO: 206)
AVLATLL (SEQ ID NO: 207)
TLKAGDNLKIKQ (SEQ ID NO: 208)
FTYSLKKDLTDLTSV (SEQ ID NO: 209)
TEKLSFGANG (SEQ ID NO: 210)
KVNITSDTKGLNFAKETAGTNGD (SEQ ID NO: 211)
TVHLNGIGSTLTDTL (SEQ ID NO: 212)
RAAS (V/I) KDVLNAGWNIKGVK (SEQ ID NO: 213)
NVDFVRTYDTVEFLSADTKTTTVNVESKDNGKKTEVKIGAKTSVIKEKDG

KLVTGK (SEQ ID NO: 214)
KGENGSSTDEGEGLVTAKEVIDAVNKAGWRMKTTTANGQTGQADKFETVT

SGT (SEQ ID NO: 215)
GTTATVSKDDQGNITV (SEQ ID NO: 216)
YDVNVGDALNVNQLQNSGWNLDSKAVAGSSCKVISGNVSPSKGKMDETVN

INAGNNIEITRNGKNIDIATSM (SEQ ID NO: 217)
PQFSSVSLGAGADAPTLSVD (SEQ ID NO: 218)
NYPVRITNVAPGVKEGDVTNVAQLKGVAQNLNNRIDNVDGNARACIAQAI

ATAGLVQAYLPGKSMMAIGGGTYRGEAGYAIGYSSISDGGNWIIKGTASG

NSRGHFGASASVGYQW.
```

Example 2

Example 26 of WO99/24578 discloses the cloning and expression of a Neisserial protein referred to as "ORF4".

Protein and DNA sequences from serogroup A and B *N. meningitidis* are disclosed, along with sequences from *N. gonorrhoeae*. The identity between the sequences at an amino acid level are:

| | *N. meningitidis* A | *N. gonorrhoeae* |
|---|---|---|
| *N. meningitidis* B | 99.7% over 287 aa | 97.6% over 288 aa |

ORF4 was sequenced for a reference population of 32 strains of *Neisseria*:

| Identification number | Strain | Reference |
|---|---|---|
| | Group B | |
| zv01_4 | NG6/88 | Seiler et al. (1996) |
| zv02_4 | BZ198 | Seiler et al. (1996) |
| zv03_4ass | NG3/88 | Seiler et al. (1996) |
| zv04_4 | 297-0 | Seiler et al. (1996) |
| zv05_4 | 1000 | Seiler et al. (1996) |
| zv06_4 | BZ147 | Seiler et al. (1996) |
| zv07_4 | BZ169 | Seiler et al. (1996) |
| zv08_4 | 528 | Seiler et al. (1996) |
| zv09_4 | NGP165 | Seiler et al. (1996) |
| zv10_4 | BZ133 | Seiler et al. (1996) |
| zv11_4 | NGE31 | Seiler et al. (1996) |
| zv12_4ass | NGF26 | Seiler et al. (1996) |
| zv13_4 | NGE28 | Seiler et al. (1996) |
| zv15_4 | SWZ107 | Seiler et al. (1996) |
| zv16_4 | NGH15 | Seiler et al. (1996) |
| zv17_4 | NGH36 | Seiler et al. (1996) |
| zv18_4 | BZ232 | Seiler et al. (1996) |
| zv19_4 | BZ83 | Seiler et al. (1996) |
| zv20_4 | 44/76 | Seiler et al. (1996) |
| zv21_4 | MC58 | Virji et al. (1992) |
| zv96_4 | 2996 | Chiron SpA |
| | Group A | |
| zv22_4 | 205900 | Chiron SpA |
| z2491_4 | Z2491 | Maiden et al., 1998 |
| | Group C | |
| zv24_4 | 90/18311 | Chiron SpA |
| zv25_4 | 93/4286 | Chiron SpA |
| | Others | |
| zv26_4ass | A22 (group W) | Maiden et al. (1998) |
| zv27_4 | E26 (group X) | Maiden et al. (1998) |
| zv28_4 | 860800 (group Y) | Maiden et al. (1998) |
| zv29_4 | E32 (group Z) | Maiden et al. (1998) |
| | *N. gonorrhoeae* | |
| zv32_4 | Ng F62 | Maiden et al. (1998) |
| zv33_4 | Ng SN4 | R. Moxon |
| fa1090_4 | FA1090 | Dempsey et al. (1991) |

An alignment of the sequences generated using PILEUP is shown in FIGS. 2A-2C. Stretches of conserved amino acids are evident. The first 34 amino acids, for instance, are conserved, although the serine at residue 26 is not present in 100% of *Neisseria*. The C-terminal of the protein consists of 228 conserved amino acids.

The conserved regions identified in this example confirm that fragments of the full-length ORF4 protein are suitable as multi-specific vaccines or diagnostic reagents.

ORF4 was re-sequenced for 35 strains in total, and the sequences were aligned. The results are shown in FIGS. 10A-10B.

Conserved regions of particular interest are:

```
                                    (SEQ ID NO: 219)
MKTFFKTLSAAALALILAACGGQKDSAPAASASAAADNGA (SEQ ID NO: 220)
KKEIVFGTTVGDFGDMVKE (SEQ ID NO: 221)
ELEKKGYTVKLVEFTDYVRPNLALAEGELDINVFQHKPYLDDFKKEHNLD

ITEVFQVPTAPLGLYPGKLKSLEEVKDGSTVSAPNDPSNFARVLVNLDEL

GWTKLKDGINPLTASKADIAENLKNIKIVELEAAQLPRSRADVDFAVVNG

NYAISSGMKLTEALFQEPSFAYVNWSAVKTADKDSQWLKDVTEAYNSDAF

KAYAHKRFEGYKSPAAWNEGAAK
```

Example 3

Example 16 of WO99/57280 discloses the cloning and expression of a Neisserial protein referred to as "225". Protein and DNA sequences from serogroup A and B *N. meningitidis* are disclosed, along with sequences from *N. gonorrhoeae.*

225 has now been sequenced for a reference population of 34 strains of *Neisseria*:

| Identification number | Strain | Source reference |
|---|---|---|
| | Group B | |
| zo01_225 | NG6/88 | Seiler et al., 1996 |
| zo02_225 | BZ198 | Seiler et al., 1996 |
| zo03_225 | NG3/88 | Seiler et al., 1996 |
| zo04_225 | 297-0 | Seiler et al., 1996 |
| zo05_225 | 1000 | Seiler et al., 1996 |
| zo06_225 | BZ147 | Seiler et al., 1996 |
| zo07_225 | BZ169 | Seiler et al., 1996 |
| zo08_225 | 528 | Seiler et al., 1996 |
| zo09_225 | NGP165 | Seiler et al., 1996 |
| zo10_225 | BZ133 | Seiler et al., 1996 |
| zo11_225 | NGE31 | Seiler et al., 1996 |
| zo12_225 | NGF26 | Seiler et al., 1996 |
| zo13_225 | NGE28 | Seiler et al., 1996 |
| zo14_225 | NGH38 | Seiler et al., 1996 |
| zo15_225 | SWZ107 | Seiler et al., 1996 |
| zo16_225 | NGH15 | Seiler et al., 1996 |
| zo17_225 | NGH36 | Seiler et al., 1996 |
| zo18_225 | BZ232 | Seiler et al., 1996 |
| zo19_225 | BZ83 | Seiler et al., 1996 |
| zo20_225 | 44/76 | Seiler et al., 1996 |
| zo21_225 | MC58 | Chiron SpA |
| zo96_225 | 2996 | Chiron SpA |
| | Group A | |
| zo22_225 | 205900 | Chiron SpA |
| zo23_225 | F6124 | Chiron SpA |
| z2491 | Z2491 | Maiden et al., 1998 |
| | Group C | |
| zo24_225 | 90/18311 | Chiron SpA |
| zo25_225 | 93/4286 | Chiron SpA |
| | Others | |
| zo26_225 | A22 (group W) | Maiden et al., 1998 |
| zo27_225 | E26 (group X) | Maiden et al., 1998 |
| zo28_225 | 860800 (group Y) | Maiden et al., 1998 |
| zo29_225 | E32 (group Z) | Maiden et al., 1998 |
| | *Gonococcus* | |
| zo32_225 | Ng F62 | Maiden et al., 1998 |
| zo33_225 | Ng SN4 | Chiron SpA |
| fa1090 | FA1090 | Chiron SpA |

An alignment of the sequences generated using PILEUP is shown in FIGS. 3A-3C. Stretches of conserved amino acids are evident. The first 74 amino acids, for instance, are conserved, although the isoleucine at residue 51 is not present in 100% of *Neisseria*. The C-terminal of the protein consists of 148 conserved amino acids. A similar alignment is shown in FIGS. 13A-13B.

The conserved regions identified in this example confirm that fragments of the full-length 225 protein are suitable as multi-specific vaccines or diagnostic reagents.

Example 4

Example 16 of WO99/57280 discloses the cloning and expression of a Neisserial protein referred to as "235". Protein and DNA sequences from serogroup A and B *N. meningitidis* are disclosed, along with sequences from *N. gonorrhoeae*.

235 has now been sequenced for a reference population of 31 strains of *Neisseria*:

| Identification number | Strain | Reference |
|---|---|---|
| Group B | | |
| gnmzq01 | NG6/88 | Seiler et al., 1996 |
| gnmzq02 | BZ198 | Seiler et al., 1996 |
| gnmzq03 | NG3/88 | Seiler et al., 1996 |
| gnmzq04 | 1000 | Seiler et al., 1996 |
| gnmzq05 | 1000 | Seiler et al., 1996 |
| gnmzq07 | BZ169 | Seiler et al., 1996 |
| gnmzq08 | 528 | Seiler et al., 1996 |
| gnmzq09 | NGP165 | Seiler et al., 1996 |
| gnmzq10 | BZ133 | Seiler et al., 1996 |
| gnmzq11 | NGE31 | Seiler et al., 1996 |
| gnmzq13 | NGE28 | Seiler et al., 1996 |
| gnmzq14 | NGH38 | Seiler et al., 1996 |
| gnmzq15 | SWZ107 | Seiler et al., 1996 |
| gnmzq16 | NGH15 | Seiler et al., 1996 |
| gnmzq17 | NGH36 | Seiler et al., 1996 |
| gnmzq18 | BZ232 | Seiler et al., 1996 |
| gnmzq19 | BZ83 | Seiler et al., 1996 |
| gnmzq21 | MC58 | Virji et al., 1992 |
| Group A | | |
| gnmzq22 | 205900 | Chiron SpA |
| gnmzq23 | F6124 | Chiron SpA |
| z2491 | Z2491 | Maiden et al., 1998 |
| Group C | | |
| gnmzq24 | 90/18311 | Chiron SpA |
| gnmzq25 | 93/4286 | Chiron SpA |
| Others | | |
| gnmzq26 | A22 (group W) | Maiden et al., 1998 |
| gnmzq27 | E26 (group X) | Maiden et al., 1998 |
| gnmzq28 | 860800 (group Y) | Maiden et al., 1998 |
| gnmzq29 | E32 (group Z) | Maiden et al., 1998 |
| gnmzq31 | *N. lactamica* | Chiron SpA |
| Gonococcus | | |
| gnmzq32 | Ng F62 | Maiden et al., 1998 |
| gnmzq33 | Ng SN4 | Chiron SpA |
| fa1090 | FA1090 | Dempsey et al. 1991 |

Figure 4A:
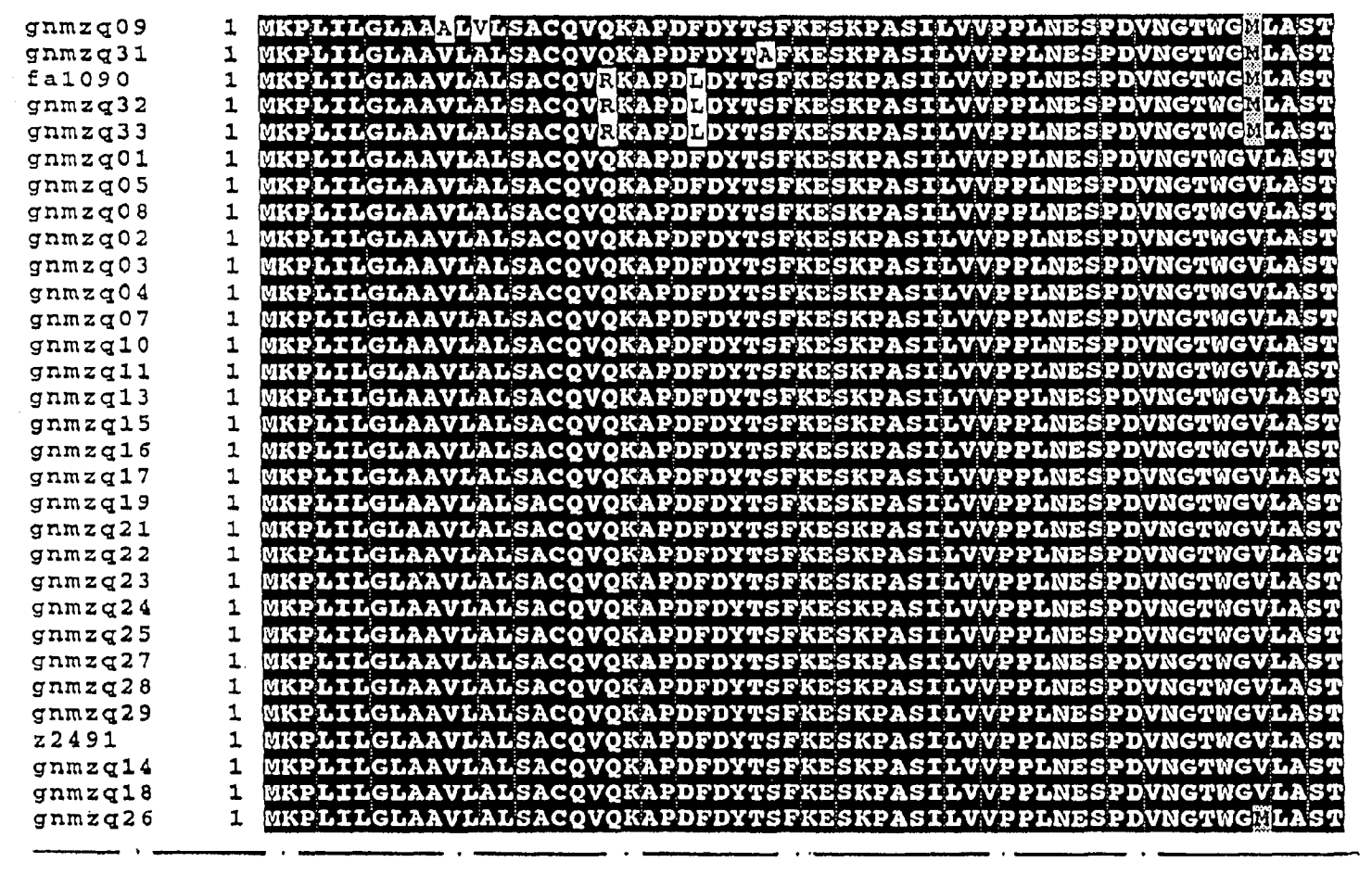
Figure 4B:
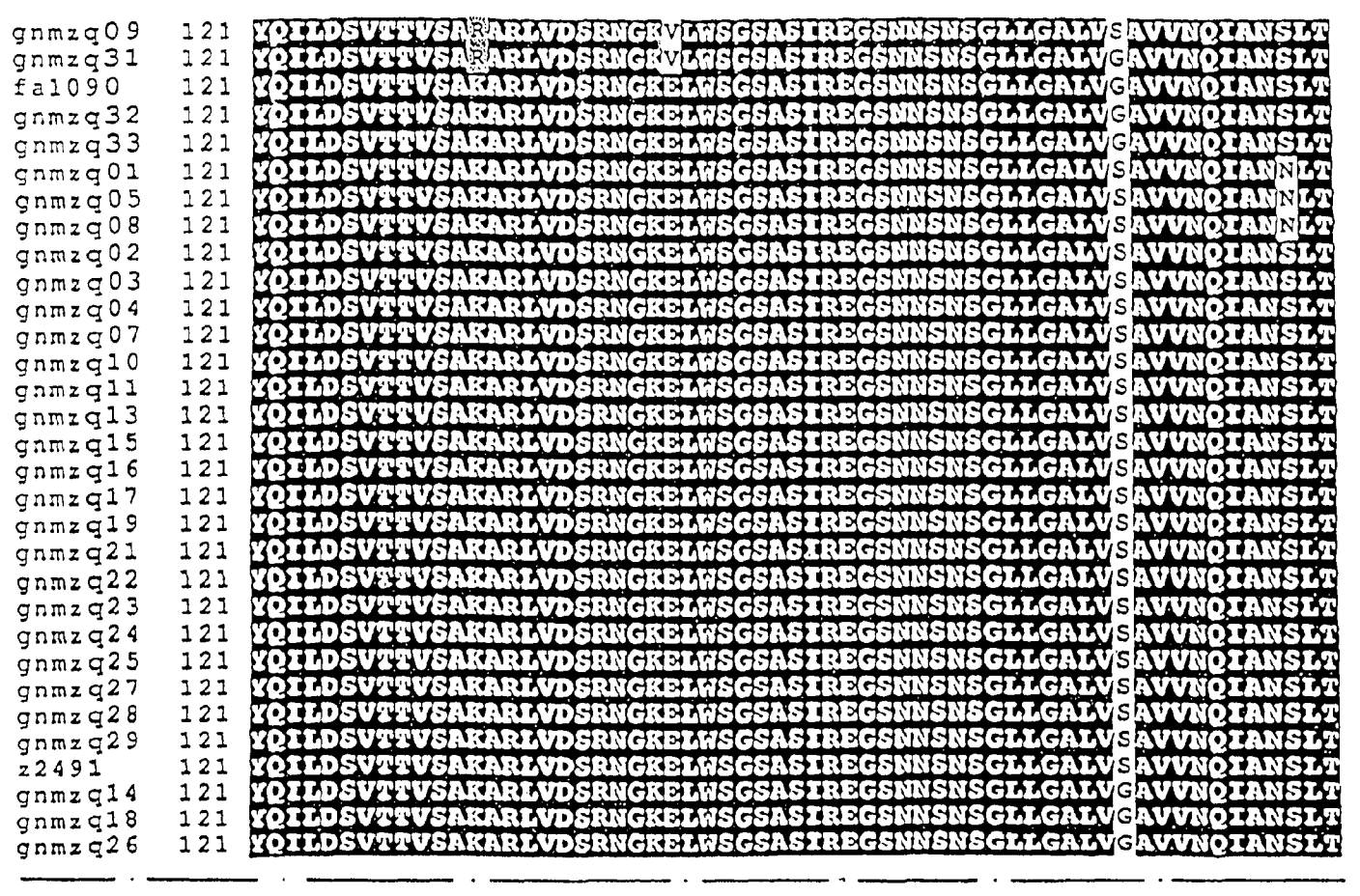
Figure 4B:
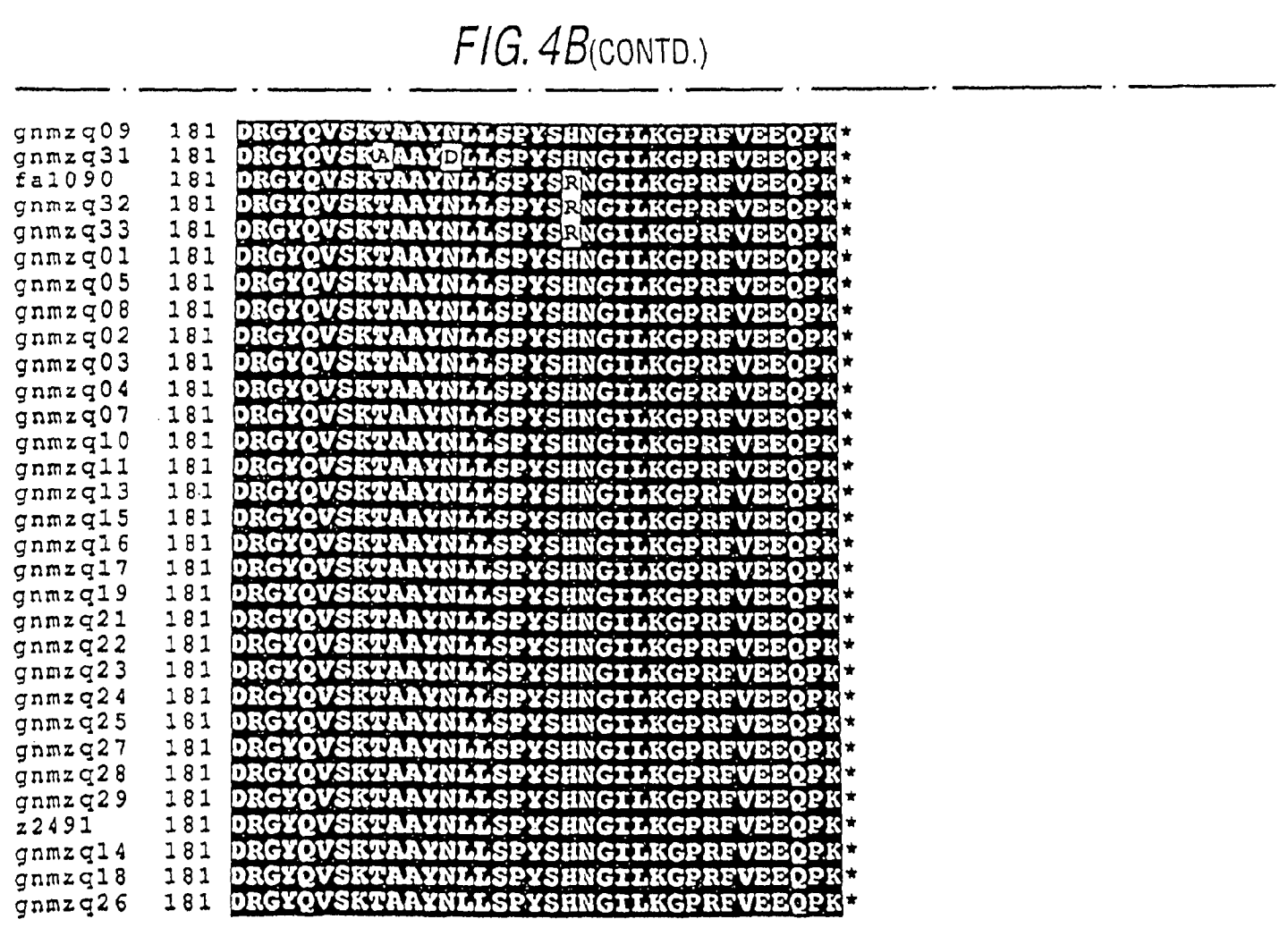

An alignment of the sequences generated using PILEUP is shown in FIGS. 4A-4B. Stretches of conserved amino acids are evident. The protein is wholly conserved, although the serine at residue 168 shows some variance.

Figure 14A:
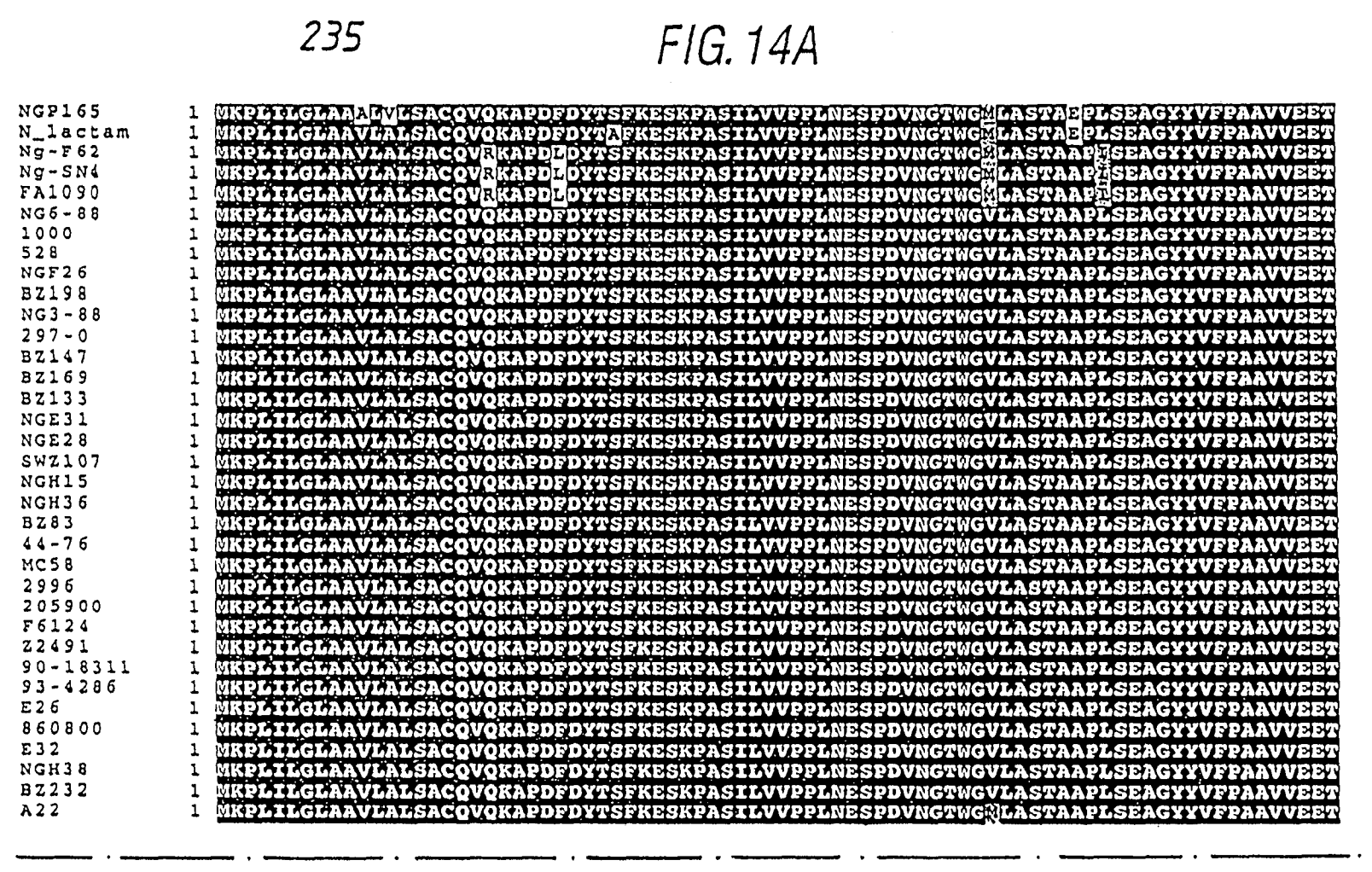
Figure 14A:
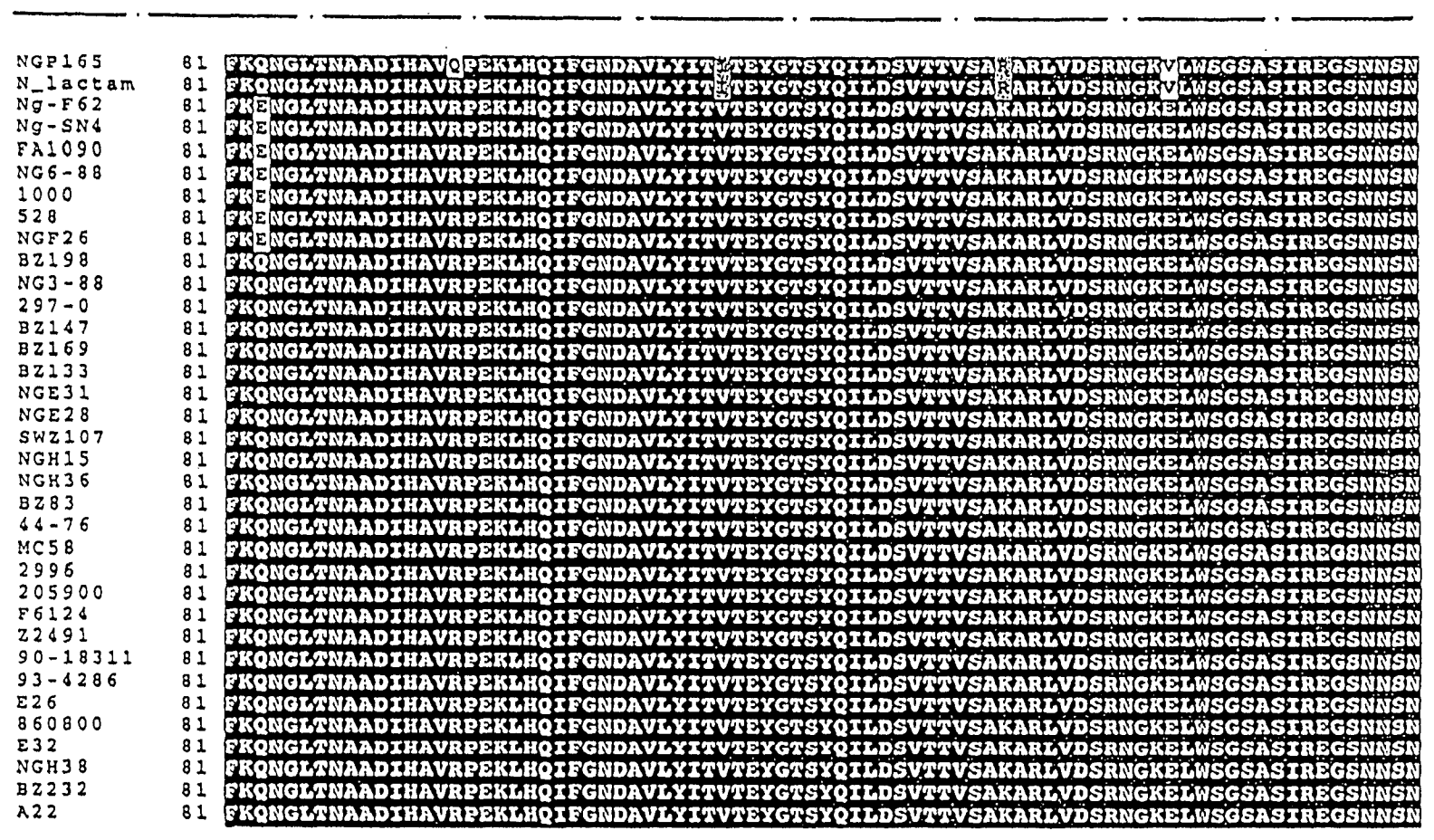
Figure 14B:
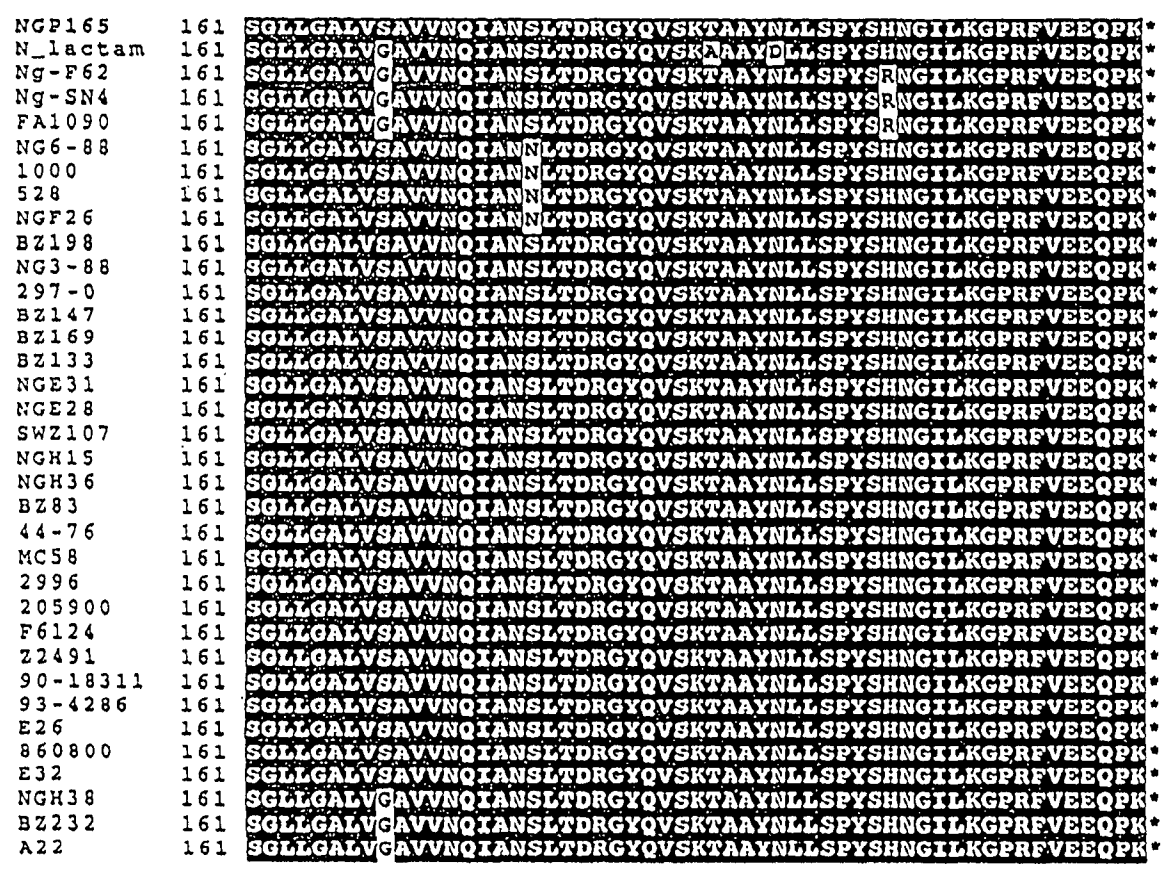

235 was re-sequenced for 35 strains in total, and the sequences were aligned. The results are shown in FIGS. 14A-14B.

Example 5

Example 16 of WO99/57280 discloses the cloning and expression of a Neisserial protein referred to as "287". Protein and DNA sequences from serogroup A and B *N. meningitidis* are disclosed, along with sequences from *N. gonorrhoeae*.

287 has now been sequenced for a reference population of 6 strains of *Neisseria*:

| Identification number | Strain | Reference |
|---|---|---|
| Group B | | |
| 287_2 | BZ198 | Seiler et al. (1996) |
| 287_9 | NGP165 | Seiler et al. (1996) |
| 287_14 | NGH38 | Seiler et al. (1996) |
| 287_21 | MC58 | Virji et al. (1992) |
| Group A | | |
| z2491 | Z2491 | Maiden et al. (1998) |
| Gonococcus | | |
| fa1090 | FA1090 | Dempsey et al. (1991) |

Figure 5:
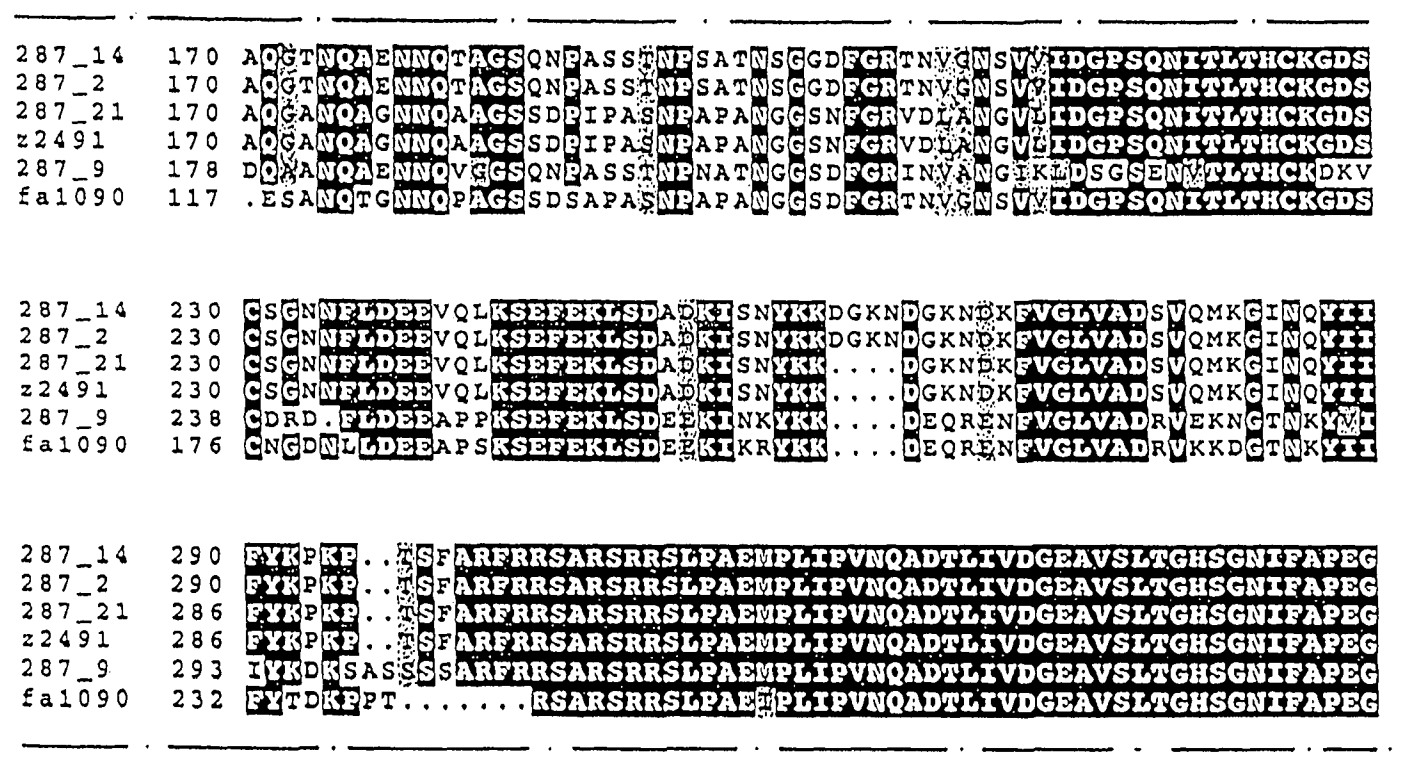
Figure 5:
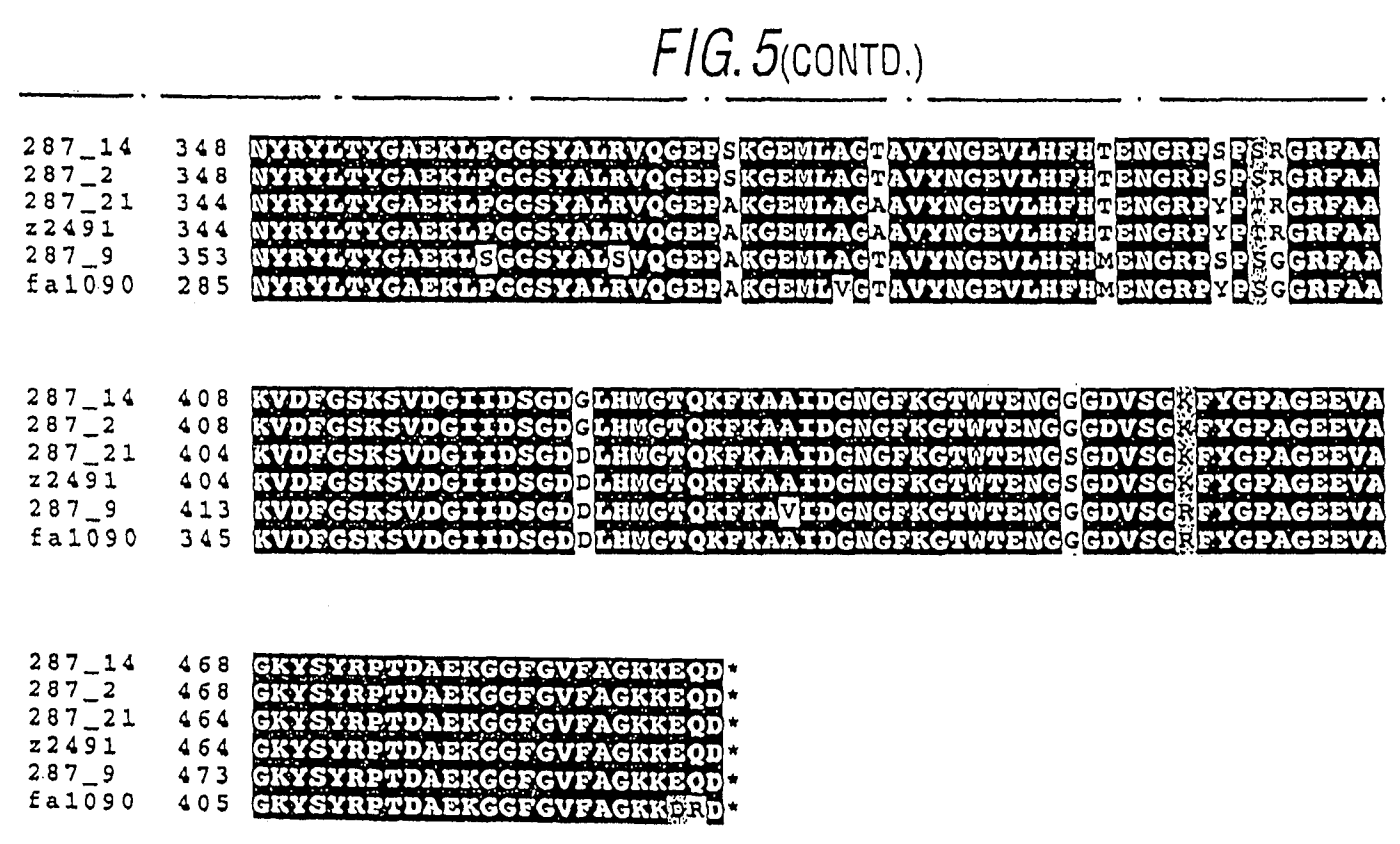

An alignment of the sequences generated using PILEUP is shown in FIG. 5. Stretches of conserved amino acids are evident. The first 42 amino acids, for instance, are well conserved and a long conserved region can be seen at the C-terminus.

The conserved regions identified in this example confirm that fragments of the full-length 287 protein are suitable as multi-specific vaccines or diagnostic reagents.

287 was re-sequenced for 35 strains in total (including C1 1, a serogroup C *N. meningitidis* strain), and the sequences were aligned. The results are shown in FIGS. 15A-15E.

Conserved regions of particular interest are:

```
                                           (SEQ ID NO: 222)
MFKRSVIAMACI (SEQ ID NO: 223)
ALSACGGGGGGSPDVKSADT (SEQ ID NO: 224)
SKPAAPVV (SEQ ID NO: 225)
QDMAAVS (SEQ ID NO: 226)
ENTGNGGAATTD (SEQ ID NO: 254)
QNDMPQ (SEQ ID NO: 227)
DGPSQNITLTHCK (SEQ ID NO: 255)
KSEFE (SEQ ID NO: 228)
RRSARSRRSLPAEMPLIPVNQADTLIVDGEAVSLTGHSGNIFAPEGNYRY
LTYCAEKL (SEQ ID NO: 256)
GGSYAL (SEQ ID NO: 229)
VQGEPAKGENLAGTAVYNGEVLHFH (SEQ ID NO: 230)
GRFAAKVDFGSKSVDGIIDSGDDLHMG
```

-continued (SEQ ID NO: 231)
QKFKAAIDGNGFKGTWTENGGGDVSG (R/K) FYGPAGEEVAGKYSYRP

TDAEKGGFGVFAGKKDRD

Example 6

Example 16 of WO99/57280 discloses the cloning and expression of a Neisserial protein referred to as "519". Protein and DNA sequences from serogroup A and B *N. meningitidis* are disclosed, along with sequences from *N. gonorrhoeae*.

519 has now been sequenced for a reference population of 22 strains of *Neisseria*:

| Identification number | Strain | Source |
|---|---|---|
| Group B | | |
| zv01_519 | NG6/88 | Seiler et al., 1996 |
| zv02_519 | BZ198 | Seiler et al., 1996 |
| zv03_519ass | NG3/88 | Seiler et al., 1996 |
| zv04_519 | 297-0 | Seiler et al., 1996 |
| zv05_519 | 1000 | Seiler et al., 1996 |
| zv06_519ass | BZ147 | Seiler et al., 1996 |
| zv07_519 | BZ169 | Seiler et al., 1996 |
| zv11_519 | NGE31 | Seiler et al., 1996 |
| zv12_519 | NGF26 | Seiler et al., 1996 |
| zv18_519 | BZ232 | Seiler et al., 1996 |
| zv19_519 | BZ83 | Seiler et al., 1996 |
| zv20_519ass | 44/76 | Seiler et al., 1996 |
| zv21_519ass | MC58 | Chiron SpA |
| zv96_519 | 2996 | Chiron SpA |
| Group A | | |
| zv22_519ass | 205900 | Chiron SpA |
| z2491_519 | Z2491 | Maiden et al., 1998 |
| Others | | |
| zv26_519 | A22 (group W) | Maiden et al., 1998 |
| zv27_519 | E26 (group X) | Maiden et al., 1998 |
| zv28_519 | 860800 (group Y) | Maiden et al., 1998 |
| zv29_519ass | E32 (group Z) | Maiden et al., 1998 |
| Gonococcus | | |
| zv32_519 | Ng F62 | Maiden et al., 1998 |
| fa1090_519 | FA1090 | Chiron SpA |

Figure 6A:
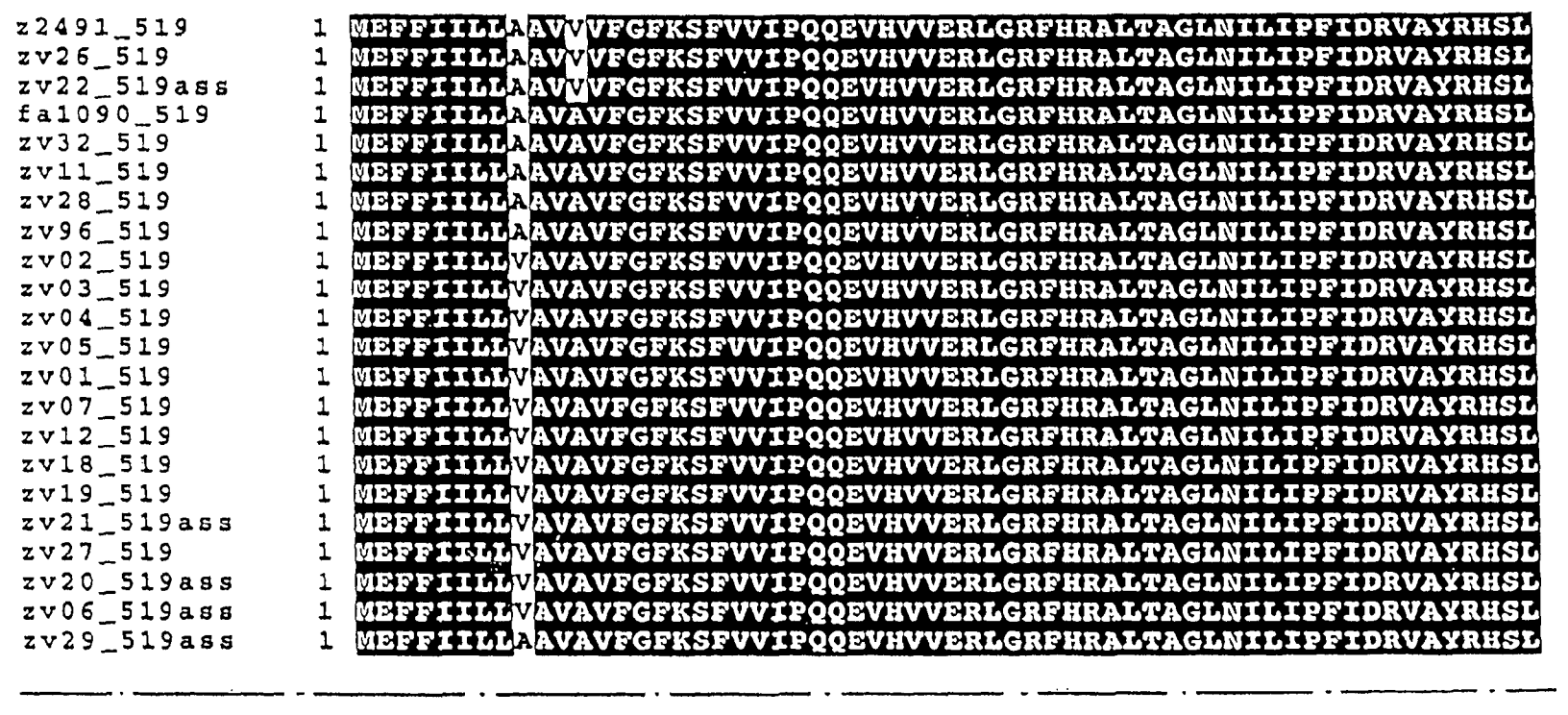
Figure 6A:
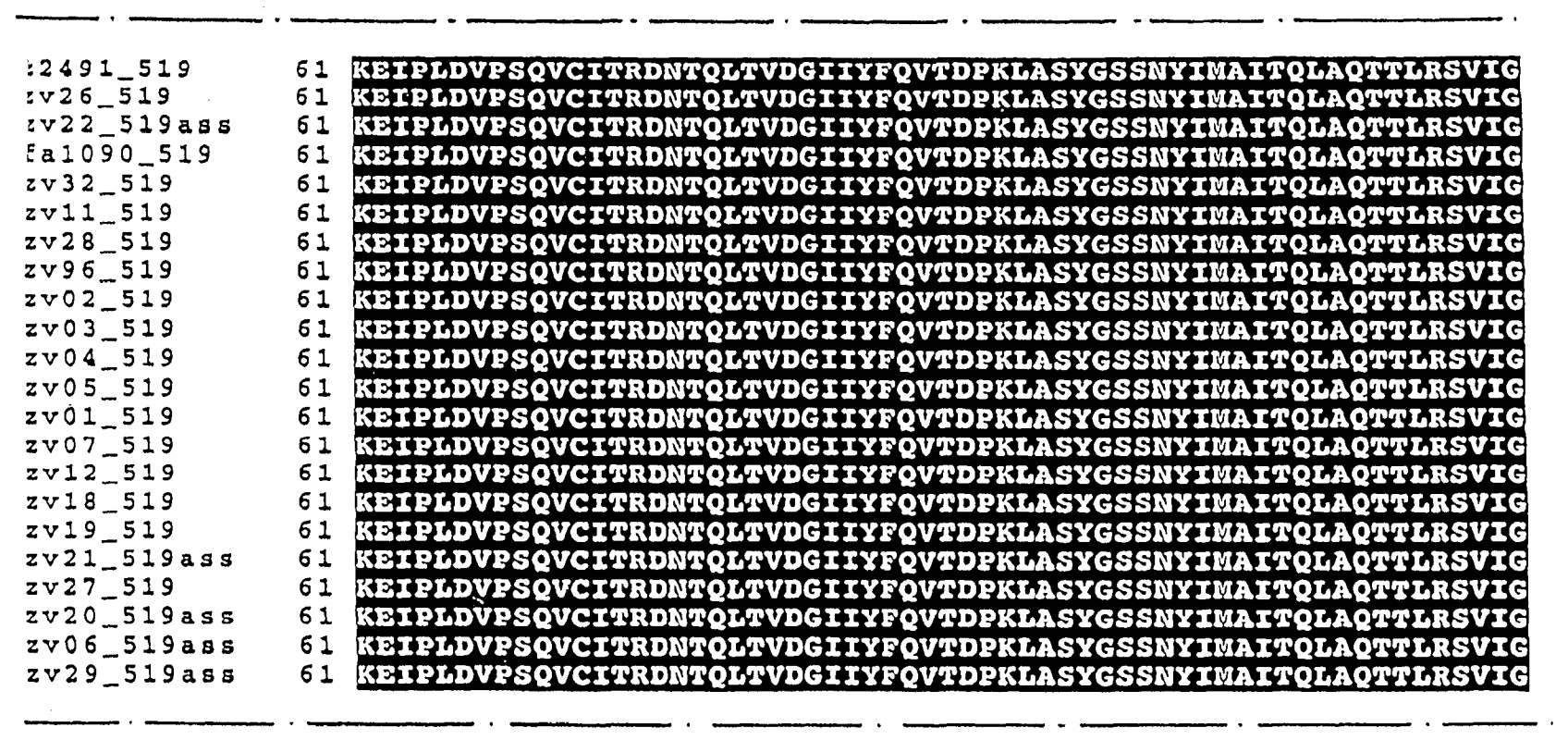
Figure 6A:
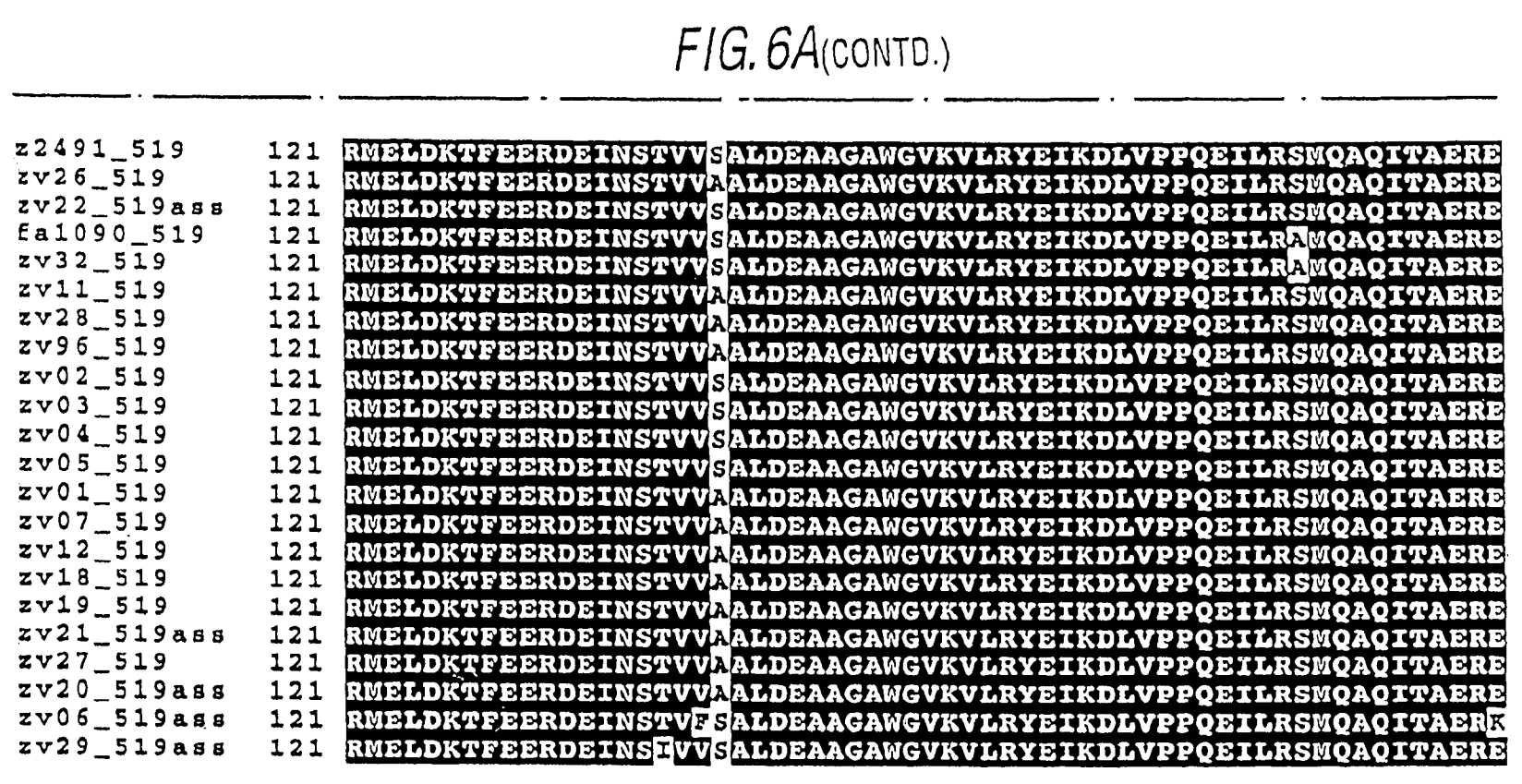
Figure 6B:
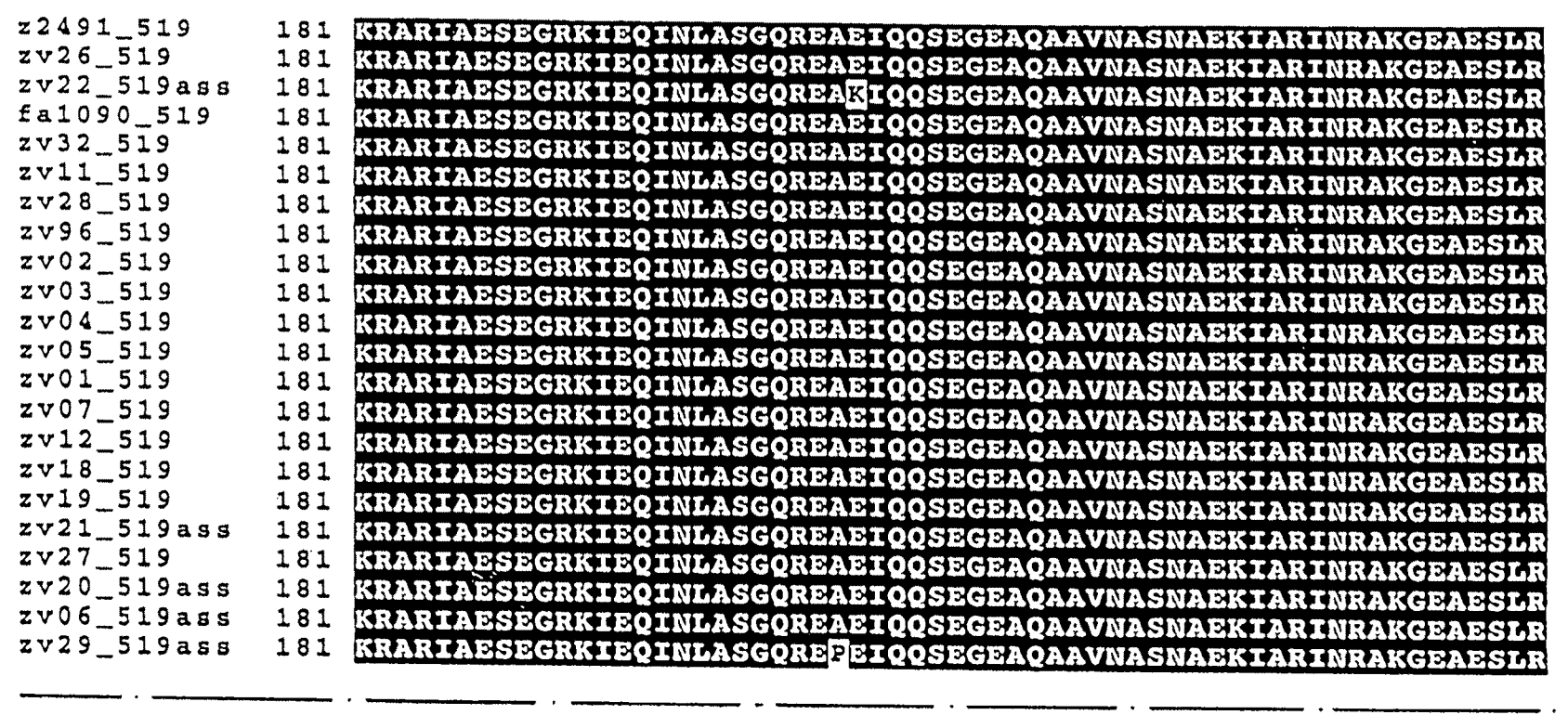

An alignment of the sequences generated using PILEUP is shown in FIGS. 6A-6B. Stretches of conserved amino acids are evident, and the protein shows conservation along its complete length.

Figure 16A:
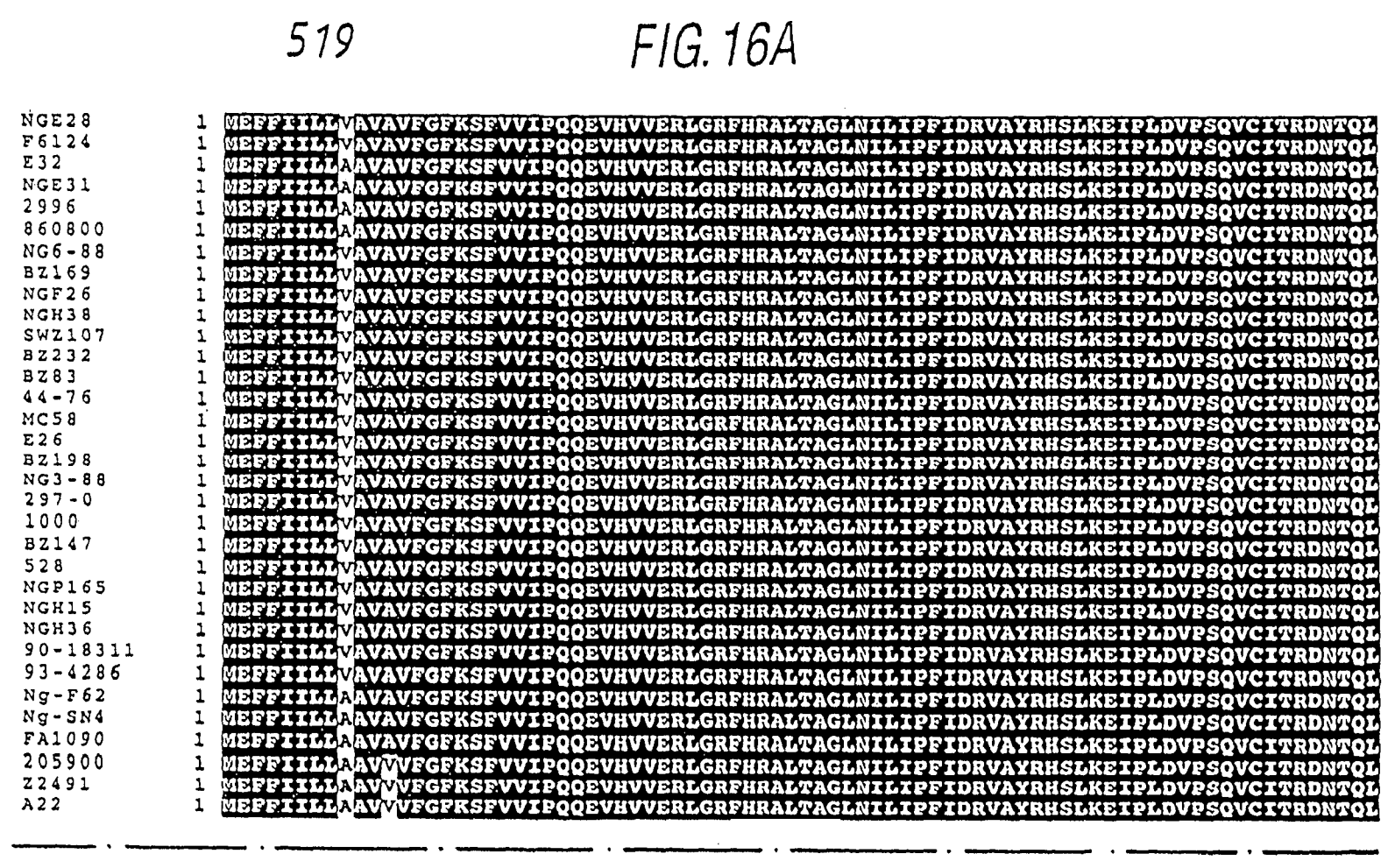
Figure 16A:
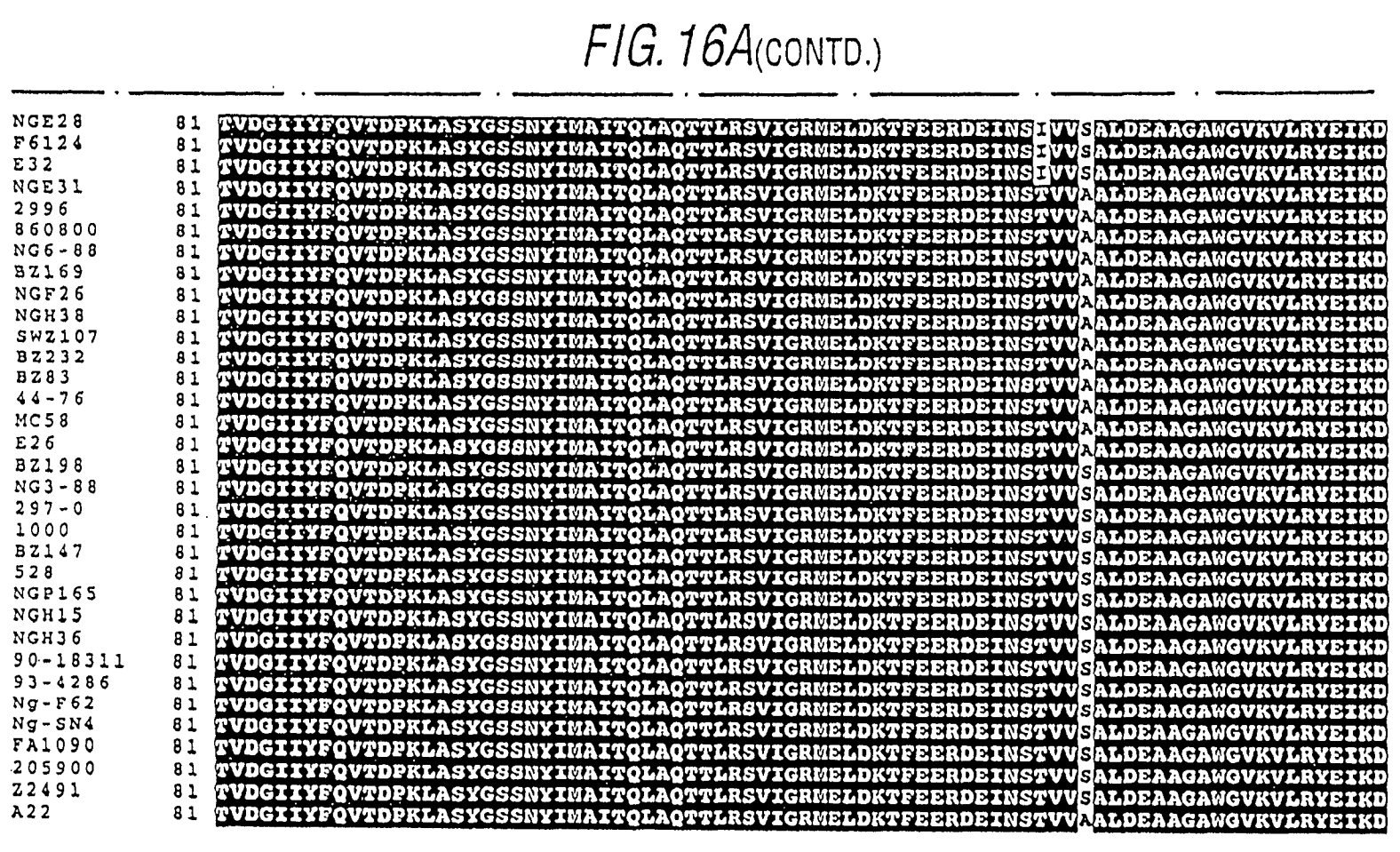
Figure 16B:
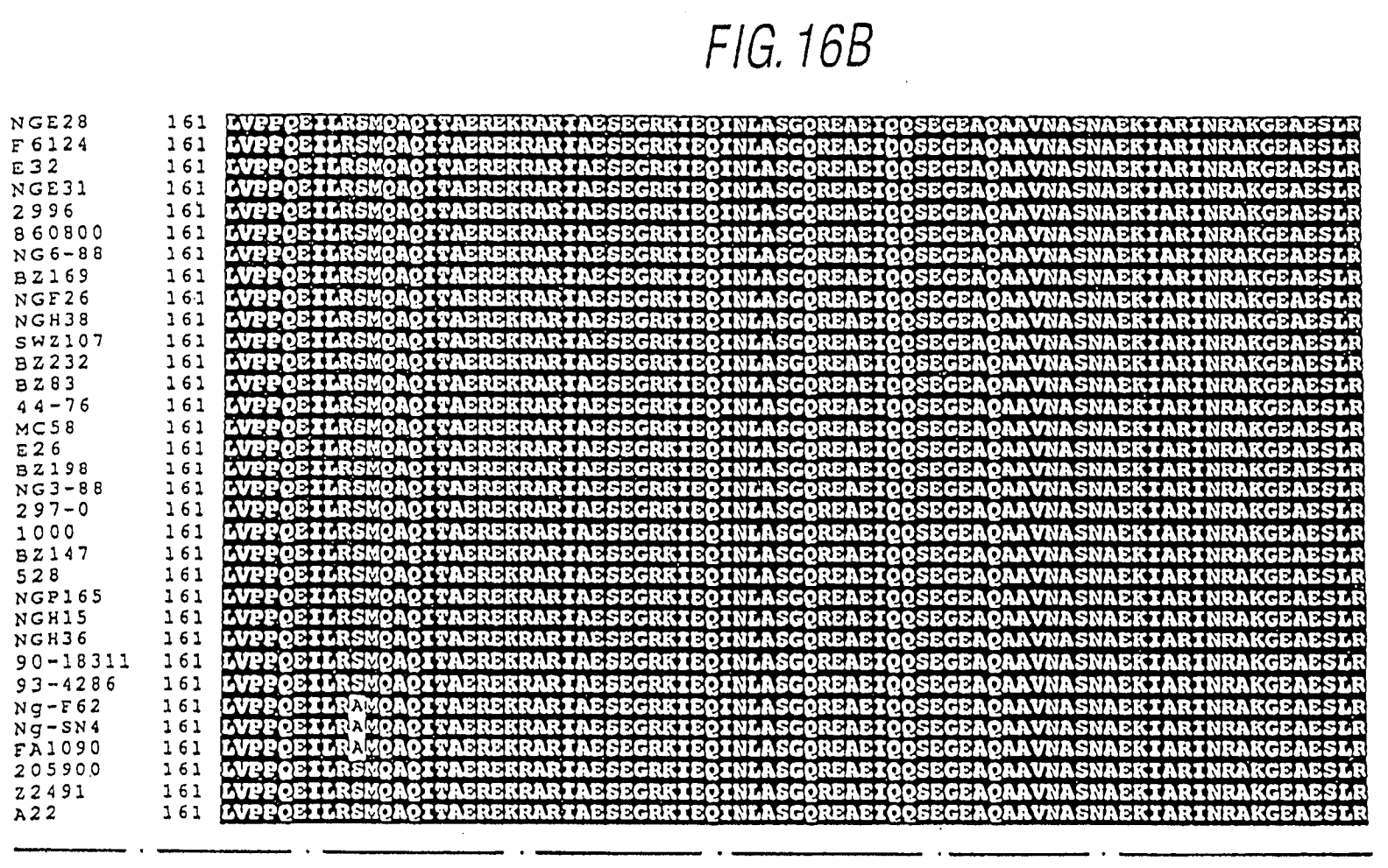
Figure 16B:
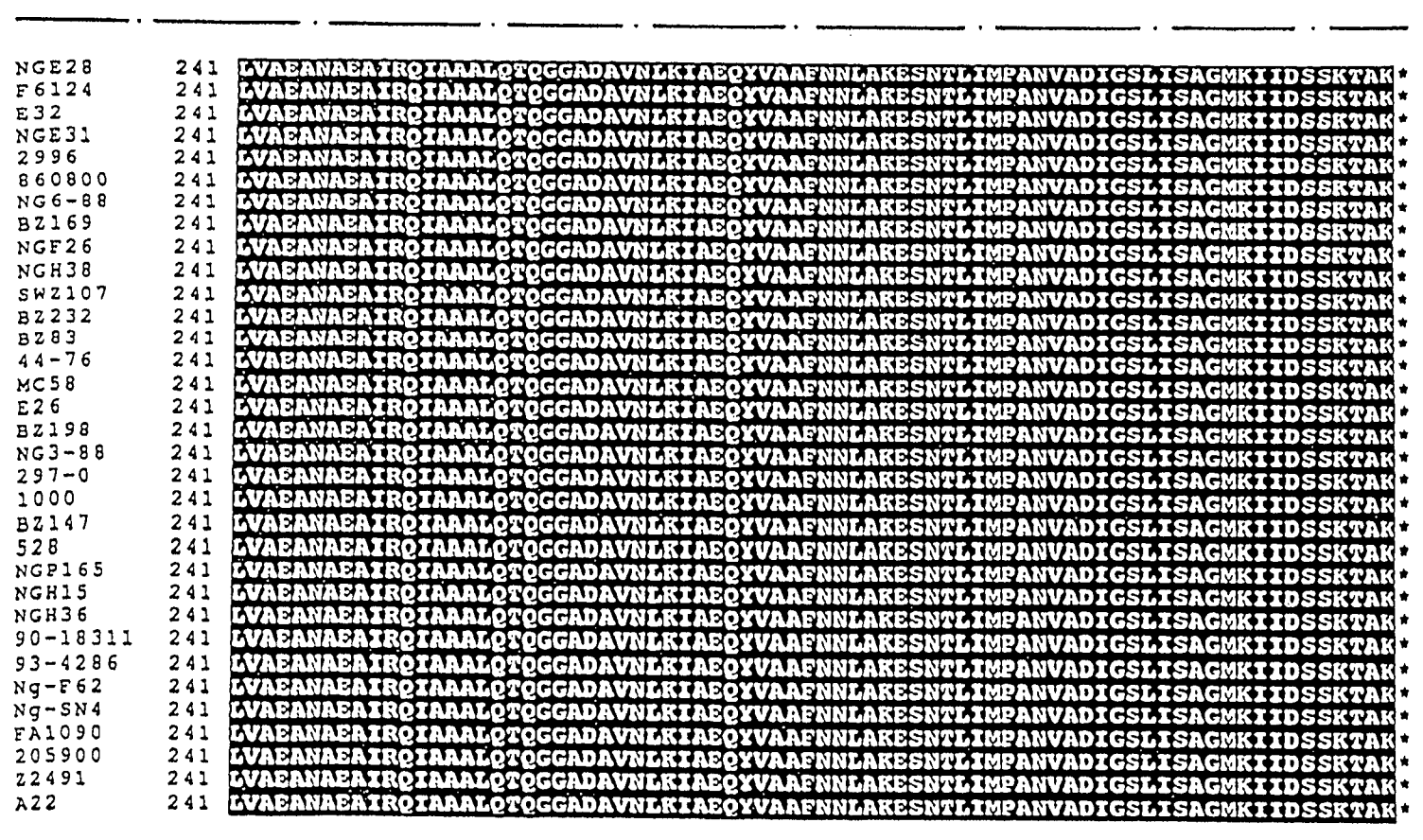

519 was re-sequenced for 33 strains in total, and the sequences were aligned. The results are shown in FIGS. 16A-16B.

The conserved regions identified in this example confirm that fragments of the full-length 519 protein are suitable as multi-specific vaccines or diagnostic reagents.

519 was re-sequenced for 33 strains in total, and the sequences were aligned. The results are shown in FIG. 16.

Conserved regions of particular interest are:

(SEQ ID NO: 232)
MEFFIILL (SEQ ID NO: 233)
AVAVFGPKSFVVIPQQEVHVVERLGRFHRALTAGLNILIPFIDRVAYRHS

LKEIPLDVPSQVCITRDNTQLTVDGIIYFQVTDPKLASYGSSNYIMAITQ

LAQTTLRSVIGRMELDKTFEERDEINSTVV (SEQ ID NO: 234)
ALDEAAGAWGVKVLRYEIKDLVPPQETLRSMQAQITAEREKRARIAESEG

RKIEQINLASGQREAEIQQSEGEAQAAVNASNAEKIARINRAKGEAESLR

LVAEANAEANRQIAAALQTQSGADAVNLKIAGQYVTAFKNLAKEDNTRIK

PAKVAEIGNPNFRRHEKFSPEAKTAK

Example 7

Example 16 of WO99/57280 discloses the cloning and expression of a Neisserial protein referred to as "919". Protein and DNA sequences from serogroup A and B *N. meningitidis* are disclosed, along with sequences from *N. gonorrhoeae*.

919 has now been sequenced for a reference population of 35 strains of *Neisseria*:

| Identification number | Strains | Source |
|---|---|---|
| Group B | | |
| zm01 | NG6/88 | Seiler et al., 1996 |
| zm02 | BZ198 | Seiler et al., 1996 |
| zm03 | NG3/88 | Seiler et al., 1996 |
| zm04 | 297-0 | Seiler et al., 1996 |
| zm05 | 1000 | Seiler et al., 1996 |
| zm06 | BZ147 | Seiler et al., 1996 |
| zm07 | BZ169 | Seiler et al., 1996 |
| zm08n | 528 | Seiler et al., 1996 |
| zm09 | NGP165 | Seiler et al., 1996 |
| zm10 | BZ133 | Seiler et al., 1996 |
| zm11asbc | NGE31 | Seiler et al., 1996 |
| zm12 | NGF26 | Seiler et al., 1996 |
| zm13 | NGE28 | Seiler et al., 1996 |
| zm14 | NGH38 | Seiler et al., 1996 |
| zm15 | SWZ107 | Seiler et al., 1996 |
| zm16 | NGH15 | Seiler et al., 1996 |
| zm17 | NGH36 | Seiler et al., 1996 |
| zm18 | BZ232 | Seiler et al., 1996 |
| zm19 | BZ83 | Seiler et al., 1996 |
| zm20 | 44/76 | Seiler et al., 1996 |
| zm21 | MC58 | Chiron SpA |
| zm96 | 2996 | Chiron SpA |
| Group A | | |
| zm22 | 205900 | Chiron SpA |
| zm23asbc | F6124 | Chiron SpA |
| z2491 | Z2491 | Maiden et al., 1998 |
| Group C | | |
| zm24 | 90/18311 | Chiron SpA |
| zm25 | 93/4286 | Chiron SpA |
| Others | | |
| zm26 | A22 (group W) | Maiden et al., 1998 |
| zm27bc | E26 (group X) | Maiden et al., 1998 |
| zm28 | 860800 (group Y) | Maiden et al., 1998 |
| zm29asbc | E32 (group Z) | Maiden et al., 1998 |
| zm31asbc | *N. lactamica* | Chiron SpA |
| Gonococcus | | |
| zm32asbc | Ng F62 | Maiden et al., 1998 |
| zm33asbc | Ng SN4 | Chiron SpA |
| fa1090 | FA1090 | Chiron SpA |

Figure 18A:
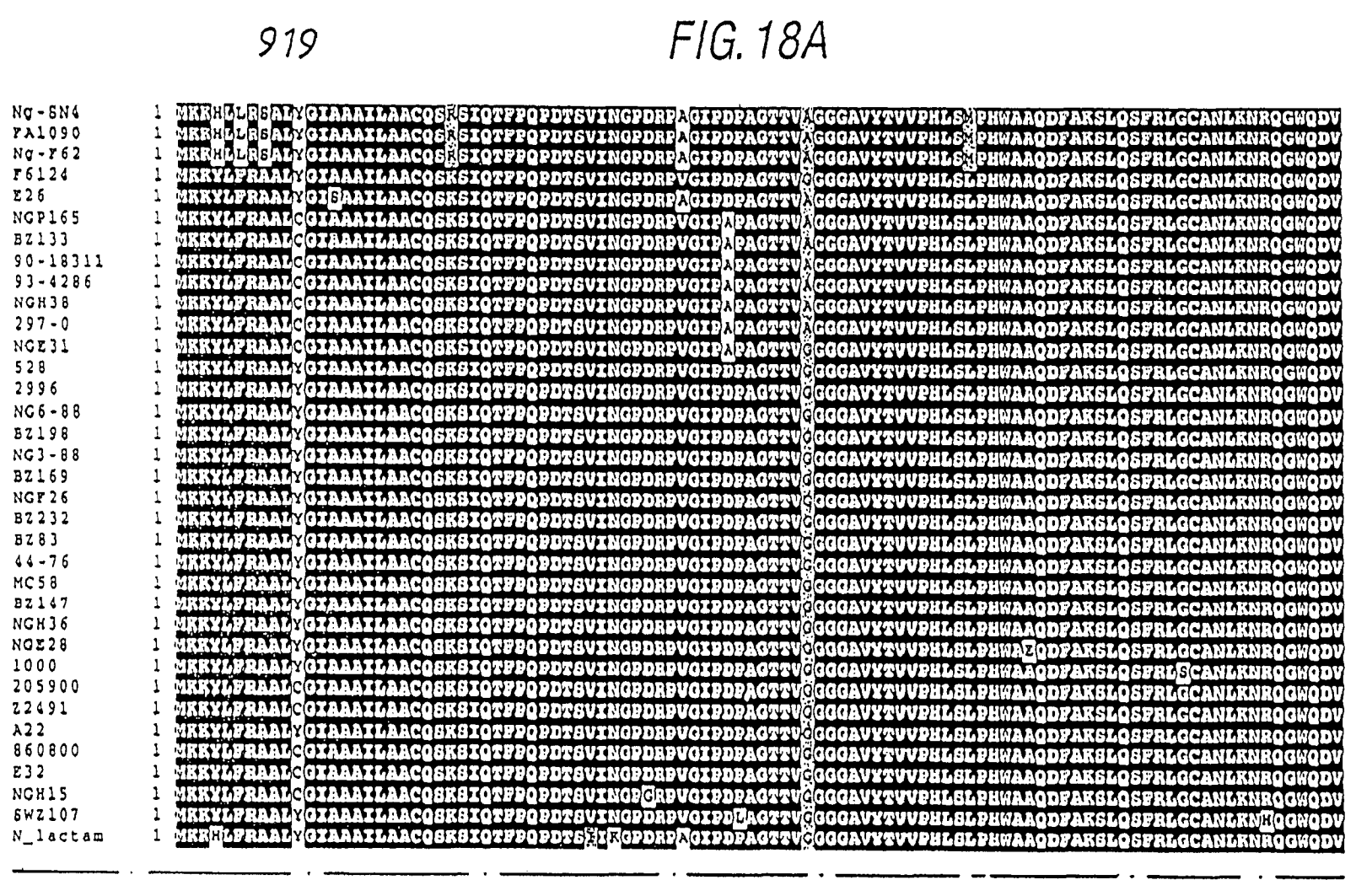
Figure 18A:
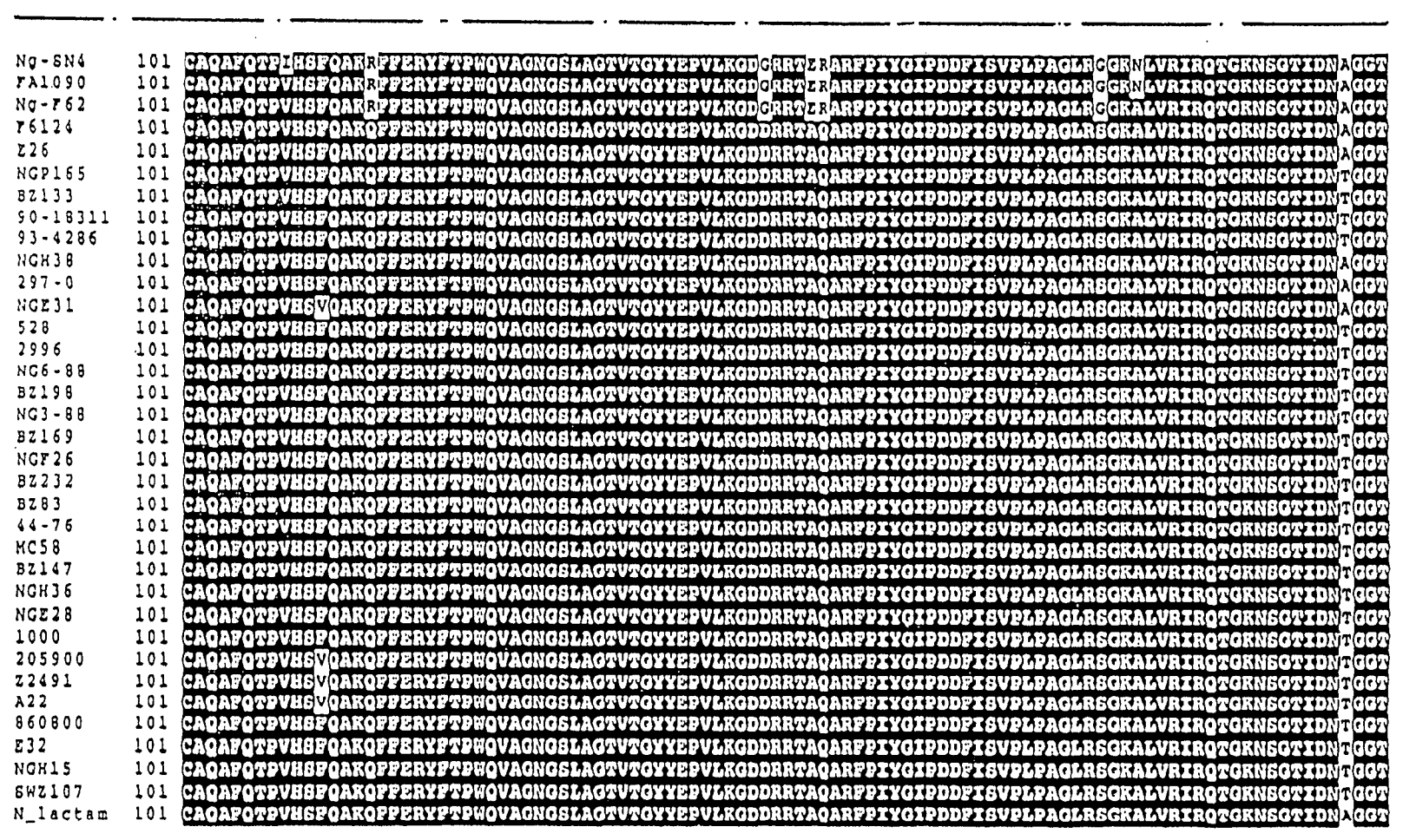
Figure 18B:
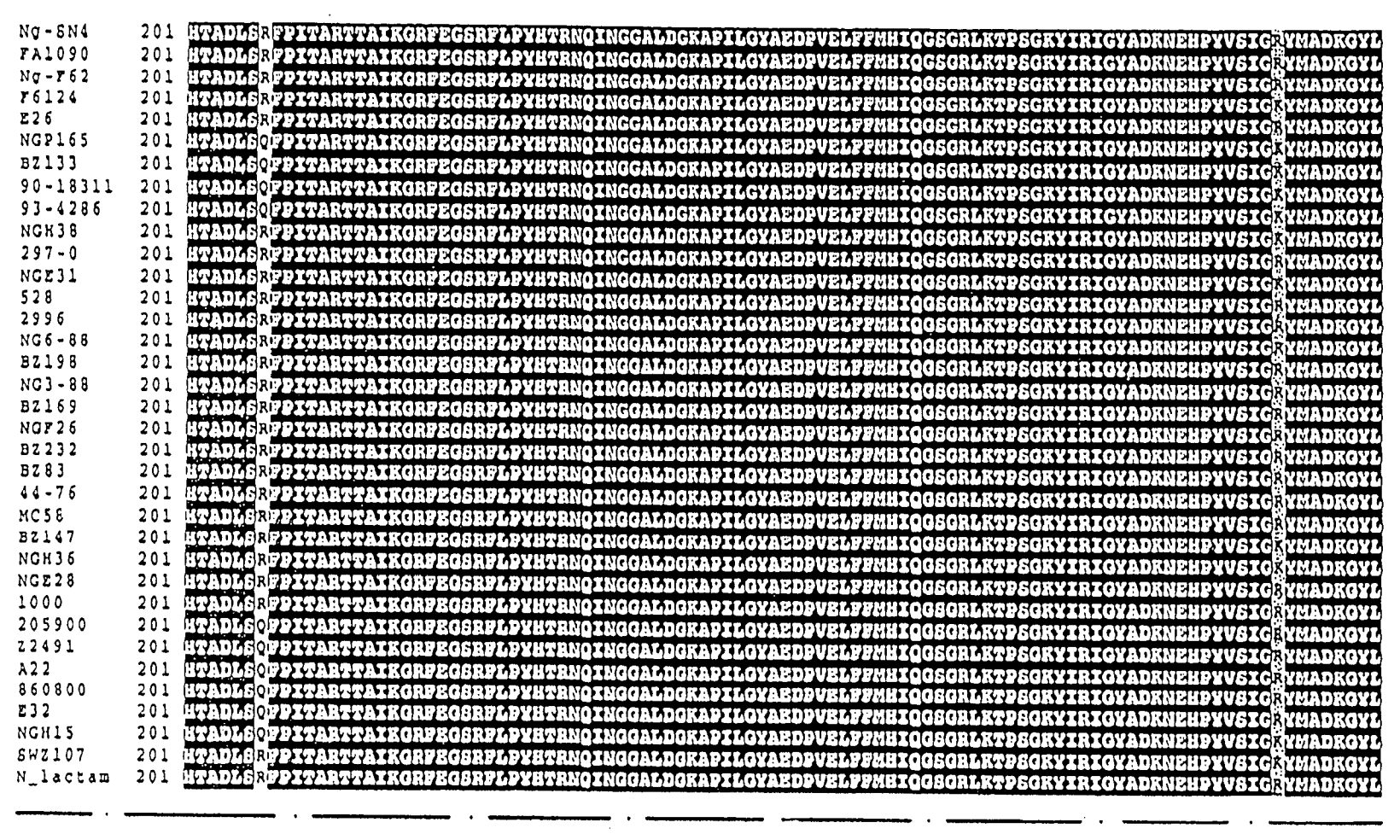
Figure 18B:
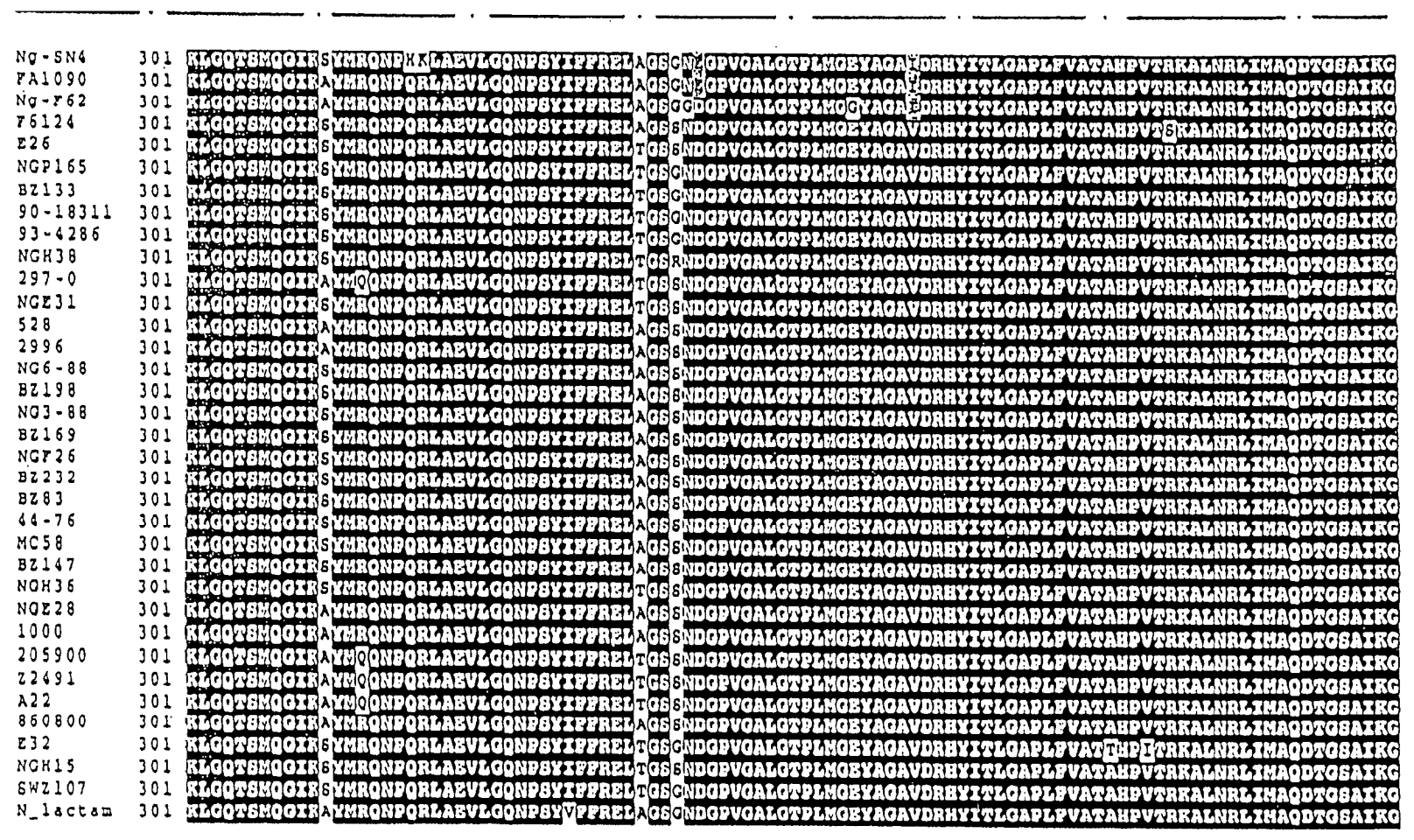
Figure 18C:
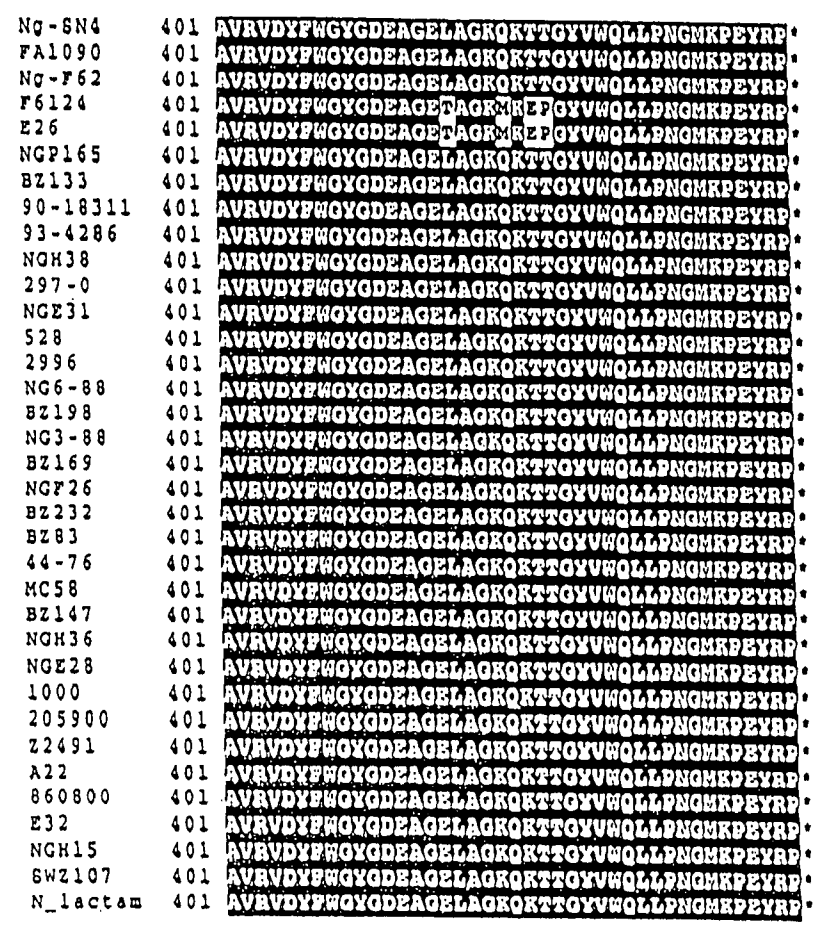

An alignment of the sequences generated using PILEUP is shown in FIGS. 7A-7D. Another alignment is shown in FIGS. 18A-18C. Stretches of conserved amino acids are evident. The protein shows almost complete conservation.

The conserved regions identified in this example confirm that fragments of the full-length 919 protein are suitable as multi-specific vaccines or diagnostic reagents.

Conserved regions of particular interest are:

(SEQ ID NO: 235)
MKKYLFPAAL (SEQ ID NO: 236)
GIAAAILAACQSKSIQTFPQPDTSVINGPDRPVGIPDPAGTTV (G/A)

GGGAVYTVVPHLSLPHWAAQDFAKSLQSFRLGCANLKNRQGWQDVCAQAF

QTPVHSFQAKQFFERYFTPWQVAGNGSLAGTVTGYYEPVLKGDDRRTAQA

RFPIYGIPDDFISVPLPAGLRSGKALATRIRQTGKNSGTIDN (SEQ ID NO: 237)
GGTHTADLS (SEQ ID NO: 238)
FPITARTTAIKGRFEGSRFLPYHTRNQINGGALDGKAPILGYAEDPVELF

FMHIQGSGRLKTPSGKYIRIGYADKNEHPYVSIG (R/K) YMADKGYLK

LGQTSMQGIK (SEQ ID NO: 239)
YMRQNPQRLAEVLGQNPSYIFFREL (SEQ ID NO: 240)
NDGPVGALGTPLMGEYAGAVDRHYITLGAPLFVATAHPVTRKALNRLIMA

QDTGSAIKGAVRVDYFWGYGDEAGELAGKQKTTGYVWQLLPNGMKPEYRP

Example 8

Example 55 of WO99/23578 discloses the cloning and expression of a Neisserial protein referred to as "ORF46". Protein and DNA sequences from serogroups A and B *N. meningitidis* are disclosed, along with sequences from *N. gonorrhoeae.*

Full-length ORF46 has been sequenced for a reference population of 6 strains of serogroup B. An alignment of these sequences is shown in FIGS. 12A-12B, from which stretches of conserved amino acids are evident.

Conserved regions of particular interest are:

(SEQ ID NO: 241)
RKISLILSILAVCLPMHAHASDLANDSFIRQVLDRQHFEPDGKYHLFGSR
GELAERSGHIGLG (SEQ ID NO: 242)
IQSHQLGNLMIQQAAIKGNIGYIVRFSDHGHEVHSPFDNHASHSDSDEAG
SPVDGFSLYRIHWDGYEHHPADGYDGPQCGGYPAPKGARDIYSYDIKGVA
QNIRLNLTDNRSTGQRLADRFHNAG (SEQ ID NO: 243)
MLTQGVGDGFKRATRYSPELDRSGNAAEAFNGTADIVKNIIGAAGEIVGA
GDAVQGISEGSNIAVMHGLGLLSTENKMARINDLADMAQLKDYAAAAIRD
WAVQNPNAAQGIEAVSNIF (SEQ ID NO: 244)
IPIKGIGAVRGKYGLGGITAHP (V/I) KRSQMGEIALPKGKSAVS (SEQ ID NO: 245)
NFADAAYAKYPSPYHSRNIRSNLEQRYGKENITSSTVPPSNGKNVKLANK
RHPKTKVPFDGKGFPNFEKDVKY

The conserved regions in ORF46 confirm that fragments of this protein are suitable as multi-specific vaccines or diagnostic reagents.

Example 9

WO99/57280 discloses the cloning and expression of a Neisserial protein referred to as "726". Protein and DNA sequences from serogroups A and B *N. meningitidis* are disclosed.

726 has been sequenced for a reference population of 7 *N. meningitidis* strains in serogroups A, B and C. An alignment of these sequences is shown in FIG. 17, from which stretches of conserved amino acids are evident.

Conserved regions of particular interest are:

(SEQ ID NO: 246)
IYFKNGFYDDTLG (SEQ ID NO: 247)
IPEGAVAVRAEEYAALLAGQAQGGQIAADSDCRPVLTPPRPS (D/E) Y
HEWDGKKW (SEQ ID NO: 248)
AAAAARFAEQKTATAFRLA (SEQ ID NO: 249)
KADELKNSLLAGYPQVEIDSFYRQEKEALARQADNNAPTPMLAQIAAARG
VELDVLIEKV (I/V) EKSARLAVAAGAIIGKRQQLEDKLN (SEQ ID NO: 250)
IETAPGLDALEKEIEEWT

The conserved regions in 726 confirm that fragments of this protein are suitable as multi-specific vaccines or diagnostic reagents.

Example 10

WO99/57280 discloses the cloning and expression of a Neisserial protein referred to as "953". Protein and DNA sequences from serogroups A and B *N. meningitidis* are disclosed, along with sequences from *N. gonorrhoeae.*

953 has been sequenced for a reference population of 8 strains of *N. meningitidis* serogroups A, B and C. An alignment of these sequences is shown in FIG. 19, from which stretches of conserved amino acids are evident. The protein is well-conserved.

Conserved regions of particular interest are:

(SEQ ID NO: 251)
MKKIIFAALAAAAVGTASAATYKVDEYHANARFAIDHFNTSTNVGGFYGL
TGSVEFDQAKRDGKIDIT IP (I/V) ANLQSGSQHFTDHLKSADIFDA
AQYPDIRFVSTKFNFNGKKLVSVDGNLTMHGKTAPVKLKAEKFNCYQSPM (SEQ ID NO: 252)
ATYKVDEYHANARFAIDHFNTSTNVGGFYGLTGSVEFDQAKRDGKIDITI
P (I/V) ANLQSGSQHFTDHLKSADIFDAAQYPDIRFVSTKFNFNGKKL
VSVDGNLTMHGKTAPVKLKAEKFNCYQSPM (SEQ ID NO: 253)
KTEVCGGDPSTTIDRTKWG (M/V) DYLVNVGMTKSVRIDIQIEAAKQ

The conserved regions in 953 confirm that fragments of this protein are suitable as multi-specific vaccines or diagnostic reagents.

Phylogenetic Tree

FIG. 8 is a dendrogram showing the genetic relationship among 107 *N. meningitidis* strains, based on MLST analysis of six gene fragments [adapted from Maiden et al. (1998)

*PNAS USA* 95:3140]. The dendrogram can be used to select strains representative of meningococcus serogroup B (arrows). Five additional strains, for which genetic assignment to hypervirulent lineages has been independently determined by Wang et al. [*J. Infect. Dis* (1993) 167:1320], Seiler et al. [*Mol. Microbiol.* (1996) 19:841], and Virji et al. [*Mol. Microbiol.* (1992) 6:1271] are superimposed on the dendrogram and indicated by asterisks. In addition to the 22 strains of MenB, three strains of MenA, two strains of MenC, and one strain each of Men Y, X, Z and W135 were used. These are indicated by bold letters before the name. Where phylogenetic data were not available, the strains are shown outside the tree. The hypervirulent strains ET-5, ET-37 and IV-1 are indicated.

Sequence Variability

FIG. 9*a* is a schematic representation of amino acid sequence variability with *N. meningitidis* for proteins 225, 235, 287, 519, 919, ORF4 and ORF40. The horizontal axis represents the sequence of MC58. Amino acid differences within MenB strains are indicated by vertical lines above the horizontal axis; differences within serogroups A, C, Y, X, Z and W135 are indicated by lines below the axis. The height of the vertical lines represents the number of strains with amino acid differences. Peaks thus show variable regions. The bard below 225 and 287 represent sequence segments that are missing from some strains.

FIG. 9*b* is a dendrogram of *N. meningitidis* strains obtained using the same 7 proteins. The phylogenetic analysis based on these genes provided a dendrogram which clusters the hypervirulent strains in agreement with FIG. 8. Bars indicate strains which cluster with 100% bootstrap support in agreement with MLST analysis. Numbers at the base of each node are bootstrap scores (only those >80% are reported). Gene sequences from different strains were aligned with the program PILEUP from the GCG package. The phylogenetic analysis was performed using the neighbour-joining algorithm [Saitou & Nei (1987) *Mol. Biol. Evol.* 4:406] as implemented in the NEIGHBOR program of the PHYLIP package. Pairwise distances were calculated using the Kimura-two parameter [Kimura (1980) *J. Mol. Evol.* 16:111] on the 31 *N. meningitidis* strains. The N-terminal region of ORF40, the entire 287, and the tandem repeats of 225 were excluded from the analysis. A total of 1000 bootstrap replicates were allowed to evaluate the level of support. The clustering of the hypervirulent strains was confirmed by maximum parsimony analysis.

Western Blots

Western blots Antigens ORF4, 225, 235, 519 and 919 were analysed by Western blot for various strains. The results are shown in FIGS. 20A-20E. In the case of 225, the blot shows fragments of different sizes in the different strains, with arrows indicating the band of correct size. 225 contains regions of deletion and insertion of a defined repeat and the size of the fragments on the blots matches the gene variability data.

The strains used for FIGS. 20A-20E are as follows:

*N. meningitidis* Serogroup B:
1=NG6/88 2=BZ198 3=NG3/88 4=297-0 5=1000 6=BZ147 7=BZ169 8=528 9=NGP165 10=BZ133 11=NGE31 12=NGF26 13=NGE28 14=NGH38 15=SWZ107 16=NGH15 17=NGH36 18=BZ232 19=BZ83 20=44/76 21=MC58 96=2996

*N. meningitidis* Serogroup A:
22=205900 23=F6124

*N. meningitidis* Serogroup C:
24=90/18311 25=93/4286

Other *N. meningitidis*
26=A22 (serogroup W)
27=E26 (serogroup X)
28=860800 (serogroup Y)
29=E32 (serogroup Z)

Other *Neisseria*
30=*N. cinerea*
L17=*N. lactamica*
L19=*N. lactamica*
31=*N. gonorrhoeae* F62
32=*N. gonorrhoeae* SN4

It will be appreciated that the invention has been described by means of example only, and that modifications may be made whilst remaining within the spirit and scope of the invention.

The invention claimed is:

1. An immunogenic composition comprising a pharmaceutically acceptable excipient, an adjuvant, and an isolated polypeptide comprising a fragment conserved in SEQ ID NOs: 119-124, wherein the fragment conserved in SEQ ID NOs: 119-124 includes at least 10 or more contiguous amino acids in any of SEQ ID NOs: 222, 223, 226, 227, 228, 229, 230, and 231, provided that said polypeptide does not comprise a full-length Neisserial protein selected from SEQ ID NOs: 119-124.

2. The immunogenic composition of claim 1, wherein said fragment consists of 20 or more consecutive conserved amino acids.

3. The immunogenic composition of claim 1, where in the adjuvant comprises an aluminum salt.

4. A method of inducing an immune response against a Neisserial bacteria in a subject comprising administering the immunogenic composition of claim 1 to the subject.

5. A method of inducing an immune response against a Neisserial bacteria in a subject comprising administering the immunogenic composition of claim 3 to the subject.

* * * * *

SEQUENCE LISTING

```
<160> NUMBER OF SEQ ID NOS: 256

<210> SEQ ID NO 1
<211> LENGTH: 591
<212> TYPE: PRT
<213> ORGANISM: Neisseria meningitidis

<400> SEQUENCE: 1

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95
```

```
Phe Asn Glu Lys Gly Val Leu Thr Ala Arg Glu Ile Thr Leu Lys Ala
            100                 105                 110
Gly Asp Asn Leu Lys Ile Lys Gln Asn Gly Thr Asn Phe Thr Tyr Ser
            115                 120                 125
Leu Lys Lys Asp Leu Thr Asp Leu Thr Ser Val Gly Thr Glu Lys Leu
            130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Leu Asn
            180                 185                 190
Thr Gly Ala Thr Thr Asn Val Thr Asn Asp Asn Val Thr Asp Asp Glu
            195                 200                 205
Lys Lys Arg Ala Ala Ser Val Lys Asp Val Leu Asn Ala Gly Trp Asn
            210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Thr Lys Thr
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
            275                 280                 285
Val Thr Gly Lys Asp Lys Gly Glu Asn Gly Ser Ser Thr Asp Glu Gly
            290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
            355                 360                 365
Thr Val Met Tyr Asp Val Asn Val Gly Asp Ala Leu Asn Val Asn Gln
            370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
            435                 440                 445
Ser Val Ser Leu Gly Ala Gly Ala Asp Ala Pro Thr Leu Ser Val Asp
            450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
            500                 505                 510
```

```
Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
        530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 2
<211> LENGTH: 591
<212> TYPE: PRT
<213> ORGANISM: Neisseria meningitidis

<400> SEQUENCE: 2

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
        115                 120                 125

Leu Lys Lys Asp Leu Thr Asp Leu Thr Ser Val Gly Thr Glu Lys Leu
    130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300
```

```
Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
            355                 360                 365

Thr Val Met Tyr Asp Val Asn Val Gly Asp Ala Leu Asn Val Asn Gln
            370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
            435                 440                 445

Ser Val Ser Leu Gly Ala Gly Ala Asp Ala Pro Thr Leu Ser Val Asp
            450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510

Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
            580                 585                 590

<210> SEQ ID NO 3
<211> LENGTH: 591
<212> TYPE: PRT
<213> ORGANISM: Neisseria meningitidis

<400> SEQUENCE: 3

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Ser Ala Asn Asn Glu Glu Gln Glu Glu Asp Leu Tyr Leu Asp Pro
        50                  55                  60

Val Gln Arg Thr Val Ala Val Leu Ile Val Asn Ser Asp Lys Glu Gly
65              70                  75                  80

Thr Gly Glu Lys Glu Lys Val Glu Glu Asn Ser Asp Trp Ala Val Tyr
```

```
                   85                  90                  95
Phe Asn Glu Lys Gly Val Leu Thr Ala Arg Glu Ile Thr Leu Lys Ala
                100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
        130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
                180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
        210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
            420                 425                 430

Asn Gly Lys Asn Ile Asp Ile Ala Thr Ser Met Thr Pro Gln Phe Ser
        435                 440                 445

Ser Val Ser Leu Gly Ala Gly Ala Asp Ala Pro Thr Leu Ser Val Asp
    450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
            500                 505                 510
```

```
Val Asp Gly Asn Ala Arg Ala Gly Ile Ala Gln Ala Ile Ala Thr Ala
            515                 520                 525

Gly Leu Val Gln Ala Tyr Leu Pro Gly Lys Ser Met Met Ala Ile Gly
            530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
            565                 570                 575

Ser Arg Gly His Phe Gly Ala Ser Ala Ser Val Gly Tyr Gln Trp
            580                 585                 590

<210> SEQ ID NO 4
<211> LENGTH: 591
<212> TYPE: PRT
<213> ORGANISM: Neisseria meningitidis

<400> SEQUENCE: 4

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Glu Thr Ala Val Leu Ala Thr Leu Leu Phe Ala Thr Val Gln
        35                  40                  45

Ala Ser Ala Asn Asn Glu Glu Gln Glu Glu Asp Leu Tyr Leu Asp Pro
    50                  55                  60

Val Gln Arg Thr Val Ala Val Leu Ile Val Asn Ser Asp Lys Glu Gly
65                  70                  75                  80

Thr Gly Glu Lys Glu Lys Val Glu Glu Asn Ser Asp Trp Ala Val Tyr
                85                  90                  95

Phe Asn Glu Lys Gly Val Leu Thr Ala Arg Glu Ile Thr Leu Lys Ala
            100                 105                 110

Gly Asp Asn Leu Lys Ile Lys Gln Asn Gly Thr Asn Phe Thr Tyr Ser
            115                 120                 125

Leu Lys Lys Asp Leu Thr Asp Leu Thr Ser Val Gly Thr Glu Lys Leu
130                 135                 140

Ser Phe Ser Ala Asn Gly Asn Lys Val Asn Ile Thr Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Leu Asn
            180                 185                 190

Thr Gly Ala Thr Thr Asn Val Thr Asn Asp Asn Val Thr Asp Asp Glu
            195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Asp Lys Gly Glu Asn Gly Ser Ser Thr Asp Glu Gly
```

```
            290                 295                 300
Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
                340                 345                 350

Gly Lys Gly Thr Thr Ala Thr Val Ser Lys Asp Asp Gln Gly Asn Ile
                355                 360                 365

Thr Val Met Tyr Asp Val Asn Val Gly Asp Ala Leu Asn Val Asn Gln
                370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Thr Arg
                420                 425                 430

Asn Gly Lys Asn Ile Asp Ile Ala Thr Ser Met Thr Pro Gln Phe Ser
                435                 440                 445

Ser Val Ser Leu Gly Ala Gly Ala Asp Ala Pro Thr Leu Ser Val Asp
                450                 455                 460

Gly Asp Ala Leu Asn Val Gly Ser Lys Lys Asp Asn Lys Pro Val Arg
465                 470                 475                 480

Ile Thr Asn Val Ala Pro Gly Val Lys Glu Gly Asp Val Thr Asn Val
                485                 490                 495

Ala Gln Leu Lys Gly Val Ala Gln Asn Leu Asn Asn Arg Ile Asp Asn
                500                 505                 510

Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
                530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 5
<211> LENGTH: 591
<212> TYPE: PRT
<213> ORGANISM: Neisseria meningitidis

<400> SEQUENCE: 5

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
                35                  40                  45

Ala Ser Ala Asn Asn Glu Glu Gln Glu Glu Asp Leu Tyr Leu Asp Pro
            50                  55                  60

Val Gln Arg Thr Val Ala Val Leu Ile Val Asn Ser Asp Lys Glu Gly
65                  70                  75                  80
```

-continued

```
Thr Gly Glu Lys Glu Lys Val Glu Glu Asn Ser Asp Trp Ala Val Tyr
                 85                  90                  95
Phe Asn Glu Lys Gly Val Leu Thr Ala Arg Glu Ile Thr Leu Lys Ala
            100                 105                 110
Gly Asp Asn Leu Lys Ile Lys Gln Asn Gly Thr Asn Phe Thr Tyr Ser
        115                 120                 125
Leu Lys Lys Asp Leu Thr Asp Leu Thr Ser Val Gly Thr Glu Lys Leu
    130                 135                 140
Ser Phe Ser Ala Asn Gly Asn Lys Val Asn Ile Thr Ser Asp Thr Lys
145                 150                 155                 160
Gly Leu Asn Phe Ala Lys Glu Thr Ala Gly Thr Asn Gly Asp Thr Thr
                165                 170                 175
Val His Leu Asn Gly Ile Gly Ser Thr Leu Thr Asp Thr Leu Leu Asn
            180                 185                 190
Thr Gly Ala Thr Thr Asn Val Thr Asn Asp Asn Val Thr Asp Asp Glu
        195                 200                 205
Lys Lys Arg Ala Ala Ser Val Lys Asp Val Leu Asn Ala Gly Trp Asn
    210                 215                 220
Ile Lys Gly Val Lys Pro Gly Thr Thr Ala Ser Asp Asn Val Asp Phe
225                 230                 235                 240
Val Arg Thr Tyr Asp Thr Val Glu Phe Leu Ser Ala Asp Thr Lys Thr
                245                 250                 255
Thr Thr Val Asn Val Glu Ser Lys Asp Asn Gly Lys Lys Thr Glu Val
            260                 265                 270
Lys Ile Gly Ala Lys Thr Ser Val Ile Lys Glu Lys Asp Gly Lys Leu
        275                 280                 285
Val Thr Gly Lys Asp Lys Gly Glu Asn Gly Ser Ser Thr Asp Glu Gly
    290                 295                 300
Glu Gly Leu Val Thr Ala Lys Glu Val Ile Asp Ala Val Asn Lys Ala
305                 310                 315                 320
Gly Trp Arg Met Lys Thr Thr Thr Ala Asn Gly Gln Thr Gly Gln Ala
                325                 330                 335
Asp Lys Phe Glu Thr Val Thr Ser Gly Thr Asn Val Thr Phe Ala Ser
            340                 345                 350
Gly Lys Gly Thr Thr Ala Thr Val Ser Lys Asp Asp Gln Gly Asn Ile
        355                 360                 365
Thr Val Met Tyr Asp Val Asn Val Gly Asp Ala Leu Asn Val Asn Gln
    370                 375                 380
Leu Gln Asn Ser Gly Trp Asn Leu Asp Ser Lys Ala Val Ala Gly Ser
385                 390                 395                 400
Ser Gly Lys Val Ile Ser Gly Asn Val Ser Pro Ser Lys Gly Lys Met
                405                 410                 415
Asp Glu Thr Val Asn Ile Asn Ala Gly Asn Asn Ile Glu Ile Thr Arg
            420                 425                 430
Asn Gly Lys Asn Ile Asp Ile Ala Thr Ser Met Thr Pro Gln Phe Ser
        435                 440                 445
Ser Val Ser Leu Gly Ala Gly Ala Asp Ala Pro Thr Leu Ser Val Asp
    450                 455                 460
Gly Asp Ala Leu Asn Val Gly Ser Lys Lys Asp Asn Lys Pro Val Arg
465                 470                 475                 480
Ile Thr Asn Val Ala Pro Gly Val Lys Glu Gly Asp Val Thr Asn Val
                485                 490                 495
Ala Gln Leu Lys Gly Val Ala Gln Asn Leu Asn Asn Arg Ile Asp Asn
```

```
                    500                 505                 510
Val Asp Gly Asn Ala Arg Ala Gly Ile Ala Gln Ala Ile Ala Thr Ala
                515                 520                 525

Gly Leu Val Gln Ala Tyr Leu Pro Gly Lys Ser Met Met Ala Ile Gly
            530                 535                 540

Gly Gly Thr Tyr Arg Gly Glu Ala Gly Tyr Ala Ile Gly Tyr Ser Ser
545                 550                 555                 560

Ile Ser Asp Gly Gly Asn Trp Ile Ile Lys Gly Thr Ala Ser Gly Asn
                565                 570                 575

Ser Arg Gly His Phe Gly Ala Ser Ala Ser Val Gly Tyr Gln Trp
                580                 585                 590

<210> SEQ ID NO 6
<211> LENGTH: 594
<212> TYPE: PRT
<213> ORGANISM: Neisseria meningitidis

<400> SEQUENCE: 6

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Asp Asp Leu Tyr Leu Glu Pro Val Gln Arg
    50                  55                  60

Thr Ala Pro Val Leu Ser Phe His Ala Asp Ser Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285
```

Lys Leu Val Thr Gly Lys Asp Lys Gly Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Ala Asn Gly Gln Thr Gly
            325                 330                 335

Gln Ala Asp Lys Phe Glu Thr Val Ser Gly Thr Lys Val Thr Phe
            340                 345                 350

Ala Ser Gly Asn Gly Thr Thr Ala Thr Val Ser Lys Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
    435                 440                 445

Phe Ser Ser Val Ser Leu Gly Ala Gly Ala Asp Ala Pro Thr Leu Ser
450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
    515                 520                 525

Ala Thr Ala Gly Leu Val Gln Ala Tyr Leu Pro Gly Lys Ser Met Met
530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 7
<211> LENGTH: 594
<212> TYPE: PRT
<213> ORGANISM: Neisseria meningitidis

<400> SEQUENCE: 7

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Ala Thr Ala Val Leu Ala Thr Leu Phe Ala Thr Val Gln
        35                  40                  45

Ala Ser Thr Thr Asp Asp Asp Leu Tyr Leu Glu Pro Val Gln Arg
    50                  55                  60

```
Thr Ala Pro Val Leu Ser Phe His Ala Asp Ser Glu Gly Thr Gly Glu
 65                  70                  75                  80

Lys Glu Val Thr Glu Asp Ser Asn Trp Gly Val Tyr Phe Asp Lys Lys
                 85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
    130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
    210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
            260                 265                 270

Glu Val Lys Ile Gly Ala Lys Thr Ser Val Ile Lys Glu Lys Asp Gly
        275                 280                 285

Lys Leu Val Thr Gly Lys Asp Lys Gly Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Lys Val Thr Phe
            340                 345                 350

Ala Ser Gly Asn Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
```

```
                485                 490                 495
Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 8
<211> LENGTH: 594
<212> TYPE: PRT
<213> ORGANISM: Neisseria meningitidis

<400> SEQUENCE: 8

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
        35                  40                  45

Ala Ser Thr Thr Asp Asp Asp Leu Tyr Leu Glu Pro Val Gln Arg
50                  55                  60

Thr Ala Pro Val Leu Ser Phe His Ala Asp Ser Gly Thr Gly Glu
65                  70                  75                  80

Lys Glu Val Thr Glu Asp Ser Asn Trp Gly Val Tyr Phe Asp Lys Lys
                85                  90                  95

Gly Val Leu Thr Ala Gly Thr Ile Thr Leu Lys Ala Gly Asp Asn Leu
            100                 105                 110

Lys Ile Lys Gln Asn Thr Asp Glu Asn Thr Asn Ala Ser Ser Phe Thr
        115                 120                 125

Tyr Ser Leu Lys Lys Asp Leu Thr Asp Leu Thr Ser Val Glu Thr Glu
130                 135                 140

Lys Leu Ser Phe Gly Ala Asn Gly Lys Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Thr Thr Val His Leu Asn Gly Ile Gly Ser Thr Leu Thr Asp Thr Leu
            180                 185                 190

Leu Asn Thr Gly Ala Thr Thr Asn Val Thr Asn Asp Asn Val Thr Asp
        195                 200                 205

Asp Glu Lys Lys Arg Ala Ala Ser Val Lys Asp Val Leu Asn Ala Gly
210                 215                 220

Trp Asn Ile Lys Gly Val Lys Pro Gly Thr Thr Ala Ser Asp Asn Val
225                 230                 235                 240

Asp Phe Val Arg Thr Tyr Asp Thr Val Glu Phe Leu Ser Ala Asp Thr
                245                 250                 255

Lys Thr Thr Thr Val Asn Val Glu Ser Lys Asp Asn Gly Lys Lys Thr
```

```
            260                 265                 270
Glu Val Lys Ile Gly Ala Lys Thr Ser Val Ile Lys Glu Lys Asp Gly
        275                 280                 285

Lys Leu Val Thr Gly Lys Asp Lys Gly Glu Asn Gly Ser Ser Thr Asp
    290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Thr Ala Asn Gly Gln Thr Gly
                325                 330                 335

Gln Ala Asp Lys Phe Glu Thr Val Thr Ser Gly Thr Lys Val Thr Phe
            340                 345                 350

Ala Ser Gly Asn Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Thr Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Ala Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn His
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Gly Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 9
<211> LENGTH: 594
<212> TYPE: PRT
<213> ORGANISM: Neisseria meningitidis

<400> SEQUENCE: 9

Met Asn Lys Ile Tyr Arg Ile Ile Trp Asn Ser Ala Leu Asn Ala Trp
1               5                   10                  15

Val Val Ser Glu Leu Thr Arg Asn His Thr Lys Arg Ala Ser Ala
            20                  25                  30

Thr Val Ala Thr Ala Val Leu Ala Thr Leu Leu Phe Ala Thr Val Gln
```

```
                 35                  40                  45
Ala Asn Ala Thr Asp Asp Asp Leu Tyr Leu Glu Pro Val Gln Arg
             50                  55                  60
Thr Ala Val Val Leu Ser Phe Arg Ser Asp Lys Glu Gly Thr Gly Glu
65                  70                  75                  80
Lys Glu Gly Thr Glu Asp Ser Asn Trp Ala Val Tyr Phe Asp Glu Lys
                 85                  90                  95
Arg Val Leu Lys Ala Gly Ala Ile Thr Leu Lys Ala Gly Asp Asn Leu
            100                 105                 110
Lys Ile Lys Gln Asn Thr Asn Glu Asn Thr Asn Asp Ser Ser Phe Thr
            115                 120                 125
Tyr Ser Leu Lys Lys Asp Leu Thr Asp Leu Thr Ser Val Glu Thr Glu
            130                 135                 140
Lys Leu Ser Phe Gly Ala Asn Gly Asn Lys Val Asn Ile Thr Ser Asp
145                 150                 155                 160
Thr Lys Gly Leu Asn Phe Ala Lys Glu Thr Ala Gly Thr Asn Gly Asp
                165                 170                 175
Pro Thr Val His Leu Asn Gly Ile Gly Ser Thr Leu Thr Asp Thr Leu
                180                 185                 190
Leu Asn Thr Gly Ala Thr Thr Asn Val Thr Asn Asp Asn Val Thr Asp
            195                 200                 205
Asp Glu Lys Lys Arg Ala Ala Ser Val Lys Asp Val Leu Asn Ala Gly
            210                 215                 220
Trp Asn Ile Lys Gly Val Lys Pro Gly Thr Thr Ala Ser Asp Asn Val
225                 230                 235                 240
Asp Phe Val Arg Thr Tyr Asp Thr Val Glu Phe Leu Ser Ala Asp Thr
                245                 250                 255
Lys Thr Thr Thr Val Asn Val Glu Ser Lys Asp Asn Gly Lys Lys Thr
            260                 265                 270
Glu Val Lys Ile Gly Ala Lys Thr Ser Val Ile Lys Glu Lys Asp Gly
            275                 280                 285
Lys Leu Val Thr Gly Lys Gly Lys Asp Glu Asn Gly Ser Ser Thr Asp
            290                 295                 300
Glu Gly Glu Gly Leu Val Thr Ala Lys Glu Val Ile Asp Ala Val Asn
305                 310                 315                 320
Lys Ala Gly Trp Arg Met Lys Thr Thr Thr Ala Asn Gly Gln Thr Gly
                325                 330                 335
Gln Ala Asp Lys Phe Glu Thr Val Thr Ser Gly Thr Asn Val Thr Phe
            340                 345                 350
Ala Ser Gly Lys Gly Thr Thr Ala Thr Val Ser Lys Asp Asp Gln Gly
            355                 360                 365
Asn Ile Thr Val Lys Tyr Asp Val Asn Val Gly Asp Ala Leu Asn Val
            370                 375                 380
Asn Gln Leu Gln Asn Ser Gly Trp Asn Leu Asp Ser Lys Ala Val Ala
385                 390                 395                 400
Gly Ser Ser Gly Lys Val Ile Ser Gly Asn Val Ser Pro Ser Lys Gly
                405                 410                 415
Lys Met Asp Glu Thr Val Asn Ile Asn Ala Gly Asn Asn Ile Glu Ile
            420                 425                 430
Thr Arg Asn Gly Lys Asn Ile Asp Ile Ala Thr Ser Met Ala Pro Gln
            435                 440                 445
Phe Ser Ser Val Ser Leu Gly Ala Gly Ala Asp Ala Pro Thr Leu Ser
450                 455                 460
```

```
Val Asp Asp Glu Gly Ala Leu Asn Val Gly Ser Lys Asp Thr Asn Lys
465                 470                 475                 480

Pro Val Arg Ile Thr Asn Val Ala Pro Gly Val Lys Glu Gly Asp Val
                    485                 490                 495

Thr Asn Val Ala Gln Leu Lys Gly Val Ala Gln Asn Leu Asn Asn Arg
                500                 505                 510

Ile Asp Asn Val Asp Gly Asn Ala Arg Ala Gly Ile Ala Gln Ala Ile
            515                 520                 525

Ala Thr Ala Gly Leu Val Gln Ala Tyr Leu Pro Gly Lys Ser Met Met
530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
                580                 585                 590

Gln Trp

<210> SEQ ID NO 10
<211> LENGTH: 594
<212> TYPE: PRT
<213> ORGANISM: Neisseria meningitidis

<400> SEQUENCE: 10

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Leu Phe Ala Thr Val Gln
            35                  40                  45

Ala Asn Ala Thr Asp Asp Asp Leu Tyr Leu Glu Pro Val Gln Arg
50                  55                  60

Thr Ala Val Val Leu Ser Phe Arg Ser Asp Lys Glu Gly Thr Gly Glu
65                  70                  75                  80

Lys Glu Gly Thr Glu Asp Ser Asn Trp Ala Val Tyr Phe Asp Glu Lys
                85                  90                  95

Arg Val Leu Lys Ala Gly Ala Ile Thr Leu Lys Ala Gly Asp Asn Leu
                100                 105                 110

Lys Ile Lys Gln Asn Thr Asn Glu Asn Thr Asn Asp Ser Ser Phe Thr
            115                 120                 125

Tyr Ser Leu Lys Lys Asp Leu Thr Asp Leu Thr Ser Val Glu Thr Glu
130                 135                 140

Lys Leu Ser Phe Gly Ala Asn Gly Asn Lys Val Asn Ile Thr Ser Asp
145                 150                 155                 160

Thr Lys Gly Leu Asn Phe Ala Lys Glu Thr Ala Gly Thr Asn Gly Asp
                165                 170                 175

Pro Thr Val His Leu Asn Gly Ile Gly Ser Thr Leu Thr Asp Thr Leu
                180                 185                 190

Leu Asn Thr Gly Ala Thr Thr Asn Val Thr Asn Asp Asn Val Thr Asp
            195                 200                 205

Asp Glu Lys Lys Arg Ala Ala Ser Val Lys Asp Val Leu Asn Ala Gly
210                 215                 220

Trp Asn Ile Lys Gly Val Lys Pro Gly Thr Thr Ala Ser Asp Asn Val
225                 230                 235                 240
```

Asp Phe Val Arg Thr Tyr Asp Thr Val Glu Phe Leu Ser Ala Asp Thr
            245                 250                 255

Lys Thr Thr Thr Val Asn Val Glu Ser Lys Asp Asn Gly Lys Lys Thr
        260                 265                 270

Glu Val Lys Ile Gly Ala Lys Thr Ser Val Ile Lys Glu Lys Asp Gly
    275                 280                 285

Lys Leu Val Thr Gly Lys Gly Lys Asp Glu Asn Gly Ser Ser Thr Asp
290                 295                 300

Glu Gly Glu Gly Leu Val Thr Ala Lys Glu Val Ile Asp Ala Val Asn
305                 310                 315                 320

Lys Ala Gly Trp Arg Met Lys Thr Thr Ala Asn Gly Gln Thr Gly
                325                 330                 335

Gln Ala Asp Lys Phe Glu Thr Val Thr Ser Gly Thr Asn Val Thr Phe
            340                 345                 350

Ala Ser Gly Lys Gly Thr Thr Ala Thr Val Ser Lys Asp Asp Gln Gly
        355                 360                 365

Asn Ile Thr Val Lys Tyr Asp Val Asn Val Gly Asp Ala Leu Asn Val
    370                 375                 380

Asn Gln Leu Gln Asn Ser Gly Trp Asn Leu Asp Ser Lys Ala Val Ala
385                 390                 395                 400

Gly Ser Ser Gly Lys Val Ile Ser Gly Asn Val Ser Pro Ser Lys Gly
                405                 410                 415

Lys Met Asp Glu Thr Val Asn Ile Asn Ala Gly Asn Asn Ile Glu Ile
            420                 425                 430

Thr Arg Asn Gly Lys Asn Ile Asp Ile Ala Thr Ser Met Ala Pro Gln
        435                 440                 445

Phe Ser Ser Val Ser Leu Gly Ala Gly Ala Asp Ala Pro Thr Leu Ser
    450                 455                 460

Val Asp Asp Glu Gly Ala Leu Asn Val Gly Ser Lys Asp Thr Asn Lys
465                 470                 475                 480

Pro Val Arg Ile Thr Asn Val Ala Pro Gly Val Lys Glu Gly Asp Val
                485                 490                 495

Thr Asn Val Ala Gln Leu Lys Gly Val Ala Gln Asn Leu Asn Asn Arg
            500                 505                 510

Ile Asp Asn Val Asp Gly Asn Ala Arg Ala Gly Ile Ala Gln Ala Ile
        515                 520                 525

Ala Thr Ala Gly Leu Val Gln Ala Tyr Leu Pro Gly Lys Ser Met Met
    530                 535                 540

Ala Ile Gly Gly Asp Thr Tyr Arg Gly Glu Ala Gly Tyr Ala Ile Gly
545                 550                 555                 560

Tyr Ser Ser Ile Ser Asp Gly Gly Asn Trp Ile Ile Lys Gly Thr Ala
                565                 570                 575

Ser Gly Asn Ser Arg Gly His Phe Gly Ala Ser Ala Ser Val Gly Tyr
            580                 585                 590

Gln Trp

<210> SEQ ID NO 11
<211> LENGTH: 598
<212> TYPE: PRT
<213> ORGANISM: Neisseria meningitidis

<400> SEQUENCE: 11

Met Asn Lys Ile Tyr Arg Ile Ile Trp Asn Ser Ala Leu Asn Ala Trp
1               5                   10                  15

```
Val Val Val Ser Glu Leu Thr Arg Asn His Thr Lys Arg Ala Ser Ala
             20                  25                  30

Thr Val Ala Thr Ala Val Leu Ala Thr Leu Leu Phe Ala Thr Val Gln
             35                  40                  45

Ala Asn Ala Thr Asp Asp Asp Leu Tyr Leu Glu Pro Val Gln Arg
 50                  55                  60

Thr Ala Val Val Leu Ser Phe Arg Ser Asp Lys Glu Gly Thr Gly Glu
 65                  70                  75                  80

Lys Glu Gly Thr Glu Asp Ser Asn Trp Ala Val Tyr Phe Asp Glu Lys
                 85                  90                  95

Arg Val Leu Lys Ala Gly Ala Ile Thr Leu Lys Ala Gly Asp Asn Leu
             100                 105                 110

Lys Ile Lys Gln Asn Thr Asn Glu Asn Thr Asn Glu Asn Thr Asn Asp
         115                 120                 125

Ser Ser Phe Thr Tyr Ser Leu Lys Lys Asp Leu Thr Asp Leu Thr Ser
130                 135                 140

Val Glu Thr Glu Lys Leu Ser Phe Gly Ala Asn Gly Asn Lys Val Asn
145                 150                 155                 160

Ile Thr Ser Asp Thr Lys Gly Leu Asn Phe Ala Lys Glu Thr Ala Gly
             165                 170                 175

Thr Asn Gly Asp Pro Thr Val His Leu Asn Gly Ile Gly Ser Thr Leu
             180                 185                 190

Thr Asp Thr Leu Leu Asn Thr Gly Ala Thr Thr Asn Val Thr Asn Asp
         195                 200                 205

Asn Val Thr Asp Asp Glu Lys Lys Arg Ala Ala Ser Val Lys Asp Val
         210                 215                 220

Leu Asn Ala Gly Trp Asn Ile Lys Gly Val Lys Pro Gly Thr Thr Ala
225                 230                 235                 240

Ser Asp Asn Val Asp Phe Val Arg Thr Tyr Asp Thr Val Glu Phe Leu
             245                 250                 255

Ser Ala Asp Thr Lys Thr Thr Val Asn Val Glu Ser Lys Asp Asn
             260                 265                 270

Gly Lys Lys Thr Glu Val Lys Ile Gly Ala Lys Thr Ser Val Ile Lys
         275                 280                 285

Glu Lys Asp Gly Lys Leu Val Thr Gly Lys Gly Lys Asp Glu Asn Gly
290                 295                 300

Ser Ser Thr Asp Glu Gly Glu Gly Leu Val Thr Ala Lys Glu Val Ile
305                 310                 315                 320

Asp Ala Val Asn Lys Ala Gly Trp Arg Met Lys Thr Thr Thr Ala Asn
             325                 330                 335

Gly Gln Thr Gly Gln Ala Asp Lys Phe Glu Thr Val Thr Ser Gly Thr
             340                 345                 350

Lys Val Thr Phe Ala Ser Gly Asn Gly Thr Thr Ala Thr Val Ser Lys
             355                 360                 365

Asp Asp Gln Gly Asn Ile Thr Val Lys Tyr Asp Val Asn Val Gly Asp
         370                 375                 380

Ala Leu Asn Val Asn Gln Leu Gln Asn Ser Gly Trp Asn Leu Asp Ser
385                 390                 395                 400

Lys Ala Val Ala Gly Ser Ser Gly Lys Val Ile Ser Gly Asn Val Ser
             405                 410                 415

Pro Ser Lys Gly Lys Met Asp Glu Thr Val Asn Ile Asn Ala Gly Asn
         420                 425                 430
```

```
Asn Ile Glu Ile Thr Arg Asn Gly Lys Asn Ile Asp Ile Ala Thr Ser
            435                 440                 445

Met Thr Pro Gln Phe Ser Ser Val Ser Leu Gly Ala Gly Ala Asp Ala
    450                 455                 460

Pro Thr Leu Ser Val Asp Asp Glu Gly Ala Leu Asn Val Gly Ser Lys
465                 470                 475                 480

Asp Ala Asn Lys Pro Val Arg Ile Thr Asn Val Ala Pro Gly Val Lys
                485                 490                 495

Glu Gly Asp Val Thr Asn Val Ala Gln Leu Lys Gly Val Ala Gln Asn
                500                 505                 510

Leu Asn Asn Arg Ile Asp Asn Val Asp Gly Asn Ala Arg Ala Gly Ile
            515                 520                 525

Ala Gln Ala Ile Ala Thr Ala Gly Leu Ala Gln Ala Tyr Leu Pro Gly
    530                 535                 540

Lys Ser Met Met Ala Ile Gly Gly Gly Thr Tyr Arg Gly Glu Ala Gly
545                 550                 555                 560

Tyr Ala Ile Gly Tyr Ser Ser Ile Ser Asp Thr Gly Asn Trp Val Ile
                565                 570                 575

Lys Gly Thr Ala Ser Gly Asn Ser Arg Gly His Phe Gly Ala Ser Ala
            580                 585                 590

Ser Val Gly Tyr Gln Trp
            595

<210> SEQ ID NO 12
<211> LENGTH: 599
<212> TYPE: PRT
<213> ORGANISM: Neisseria meningitidis

<400> SEQUENCE: 12

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
                20                  25                  30

Thr Val Lys Thr Ala Val Leu Ala Thr Leu Leu Phe Ala Thr Val Gln
            35                  40                  45

Ala Asn Ala Thr Asp Glu Asp Glu Glu Glu Leu Glu Pro Val Val
    50                  55                  60

Arg Ser Ala Leu Val Leu Gln Phe Met Ile Asp Lys Glu Gly Asn Gly
65                  70                  75                  80

Glu Asn Glu Ser Thr Gly Asn Ile Gly Trp Ser Ile Tyr Tyr Asp Asn
                85                  90                  95

His Asn Thr Leu His Gly Ala Thr Val Thr Leu Lys Ala Gly Asp Asn
                100                 105                 110

Leu Lys Ile Lys Gln Asn Thr Asn Lys Asn Thr Asn Glu Asn Thr Asn
            115                 120                 125

Asp Ser Ser Phe Thr Tyr Ser Leu Lys Lys Asp Leu Thr Asp Leu Thr
    130                 135                 140

Ser Val Glu Thr Glu Lys Leu Ser Phe Gly Ala Asn Gly Asn Lys Val
145                 150                 155                 160

Asn Ile Thr Ser Asp Thr Lys Gly Leu Asn Phe Ala Lys Glu Thr Ala
                165                 170                 175

Gly Thr Asn Gly Asp Thr Thr Val His Leu Asn Gly Ile Gly Ser Thr
            180                 185                 190

Leu Thr Asp Thr Leu Leu Asn Thr Gly Ala Thr Thr Asn Val Thr Asn
    195                 200                 205
```

Asp Asn Val Thr Asp Asp Lys Lys Arg Ala Ala Ser Val Lys Asp
210                 215                 220

Val Leu Asn Ala Gly Trp Asn Ile Lys Gly Val Lys Pro Gly Thr Thr
225                 230                 235                 240

Ala Ser Asp Asn Val Asp Phe Val His Thr Tyr Asp Thr Val Glu Phe
            245                 250                 255

Leu Ser Ala Asp Thr Lys Thr Thr Val Asn Val Glu Ser Lys Asp
        260                 265                 270

Asn Gly Lys Arg Thr Glu Val Lys Ile Gly Ala Lys Thr Ser Val Ile
    275                 280                 285

Lys Glu Lys Asp Gly Lys Leu Val Thr Gly Lys Gly Lys Gly Glu Asn
290                 295                 300

Gly Ser Ser Thr Asp Glu Gly Glu Gly Leu Val Thr Ala Lys Glu Val
305                 310                 315                 320

Ile Asp Ala Val Asn Lys Ala Gly Trp Arg Met Lys Thr Thr Thr Ala
                325                 330                 335

Asn Gly Gln Thr Gly Gln Ala Asp Lys Phe Glu Thr Val Thr Ser Gly
            340                 345                 350

Thr Asn Val Thr Phe Ala Ser Gly Lys Gly Thr Thr Ala Thr Val Ser
        355                 360                 365

Lys Asp Asp Gln Gly Asn Ile Thr Val Lys Tyr Asp Val Asn Val Gly
370                 375                 380

Asp Ala Leu Asn Val Asn Gln Leu Gln Asn Ser Gly Trp Asn Leu Asp
385                 390                 395                 400

Ser Lys Ala Val Ala Gly Ser Ser Gly Lys Val Ile Ser Gly Asn Val
                405                 410                 415

Ser Pro Ser Lys Gly Lys Met Asp Glu Thr Val Asn Ile Asn Ala Gly
            420                 425                 430

Asn Asn Ile Glu Ile Thr Arg Asn Gly Lys Asn Ile Asp Ile Ala Thr
        435                 440                 445

Ser Met Thr Pro Gln Phe Ser Ser Val Ser Leu Gly Ala Gly Ala Asp
450                 455                 460

Ala Pro Thr Leu Ser Val Asp Asp Lys Gly Ala Leu Asn Val Gly Ser
465                 470                 475                 480

Lys Asp Ala Asn Lys Pro Val Arg Ile Thr Asn Val Ala Pro Gly Val
                485                 490                 495

Lys Glu Gly Asp Val Thr Asn Val Ala Gln Leu Lys Gly Val Ala Gln
            500                 505                 510

Asn Leu Asn Asn Arg Ile Asp Asn Val Asp Gly Asn Ala Arg Ala Gly
        515                 520                 525

Ile Ala Gln Ala Ile Ala Thr Ala Gly Leu Val Gln Ala Tyr Leu Pro
530                 535                 540

Gly Lys Ser Met Met Ala Ile Gly Gly Gly Thr Tyr Arg Gly Glu Ala
545                 550                 555                 560

Gly Tyr Ala Ile Gly Tyr Ser Ser Ile Ser Asp Gly Gly Asn Trp Ile
                565                 570                 575

Ile Lys Gly Thr Ala Ser Gly Asn Ser Arg Gly His Phe Gly Ala Ser
            580                 585                 590

Ala Ser Val Gly Tyr Gln Trp
        595

<210> SEQ ID NO 13
<211> LENGTH: 592

```
<212> TYPE: PRT
<213> ORGANISM: Neisseria meningitidis

<400> SEQUENCE: 13

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
50                  55                      60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Gln Gly Asn Ile
        355                 360                 365

Thr Val Met Tyr Asp Val Asn Val Gly Asp Ala Leu Asn Val Asn Gln
370                 375                 380

Leu Gln Asn Ser Gly Trp Asn Leu Asp Ser Lys Ala Val Ala Gly Ser
385                 390                 395                 400
```

```
Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
            435                 440                 445

Ser Val Ser Leu Gly Ala Gly Ala Asp Ala Pro Thr Leu Ser Val Asp
            450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
            485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
            515                 520                 525

Ala Gly Leu Val Gln Ala Tyr Leu Pro Gly Lys Ser Met Met Ala Ile
            530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
            580                 585                 590
```

<210> SEQ ID NO 14
<211> LENGTH: 592
<212> TYPE: PRT
<213> ORGANISM: Neisseria meningitidis

<400> SEQUENCE: 14

```
Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Phe Ala Thr Val Gln
            35                  40                  45

Ala Asn Ala Thr Asp Glu Asp Glu Glu Glu Leu Glu Ser Val Gln
50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
            85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
            115                 120                 125

Leu Lys Lys Asp Leu Thr Gly Leu Ile Asn Val Glu Thr Glu Lys Leu
            130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
            165                 170                 175

Val His Leu Asn Gly Ile Gly Ser Thr Leu Thr Asp Thr Leu Ala Gly
```

```
            180              185              190
Ser Ser Ala Ser His Val Asp Ala Gly Asn Gln Ser Thr His Tyr Thr
        195              200              205

Arg Ala Ala Ser Ile Lys Asp Val Leu Asn Ala Gly Trp Asn Ile Lys
        210              215              220

Gly Val Lys Thr Gly Ser Thr Thr Gly Gln Ser Glu Asn Val Asp Phe
225              230              235              240

Val Arg Thr Tyr Asp Thr Val Glu Phe Leu Ser Ala Asp Thr Lys Thr
                245              250              255

Thr Thr Val Asn Val Glu Ser Lys Asp Asn Gly Lys Arg Thr Glu Val
            260              265              270

Lys Ile Gly Ala Lys Thr Ser Val Ile Lys Glu Lys Asp Gly Lys Leu
        275              280              285

Val Thr Gly Lys Gly Lys Gly Glu Asn Gly Ser Ser Thr Asp Glu Gly
        290              295              300

Glu Gly Leu Val Thr Ala Lys Glu Val Ile Asp Ala Val Asn Lys Ala
305              310              315              320

Gly Trp Arg Met Lys Thr Thr Ala Asn Gly Gln Thr Gly Gln Ala
                325              330              335

Asp Lys Phe Glu Thr Val Thr Ser Gly Thr Asn Val Thr Phe Ala Ser
                340              345              350

Gly Lys Gly Thr Thr Ala Thr Val Ser Lys Asp Gln Gly Asn Ile
            355              360              365

Thr Val Met Tyr Asp Val Asn Val Gly Asp Ala Leu Asn Val Asn Gln
        370              375              380

Leu Gln Asn Ser Gly Trp Asn Leu Asp Ser Lys Ala Val Ala Gly Ser
385              390              395              400

Ser Gly Lys Val Ile Ser Gly Asn Val Ser Pro Ser Lys Gly Lys Met
                405              410              415

Asp Glu Thr Val Asn Ile Asn Ala Gly Asn Asn Ile Glu Ile Ser Arg
                420              425              430

Asn Gly Lys Asn Ile Asp Ile Ala Thr Ser Met Ala Pro Gln Phe Ser
            435              440              445

Ser Val Ser Leu Gly Ala Gly Ala Asp Ala Pro Thr Leu Ser Val Asp
        450              455              460

Asp Glu Gly Ala Leu Asn Val Gly Ser Lys Asp Ala Asn Lys Pro Val
465              470              475              480

Arg Ile Thr Asn Val Ala Pro Gly Val Lys Glu Gly Asp Val Thr Asn
                485              490              495

Val Ala Gln Leu Lys Gly Val Ala Gln Asn Leu Asn Asn Arg Ile Asp
            500              505              510

Asn Val Asp Gly Asn Ala Arg Ala Gly Ile Ala Gln Ala Ile Ala Thr
        515              520              525

Ala Gly Leu Val Gln Ala Tyr Leu Pro Gly Lys Ser Met Met Ala Ile
        530              535              540

Gly Gly Gly Thr Tyr Arg Gly Glu Ala Gly Tyr Ala Ile Gly Tyr Ser
545              550              555              560

Ser Ile Ser Asp Gly Gly Asn Trp Ile Ile Lys Gly Thr Ala Ser Gly
                565              570              575

Asn Ser Arg Gly His Phe Gly Ala Ser Ala Ser Val Gly Tyr Gln Trp
            580              585              590

<210> SEQ ID NO 15
```

<211> LENGTH: 592
<212> TYPE: PRT
<213> ORGANISM: Neisseria meningitidis

<400> SEQUENCE: 15

```
Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
    50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
```

```
                385                 390                 395                 400
        Ser Gly Lys Val Ile Ser Gly Asn Val Ser Pro Ser Lys Gly Lys Met
                            405                 410                 415

Asp Glu Thr Val Asn Ile Asn Ala Gly Asn Asn Ile Glu Ile Ser Arg
                            420                 425                 430

Asn Gly Lys Asn Ile Asp Ile Ala Thr Ser Met Ala Pro Gln Phe Ser
                            435                 440                 445

Ser Val Ser Leu Gly Ala Gly Ala Asp Ala Pro Thr Leu Ser Val Asp
                    450                 455                 460

Asp Glu Gly Ala Leu Asn Val Gly Ser Lys Asp Ala Asn Lys Pro Val
        465                 470                 475                 480

Arg Ile Thr Asn Val Ala Pro Gly Val Lys Glu Gly Asp Val Thr Asn
                            485                 490                 495

Val Ala Gln Leu Lys Gly Val Ala Gln Asn Leu Asn Asn Arg Ile Asp
                        500                 505                 510

Asn Val Asp Gly Asn Ala Arg Ala Gly Ile Ala Gln Ala Ile Ala Thr
                        515                 520                 525

Ala Gly Leu Val Gln Ala Tyr Leu Pro Gly Lys Ser Met Met Ala Ile
                530                 535                 540

Gly Gly Gly Thr Tyr Arg Gly Glu Ala Gly Tyr Ala Ile Gly Tyr Ser
        545                 550                 555                 560

Ser Ile Ser Asp Gly Gly Asn Trp Ile Ile Lys Gly Thr Ala Ser Gly
                            565                 570                 575

Asn Ser Arg Gly His Phe Gly Ala Ser Ala Ser Val Gly Tyr Gln Trp
                        580                 585                 590

<210> SEQ ID NO 16
<211> LENGTH: 592
<212> TYPE: PRT
<213> ORGANISM: Neisseria meningitidis

<400> SEQUENCE: 16

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
    50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175
```

Val His Leu Asn Gly Ile Gly Ser Thr Leu Thr Asp Thr Leu Ala Gly
            180                 185                 190

Ser Ser Ala Ser His Val Asp Ala Gly Asn Gln Ser Thr His Tyr Thr
        195                 200                 205

Arg Ala Ala Ser Ile Lys Asp Val Leu Asn Ala Gly Trp Asn Ile Lys
    210                 215                 220

Gly Val Lys Thr Gly Ser Thr Thr Gly Gln Ser Glu Asn Val Asp Phe
225                 230                 235                 240

Val Arg Thr Tyr Asp Thr Val Glu Phe Leu Ser Ala Thr Lys Thr
                245                 250                 255

Thr Thr Val Asn Val Glu Ser Lys Asp Asn Gly Lys Arg Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Glu Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380

Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
                405                 410                 415

Asp Glu Thr Val Asn Ile Asn Ala Gly Asn Asn Ile Glu Ile Ser Arg
            420                 425                 430

Asn Gly Lys Asn Ile Asp Ile Ala Thr Ser Met Ala Pro Gln Phe Ser
        435                 440                 445

Ser Val Ser Leu Gly Ala Gly Ala Asp Ala Pro Thr Leu Ser Val Asp
    450                 455                 460

Asp Glu Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
                485                 490                 495

Val Ala Gln Leu Lys Gly Val Ala Gln Asn Leu Asn Asn Arg Ile Asp
            500                 505                 510

Asn Val Asp Gly Asn Ala Arg Ala Gly Ile Ala Gln Ala Ile Ala Thr
        515                 520                 525

Ala Gly Leu Val Gln Ala Tyr Leu Pro Gly Lys Ser Met Met Ala Ile
    530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
                565                 570                 575

Asn Ser Arg Gly His Phe Gly Ala Ser Ala Ser Val Gly Tyr Gln Trp
            580                 585                 590

```
<210> SEQ ID NO 17
<211> LENGTH: 592
<212> TYPE: PRT
<213> ORGANISM: Neisseria meningitidis

<400> SEQUENCE: 17

Met Asn Lys Ile Tyr Arg Ile Ile Trp Asn Ser Ala Leu Asn Ala Trp
1               5                   10                  15

Val Ala Val Ser Glu Leu Thr Arg Asn His Thr Lys Arg Ala Ser Ala
            20                  25                  30

Thr Val Lys Thr Ala Val Leu Ala Thr Leu Leu Phe Ala Thr Val Gln
        35                  40                  45

Ala Asn Ala Thr Asp Glu Asp Glu Glu Glu Leu Glu Ser Val Gln
    50                  55                  60

Arg Ser Val Val Gly Ser Ile Gln Ala Ser Met Glu Gly Ser Gly Glu
65                  70                  75                  80

Leu Glu Thr Ile Ser Leu Ser Met Thr Asn Asp Ser Lys Glu Phe Val
                85                  90                  95

Asp Pro Tyr Ile Val Val Thr Leu Lys Ala Gly Asp Asn Leu Lys Ile
            100                 105                 110

Lys Gln Asn Thr Asn Glu Asn Thr Asn Ala Ser Ser Phe Thr Tyr Ser
        115                 120                 125

Leu Lys Lys Asp Leu Thr Gly Leu Ile Asn Val Glu Thr Glu Lys Leu
    130                 135                 140

Ser Phe Gly Ala Asn Gly Lys Lys Val Asn Ile Ile Ser Asp Thr Lys
145                 150                 155                 160

Gly Leu Asn Phe Ala Lys Glu Thr Ala Gly Thr Asn Gly Asp Thr Thr
                165                 170                 175

Val His Leu Asn Gly Ile Gly Ser Thr Leu Thr Asp Met Leu Leu Asn
            180                 185                 190

Thr Gly Ala Thr Thr Asn Val Thr Asn Asp Asn Val Thr Asp Asp Glu
        195                 200                 205

Lys Lys Arg Ala Ala Ser Val Lys Asp Val Leu Asn Ala Gly Trp Asn
    210                 215                 220

Ile Lys Gly Val Lys Pro Gly Thr Thr Ala Ser Asp Asn Val Asp Phe
225                 230                 235                 240

Val Arg Thr Tyr Asp Thr Val Glu Phe Leu Ser Ala Asp Thr Lys Thr
                245                 250                 255

Thr Thr Val Asn Val Glu Ser Lys Asp Asn Gly Lys Lys Thr Glu Val
            260                 265                 270

Lys Ile Gly Ala Lys Thr Ser Val Ile Lys Glu Lys Asp Gly Lys Leu
        275                 280                 285

Val Thr Gly Lys Gly Lys Gly Asn Gly Ser Ser Thr Asp Glu Gly
    290                 295                 300

Glu Gly Leu Val Thr Ala Lys Glu Val Ile Asp Ala Val Asn Lys Ala
305                 310                 315                 320

Gly Trp Arg Met Lys Thr Thr Ala Asn Gly Gln Thr Gly Gln Ala
                325                 330                 335

Asp Lys Phe Glu Thr Val Thr Ser Gly Thr Asn Val Thr Phe Ala Ser
            340                 345                 350

Gly Lys Gly Thr Thr Ala Thr Val Ser Lys Asp Asp Gln Gly Asn Ile
        355                 360                 365

Thr Val Met Tyr Asp Val Asn Val Gly Asp Ala Leu Asn Val Asn Gln
    370                 375                 380
```

```
Leu Gln Asn Ser Gly Trp Asn Leu Asp Ser Lys Ala Val Ala Gly Ser
385                 390                 395                 400

Ser Gly Lys Val Ile Ser Gly Asn Val Ser Pro Ser Lys Gly Lys Met
            405                 410                 415

Asp Glu Thr Val Asn Ile Asn Ala Gly Asn Asn Ile Glu Ile Thr Arg
        420                 425                 430

Asn Gly Lys Asn Ile Asp Ile Ala Thr Ser Met Thr Pro Gln Phe Ser
    435                 440                 445

Ser Val Ser Leu Gly Ala Gly Ala Asp Ala Pro Thr Leu Ser Val Asp
450                 455                 460

Asp Lys Gly Ala Leu Asn Val Gly Ser Lys Asp Ala Asn Lys Pro Val
465                 470                 475                 480

Arg Ile Thr Asn Val Ala Pro Gly Val Lys Glu Gly Asp Val Thr Asn
            485                 490                 495

Val Ala Gln Leu Lys Gly Val Ala Gln Asn Leu Asn Asn Arg Ile Asp
        500                 505                 510

Asn Val Asp Gly Asn Ala Arg Ala Gly Ile Ala Gln Ala Ile Ala Thr
    515                 520                 525

Ala Gly Leu Val Gln Ala Tyr Leu Pro Gly Lys Ser Met Met Ala Ile
530                 535                 540

Gly Gly Gly Thr Tyr Arg Gly Glu Ala Gly Tyr Ala Ile Gly Tyr Ser
545                 550                 555                 560

Ser Ile Ser Asp Gly Gly Asn Trp Ile Ile Lys Gly Thr Ala Ser Gly
            565                 570                 575

Asn Ser Arg Gly His Phe Gly Ala Ser Ala Ser Val Gly Tyr Gln Trp
        580                 585                 590

<210> SEQ ID NO 18
<211> LENGTH: 589
<212> TYPE: PRT
<213> ORGANISM: Neisseria meningitidis

<400> SEQUENCE: 18

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
                20                  25                  30

Thr Val Ala Thr Ala Val Leu Ala Thr Leu Leu Ser Ala Thr Val Gln
            35                  40                  45

Ala Asn Ala Thr Asp Thr Asp Glu Asp Glu Glu Leu Glu Ser Val Val
        50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
                85                  90                  95

His Asn Thr Leu His Gly Ala Thr Val Thr Leu Lys Ala Gly Asp Asn
            100                 105                 110

Leu Lys Ile Lys Gln Ser Gly Lys Asp Phe Thr Tyr Ser Leu Lys Lys
        115                 120                 125

Glu Leu Lys Asp Leu Thr Ser Val Glu Thr Lys Leu Ser Phe Gly
        130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175
```

```
Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
            195                 200                 205

Ser Ile Lys Asp Val Leu Asn Ala Gly Trp Asn Ile Lys Gly Val Lys
            210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
            275                 280                 285

Lys Gly Lys Gly Glu Asn Gly Ser Ser Thr Asp Glu Gly Glu Gly Leu
290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
                340                 345                 350

Thr Thr Ala Thr Val Ser Lys Asp Asp Gln Gly Asn Ile Thr Val Lys
            355                 360                 365

Tyr Asp Val Asn Val Gly Asp Ala Leu Asn Val Asn Gln Leu Gln Asn
            370                 375                 380

Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
                405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
            435                 440                 445

Leu Gly Ala Gly Ala Asp Ala Pro Thr Leu Ser Val Asp Asp Glu Gly
450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
                485                 490                 495

Leu Lys Gly Val Ala Gln Asn Leu Asn Asn Arg Ile Asp Asn Val Asp
            500                 505                 510

Gly Asn Ala Arg Ala Gly Ile Ala Gln Ala Ile Ala Thr Ala Gly Leu
            515                 520                 525

Ala Gln Ala Tyr Leu Pro Gly Lys Ser Met Met Ala Ile Gly Gly Gly
            530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
                565                 570                 575

Gly His Phe Gly Thr Ser Ala Ser Val Gly Tyr Gln Trp
            580                 585
```

<210> SEQ ID NO 19
<211> LENGTH: 589
<212> TYPE: PRT
<213> ORGANISM: Neisseria meningitidis

<400> SEQUENCE: 19

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Ser Ala Thr Val Gln
        35                  40                  45

Ala Asn Ala Thr Asp Thr Asp Glu Asp Glu Glu Leu Glu Ser Val Val
    50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
                85                  90                  95

His Asn Thr Leu His Gly Ala Thr Val Thr Leu Lys Ala Gly Asp Asn
            100                 105                 110

Leu Lys Ile Lys Gln Ser Gly Lys Asp Phe Thr Tyr Ser Leu Lys Lys
        115                 120                 125

Glu Leu Lys Asp Leu Thr Ser Val Thr Glu Lys Leu Ser Phe Gly
    130                 135                 140

Ala Asn Gly Asn Lys Val Asn Ile Thr Ser Asp Thr Lys Gly Leu Asn
145                 150                 155                 160

Phe Ala Lys Glu Thr Ala Gly Thr Asn Gly Asp Pro Thr Val His Leu
                165                 170                 175

Asn Gly Ile Gly Ser Thr Leu Thr Asp Thr Leu Ala Gly Ser Ser Ala
            180                 185                 190

Ser His Val Asp Ala Gly Asn Gln Ser Thr His Tyr Thr Arg Ala Ala
        195                 200                 205

Ser Ile Lys Asp Val Leu Asn Ala Gly Trp Asn Ile Lys Gly Val Lys
    210                 215                 220

Thr Gly Ser Thr Thr Gly Gln Ser Glu Asn Val Asp Phe Val Arg Thr
225                 230                 235                 240

Tyr Asp Thr Val Glu Phe Leu Ser Ala Asp Thr Lys Thr Thr Thr Val
                245                 250                 255

Asn Val Glu Ser Lys Asp Asn Gly Lys Arg Thr Glu Val Lys Ile Gly
            260                 265                 270

Ala Lys Thr Ser Val Ile Lys Glu Lys Asp Gly Lys Leu Val Thr Gly
        275                 280                 285

Lys Gly Lys Gly Glu Asn Gly Ser Ser Thr Asp Glu Gly Glu Gly Leu
    290                 295                 300

Val Thr Ala Lys Glu Val Ile Asp Ala Val Asn Lys Ala Gly Trp Arg
305                 310                 315                 320

Met Lys Thr Thr Thr Ala Asn Gly Gln Thr Gly Gln Ala Asp Lys Phe
                325                 330                 335

Glu Thr Val Thr Ser Gly Thr Lys Val Thr Phe Ala Ser Gly Asn Gly
            340                 345                 350

Thr Thr Ala Thr Val Ser Lys Asp Asp Gln Gly Asn Ile Thr Val Lys
        355                 360                 365

Tyr Asp Val Asn Val Gly Asp Ala Leu Asn Val Asn Gln Leu Gln Asn
    370                 375                 380

```
Ser Gly Trp Asn Leu Asp Ser Lys Ala Val Ala Gly Ser Ser Gly Lys
385                 390                 395                 400

Val Ile Ser Gly Asn Val Ser Pro Ser Lys Gly Lys Met Asp Glu Thr
            405                 410                 415

Val Asn Ile Asn Ala Gly Asn Asn Ile Glu Ile Thr Arg Asn Gly Lys
            420                 425                 430

Asn Ile Asp Ile Ala Thr Ser Met Thr Pro Gln Phe Ser Ser Val Ser
            435                 440                 445

Leu Gly Ala Gly Ala Asp Ala Pro Thr Leu Ser Val Asp Asp Glu Gly
            450                 455                 460

Ala Leu Asn Val Gly Ser Lys Asp Ala Asn Lys Pro Val Arg Ile Thr
465                 470                 475                 480

Asn Val Ala Pro Gly Val Lys Glu Gly Asp Val Thr Asn Val Ala Gln
            485                 490                 495

Leu Lys Gly Val Ala Gln Asn Leu Asn Asn Arg Ile Asp Asn Val Asp
            500                 505                 510

Gly Asn Ala Arg Ala Gly Ile Ala Gln Ala Ile Ala Thr Ala Gly Leu
            515                 520                 525

Ala Gln Ala Tyr Leu Pro Gly Lys Ser Met Met Ala Ile Gly Gly Gly
            530                 535                 540

Thr Tyr Arg Gly Glu Ala Gly Tyr Ala Ile Gly Tyr Ser Ser Ile Ser
545                 550                 555                 560

Asp Thr Gly Asn Trp Val Ile Lys Gly Thr Ala Ser Gly Asn Ser Arg
            565                 570                 575

Gly His Phe Gly Thr Ser Ala Ser Val Gly Tyr Gln Trp
            580                 585

<210> SEQ ID NO 20
<211> LENGTH: 595
<212> TYPE: PRT
<213> ORGANISM: Neisseria meningitidis

<400> SEQUENCE: 20

Met Asn Lys Ile Tyr Arg Ile Ile Trp Asn Ser Ala Leu Asn Ala Trp
1               5                   10                  15

Val Val Val Ser Glu Leu Thr Arg Asn His Thr Lys Arg Ala Ser Ala
            20                  25                  30

Thr Val Glu Thr Ala Val Leu Ala Thr Leu Phe Ala Thr Val Gln
            35                  40                  45

Ala Asn Ala Thr Asp Thr Asp Glu Asp Glu Leu Glu Pro Val Val
50                  55                  60

Arg Ser Ala Leu Val Leu Gln Phe Met Ile Asp Lys Glu Gly Asn Gly
65                  70                  75                  80

Glu Ile Glu Ser Thr Gly Asp Ile Gly Trp Ser Ile Tyr Tyr Asp Asp
            85                  90                  95

His Asn Thr Leu His Gly Ala Thr Val Thr Leu Lys Ala Gly Asp Asn
            100                 105                 110

Leu Lys Ile Lys Gln Asn Thr Asp Glu Asn Thr Asn Ala Ser Ser Phe
            115                 120                 125

Thr Tyr Ser Leu Lys Lys Asp Leu Thr Asp Leu Thr Ser Val Gly Thr
            130                 135                 140

Glu Glu Leu Ser Phe Gly Ala Asn Gly Asn Lys Val Asn Ile Thr Ser
145                 150                 155                 160

Asp Thr Lys Gly Leu Asn Phe Ala Lys Lys Thr Ala Gly Thr Asn Gly
```

-continued

```
                165                 170                 175
Asp Thr Thr Val His Leu Asn Gly Ile Gly Ser Thr Leu Thr Asp Thr
                    180                 185                 190

Leu Ala Gly Ser Ser Ala Ser His Val Asp Ala Gly Asn Gln Ser Thr
                195                 200                 205

His Tyr Thr Arg Ala Ala Ser Ile Lys Asp Val Leu Asn Ala Gly Trp
            210                 215                 220

Asn Ile Lys Gly Val Lys Thr Gly Ser Thr Thr Gly Gln Ser Glu Asn
225                 230                 235                 240

Val Asp Phe Val Arg Thr Tyr Asp Thr Val Glu Phe Leu Ser Ala Asp
                245                 250                 255

Thr Lys Thr Thr Thr Val Asn Val Glu Ser Lys Asp Asn Gly Lys Arg
                260                 265                 270

Thr Glu Val Lys Ile Gly Ala Lys Thr Ser Val Ile Lys Glu Lys Asp
            275                 280                 285

Gly Lys Leu Val Thr Gly Lys Gly Lys Gly Glu Asn Gly Ser Ser Thr
        290                 295                 300

Asp Glu Gly Glu Gly Leu Val Thr Ala Lys Glu Val Ile Asp Ala Val
305                 310                 315                 320

Asn Lys Ala Gly Trp Arg Met Lys Thr Thr Thr Ala Asn Gly Gln Thr
                325                 330                 335

Gly Gln Ala Asp Lys Phe Glu Thr Val Thr Ser Gly Thr Asn Val Thr
            340                 345                 350

Phe Ala Ser Gly Lys Gly Thr Thr Ala Thr Val Ser Lys Asp Asp Gln
        355                 360                 365

Gly Asn Ile Thr Val Lys Tyr Asp Val Asn Val Gly Asp Ala Leu Asn
    370                 375                 380

Val Asn Gln Leu Gln Asn Ser Gly Trp Asn Leu Asp Ser Lys Ala Val
385                 390                 395                 400

Ala Gly Ser Ser Gly Lys Val Ile Ser Gly Asn Val Ser Pro Ser Lys
                405                 410                 415

Gly Lys Met Asp Glu Thr Val Asn Ile Asn Ala Gly Asn Asn Ile Glu
            420                 425                 430

Ile Thr Arg Asn Gly Lys Asn Ile Asp Ile Ala Thr Ser Met Thr Pro
        435                 440                 445

Gln Phe Ser Ser Val Ser Leu Gly Ala Gly Ala Asp Ala Pro Thr Leu
    450                 455                 460

Ser Val Asp Asp Glu Gly Ala Leu Asn Val Gly Ser Lys Asp Ala Asn
465                 470                 475                 480

Lys Pro Val Arg Ile Thr Asn Val Ala Pro Gly Val Lys Glu Gly Asp
                485                 490                 495

Val Thr Asn Val Ala Gln Leu Lys Gly Val Ala Gln Asn Leu Asn Asn
            500                 505                 510

His Ile Asp Asn Val Asp Gly Asn Ala Arg Ala Gly Ile Ala Gln Ala
        515                 520                 525

Ile Ala Thr Ala Gly Leu Val Gln Ala Tyr Leu Pro Gly Lys Ser Met
    530                 535                 540

Met Ala Ile Gly Gly Gly Thr Tyr Arg Gly Glu Ala Gly Tyr Ala Ile
545                 550                 555                 560

Gly Tyr Ser Ser Ile Ser Asp Gly Gly Asn Trp Ile Ile Lys Gly Thr
                565                 570                 575

Ala Ser Gly Asn Ser Arg Gly His Phe Gly Ala Ser Ala Ser Val Gly
            580                 585                 590
```

Tyr Gln Trp
        595

<210> SEQ ID NO 21
<211> LENGTH: 600
<212> TYPE: PRT
<213> ORGANISM: Neisseria meningitidis

<400> SEQUENCE: 21

Met Asn Lys Ile Tyr Arg Ile Ile Trp Asn Ile Ala Leu Asn Ala Trp
1               5                   10                  15

Val Val Val Ser Glu Leu Thr Arg Asn His Thr Lys Arg Ala Ser Ala
            20                  25                  30

Thr Val Ala Thr Ala Val Leu Ala Thr Leu Leu Ser Ala Thr Val Gln
        35                  40                  45

Ala Asn Ala Thr Asp Glu Glu Asp Asn Glu Asp Leu Glu Pro Val Val
    50                  55                  60

Arg Thr Ala Pro Val Leu Ser Phe His Ser Asp Lys Glu Gly Thr Gly
65                  70                  75                  80

Glu Lys Glu Glu Val Gly Ala Ser Ser Asn Leu Thr Val Tyr Phe Asp
                85                  90                  95

Lys Asn Arg Val Leu Lys Ala Gly Thr Ile Thr Leu Lys Ala Gly Asp
            100                 105                 110

Asn Leu Lys Ile Lys Gln Asn Thr Asn Glu Asn Thr Asn Glu Asn Thr
        115                 120                 125

Asn Ala Ser Ser Phe Thr Tyr Ser Leu Lys Lys Asp Leu Thr Gly Leu
    130                 135                 140

Ile Asn Val Glu Thr Glu Lys Leu Ser Phe Gly Ala Asn Gly Lys Lys
145                 150                 155                 160

Val Asn Ile Ile Ser Asp Thr Lys Gly Leu Asn Phe Ala Lys Glu Thr
                165                 170                 175

Ala Gly Thr Asn Gly Asp Pro Thr Val His Leu Asn Gly Ile Gly Ser
            180                 185                 190

Thr Leu Thr Asp Thr Leu Ala Gly Ser Ser Ala Ser His Val Asp Ala
        195                 200                 205

Gly Asn Gln Ser Thr His Tyr Thr Arg Ala Ala Ser Ile Lys Asp Val
    210                 215                 220

Leu Asn Ala Gly Trp Asn Ile Lys Gly Val Lys Thr Gly Ser Thr Thr
225                 230                 235                 240

Gly Gln Ser Glu Asn Val Asp Phe Val Arg Thr Tyr Asp Thr Val Glu
                245                 250                 255

Phe Leu Ser Ala Asp Thr Lys Thr Thr Thr Val Asn Val Glu Ser Lys
            260                 265                 270

Asp Asn Gly Lys Arg Thr Glu Val Lys Ile Gly Ala Lys Thr Ser Val
        275                 280                 285

Ile Lys Glu Lys Asp Gly Lys Leu Val Thr Gly Lys Gly Lys Gly Glu
    290                 295                 300

Asn Gly Ser Ser Thr Asp Glu Gly Glu Gly Leu Val Thr Ala Lys Glu
305                 310                 315                 320

Val Ile Asp Ala Val Asn Lys Ala Gly Trp Arg Met Lys Thr Thr Thr
                325                 330                 335

Ala Asn Gly Gln Thr Gly Gln Ala Asp Lys Phe Glu Thr Val Thr Ser
            340                 345                 350

Gly Thr Lys Val Thr Phe Ala Ser Gly Asn Gly Thr Thr Ala Thr Val

```
                355                 360                 365
Ser Lys Asp Asp Gln Gly Asn Ile Thr Val Lys Tyr Asp Val Asn Val
370                 375                 380

Gly Asp Ala Leu Asn Val Asn Gln Leu Gln Asn Ser Gly Trp Asn Leu
385                 390                 395                 400

Asp Ser Lys Ala Val Ala Gly Ser Ser Lys Val Ile Ser Gly Asn
                405                 410                 415

Val Ser Pro Ser Lys Gly Lys Met Asp Glu Thr Val Asn Ile Asn Ala
                420                 425                 430

Gly Asn Asn Ile Glu Ile Thr Arg Asn Gly Lys Asn Ile Asp Ile Ala
                435                 440                 445

Thr Ser Met Thr Pro Gln Phe Ser Ser Val Ser Leu Gly Ala Gly Ala
            450                 455                 460

Asp Ala Pro Thr Leu Ser Val Asp Asp Gly Ala Leu Asn Val Gly
465                 470                 475                 480

Ser Lys Asp Ala Asn Lys Pro Val Arg Ile Thr Asn Val Ala Pro Gly
                485                 490                 495

Val Lys Glu Gly Asp Val Thr Asn Val Ala Gln Leu Lys Gly Val Ala
                500                 505                 510

Gln Asn Leu Asn Asn Arg Ile Asp Asn Val Asp Gly Asn Ala Arg Ala
                515                 520                 525

Gly Ile Ala Gln Ala Ile Ala Thr Ala Gly Leu Val Gln Ala Tyr Leu
                530                 535                 540

Pro Gly Lys Ser Met Met Ala Ile Gly Gly Thr Tyr Arg Gly Glu
545                 550                 555                 560

Ala Gly Tyr Ala Ile Gly Tyr Ser Ser Ile Ser Asp Gly Asn Trp
                565                 570                 575

Ile Ile Lys Gly Thr Ala Ser Gly Asn Ser Arg Gly His Phe Gly Ala
                580                 585                 590

Ser Ala Ser Val Gly Tyr Gln Trp
                595                 600

<210> SEQ ID NO 22
<211> LENGTH: 288
<212> TYPE: PRT
<213> ORGANISM: Neisseria gonorrhoeae

<400> SEQUENCE: 22

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ala Ala Pro Ser Ala Asp Asn Gly Ala Ala Lys Lys Glu Ile Val Phe
            35                  40                  45

Gly Thr Thr Val Gly Asp Phe Gly Asp Met Val Lys Glu Gln Ile Gln
50                  55                  60

Ala Glu Leu Glu Lys Lys Gly Tyr Thr Val Lys Leu Val Glu Phe Thr
65                  70                  75                  80

Asp Tyr Val Arg Pro Asn Leu Ala Leu Ala Glu Gly Glu Leu Asp Ile
                85                  90                  95

Asn Val Phe Gln His Lys Pro Tyr Leu Asp Asp Phe Lys Lys Glu His
                100                 105                 110

Asn Leu Asp Ile Thr Glu Ala Phe Gln Val Pro Thr Ala Pro Leu Gly
            115                 120                 125
```

```
Leu Tyr Pro Gly Lys Leu Lys Ser Leu Glu Glu Val Lys Asp Gly Ser
    130                 135                 140

Thr Val Ser Ala Pro Asn Asp Pro Ser Asn Phe Ala Arg Ala Leu Val
145                 150                 155                 160

Met Leu Asn Glu Leu Gly Trp Ile Lys Leu Lys Asp Gly Ile Asn Pro
                165                 170                 175

Leu Thr Ala Ser Lys Ala Asp Ile Ala Glu Asn Leu Lys Asn Ile Lys
                180                 185                 190

Ile Val Glu Leu Glu Ala Ala Gln Leu Pro Arg Ser Arg Ala Asp Val
            195                 200                 205

Asp Phe Ala Val Val Asn Gly Asn Tyr Ala Ile Ser Ser Gly Met Lys
210                 215                 220

Leu Thr Glu Ala Leu Phe Gln Glu Pro Ser Phe Ala Tyr Val Asn Trp
225                 230                 235                 240

Ser Ala Val Lys Thr Ala Asp Lys Asp Ser Gln Trp Leu Lys Asp Val
                245                 250                 255

Thr Glu Ala Tyr Asn Ser Asp Ala Phe Lys Ala Tyr Ala His Lys Arg
                260                 265                 270

Phe Glu Gly Tyr Lys Tyr Pro Ala Ala Trp Asn Glu Gly Ala Ala Lys
                275                 280                 285

<210> SEQ ID NO 23
<211> LENGTH: 288
<212> TYPE: PRT
<213> ORGANISM: Neisseria gonorrhoeae

<400> SEQUENCE: 23

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ala Ala Pro Ser Ala Asp Asn Gly Ala Ala Lys Lys Glu Ile Val Phe
            35                  40                  45

Gly Thr Thr Val Gly Asp Phe Gly Asp Met Val Lys Glu Gln Ile Gln
50                  55                  60

Ala Glu Leu Glu Lys Lys Gly Tyr Thr Val Lys Leu Val Glu Phe Thr
65                  70                  75                  80

Asp Tyr Val Arg Pro Asn Leu Ala Leu Ala Glu Gly Glu Leu Asp Ile
                85                  90                  95

Asn Val Phe Gln His Lys Pro Tyr Leu Asp Asp Phe Lys Lys Glu His
            100                 105                 110

Asn Leu Asp Ile Thr Glu Ala Phe Gln Val Pro Thr Ala Pro Leu Gly
        115                 120                 125

Leu Tyr Pro Gly Lys Leu Lys Ser Leu Glu Glu Val Lys Asp Gly Ser
    130                 135                 140

Thr Val Ser Ala Pro Asn Asp Pro Ser Asn Phe Ala Arg Ala Leu Val
145                 150                 155                 160

Met Leu Asn Glu Leu Gly Trp Ile Lys Leu Lys Asp Gly Ile Asn Pro
                165                 170                 175

Leu Thr Ala Ser Lys Ala Asp Ile Ala Glu Asn Leu Lys Asn Ile Lys
                180                 185                 190

Ile Val Glu Leu Glu Ala Ala Gln Leu Pro Arg Ser Arg Ala Asp Val
            195                 200                 205

Asp Phe Ala Val Val Asn Gly Asn Tyr Ala Ile Ser Ser Gly Met Lys
210                 215                 220
```

Leu Thr Glu Ala Leu Phe Gln Glu Pro Ser Phe Ala Tyr Val Asn Trp
225                 230                 235                 240

Ser Ala Val Lys Thr Ala Asp Lys Asp Ser Gln Trp Leu Lys Asp Val
            245                 250                 255

Thr Glu Ala Tyr Asn Ser Asp Ala Phe Lys Ala Tyr Ala His Lys Arg
        260                 265                 270

Phe Glu Gly Tyr Lys Tyr Pro Ala Ala Trp Asn Glu Gly Ala Ala Lys
    275                 280                 285

<210> SEQ ID NO 24
<211> LENGTH: 288
<212> TYPE: PRT
<213> ORGANISM: Neisseria gonorrhoeae

<400> SEQUENCE: 24

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ser Ala
            20                  25                  30

Ala Ala Pro Ser Ala Asp Asn Gly Ala Ala Lys Lys Glu Ile Val Phe
        35                  40                  45

Gly Thr Thr Val Gly Asp Phe Gly Asp Met Val Lys Glu Gln Ile Gln
    50                  55                  60

Ala Glu Leu Glu Lys Lys Gly Tyr Thr Val Lys Leu Val Glu Phe Thr
65                  70                  75                  80

Asp Tyr Val Arg Pro Asn Leu Ala Leu Ala Glu Gly Glu Leu Asp Ile
                85                  90                  95

Asn Val Phe Gln His Lys Pro Tyr Leu Asp Asp Phe Lys Lys Glu His
            100                 105                 110

Asn Leu Asp Ile Thr Glu Ala Phe Gln Val Pro Thr Ala Pro Leu Gly
        115                 120                 125

Leu Tyr Pro Gly Lys Leu Lys Ser Leu Glu Glu Val Lys Asp Gly Ser
    130                 135                 140

Thr Val Ser Ala Pro Asn Asp Pro Ser Asn Phe Ala Arg Ala Leu Val
145                 150                 155                 160

Met Leu Asn Glu Leu Gly Trp Ile Lys Leu Lys Asp Gly Ile Asn Pro
                165                 170                 175

Leu Thr Ala Ser Lys Ala Asp Ile Ala Glu Asn Leu Lys Asn Ile Lys
            180                 185                 190

Ile Val Glu Leu Glu Ala Ala Gln Leu Pro Arg Ser Arg Ala Asp Val
        195                 200                 205

Asp Phe Ala Val Val Asn Gly Asn Tyr Ala Ile Ser Ser Gly Met Lys
    210                 215                 220

Leu Thr Glu Ala Leu Phe Gln Glu Pro Ser Phe Ala Tyr Val Asn Trp
225                 230                 235                 240

Ser Ala Val Lys Thr Ala Asp Lys Asp Ser Gln Trp Leu Lys Asp Val
                245                 250                 255

Thr Glu Ala Tyr Asn Ser Asp Ala Phe Lys Ala Tyr Ala His Lys Arg
            260                 265                 270

Phe Glu Gly Tyr Lys Tyr Pro Ala Ala Trp Asn Glu Gly Ala Ala Lys
        275                 280                 285

<210> SEQ ID NO 25
<211> LENGTH: 287
<212> TYPE: PRT

<213> ORGANISM: Neisseria meningitidis

<400> SEQUENCE: 25

Met Lys Thr Phe Phe Lys Thr Leu Ser Ala Ala Leu Ala Leu Ile
1               5                   10                  15

Leu Ala Ala Cys Gly Gly Gln Lys Asp Ser Pro Ala Ala Ser Ala
                20                  25                  30

Ser Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 26
<211> LENGTH: 287
<212> TYPE: PRT
<213> ORGANISM: Neisseria meningitidis

<400> SEQUENCE: 26

Met Lys Thr Phe Phe Lys Thr Leu Ser Ala Ala Leu Ala Leu Ile
1               5                   10                  15

Leu Ala Ala Cys Gly Gly Gln Lys Asp Ser Pro Ala Ala Ser Ala
                20                  25                  30

Ser Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp

```
                65                  70                  75                  80
Tyr Val Arg Pro Asn Leu Ala Leu Ala Glu Gly Glu Leu Asp Ile Asn
                    85                  90                  95
Val Phe Gln His Lys Pro Tyr Leu Asp Asp Phe Lys Lys Glu His Asn
                100                 105                 110
Leu Asp Ile Thr Glu Val Phe Gln Val Pro Thr Ala Pro Leu Gly Leu
                115                 120                 125
Tyr Pro Gly Lys Leu Lys Ser Leu Glu Glu Val Lys Asp Gly Ser Thr
            130                 135                 140
Val Ser Ala Pro Asn Asp Pro Ser Asn Phe Ala Arg Val Leu Val Met
145                 150                 155                 160
Leu Asp Glu Leu Gly Trp Ile Lys Leu Lys Asp Gly Ile Asn Pro Leu
                165                 170                 175
Thr Ala Ser Lys Ala Asp Ile Ala Glu Asn Leu Lys Asn Ile Lys Ile
                180                 185                 190
Val Glu Leu Glu Ala Ala Gln Leu Pro Arg Ser Arg Ala Asp Val Asp
            195                 200                 205
Phe Ala Val Val Asn Gly Asn Tyr Ala Ile Ser Ser Gly Met Lys Leu
    210                 215                 220
Thr Glu Ala Leu Phe Gln Glu Pro Ser Phe Ala Tyr Val Asn Trp Ser
225                 230                 235                 240
Ala Val Lys Thr Ala Asp Lys Asp Ser Gln Trp Leu Lys Asp Val Thr
                245                 250                 255
Glu Ala Tyr Asn Ser Asp Ala Phe Lys Ala Tyr Ala His Lys Arg Phe
                260                 265                 270
Glu Gly Tyr Lys Ser Pro Ala Ala Trp Asn Glu Gly Ala Ala Lys
            275                 280                 285

<210> SEQ ID NO 27
<211> LENGTH: 287
<212> TYPE: PRT
<213> ORGANISM: Neisseria meningitidis

<400> SEQUENCE: 27

Met Lys Thr Phe Phe Lys Thr Leu Ser Ala Ala Ala Leu Ala Leu Ile
1               5                   10                  15
Leu Ala Ala Cys Gly Gly Gln Lys Asp Ser Ala Pro Ala Ala Ser Ala
                20                  25                  30
Ser Ala Ala Ala Asp Asn Gly Ala Glu Lys Lys Glu Ile Val Phe Gly
            35                  40                  45
Thr Thr Val Gly Asp Phe Gly Asp Met Val Lys His Ile Gln Pro
    50                  55                  60
Glu Leu Glu Lys Lys Gly Tyr Thr Val Lys Leu Val Glu Phe Thr Asp
65                  70                  75                  80
Tyr Val Arg Pro Asn Leu Ala Leu Ala Glu Gly Glu Leu Asp Ile Asn
                85                  90                  95
Val Phe Gln His Lys Pro Tyr Leu Asp Asp Phe Lys Lys Glu His Asn
                100                 105                 110
Leu Asp Ile Thr Glu Val Phe Gln Val Pro Thr Ala Pro Leu Gly Leu
            115                 120                 125
Tyr Pro Gly Lys Leu Lys Ser Leu Glu Glu Val Lys Asp Gly Ser Thr
    130                 135                 140
Val Ser Ala Pro Asn Asp Pro Ser Asn Phe Ala Arg Val Leu Val Met
145                 150                 155                 160
```

```
Leu Asp Glu Leu Gly Trp Ile Lys Leu Lys Asp Gly Ile Asn Pro Leu
            165                 170                 175

Thr Ala Ser Lys Ala Asp Ile Ala Glu Asn Leu Lys Asn Ile Lys Ile
        180                 185                 190

Val Glu Leu Glu Ala Ala Gln Leu Pro Arg Ser Arg Ala Asp Val Asp
            195                 200                 205

Phe Ala Val Val Asn Gly Asn Tyr Ala Ile Ser Ser Gly Met Lys Leu
        210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
        260                 265                 270

Glu Gly Tyr Lys Ser Pro Ala Ala Trp Asn Glu Gly Ala Ala Lys
            275                 280                 285

<210> SEQ ID NO 28
<211> LENGTH: 287
<212> TYPE: PRT
<213> ORGANISM: Neisseria meningitidis

<400> SEQUENCE: 28

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala Glu Lys Lys Glu Ile Val Phe Gly
        35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255
```

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Gly Ala Ala Lys
            275                 280                 285

<210> SEQ ID NO 29
<211> LENGTH: 287
<212> TYPE: PRT
<213> ORGANISM: Neisseria meningitidis

<400> SEQUENCE: 29

Met Lys Thr Phe Phe Lys Thr Leu Ser Ala Ala Leu Ala Leu Ile
1               5                   10                  15

Leu Ala Ala Cys Gly Gly Gln Lys Asp Ser Pro Ala Ala Ser Ala
                20                  25                  30

Ser Ala Ala Ala Asp Asn Gly Ala Glu Lys Lys Glu Ile Val Phe Gly
                35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
                115                 120                 125

Tyr Pro Gly Lys Leu Lys Ser Leu Glu Glu Val Lys Asp Gly Ser Thr
        130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Gly Ala Ala Lys
            275                 280                 285

<210> SEQ ID NO 30
<211> LENGTH: 287
<212> TYPE: PRT
<213> ORGANISM: Neisseria meningitidis

<400> SEQUENCE: 30

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285

<210> SEQ ID NO 31
<211> LENGTH: 287
<212> TYPE: PRT
<213> ORGANISM: Neisseria meningitidis

<400> SEQUENCE: 31

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn

```
                    100                 105                 110
Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
        130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 32
<211> LENGTH: 287
<212> TYPE: PRT
<213> ORGANISM: Neisseria meningitidis

<400> SEQUENCE: 32

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala Glu Lys Lys Glu Ile Val Phe Gly
        35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190
```

```
Val Glu Leu Glu Ala Ala Gln Leu Pro Arg Ser Arg Ala Asp Val Asp
            195                 200                 205

Phe Ala Val Val Asn Gly Asn Tyr Ala Ile Ser Ser Gly Met Lys Leu
        210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285

<210> SEQ ID NO 33
<211> LENGTH: 287
<212> TYPE: PRT
<213> ORGANISM: Neisseria meningitidis

<400> SEQUENCE: 33

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala Glu Lys Lys Glu Ile Val Phe Gly
        35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285
```

<210> SEQ ID NO 34
<211> LENGTH: 287
<212> TYPE: PRT
<213> ORGANISM: Neisseria meningitidis

<400> SEQUENCE: 34

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Pro Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 35
<211> LENGTH: 287
<212> TYPE: PRT
<213> ORGANISM: Neisseria meningitidis

<400> SEQUENCE: 35

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
                115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
    195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
    275                 280                 285

<210> SEQ ID NO 36
<211> LENGTH: 287
<212> TYPE: PRT
<213> ORGANISM: Neisseria meningitidis

<400> SEQUENCE: 36

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu His Ile Gln Pro
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
                115                 120                 125

Tyr Pro Gly Lys Leu Lys Ser Leu Glu Glu Val Lys Asp Gly Ser Thr

```
                130                 135                 140
Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
                195                 200                 205

Phe Ala Val Val Asn Gly Asn Tyr Ala Ile Ser Ser Gly Met Lys Leu
        210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285

<210> SEQ ID NO 37
<211> LENGTH: 287
<212> TYPE: PRT
<213> ORGANISM: Neisseria meningitidis

<400> SEQUENCE: 37

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Glu Lys Lys Glu Ile Val Phe Gly
            35                  40                  45

Thr Thr Val Gly Asp Phe Gly Asp Met Val Lys Glu Gln Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
        130                 135                 140

Val Ser Ala Pro Asn Asp Pro Ser Asn Phe Ala Arg Ala Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
                195                 200                 205

Phe Ala Val Val Asn Gly Asn Tyr Ala Ile Ser Ser Gly Met Lys Leu
        210                 215                 220
```

```
Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
        260                 265                 270

Glu Gly Tyr Lys Ser Pro Ala Ala Trp Asn Glu Gly Ala Ala Lys
    275                 280                 285
```

<210> SEQ ID NO 38
<211> LENGTH: 287
<212> TYPE: PRT
<213> ORGANISM: Neisseria meningitidis

<400> SEQUENCE: 38

```
Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala Glu Lys Lys Glu Ile Val Phe Gly
        35                  40                  45

Thr Thr Val Gly Asp Phe Gly Asp Met Val Lys Glu Gln Ile Gln Ala
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
        260                 265                 270

Glu Gly Tyr Lys Ser Pro Ala Ala Trp Asn Glu Gly Ala Ala Lys
    275                 280                 285
```

<210> SEQ ID NO 39
<211> LENGTH: 287
<212> TYPE: PRT
<213> ORGANISM: Neisseria meningitidis

<400> SEQUENCE: 39

| Met | Lys | Thr | Phe | Phe | Lys | Thr | Leu | Ser | Ala | Ala | Leu | Ala | Leu | Ile |
|---|---|---|---|---|---|---|---|---|---|---|---|---|---|---|
| 1 | | | | 5 | | | | | 10 | | | | | 15 |

| Leu | Ala | Ala | Cys | Gly | Gly | Gln | Lys | Asp | Ser | Ala | Pro | Ala | Ala | Ser | Ala |
|---|---|---|---|---|---|---|---|---|---|---|---|---|---|---|---|
| | | | 20 | | | | | 25 | | | | | 30 | | |

| Ser | Ala | Ala | Ala | Asp | Asn | Gly | Ala | Glu | Lys | Lys | Glu | Ile | Val | Phe | Gly |
|---|---|---|---|---|---|---|---|---|---|---|---|---|---|---|---|
| | | | 35 | | | | | 40 | | | | | 45 | | |

| Thr | Thr | Val | Gly | Asp | Phe | Gly | Asp | Met | Val | Lys | Glu | Gln | Ile | Gln | Ala |
|---|---|---|---|---|---|---|---|---|---|---|---|---|---|---|---|
| | 50 | | | | | 55 | | | | | 60 | | | | |

| Glu | Leu | Glu | Lys | Lys | Gly | Tyr | Thr | Val | Lys | Leu | Val | Glu | Phe | Thr | Asp |
|---|---|---|---|---|---|---|---|---|---|---|---|---|---|---|---|
| 65 | | | | | 70 | | | | | 75 | | | | | 80 |

| Tyr | Val | Arg | Pro | Asn | Leu | Ala | Leu | Ala | Glu | Gly | Leu | Asp | Ile | Asn |
|---|---|---|---|---|---|---|---|---|---|---|---|---|---|---|
| | | | | 85 | | | | | 90 | | | | | 95 |

| Val | Phe | Gln | His | Lys | Pro | Tyr | Leu | Asp | Asp | Phe | Lys | Lys | Glu | His | Asn |
|---|---|---|---|---|---|---|---|---|---|---|---|---|---|---|---|
| | | | 100 | | | | | 105 | | | | | 110 | | |

| Leu | Asp | Ile | Thr | Glu | Val | Phe | Gln | Val | Pro | Thr | Ala | Pro | Leu | Gly | Leu |
|---|---|---|---|---|---|---|---|---|---|---|---|---|---|---|---|
| | | | 115 | | | | | 120 | | | | | 125 | | |

| Tyr | Pro | Gly | Lys | Leu | Lys | Ser | Leu | Glu | Glu | Val | Lys | Asp | Gly | Ser | Thr |
|---|---|---|---|---|---|---|---|---|---|---|---|---|---|---|---|
| | | 130 | | | | | 135 | | | | | 140 | | | |

| Val | Ser | Ala | Pro | Asn | Asp | Pro | Ser | Asn | Phe | Ala | Arg | Val | Leu | Val | Met |
|---|---|---|---|---|---|---|---|---|---|---|---|---|---|---|---|
| 145 | | | | | 150 | | | | | 155 | | | | | 160 |

| Leu | Asp | Glu | Leu | Gly | Trp | Ile | Lys | Leu | Lys | Asp | Gly | Ile | Asn | Pro | Leu |
|---|---|---|---|---|---|---|---|---|---|---|---|---|---|---|---|
| | | | | 165 | | | | | 170 | | | | | 175 | |

| Thr | Ala | Ser | Lys | Ala | Asp | Ile | Ala | Glu | Asn | Leu | Lys | Asn | Ile | Lys | Ile |
|---|---|---|---|---|---|---|---|---|---|---|---|---|---|---|---|
| | | | 180 | | | | | 185 | | | | | 190 | | |

| Val | Glu | Leu | Glu | Ala | Ala | Gln | Leu | Pro | Arg | Ser | Arg | Ala | Asp | Val | Asp |
|---|---|---|---|---|---|---|---|---|---|---|---|---|---|---|---|
| | | | 195 | | | | | 200 | | | | | 205 | | |

| Phe | Ala | Val | Val | Asn | Gly | Asn | Tyr | Ala | Ile | Ser | Ser | Gly | Met | Lys | Leu |
|---|---|---|---|---|---|---|---|---|---|---|---|---|---|---|---|
| | 210 | | | | | 215 | | | | | 220 | | | | |

| Thr | Glu | Ala | Leu | Phe | Gln | Glu | Pro | Ser | Phe | Ala | Tyr | Val | Asn | Trp | Ser |
|---|---|---|---|---|---|---|---|---|---|---|---|---|---|---|---|
| 225 | | | | | 230 | | | | | 235 | | | | | 240 |

| Ala | Val | Lys | Thr | Ala | Asp | Lys | Asp | Ser | Gln | Trp | Leu | Lys | Asp | Val | Thr |
|---|---|---|---|---|---|---|---|---|---|---|---|---|---|---|---|
| | | | | 245 | | | | | 250 | | | | | 255 | |

| Glu | Ala | Tyr | Asn | Ser | Asp | Ala | Phe | Lys | Ala | Tyr | Ala | His | Lys | Arg | Phe |
|---|---|---|---|---|---|---|---|---|---|---|---|---|---|---|---|
| | | | 260 | | | | | 265 | | | | | 270 | | |

| Glu | Gly | Tyr | Lys | Ser | Pro | Ala | Ala | Trp | Asn | Gly | Ala | Ala | Lys |
|---|---|---|---|---|---|---|---|---|---|---|---|---|---|
| | | | 275 | | | | | 280 | | | | | 285 |

<210> SEQ ID NO 40
<211> LENGTH: 287
<212> TYPE: PRT
<213> ORGANISM: Neisseria meningitidis

<400> SEQUENCE: 40

| Met | Lys | Thr | Phe | Phe | Lys | Thr | Leu | Ser | Ala | Ala | Leu | Ala | Leu | Ile |
|---|---|---|---|---|---|---|---|---|---|---|---|---|---|---|
| 1 | | | | 5 | | | | | 10 | | | | | 15 |

| Leu | Ala | Ala | Cys | Gly | Gly | Gln | Lys | Asp | Ser | Ala | Pro | Ala | Ala | Ser | Ala |
|---|---|---|---|---|---|---|---|---|---|---|---|---|---|---|---|
| | | | 20 | | | | | 25 | | | | | 30 | | |

| Ser | Ala | Ala | Ala | Asp | Asn | Gly | Ala | Glu | Lys | Lys | Glu | Ile | Val | Phe | Gly |
|---|---|---|---|---|---|---|---|---|---|---|---|---|---|---|---|
| | | | 35 | | | | | 40 | | | | | 45 | | |

| Thr | Thr | Val | Gly | Asp | Phe | Gly | Asp | Met | Val | Lys | Glu | Gln | Ile | Gln | Ala |
|---|---|---|---|---|---|---|---|---|---|---|---|---|---|---|---|
| | 50 | | | | | 55 | | | | | 60 | | | | |

| Glu | Leu | Glu | Lys | Lys | Gly | Tyr | Thr | Val | Lys | Leu | Val | Glu | Phe | Thr | Asp |
|---|---|---|---|---|---|---|---|---|---|---|---|---|---|---|---|
| 65 | | | | | 70 | | | | | 75 | | | | | 80 |

```
Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Gly Ala Ala Lys
        275                 280                 285

<210> SEQ ID NO 41
<211> LENGTH: 287
<212> TYPE: PRT
<213> ORGANISM: Neisseria meningitidis

<400> SEQUENCE: 41

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala Ala Lys Lys Glu Ile Val Phe Gly
        35                  40                  45

Thr Thr Val Gly Asp Phe Gly Asp Met Val Lys Glu Gln Ile Gln Ala
    50                  55                  60

Glu Leu Glu Lys Lys Gly Tyr Thr Val Glu Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
```

```
                    165                 170                 175
Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
            195                 200                 205

Phe Ala Val Val Asn Gly Asn Tyr Ala Ile Ser Ser Gly Met Lys Leu
        210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 42
<211> LENGTH: 287
<212> TYPE: PRT
<213> ORGANISM: Neisseria meningitidis

<400> SEQUENCE: 42

Met Lys Thr Phe Phe Lys Thr Leu Ser Ala Ala Leu Ala Leu Ile
1               5                  10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Ala
        50                  55                  60

Glu Leu Glu Lys Lys Gly Tyr Thr Val Glu Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255
```

```
Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285

<210> SEQ ID NO 43
<211> LENGTH: 287
<212> TYPE: PRT
<213> ORGANISM: Neisseria meningitidis

<400> SEQUENCE: 43

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Pro
50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
            275                 280                 285

<210> SEQ ID NO 44
<211> LENGTH: 287
<212> TYPE: PRT
<213> ORGANISM: Neisseria meningitidis

<400> SEQUENCE: 44

Met Lys Thr Phe Phe Lys Thr Leu Ser Ala Ala Leu Ala Leu Ile
1               5                   10                  15
```

```
Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 45
<211> LENGTH: 287
<212> TYPE: PRT
<213> ORGANISM: Neisseria meningitidis

<400> SEQUENCE: 45

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110
```

```
Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
                195                 200                 205

Phe Ala Val Val Asn Gly Asn Tyr Ala Ile Ser Ser Gly Met Lys Leu
                210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
                275                 280                 285

<210> SEQ ID NO 46
<211> LENGTH: 287
<212> TYPE: PRT
<213> ORGANISM: Neisseria meningitidis

<400> SEQUENCE: 46

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Ala
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
```

```
                    195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 47
<211> LENGTH: 287
<212> TYPE: PRT
<213> ORGANISM: Neisseria meningitidis

<400> SEQUENCE: 47

Met Lys Thr Phe Phe Lys Thr Leu Ser Ala Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Ala
    50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
    130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
    210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285
```

<210> SEQ ID NO 48
<211> LENGTH: 287
<212> TYPE: PRT
<213> ORGANISM: Neisseria meningitidis

<400> SEQUENCE: 48

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ser Ala
                20                  25                  30

Ser Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Ala
50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
        115                 120                 125

Tyr Pro Gly Lys Leu Lys Ser Leu Glu Glu Val Lys Asp Gly Ser Thr
130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285

<210> SEQ ID NO 49
<211> LENGTH: 287
<212> TYPE: PRT
<213> ORGANISM: Neisseria meningitidis

<400> SEQUENCE: 49

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ser Ala
                20                  25                  30

Ser Ala Ala Asp Asn Gly Ala Ala Lys Lys Glu Ile Val Phe Gly
            35                  40                  45

```
Thr Thr Val Gly Asp Phe Gly Asp Met Val Lys Glu Gln Ile Gln Val
    50                  55                  60
Glu Leu Glu Lys Lys Gly Tyr Thr Val Lys Leu Val Glu Phe Thr Asp
65                  70                  75                  80
Tyr Val Arg Pro Asn Leu Ala Leu Ala Glu Gly Leu Asp Ile Asn
                85                  90                  95
Val Phe Gln His Lys Pro Tyr Leu Asp Asp Phe Lys Lys Glu His Asn
            100                 105                 110
Leu Asp Ile Thr Glu Val Phe Gln Val Pro Thr Ala Pro Leu Gly Leu
        115                 120                 125
Tyr Pro Gly Lys Leu Lys Ser Leu Glu Glu Val Lys Asp Gly Ser Thr
    130                 135                 140
Val Ser Ala Pro Asn Asp Pro Ser Asn Phe Ala Arg Val Leu Val Met
145                 150                 155                 160
Leu Asp Glu Leu Gly Trp Ile Lys Leu Lys Asp Gly Ile Asn Pro Leu
                165                 170                 175
Thr Ala Ser Lys Ala Asp Ile Ala Glu Asn Leu Lys Asn Ile Lys Ile
            180                 185                 190
Val Glu Leu Glu Ala Ala Gln Leu Pro Arg Ser Arg Ala Asp Val Asp
        195                 200                 205
Phe Ala Val Val Asn Gly Asn Tyr Ala Ile Ser Ser Gly Met Lys Leu
    210                 215                 220
Thr Glu Ala Leu Phe Gln Glu Pro Ser Phe Ala Tyr Val Asn Trp Ser
225                 230                 235                 240
Ala Val Lys Thr Ala Asp Lys Asp Ser Gln Trp Leu Lys Asp Val Thr
                245                 250                 255
Glu Ala Tyr Asn Ser Asp Ala Phe Lys Ala Tyr Ala His Lys Arg Phe
            260                 265                 270
Glu Gly Tyr Lys Ser Pro Ala Ala Trp Asn Glu Gly Ala Ala Lys
        275                 280                 285

<210> SEQ ID NO 50
<211> LENGTH: 287
<212> TYPE: PRT
<213> ORGANISM: Neisseria meningitidis

<400> SEQUENCE: 50

Met Lys Thr Phe Phe Lys Thr Leu Ser Ala Ala Ala Leu Ala Leu Ile
1               5                   10                  15
Leu Ala Ala Cys Gly Gly Gln Lys Asp Ser Ala Pro Ala Ala Ser Ala
            20                  25                  30
Ser Ala Ala Ala Asp Asn Gly Ala Ala Lys Lys Glu Ile Val Phe Gly
        35                  40                  45
Thr Thr Val Gly Asp Phe Gly Asp Met Val Lys Glu Gln Ile Gln Val
    50                  55                  60
Glu Leu Glu Lys Lys Gly Tyr Thr Val Lys Leu Val Glu Phe Thr Asp
65                  70                  75                  80
Tyr Val Arg Pro Asn Leu Ala Leu Ala Glu Gly Leu Asp Ile Asn
                85                  90                  95
Val Phe Gln His Lys Pro Tyr Leu Asp Asp Phe Lys Lys Glu His Asn
            100                 105                 110
Leu Asp Ile Thr Glu Val Phe Gln Val Pro Thr Ala Pro Leu Gly Leu
        115                 120                 125
Tyr Pro Gly Lys Leu Lys Ser Leu Glu Glu Val Lys Asp Gly Ser Thr
    130                 135                 140
```

```
Val Ser Ala Pro Asn Asp Pro Ser Asn Phe Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
                195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
                275                 280                 285
```

<210> SEQ ID NO 51
<211> LENGTH: 287
<212> TYPE: PRT
<213> ORGANISM: Neisseria meningitidis

<400> SEQUENCE: 51

```
Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
            35                  40                  45

Thr Thr Val Gly Asp Phe Gly Asp Met Val Lys Glu Gln Ile Gln Pro
50                  55                  60

Glu Leu Glu Lys Lys Gly Tyr Thr Val Glu Leu Val Glu Phe Thr Asp
65                  70                  75                  80

Tyr Val Arg Pro Asn Leu Ala Leu Ala Glu Gly Glu Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
130                 135                 140

Val Ser Ala Pro Asn Asp Pro Ser Asn Phe Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
                195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
```

```
                    225                 230                 235                 240
Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
                275                 280                 285

<210> SEQ ID NO 52
<211> LENGTH: 287
<212> TYPE: PRT
<213> ORGANISM: Neisseria meningitidis

<400> SEQUENCE: 52

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Ala Asp Asn Gly Ala Ala Lys Lys Glu Ile Val Phe Gly
                35                  40                  45

Thr Thr Val Gly Asp Phe Gly Asp Met Val Lys Glu Gln Ile Gln Ala
            50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn
                100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
        130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
                180                 185                 190

Val Glu Leu Glu Ala Ala Gln Leu Pro Arg Ser Arg Ala Asp Val Asp
            195                 200                 205

Phe Ala Val Val Asn Gly Asn Tyr Ala Ile Ser Ser Gly Met Lys Leu
        210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
                245                 250                 255

Glu Ala Tyr Asn Ser Asp Ala Phe Lys Ala Tyr Ala His Lys Arg Phe
                260                 265                 270

Glu Gly Tyr Lys Ser Pro Ala Ala Trp Asn Glu Gly Ala Ala Lys
                275                 280                 285

<210> SEQ ID NO 53
<211> LENGTH: 287
<212> TYPE: PRT
<213> ORGANISM: Neisseria meningitidis
```

<400> SEQUENCE: 53

```
Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
                20                  25                  30

Ser Ala Ala Asp Asn Gly Ala Glu Lys Lys Glu Ile Val Phe Gly
            35                  40                  45

Thr Thr Val Gly Asp Phe Gly Asp Met Val Lys Glu His Ile Gln Pro
        50                  55                  60

Glu Leu Glu Lys Lys Gly Tyr Thr Val Lys Leu Val Glu Phe Thr Asp
65                  70                  75                  80

Tyr Val Arg Pro Asn Leu Ala Leu Ala Glu Gly Leu Asp Ile Asn
                85                  90                  95

Val Phe Gln His Lys Pro Tyr Leu Asp Asp Phe Lys Lys Glu His Asn
            100                 105                 110

Leu Asp Ile Thr Glu Val Phe Gln Val Pro Thr Ala Pro Leu Gly Leu
            115                 120                 125

Tyr Pro Gly Lys Leu Lys Ser Leu Glu Glu Val Lys Asp Gly Ser Thr
        130                 135                 140

Val Ser Ala Pro Asn Asp Pro Ser Asn Phe Ala Arg Val Leu Val Met
145                 150                 155                 160

Leu Asp Glu Leu Gly Trp Ile Lys Leu Lys Asp Gly Ile Asn Pro Leu
                165                 170                 175

Thr Ala Ser Lys Ala Asp Ile Ala Glu Asn Leu Lys Asn Ile Lys Ile
            180                 185                 190

Val Glu Leu Glu Ala Ala Gln Leu Pro Arg Ser Arg Ala Asp Val Asp
        195                 200                 205

Phe Ala Val Val Asn Gly Asn Tyr Ala Ile Ser Ser Gly Met Lys Leu
210                 215                 220

Thr Glu Ala Leu Phe Gln Glu Pro Ser Phe Ala Tyr Val Asn Trp Ser
225                 230                 235                 240

Ala Val Lys Thr Ala Asp Lys Asp Ser Gln Trp Leu Lys Asp Val Thr
            245                 250                 255

Glu Ala Tyr Asn Ser Asp Ala Phe Lys Ala Tyr Ala His Lys Arg Phe
            260                 265                 270

Glu Gly Tyr Lys Ser Pro Ala Ala Trp Asn Glu Gly Ala Ala Lys
        275                 280                 285
```

<210> SEQ ID NO 54
<211> LENGTH: 251
<212> TYPE: PRT
<213> ORGANISM: Neisseria meningitidis

<400> SEQUENCE: 54

```
Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80
```

```
Asn Arg Val Pro Ala Arg Arg Ala Gly Asn Ala Asp Glu Leu Ile Gly
                85                  90                  95

Ser Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 55
<211> LENGTH: 251
<212> TYPE: PRT
<213> ORGANISM: Neisseria meningitidis

<400> SEQUENCE: 55

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Ser Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205
```

```
Asn Arg Phe Ile His Ala Pro Arg Thr Gly Lys Asn Ile Glu Ile Thr
            210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 56
<211> LENGTH: 280
<212> TYPE: PRT
<213> ORGANISM: Neisseria meningitidis

<400> SEQUENCE: 56

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Val
                100                 105                 110

Pro Ala Arg Arg Ala Gly Asn Ala Asp Glu Leu Ile Gly Asn Ala Met
            115                 120                 125

Gly Leu Asn Glu Gln Pro Val Leu Pro Val Asn Arg Ala Pro Ala Arg
130                 135                 140

Arg Ala Gly Asn Ala Asp Glu Leu Ile Gly Asn Ala Met Gly Leu Leu
145                 150                 155                 160

Gly Ile Ala Tyr Arg Tyr Gly Gly Thr Ser Ile Ser Thr Gly Phe Asp
                165                 170                 175

Cys Ser Gly Phe Met Gln His Ile Phe Lys Arg Ala Met Gly Ile Asn
                180                 185                 190

Leu Pro Arg Thr Ser Ala Glu Gln Ala Arg Met Gly Thr Pro Val Ala
            195                 200                 205

Arg Ser Glu Leu Gln Pro Gly Asp Met Val Phe Phe Arg Thr Leu Gly
210                 215                 220

Gly Ser Arg Ile Ser His Val Gly Leu Tyr Ile Gly Asn Asn Arg Phe
225                 230                 235                 240

Ile His Ala Pro Arg Thr Gly Lys Asn Ile Glu Ile Thr Ser Leu Ser
                245                 250                 255

His Lys Tyr Trp Ser Gly Lys Tyr Ala Phe Ala Arg Arg Val Lys Lys
                260                 265                 270

Asn Asp Pro Ser Arg Phe Leu Asn
        275                 280

<210> SEQ ID NO 57
<211> LENGTH: 280
<212> TYPE: PRT
<213> ORGANISM: Neisseria meningitidis

<400> SEQUENCE: 57
```

```
Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Asn Glu Gln Pro Val Leu Pro Val Asn Arg Ala Pro Ala Arg
    130                 135                 140

Arg Ala Gly Asn Ala Asp Glu Leu Ile Gly Asn Ala Met Gly Leu Leu
145                 150                 155                 160

Gly Ile Ala Tyr Arg Tyr Gly Gly Thr Ser Val Ser Thr Gly Phe Asp
                165                 170                 175

Cys Ser Gly Phe Met Gln His Ile Phe Lys Arg Ala Met Gly Ile Asn
            180                 185                 190

Leu Pro Arg Thr Ser Ala Glu Gln Ala Arg Met Gly Thr Pro Val Ala
        195                 200                 205

Arg Ser Glu Leu Gln Pro Gly Asp Met Val Phe Phe Arg Thr Leu Gly
210                 215                 220

Gly Ser Arg Ile Ser His Val Gly Leu Tyr Ile Gly Asn Asn Arg Phe
225                 230                 235                 240

Ile His Ala Pro Arg Thr Gly Lys Asn Ile Glu Ile Thr Ser Leu Ser
                245                 250                 255

His Lys Tyr Trp Ser Gly Lys Tyr Ala Phe Ala Arg Arg Val Lys Lys
            260                 265                 270

Asn Asp Pro Ser Arg Phe Leu Asn
        275                 280

<210> SEQ ID NO 58
<211> LENGTH: 280
<212> TYPE: PRT
<213> ORGANISM: Neisseria meningitidis

<400> SEQUENCE: 58

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Ile
65                  70                  75                  80

Asn Arg Ala Pro Ala Arg Arg Ala Gly Asn Ala Asp Glu Leu Ile Gly
```

```
            85                  90                  95
Ser Ala Met Gly Leu Asn Glu Gln Pro Val Leu Pro Val Asn Arg Val
            100                 105                 110

Pro Ala Arg Arg Ala Gly Asn Ala Asp Glu Leu Ile Gly Asn Ala Met
            115                 120                 125

Gly Leu Asn Glu Gln Pro Val Leu Pro Val Asn Arg Ala Pro Ala Arg
    130                 135                 140

Arg Ala Gly Asn Ala Asp Glu Leu Ile Gly Asn Ala Met Gly Leu Leu
145                 150                 155                 160

Gly Ile Ala Tyr Arg Tyr Gly Gly Thr Ser Val Ser Thr Gly Phe Asp
                165                 170                 175

Cys Ser Gly Phe Met Gln His Ile Phe Lys Arg Ala Met Gly Ile Asn
                180                 185                 190

Leu Pro Arg Thr Ser Ala Glu Gln Ala Arg Met Gly Thr Pro Val Ala
                195                 200                 205

Arg Ser Glu Leu Gln Pro Gly Asp Met Val Phe Phe Arg Thr Leu Gly
    210                 215                 220

Gly Ser Arg Ile Ser His Val Gly Leu Tyr Ile Gly Asn Asn Arg Phe
225                 230                 235                 240

Ile His Ala Pro Arg Thr Gly Lys Asn Ile Glu Ile Thr Ser Leu Ser
                245                 250                 255

His Lys Tyr Trp Ser Gly Lys Tyr Ala Phe Ala Arg Arg Val Lys Lys
                260                 265                 270

Asn Asp Pro Ser Arg Phe Leu Asn
            275                 280

<210> SEQ ID NO 59
<211> LENGTH: 251
<212> TYPE: PRT
<213> ORGANISM: Neisseria meningitidis

<400> SEQUENCE: 59

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175
```

```
Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 60
<211> LENGTH: 251
<212> TYPE: PRT
<213> ORGANISM: Neisseria meningitidis

<400> SEQUENCE: 60

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 61
<211> LENGTH: 251
<212> TYPE: PRT
<213> ORGANISM: Neisseria meningitidis

<400> SEQUENCE: 61
```

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
        130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
            245                 250

<210> SEQ ID NO 62
<211> LENGTH: 251
<212> TYPE: PRT
<213> ORGANISM: Neisseria meningitidis

<400> SEQUENCE: 62

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

```
Gly Leu Leu Gly Ile Ala Tyr Arg Tyr Gly Thr Ser Ile Ser Thr
    130                 135                 140
Gly Phe Asp Cys Ser Gly Phe Met Gln His Ile Phe Lys Arg Ala Met
145                 150                 155                 160
Gly Ile Asn Leu Pro Arg Thr Ser Ala Glu Gln Ala Arg Met Gly Thr
                165                 170                 175
Pro Val Ala Arg Ser Glu Leu Gln Pro Gly Asp Met Val Phe Phe Arg
                180                 185                 190
Thr Leu Gly Gly Ser Arg Ile Ser His Val Gly Leu Tyr Ile Gly Asn
            195                 200                 205
Asn Arg Phe Ile His Ala Pro Arg Thr Gly Lys Asn Ile Glu Ile Thr
    210                 215                 220
Ser Leu Ser His Lys Tyr Trp Ser Gly Lys Tyr Ala Phe Ala Arg Arg
225                 230                 235                 240
Val Lys Lys Asn Asp Pro Ser Arg Phe Leu Asn
                245                 250

<210> SEQ ID NO 63
<211> LENGTH: 251
<212> TYPE: PRT
<213> ORGANISM: Neisseria meningitidis

<400> SEQUENCE: 63

Met Asp Ser Phe Phe Lys Pro Ala Val Trp Ala Val Leu Trp Leu Met
1               5                   10                  15
Phe Ala Val Arg Pro Ala Leu Ala Asp Glu Leu Thr Asn Leu Leu Ser
                20                  25                  30
Ser Arg Glu Gln Ile Leu Arg Gln Phe Ala Glu Asp Glu Gln Pro Val
            35                  40                  45
Leu Pro Ile Asn Arg Ala Pro Ala Arg Arg Ala Gly Asn Ala Asp Glu
    50                  55                  60
Leu Ile Gly Ser Ala Met Gly Leu Asn Glu Gln Pro Val Leu Pro Val
65                  70                  75                  80
Asn Arg Val Pro Ala Arg Arg Ala Gly Asn Ala Asp Glu Leu Ile Gly
                85                  90                  95
Asn Ala Met Gly Leu Asn Glu Gln Pro Val Leu Pro Val Asn Arg Ala
                100                 105                 110
Pro Ala Arg Arg Ala Gly Asn Ala Asp Glu Leu Ile Gly Asn Ala Met
            115                 120                 125
Gly Leu Leu Gly Ile Ala Tyr Arg Tyr Gly Thr Ser Ile Ser Thr
    130                 135                 140
Gly Phe Asp Cys Ser Gly Phe Met Gln His Ile Phe Lys Arg Ala Met
145                 150                 155                 160
Gly Ile Asn Leu Pro Arg Thr Ser Ala Glu Gln Ala Arg Met Gly Thr
                165                 170                 175
Pro Val Ala Arg Ser Glu Leu Gln Pro Gly Asp Met Val Phe Phe Arg
                180                 185                 190
Thr Leu Gly Gly Ser Arg Ile Ser His Val Gly Leu Tyr Ile Gly Asn
            195                 200                 205
Asn Arg Phe Ile His Ala Pro Arg Thr Gly Lys Asn Ile Glu Ile Thr
    210                 215                 220
Ser Leu Ser His Lys Tyr Trp Ser Gly Lys Tyr Ala Phe Ala Arg Arg
225                 230                 235                 240
Val Lys Lys Asn Asp Pro Ser Arg Phe Leu Asn
```

```
                        245                 250

<210> SEQ ID NO 64
<211> LENGTH: 251
<212> TYPE: PRT
<213> ORGANISM: Neisseria meningitidis

<400> SEQUENCE: 64

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 65
<211> LENGTH: 251
<212> TYPE: PRT
<213> ORGANISM: Neisseria meningitidis

<400> SEQUENCE: 65

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
```

```
                 65                  70                  75                  80
Asn Arg Val Pro Ala Arg Arg Ala Gly Asn Ala Asp Glu Leu Ile Gly
                 85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 66
<211> LENGTH: 251
<212> TYPE: PRT
<213> ORGANISM: Neisseria meningitidis

<400> SEQUENCE: 66

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190
```

```
Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 67
<211> LENGTH: 251
<212> TYPE: PRT
<213> ORGANISM: Neisseria meningitidis

<400> SEQUENCE: 67

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Ile Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 68
<211> LENGTH: 251
<212> TYPE: PRT
<213> ORGANISM: Neisseria meningitidis

<400> SEQUENCE: 68

Met Asp Ser Phe Phe Lys Pro Ala Val Trp Ala Val Leu Trp Leu Met
1               5                   10                  15
```

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 69
<211> LENGTH: 251
<212> TYPE: PRT
<213> ORGANISM: Neisseria meningitidis

<400> SEQUENCE: 69

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

-continued

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 70
<211> LENGTH: 251
<212> TYPE: PRT
<213> ORGANISM: Neisseria meningitidis

<400> SEQUENCE: 70

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
                100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
        130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

```
<210> SEQ ID NO 71
<211> LENGTH: 251
<212> TYPE: PRT
<213> ORGANISM: Neisseria meningitidis

<400> SEQUENCE: 71

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 72
<211> LENGTH: 251
<212> TYPE: PRT
<213> ORGANISM: Neisseria meningitidis

<400> SEQUENCE: 72

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
```

```
                    85                  90                  95
Asn Ala Met Gly Leu Asn Glu Gln Pro Val Leu Pro Val Asn Arg Ala
                100                 105                 110
Pro Ala Arg Arg Ala Gly Asn Ala Asp Glu Leu Ile Gly Asn Ala Met
                115                 120                 125
Gly Leu Leu Gly Ile Ala Tyr Arg Tyr Gly Gly Thr Ser Val Ser Thr
            130                 135                 140
Gly Phe Asp Cys Ser Gly Phe Met Gln His Ile Phe Lys Arg Ala Met
145                 150                 155                 160
Gly Ile Asn Leu Pro Arg Thr Ser Ala Glu Gln Ala Arg Met Gly Thr
                165                 170                 175
Pro Val Ala Arg Ser Glu Leu Gln Pro Gly Asp Met Val Phe Phe Arg
                180                 185                 190
Thr Leu Gly Gly Ser Arg Ile Ser His Val Gly Leu Tyr Ile Gly Asn
            195                 200                 205
Asn Arg Phe Ile His Ala Pro Arg Thr Gly Lys Asn Ile Glu Ile Thr
        210                 215                 220
Ser Leu Ser His Lys Tyr Trp Ser Gly Lys Tyr Ala Phe Ala Arg Arg
225                 230                 235                 240
Val Lys Lys Asn Asp Pro Ser Arg Phe Leu Asn
                245                 250

<210> SEQ ID NO 73
<211> LENGTH: 251
<212> TYPE: PRT
<213> ORGANISM: Neisseria meningitidis

<400> SEQUENCE: 73

Met Asp Ser Phe Phe Lys Pro Ala Val Trp Ala Val Leu Trp Leu Met
1               5                   10                  15
Phe Ala Val Arg Pro Ala Leu Ala Asp Glu Leu Thr Asn Leu Leu Ser
                20                  25                  30
Ser Arg Glu Gln Ile Leu Arg Gln Phe Ala Glu Asp Glu Gln Pro Val
            35                  40                  45
Leu Pro Ile Asn Arg Ala Pro Ala Arg Arg Ala Gly Asn Ala Asp Glu
        50                  55                  60
Leu Ile Gly Ser Ala Met Gly Leu Asn Glu Gln Pro Val Leu Pro Val
65                  70                  75                  80
Asn Arg Val Pro Ala Arg Arg Ala Gly Asn Ala Asp Glu Leu Ile Gly
                85                  90                  95
Asn Ala Met Gly Leu Asn Glu Gln Pro Val Leu Pro Val Asn Arg Ala
                100                 105                 110
Pro Ala Arg Arg Ala Gly Asn Ala Asp Glu Leu Ile Gly Asn Ala Met
                115                 120                 125
Gly Leu Leu Gly Ile Ala Tyr Arg Tyr Gly Gly Thr Ser Val Ser Thr
            130                 135                 140
Gly Phe Asp Cys Ser Gly Phe Met Gln His Ile Phe Lys Arg Ala Met
145                 150                 155                 160
Gly Ile Asn Leu Pro Arg Thr Ser Ala Glu Gln Ala Arg Met Gly Thr
                165                 170                 175
Pro Val Ala Arg Ser Glu Leu Gln Pro Gly Asp Met Val Phe Phe Arg
                180                 185                 190
Thr Leu Gly Gly Ser Arg Ile Ser His Val Gly Leu Tyr Ile Gly Asn
            195                 200                 205
```

```
Asn Arg Phe Ile His Ala Pro Arg Thr Gly Lys Asn Ile Glu Ile Thr
            210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 74
<211> LENGTH: 251
<212> TYPE: PRT
<213> ORGANISM: Neisseria meningitidis

<400> SEQUENCE: 74

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
                100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
            210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 75
<211> LENGTH: 251
<212> TYPE: PRT
<213> ORGANISM: Neisseria meningitidis

<400> SEQUENCE: 75

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30
```

```
Ser Arg Glu Gln Ile Leu Arg Gln Phe Ala Glu Asp Glu Gln Pro Val
         35                  40                  45

Leu Pro Ile Asn Arg Ala Pro Ala Arg Arg Ala Gly Asn Ala Asp Glu
 50                  55                  60

Leu Ile Gly Ser Ala Met Gly Leu Asn Glu Gln Pro Val Leu Pro Val
 65                  70                  75                  80

Asn Arg Val Pro Ala Arg Arg Ala Gly Asn Ala Asp Glu Leu Ile Gly
                 85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
            130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
            210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 76
<211> LENGTH: 251
<212> TYPE: PRT
<213> ORGANISM: Neisseria meningitidis

<400> SEQUENCE: 76

Met Asp Ser Phe Phe Lys Pro Ala Val Trp Ala Val Leu Trp Leu Met
 1               5                  10                  15

Phe Ala Val Arg Pro Ala Leu Ala Asp Glu Leu Thr Asn Leu Leu Ser
                 20                  25                  30

Ser Arg Glu Gln Ile Leu Arg Gln Phe Ala Glu Asp Glu Gln Pro Val
         35                  40                  45

Leu Pro Ile Asn Arg Ala Pro Ala Arg Arg Ala Gly Asn Ala Asp Glu
 50                  55                  60

Leu Ile Gly Ser Ala Met Gly Leu Asn Glu Gln Pro Val Leu Pro Val
 65                  70                  75                  80

Asn Arg Val Pro Ala Arg Arg Ala Gly Asn Ala Asp Glu Leu Ile Gly
                 85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
            130                 135                 140

Gly Phe Asp Cys Ser Gly Phe Met Gln His Ile Phe Lys Arg Ala Met
145                 150                 155                 160
```

```
Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 77
<211> LENGTH: 251
<212> TYPE: PRT
<213> ORGANISM: Neisseria meningitidis

<400> SEQUENCE: 77

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
    50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 78
<211> LENGTH: 251
<212> TYPE: PRT
```

<213> ORGANISM: Neisseria meningitidis

<400> SEQUENCE: 78

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Thr Ser Val Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 79
<211> LENGTH: 251
<212> TYPE: PRT
<213> ORGANISM: Neisseria meningitidis

<400> SEQUENCE: 79

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
            20                  25                  30

Ser Arg Glu Gln Ile Leu Arg Gln Phe Ala Glu Asp Glu Gln Pro Val
        35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala

```
                100                 105                 110
Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
            165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
            245                 250

<210> SEQ ID NO 80
<211> LENGTH: 251
<212> TYPE: PRT
<213> ORGANISM: Neisseria meningitidis

<400> SEQUENCE: 80

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
            165                 170                 175

Pro Val Ala Arg Ser Glu Leu Gln Pro Gly Asp Met Val Phe Phe Arg
            180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
210                 215                 220
```

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 81
<211> LENGTH: 251
<212> TYPE: PRT
<213> ORGANISM: Neisseria meningitidis

<400> SEQUENCE: 81

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Asn Glu Gln Pro Val Leu Pro Val Asn Arg Ala
                100                 105                 110

Pro Ala Arg Arg Ala Gly Asn Ala Asp Glu Leu Ile Gly Asn Ala Met
            115                 120                 125

Gly Leu Leu Gly Ile Ala Tyr Arg Tyr Gly Gly Thr Ser Val Ser Thr
        130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
                180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
        210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 82
<211> LENGTH: 251
<212> TYPE: PRT
<213> ORGANISM: Neisseria meningitidis

<400> SEQUENCE: 82

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

```
Leu Pro Val Asn Arg Ala Pro Ala Arg Arg Ala Gly Asn Ala Asp Glu
         50                  55                  60

Leu Ile Gly Ser Ala Met Gly Leu Asn Glu Gln Pro Val Leu Pro Val
 65                  70                  75                  80

Asn Arg Val Pro Ala Arg Arg Ala Gly Asn Ala Asp Glu Leu Ile Gly
                 85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

Gly Phe Asp Cys Ser Gly Phe Ile Gln His Ile Phe Lys Arg Ala Met
145                 150                 155                 160

Gly Ile Asn Leu Pro Arg Thr Ser Ala Glu Gln Ala Arg Met Gly Thr
                165                 170                 175

Pro Val Ala Arg Ser Glu Leu Gln Pro Gly Asp Met Val Phe Phe Arg
                180                 185                 190

Thr Leu Gly Gly Ser Arg Ile Ser His Val Gly Leu Tyr Ile Gly Asn
        195                 200                 205

Asn Arg Phe Ile His Ala Pro Arg Thr Gly Lys Asn Ile Glu Ile Thr
    210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 83
<211> LENGTH: 251
<212> TYPE: PRT
<213> ORGANISM: Neisseria meningitidis

<400> SEQUENCE: 83

Met Asp Ser Phe Phe Lys Pro Ala Val Trp Ala Val Leu Trp Leu Met
 1               5                  10                  15

Phe Ala Val Arg Leu Ala Leu Ala Asp Glu Leu Thr Asn Leu Leu Ser
                 20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
 65                  70                  75                  80

Asn Arg Val Pro Ala Arg Arg Ala Gly Asn Ala Asp Glu Leu Ile Gly
                 85                  90                  95

Asn Ala Met Gly Leu Asn Glu Gln Pro Val Leu Pro Val Asn Arg Ala
            100                 105                 110

Pro Ala Arg Arg Ala Gly Asn Ala Asp Glu Leu Ile Gly Asn Ala Met
        115                 120                 125

Gly Leu Leu Gly Ile Ala Tyr Arg Tyr Gly Gly Thr Ser Val Ser Thr
    130                 135                 140

Gly Phe Asp Cys Ser Gly Phe Met Gln His Ile Phe Lys Arg Ala Met
145                 150                 155                 160

Gly Ile Asn Leu Pro Arg Thr Ser Ala Glu Gln Ala Arg Met Gly Thr
                165                 170                 175
```

```
Pro Val Ala Arg Ser Glu Leu Gln Pro Gly Asp Met Val Phe Phe Arg
                180                 185                 190

Thr Leu Gly Gly Ser Arg Ile Ser His Val Gly Leu Tyr Ile Gly Asn
            195                 200                 205

Asn Arg Phe Ile His Ala Pro Arg Thr Gly Lys Asn Ile Glu Ile Thr
210                 215                 220

Ser Leu Ser His Lys Tyr Trp Ser Gly Lys Tyr Ala Phe Ala Arg Arg
225                 230                 235                 240

Val Lys Lys Asn Asp Pro Ser Arg Phe Leu Asn
                245                 250

<210> SEQ ID NO 84
<211> LENGTH: 222
<212> TYPE: PRT
<213> ORGANISM: Neisseria meningitidis

<400> SEQUENCE: 84

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Ile Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Val Pro Ala Arg Arg Ala Gly Asn Ala Asp Glu Leu Ile Gly
                85                  90                  95

Asn Ala Met Gly Leu Leu Gly Ile Ala Tyr Arg Tyr Gly Gly Thr Ser
                100                 105                 110

Val Ser Thr Gly Phe Asp Cys Ser Gly Phe Met Gln His Ile Phe Lys
            115                 120                 125

Arg Ala Met Gly Ile Asn Leu Pro Arg Thr Ser Ala Glu Gln Ala Arg
        130                 135                 140

Met Gly Thr Pro Val Ala Arg Ser Glu Leu Gln Pro Gly Asp Met Val
145                 150                 155                 160

Phe Phe Arg Thr Leu Gly Gly Ser Arg Ile Ser His Val Gly Leu Tyr
                165                 170                 175

Ile Gly Asn Asn Arg Phe Ile His Ala Pro Arg Thr Gly Lys Asn Ile
                180                 185                 190

Glu Ile Thr Ser Leu Ser His Lys Tyr Trp Ser Gly Lys Tyr Ala Phe
            195                 200                 205

Ala Arg Arg Val Lys Lys Asn Asp Pro Ser Arg Phe Leu Asn
        210                 215                 220

<210> SEQ ID NO 85
<211> LENGTH: 222
<212> TYPE: PRT
<213> ORGANISM: Neisseria gonorrhoeae

<400> SEQUENCE: 85

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30
```

Ser Arg Glu Gln Ile Leu Arg Gln Phe Ala Glu Asp Glu Gln Pro Val
    35                  40                  45

Leu Pro Val Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Ala Pro Ala Arg Arg Ala Gly Asn Ala Asp Glu Leu Ile Gly
                85                  90                  95

Ser Ala Met Gly Leu Leu Gly Ile Ala Tyr Arg Tyr Gly Gly Thr Ser
                100                 105                 110

Val Ser Thr Gly Phe Asp Cys Ser Gly Phe Met Gln His Ile Phe Lys
                115                 120                 125

Arg Ala Met Gly Ile Asn Leu Pro Arg Thr Ser Ala Glu Gln Ala Arg
                130                 135                 140

Met Gly Ala Pro Val Ala Arg Ser Glu Leu Gln Pro Gly Asp Met Val
145                 150                 155                 160

Phe Phe Arg Thr Leu Gly Gly Ser Arg Ile Ser His Val Gly Leu Tyr
                165                 170                 175

Ile Gly Asn Asn Arg Phe Ile His Ala Pro Arg Thr Gly Lys Asn Ile
                180                 185                 190

Glu Ile Thr Ser Leu Ser His Lys Tyr Trp Ser Gly Lys Tyr Ala Phe
                195                 200                 205

Ala Arg Arg Val Lys Lys Asn Asp Pro Ser Arg Phe Leu Asn
210                 215                 220

<210> SEQ ID NO 86
<211> LENGTH: 222
<212> TYPE: PRT
<213> ORGANISM: Neisseria gonorrhoeae

<400> SEQUENCE: 86

Met Asp Ser Phe Phe Lys Pro Ala Val Trp Ala Val Leu Trp Leu Met
1               5                   10                  15

Phe Ala Val Arg Pro Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
                35                  40                  45

Leu Pro Val Asn Arg Ala Pro Ala Arg Arg Ala Gly Asn Ala Asp Glu
50                  55                  60

Leu Ile Gly Ser Ala Met Gly Leu Asn Glu Gln Pro Val Leu Pro Val
65                  70                  75                  80

Asn Arg Ala Pro Ala Arg Arg Ala Gly Asn Ala Asp Glu Leu Ile Gly
                85                  90                  95

Ser Ala Met Gly Leu Leu Gly Ile Ala Tyr Arg Tyr Gly Gly Thr Ser
                100                 105                 110

Val Ser Thr Gly Phe Asp Cys Ser Gly Phe Met Gln His Ile Phe Lys
                115                 120                 125

Arg Ala Met Gly Ile Asn Leu Pro Arg Thr Ser Ala Glu Gln Ala Arg
                130                 135                 140

Met Gly Ala Pro Val Ala Arg Ser Glu Leu Gln Pro Gly Asp Met Val
145                 150                 155                 160

Phe Phe Arg Thr Leu Gly Gly Ser Arg Ile Ser His Val Gly Leu Tyr
                165                 170                 175

Ile Gly Asn Asn Arg Phe Ile His Ala Pro Arg Thr Gly Lys Asn Ile

```
                      180                 185                 190
Glu Ile Thr Ser Leu Ser His Lys Tyr Trp Ser Gly Lys Tyr Ala Phe
                  195                 200                 205

Ala Arg Arg Val Lys Lys Asn Asp Pro Ser Arg Phe Leu Asn
            210                 215                 220

<210> SEQ ID NO 87
<211> LENGTH: 222
<212> TYPE: PRT
<213> ORGANISM: Neisseria gonorrhoeae

<400> SEQUENCE: 87

Met Asp Ser Phe Phe Lys Pro Ala Val Trp Ala Val Leu Trp Leu Met
1               5                   10                  15

Phe Ala Val Arg Ser Ala Leu Ala Asp Glu Leu Thr Asn Leu Leu Ser
                20                  25                  30

Ser Arg Glu Gln Ile Leu Arg Gln Phe Ala Glu Asp Glu Gln Pro Val
            35                  40                  45

Leu Pro Val Asn Arg Ala Pro Ala Arg Arg Ala Gly Asn Ala Asp Glu
        50                  55                  60

Leu Ile Gly Ser Ala Met Gly Leu Asn Glu Gln Pro Val Leu Pro Val
65                  70                  75                  80

Asn Arg Ala Pro Ala Arg Arg Ala Gly Asn Ala Asp Glu Leu Ile Gly
                85                  90                  95

Ser Ala Met Gly Leu Leu Gly Ile Ala Tyr Arg Tyr Gly Gly Thr Ser
            100                 105                 110

Val Ser Thr Gly Phe Asp Cys Ser Gly Phe Met Gln His Ile Phe Lys
        115                 120                 125

Arg Ala Met Gly Ile Asn Leu Pro Arg Thr Ser Ala Glu Gln Ala Arg
130                 135                 140

Met Gly Ala Pro Val Ala Arg Ser Glu Leu Gln Pro Gly Asp Met Val
145                 150                 155                 160

Phe Phe Arg Thr Leu Gly Gly Ser Arg Ile Ser His Val Gly Leu Tyr
                165                 170                 175

Ile Gly Asn Asn Arg Phe Ile His Ala Pro Arg Thr Gly Lys Asn Ile
            180                 185                 190

Glu Ile Thr Ser Leu Ser His Lys Tyr Trp Ser Gly Lys Tyr Ala Phe
        195                 200                 205

Ala Arg Arg Ile Lys Lys Asn Asp Pro Ser Arg Phe Leu Asn
    210                 215                 220

<210> SEQ ID NO 88
<211> LENGTH: 215
<212> TYPE: PRT
<213> ORGANISM: Neisseria meningitidis

<400> SEQUENCE: 88

Met Lys Pro Leu Ile Leu Gly Leu Ala Ala Ala Leu Val Leu Ser Ala
1               5                   10                  15

Cys Gln Val Gln Lys Ala Pro Asp Phe Asp Tyr Thr Ser Phe Lys Glu
                20                  25                  30

Ser Lys Pro Ala Ser Ile Leu Val Pro Pro Leu Asn Glu Ser Pro
            35                  40                  45

Asp Val Asn Gly Thr Trp Gly Met Leu Ala Ser Thr Ala Glu Pro Leu
        50                  55                  60

Ser Glu Ala Gly Tyr Tyr Val Phe Pro Ala Ala Val Val Glu Glu Thr
```

```
                65                  70                  75                  80
Phe Lys Gln Asn Gly Leu Thr Asn Ala Ala Asp Ile His Ala Val Gln
                    85                  90                  95
Pro Glu Lys Leu His Gln Ile Phe Gly Asn Asp Ala Val Leu Tyr Ile
                100                 105                 110
Thr Ile Thr Glu Tyr Gly Thr Ser Tyr Gln Ile Leu Asp Ser Val Thr
                115                 120                 125
Thr Val Ser Ala Arg Ala Arg Leu Val Asp Ser Arg Asn Gly Lys Val
            130                 135                 140
Leu Trp Ser Gly Ser Ala Ser Ile Arg Glu Gly Ser Asn Asn Ser Asn
145                 150                 155                 160
Ser Gly Leu Leu Gly Ala Leu Val Ser Ala Val Asn Gln Ile Ala
                    165                 170                 175
Asn Ser Leu Thr Asp Arg Gly Tyr Gln Val Ser Lys Thr Ala Ala Tyr
                180                 185                 190
Asn Leu Leu Ser Pro Tyr Ser His Asn Gly Ile Leu Lys Gly Pro Arg
                195                 200                 205
Phe Val Glu Glu Gln Pro Lys
            210                 215

<210> SEQ ID NO 89
<211> LENGTH: 215
<212> TYPE: PRT
<213> ORGANISM: Neisseria meningitidis

<400> SEQUENCE: 89

Met Lys Pro Leu Ile Leu Gly Leu Ala Ala Val Leu Ala Leu Ser Ala
1               5                   10                  15
Cys Gln Val Gln Lys Ala Pro Asp Phe Asp Tyr Thr Ala Phe Lys Glu
                20                  25                  30
Ser Lys Pro Ala Ser Ile Leu Val Pro Leu Asn Glu Ser Pro
                35                  40                  45
Asp Val Asn Gly Thr Trp Gly Met Leu Ala Ser Thr Ala Glu Pro Leu
            50                  55                  60
Ser Glu Ala Gly Tyr Tyr Val Phe Pro Ala Ala Val Glu Glu Thr
65                  70                  75                  80
Phe Lys Gln Asn Gly Leu Thr Asn Ala Ala Asp Ile His Ala Val Arg
                    85                  90                  95
Pro Glu Lys Leu His Gln Ile Phe Gly Asn Asp Ala Val Leu Tyr Ile
                100                 105                 110
Thr Ile Thr Glu Tyr Gly Thr Ser Tyr Gln Ile Leu Asp Ser Val Thr
                115                 120                 125
Thr Val Ser Ala Arg Ala Arg Leu Val Asp Ser Arg Asn Gly Lys Val
            130                 135                 140
Leu Trp Ser Gly Ser Ala Ser Ile Arg Glu Gly Ser Asn Asn Ser Asn
145                 150                 155                 160
Ser Gly Leu Leu Gly Ala Leu Val Gly Ala Val Asn Gln Ile Ala
                    165                 170                 175
Asn Ser Leu Thr Asp Arg Gly Tyr Gln Val Ser Lys Ala Ala Ala Tyr
                180                 185                 190
Asp Leu Leu Ser Pro Tyr Ser His Asn Gly Ile Leu Lys Gly Pro Arg
                195                 200                 205
Phe Val Glu Glu Gln Pro Lys
            210                 215
```

<210> SEQ ID NO 90
<211> LENGTH: 215
<212> TYPE: PRT
<213> ORGANISM: Neisseria gonorrhoeae

<400> SEQUENCE: 90

Met Lys Pro Leu Ile Leu Gly Leu Ala Ala Val Leu Ala Leu Ser Ala
1               5                   10                  15

Cys Gln Val Arg Lys Ala Pro Asp Leu Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Met Leu Ala Ser Thr Ala Ala Pro Ile
    50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser Arg Asn Gly Ile Leu Lys Gly Pro Arg
        195                 200                 205

Phe Val Glu Glu Gln Pro Lys
    210                 215

<210> SEQ ID NO 91
<211> LENGTH: 215
<212> TYPE: PRT
<213> ORGANISM: Neisseria gonorrhoeae

<400> SEQUENCE: 91

Met Lys Pro Leu Ile Leu Gly Leu Ala Ala Val Leu Ala Leu Ser Ala
1               5                   10                  15

Cys Gln Val Arg Lys Ala Pro Asp Leu Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Met Leu Ala Ser Thr Ala Ala Pro Ile
    50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser Arg Asn Gly Ile Leu Lys Gly Pro Arg
            195                 200                 205

Phe Val Glu Glu Gln Pro Lys
    210                 215

<210> SEQ ID NO 92
<211> LENGTH: 215
<212> TYPE: PRT
<213> ORGANISM: Neisseria gonorrhoeae

<400> SEQUENCE: 92

Met Lys Pro Leu Ile Leu Gly Leu Ala Ala Val Leu Ala Leu Ser Ala
1               5                   10                  15

Cys Gln Val Arg Lys Ala Pro Asp Leu Asp Tyr Thr Ser Phe Lys Glu
            20                  25                  30

Ser Lys Pro Ala Ser Ile Leu Val Pro Pro Leu Asn Glu Ser Pro
            35                  40                  45

Asp Val Asn Gly Thr Trp Gly Met Leu Ala Ser Thr Ala Ala Pro Ile
    50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser Arg Asn Gly Ile Leu Lys Gly Pro Arg
            195                 200                 205

Phe Val Glu Glu Gln Pro Lys
    210                 215

<210> SEQ ID NO 93
<211> LENGTH: 215
<212> TYPE: PRT
<213> ORGANISM: Neisseria meningitidis

<400> SEQUENCE: 93

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
            35                  40                  45

Asp Val Asn Gly Thr Trp Gly Val Leu Ala Ser Thr Ala Ala Pro Leu
        50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Asn Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
                195                 200                 205

Phe Val Glu Glu Gln Pro Lys
            210                 215

<210> SEQ ID NO 94
<211> LENGTH: 215
<212> TYPE: PRT
<213> ORGANISM: Neisseria meningitidis

<400> SEQUENCE: 94

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
            35                  40                  45

Asp Val Asn Gly Thr Trp Gly Val Leu Ala Ser Thr Ala Ala Pro Leu
        50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
            165                 170                 175

Asn Asn Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
            195                 200                 205

Phe Val Glu Glu Gln Pro Lys
            210             215

<210> SEQ ID NO 95
<211> LENGTH: 215
<212> TYPE: PRT
<213> ORGANISM: Neisseria meningitidis

<400> SEQUENCE: 95

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Pro Leu Asn Glu Ser Pro
            35                  40                  45

Asp Val Asn Gly Thr Trp Gly Val Leu Ala Ser Thr Ala Ala Pro Leu
 50                  55                  60

Ser Glu Ala Gly Tyr Tyr Val Phe Pro Ala Ala Val Val Glu Glu Thr
65                  70                  75                  80

Phe Lys Glu Asn Gly Leu Thr Asn Ala Ala Asp Ile His Ala Val Arg
            85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
            130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
            165                 170                 175

Asn Asn Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
            195                 200                 205

Phe Val Glu Glu Gln Pro Lys
            210             215

<210> SEQ ID NO 96
<211> LENGTH: 215
<212> TYPE: PRT
<213> ORGANISM: Neisseria meningitidis

<400> SEQUENCE: 96

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Pro Leu Asn Glu Ser Pro
            35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
            130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
                195                 200                 205

Phe Val Glu Glu Gln Pro Lys
                210                 215

<210> SEQ ID NO 97
<211> LENGTH: 215
<212> TYPE: PRT
<213> ORGANISM: Neisseria meningitidis

<400> SEQUENCE: 97

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
                20                  25                  30

Ser Lys Pro Ala Ser Ile Leu Val Val Pro Pro Leu Asn Glu Ser Pro
            35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
            130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg

Phe Val Glu Gln Pro Lys
    210             215

<210> SEQ ID NO 98
<211> LENGTH: 215
<212> TYPE: PRT
<213> ORGANISM: Neisseria meningitidis

<400> SEQUENCE: 98

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210             215

<210> SEQ ID NO 99
<211> LENGTH: 215
<212> TYPE: PRT
<213> ORGANISM: Neisseria meningitidis

<400> SEQUENCE: 99

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg

```
                    85                  90                  95
Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
                195                 200                 205

Phe Val Glu Glu Gln Pro Lys
                210                 215

<210> SEQ ID NO 100
<211> LENGTH: 215
<212> TYPE: PRT
<213> ORGANISM: Neisseria meningitidis

<400> SEQUENCE: 100

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
                100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
                195                 200                 205

Phe Val Glu Glu Gln Pro Lys
                210                 215

<210> SEQ ID NO 101
<211> LENGTH: 215
```

<212> TYPE: PRT
<213> ORGANISM: Neisseria meningitidis

<400> SEQUENCE: 101

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215
```

<210> SEQ ID NO 102
<211> LENGTH: 215
<212> TYPE: PRT
<213> ORGANISM: Neisseria meningitidis

<400> SEQUENCE: 102

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125
```

```
Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
            195                 200                 205

Phe Val Glu Glu Gln Pro Lys
        210                 215

<210> SEQ ID NO 103
<211> LENGTH: 215
<212> TYPE: PRT
<213> ORGANISM: Neisseria meningitidis

<400> SEQUENCE: 103

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
                180                 185                 190

Asn Leu Leu Ser Pro Tyr Ser His Asn Gly Ile Leu Lys Gly Pro Arg
            195                 200                 205

Phe Val Glu Glu Gln Pro Lys
        210                 215

<210> SEQ ID NO 104
<211> LENGTH: 215
<212> TYPE: PRT
<213> ORGANISM: Neisseria meningitidis

<400> SEQUENCE: 104

Met Lys Pro Leu Ile Leu Gly Leu Ala Ala Val Leu Ala Leu Ser Ala
1               5                   10                  15
```

```
Cys Gln Val Gln Lys Ala Pro Asp Phe Asp Tyr Thr Ser Phe Lys Glu
            20                  25                  30

Ser Lys Pro Ala Ser Ile Leu Val Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 105
<211> LENGTH: 215
<212> TYPE: PRT
<213> ORGANISM: Neisseria meningitidis

<400> SEQUENCE: 105

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175
```

```
Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 106
<211> LENGTH: 215
<212> TYPE: PRT
<213> ORGANISM: Neisseria meningitidis

<400> SEQUENCE: 106

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 107
<211> LENGTH: 215
<212> TYPE: PRT
<213> ORGANISM: Neisseria meningitidis

<400> SEQUENCE: 107

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Leu Asn Glu Ser Pro
        35                  40                  45

Asp Val Asn Gly Thr Trp Gly Val Leu Ala Ser Thr Ala Ala Pro Leu
    50                  55                  60
```

```
Ser Glu Ala Gly Tyr Tyr Val Phe Pro Ala Ala Val Val Glu Glu Thr
 65                  70                  75                  80

Phe Lys Gln Asn Gly Leu Thr Asn Ala Ala Asp Ile His Ala Val Arg
             85                  90                  95

Pro Glu Lys Leu His Gln Ile Phe Gly Asn Asp Ala Val Leu Tyr Ile
        100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 108
<211> LENGTH: 215
<212> TYPE: PRT
<213> ORGANISM: Neisseria meningitidis

<400> SEQUENCE: 108

Met Lys Pro Leu Ile Leu Gly Leu Ala Ala Val Leu Ala Leu Ser Ala
 1               5                  10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
 65                  70                  75                  80

Phe Lys Gln Asn Gly Leu Thr Asn Ala Ala Asp Ile His Ala Val Arg
             85                  90                  95

Pro Glu Lys Leu His Gln Ile Phe Gly Asn Asp Ala Val Leu Tyr Ile
        100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
```

```
                210                 215

<210> SEQ ID NO 109
<211> LENGTH: 215
<212> TYPE: PRT
<213> ORGANISM: Neisseria meningitidis

<400> SEQUENCE: 109

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 110
<211> LENGTH: 215
<212> TYPE: PRT
<213> ORGANISM: Neisseria meningitidis

<400> SEQUENCE: 110

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
```

100                 105                 110
Thr Val Thr Glu Tyr Gly Thr Ser Tyr Gln Ile Leu Asp Ser Val Thr
            115                 120                 125
Thr Val Ser Ala Lys Ala Arg Leu Val Asp Ser Arg Asn Gly Lys Glu
        130                 135                 140
Leu Trp Ser Gly Ser Ala Ser Ile Arg Glu Gly Ser Asn Asn Ser Asn
145                 150                 155                 160
Ser Gly Leu Leu Gly Ala Leu Val Ser Ala Val Val Asn Gln Ile Ala
                165                 170                 175
Asn Ser Leu Thr Asp Arg Gly Tyr Gln Val Ser Lys Thr Ala Ala Tyr
            180                 185                 190
Asn Leu Leu Ser Pro Tyr Ser His Asn Gly Ile Leu Lys Gly Pro Arg
        195                 200                 205
Phe Val Glu Glu Gln Pro Lys
    210                 215

<210> SEQ ID NO 111
<211> LENGTH: 215
<212> TYPE: PRT
<213> ORGANISM: Neisseria meningitidis

<400> SEQUENCE: 111

Met Lys Pro Leu Ile Leu Gly Leu Ala Ala Val Leu Ala Leu Ser Ala
1               5                   10                  15
Cys Gln Val Gln Lys Ala Pro Asp Phe Asp Tyr Thr Ser Phe Lys Glu
            20                  25                  30
Ser Lys Pro Ala Ser Ile Leu Val Pro Pro Leu Asn Glu Ser Pro
        35                  40                  45
Asp Val Asn Gly Thr Trp Gly Val Leu Ala Ser Thr Ala Ala Pro Leu
    50                  55                  60
Ser Glu Ala Gly Tyr Tyr Val Phe Pro Ala Ala Val Val Glu Glu Thr
65                  70                  75                  80
Phe Lys Gln Asn Gly Leu Thr Asn Ala Ala Asp Ile His Ala Val Arg
                85                  90                  95
Pro Glu Lys Leu His Gln Ile Phe Gly Asn Asp Ala Val Leu Tyr Ile
            100                 105                 110
Thr Val Thr Glu Tyr Gly Thr Ser Tyr Gln Ile Leu Asp Ser Val Thr
        115                 120                 125
Thr Val Ser Ala Lys Ala Arg Leu Val Asp Ser Arg Asn Gly Lys Glu
    130                 135                 140
Leu Trp Ser Gly Ser Ala Ser Ile Arg Glu Gly Ser Asn Asn Ser Asn
145                 150                 155                 160
Ser Gly Leu Leu Gly Ala Leu Val Ser Ala Val Val Asn Gln Ile Ala
                165                 170                 175
Asn Ser Leu Thr Asp Arg Gly Tyr Gln Val Ser Lys Thr Ala Ala Tyr
            180                 185                 190
Asn Leu Leu Ser Pro Tyr Ser His Asn Gly Ile Leu Lys Gly Pro Arg
        195                 200                 205
Phe Val Glu Glu Gln Pro Lys
    210                 215

<210> SEQ ID NO 112
<211> LENGTH: 215
<212> TYPE: PRT
<213> ORGANISM: Neisseria meningitidis

<400> SEQUENCE: 112

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215
```

<210> SEQ ID NO 113
<211> LENGTH: 215
<212> TYPE: PRT
<213> ORGANISM: Neisseria meningitidis

<400> SEQUENCE: 113

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140
```

```
Leu Trp Ser Gly Ser Ala Ser Ile Arg Glu Gly Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215
```

<210> SEQ ID NO 114
<211> LENGTH: 215
<212> TYPE: PRT
<213> ORGANISM: Neisseria meningitidis

<400> SEQUENCE: 114

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215
```

<210> SEQ ID NO 115
<211> LENGTH: 215
<212> TYPE: PRT
<213> ORGANISM: Neisseria meningitidis

<400> SEQUENCE: 115

```
Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30
```

```
Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
 50                  55                  60

Ser Glu Ala Gly Tyr Tyr Val Phe Pro Ala Ala Val Val Glu Glu Thr
 65                  70                  75                  80

Phe Lys Gln Asn Gly Leu Thr Asn Ala Ala Asp Ile His Ala Val Arg
                 85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Ser Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
210                 215

<210> SEQ ID NO 116
<211> LENGTH: 215
<212> TYPE: PRT
<213> ORGANISM: Neisseria meningitidis

<400> SEQUENCE: 116

Met Lys Pro Leu Ile Leu Gly Leu Ala Ala Val Leu Ala Leu Ser Ala
 1               5                  10                  15

Cys Gln Val Gln Lys Ala Pro Asp Phe Asp Tyr Thr Ser Phe Lys Glu
             20                  25                  30

Ser Lys Pro Ala Ser Ile Leu Val Val Pro Pro Leu Asn Glu Ser Pro
        35                  40                  45

Asp Val Asn Gly Thr Trp Gly Val Leu Ala Ser Thr Ala Ala Pro Leu
 50                  55                  60

Ser Glu Ala Gly Tyr Tyr Val Phe Pro Ala Ala Val Val Glu Glu Thr
 65                  70                  75                  80

Phe Lys Gln Asn Gly Leu Thr Asn Ala Ala Asp Ile His Ala Val Arg
                 85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Val Asn Gln Ile Ala
                165                 170                 175

Asn Ser Leu Thr Asp Arg Gly Tyr Gln Val Ser Lys Thr Ala Ala Tyr
            180                 185                 190
```

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 117
<211> LENGTH: 215
<212> TYPE: PRT
<213> ORGANISM: Neisseria meningitidis

<400> SEQUENCE: 117

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Leu Asn Glu Ser Pro
        35                  40                  45

Asp Val Asn Gly Thr Trp Gly Val Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

Phe Lys Gln Asn Gly Leu Thr Asn Ala Ala Asp Ile His Ala Val Arg
                85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
        115                 120                 125

Thr Val Ser Ala Lys Ala Arg Leu Val Asp Ser Arg Asn Gly Lys Glu
    130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
        195                 200                 205

Phe Val Glu Glu Gln Pro Lys
    210                 215

<210> SEQ ID NO 118
<211> LENGTH: 215
<212> TYPE: PRT
<213> ORGANISM: Neisseria meningitidis

<400> SEQUENCE: 118

Met Lys Pro Leu Ile Leu Gly Leu Ala Ala Val Leu Ala Leu Ser Ala
1               5                   10                  15

Cys Gln Val Gln Lys Ala Pro Asp Phe Asp Tyr Thr Ser Phe Lys Glu
            20                  25                  30

Ser Lys Pro Ala Ser Ile Leu Val Pro Leu Asn Glu Ser Pro
        35                  40                  45

Asp Val Asn Gly Thr Trp Gly Met Leu Ala Ser Thr Ala Ala Pro Leu
    50                  55                  60

Ser Glu Ala Gly Tyr Tyr Val Phe Pro Ala Ala Val Val Glu Glu Thr
65                  70                  75                  80

-continued

Phe Lys Gln Asn Gly Leu Thr Asn Ala Ala Asp Ile His Ala Val Arg
            85                  90                  95

Pro Glu Lys Leu His Gln Ile Phe Gly Asn Asp Ala Val Leu Tyr Ile
            100                 105                 110

Thr Val Thr Glu Tyr Gly Thr Ser Tyr Gln Ile Leu Asp Ser Val Thr
            115                 120                 125

Thr Val Ser Ala Lys Ala Arg Leu Val Asp Ser Arg Asn Gly Lys Glu
        130                 135                 140

Leu Trp Ser Gly Ser Ala Ser Ile Arg Glu Gly Ser Asn Asn Ser Asn
145                 150                 155                 160

Ser Gly Leu Leu Gly Ala Leu Val Gly Ala Val Val Asn Gln Ile Ala
                165                 170                 175

Asn Ser Leu Thr Asp Arg Gly Tyr Gln Val Ser Lys Thr Ala Ala Tyr
            180                 185                 190

Asn Leu Leu Ser Pro Tyr Ser His Asn Gly Ile Leu Lys Gly Pro Arg
            195                 200                 205

Phe Val Glu Glu Gln Pro Lys
    210                 215

<210> SEQ ID NO 119
<211> LENGTH: 492
<212> TYPE: PRT
<213> ORGANISM: Neisseria meningitidis

<400> SEQUENCE: 119

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Ser Glu Lys Glu Thr Glu
        35                  40                  45

Ala Lys Glu Asp Ala Pro Gln Ala Gly Ser Gln Gly Gln Gly Ala Pro
    50                  55                  60

Ser Ala Gln Gly Gly Gln Asp Met Ala Ala Val Ser Glu Glu Asn Thr
65                  70                  75                  80

Gly Asn Gly Gly Ala Ala Ala Thr Asp Lys Pro Lys Asn Glu Asp Glu
            85                  90                  95

Gly Ala Gln Asn Asp Met Pro Gln Asn Ala Ala Asp Thr Asp Ser Leu
            100                 105                 110

Thr Pro Asn His Thr Pro Ala Ser Asn Met Pro Ala Gly Asn Met Glu
        115                 120                 125

Asn Gln Ala Pro Asp Ala Gly Glu Ser Glu Gln Pro Ala Asn Gln Pro
    130                 135                 140

Asp Met Ala Asn Thr Ala Asp Gly Met Gln Gly Asp Asp Pro Ser Ala
145                 150                 155                 160

Gly Gly Glu Asn Ala Gly Asn Thr Ala Ala Gln Gly Thr Asn Gln Ala
                165                 170                 175

Glu Asn Asn Gln Thr Ala Gly Ser Gln Asn Pro Ala Ser Ser Thr Asn
            180                 185                 190

Pro Ser Ala Thr Asn Ser Gly Gly Asp Phe Gly Arg Thr Asn Val Gly
            195                 200                 205

Asn Ser Val Val Ile Asp Gly Pro Ser Gln Asn Ile Thr Leu Thr His
        210                 215                 220

Cys Lys Gly Asp Ser Cys Ser Gly Asn Asn Phe Leu Asp Glu Glu Val

```
                225                 230                 235                 240
Gln Leu Lys Ser Glu Phe Glu Lys Leu Ser Asp Ala Asp Lys Ile Ser
                245                 250                 255

Asn Tyr Lys Lys Asp Gly Lys Asn Asp Gly Lys Asn Asp Lys Phe Val
                260                 265                 270

Gly Leu Val Ala Asp Ser Val Gln Met Lys Gly Ile Asn Gln Tyr Ile
                275                 280                 285

Ile Phe Tyr Lys Pro Lys Pro Thr Ser Phe Ala Arg Phe Arg Arg Ser
290                 295                 300

Ala Arg Ser Arg Arg Ser Leu Pro Ala Glu Met Pro Leu Ile Pro Val
305                 310                 315                 320

Asn Gln Ala Asp Thr Leu Ile Val Asp Gly Glu Ala Val Ser Leu Thr
                325                 330                 335

Gly His Ser Gly Asn Ile Phe Ala Pro Glu Gly Asn Tyr Arg Tyr Leu
                340                 345                 350

Thr Tyr Gly Ala Glu Lys Leu Pro Gly Gly Ser Tyr Ala Leu Arg Val
                355                 360                 365

Gln Gly Glu Pro Ser Lys Gly Glu Met Leu Ala Gly Thr Ala Val Tyr
                370                 375                 380

Asn Gly Glu Val Leu His Phe His Thr Glu Asn Gly Arg Pro Ser Pro
385                 390                 395                 400

Ser Arg Gly Arg Phe Ala Ala Lys Val Asp Phe Gly Ser Lys Ser Val
                405                 410                 415

Asp Gly Ile Ile Asp Ser Gly Asp Gly Leu His Met Gly Thr Gln Lys
                420                 425                 430

Phe Lys Ala Ala Ile Asp Gly Asn Gly Phe Lys Gly Thr Trp Thr Glu
                435                 440                 445

Asn Gly Gly Asp Val Ser Gly Lys Phe Tyr Gly Pro Ala Gly Glu
                450                 455                 460

Glu Val Ala Gly Lys Tyr Ser Tyr Arg Pro Thr Asp Ala Glu Lys Gly
465                 470                 475                 480

Gly Phe Gly Val Phe Ala Gly Lys Lys Glu Gln Asp
                485                 490

<210> SEQ ID NO 120
<211> LENGTH: 492
<212> TYPE: PRT
<213> ORGANISM: Neisseria meningitidis

<400> SEQUENCE: 120

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
                35                  40                  45

Ala Lys Glu Asp Ala Pro Gln Ala Gly Ser Gln Gly Gln Gly Ala Pro
            50                  55                  60

Ser Ala Gln Gly Gly Gln Asp Met Ala Ala Val Ser Glu Glu Asn Thr
65                  70                  75                  80

Gly Asn Gly Gly Ala Ala Ala Thr Asp Lys Pro Lys Asn Glu Asp Glu
                85                  90                  95

Gly Ala Gln Asn Asp Met Pro Gln Asn Ala Ala Asp Thr Asp Ser Leu
                100                 105                 110
```

Thr Pro Asn His Thr Pro Ala Ser Asn Met Pro Ala Gly Asn Met Glu
            115                 120                 125

Asn Gln Ala Pro Asp Ala Gly Glu Ser Glu Pro Ala Asn Gln Pro
        130                 135                 140

Asp Met Ala Asn Thr Ala Asp Gly Met Gln Gly Asp Pro Ser Ala
145                 150                 155                 160

Gly Gly Glu Asn Ala Gly Asn Thr Ala Ala Gln Gly Thr Asn Gln Ala
                165                 170                 175

Glu Asn Asn Gln Thr Ala Gly Ser Gln Asn Pro Ala Ser Ser Thr Asn
            180                 185                 190

Pro Ser Ala Thr Asn Ser Gly Gly Asp Phe Gly Arg Thr Asn Val Gly
        195                 200                 205

Asn Ser Val Val Ile Asp Gly Pro Ser Gln Asn Ile Thr Leu Thr His
210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Gly Lys Asn Asp Lys Phe Val
            260                 265                 270

Gly Leu Val Ala Asp Ser Val Gln Met Lys Gly Ile Asn Gln Tyr Ile
        275                 280                 285

Ile Phe Tyr Lys Pro Lys Pro Thr Ser Phe Ala Arg Phe Arg Arg Ser
290                 295                 300

Ala Arg Ser Arg Arg Ser Leu Pro Ala Glu Met Pro Leu Ile Pro Val
305                 310                 315                 320

Asn Gln Ala Asp Thr Leu Ile Val Asp Gly Glu Ala Val Ser Leu Thr
                325                 330                 335

Gly His Ser Gly Asn Ile Phe Ala Pro Glu Gly Asn Tyr Arg Tyr Leu
            340                 345                 350

Thr Tyr Gly Ala Glu Lys Leu Pro Gly Gly Ser Tyr Ala Leu Arg Val
        355                 360                 365

Gln Gly Glu Pro Ser Lys Gly Glu Met Leu Ala Gly Thr Ala Val Tyr
370                 375                 380

Asn Gly Glu Val Leu His Phe His Thr Glu Asn Gly Arg Pro Ser Pro
385                 390                 395                 400

Ser Arg Gly Arg Phe Ala Ala Lys Val Asp Phe Gly Ser Lys Ser Val
                405                 410                 415

Asp Gly Ile Ile Asp Ser Gly Asp Gly Leu His Met Gly Thr Gln Lys
            420                 425                 430

Phe Lys Ala Ala Ile Asp Gly Asn Gly Phe Lys Gly Thr Trp Thr Glu
        435                 440                 445

Asn Gly Gly Gly Asp Val Ser Gly Lys Phe Tyr Gly Pro Ala Gly Glu
450                 455                 460

Glu Val Ala Gly Lys Tyr Ser Tyr Arg Pro Thr Asp Ala Glu Lys Gly
465                 470                 475                 480

Gly Phe Gly Val Phe Ala Gly Lys Lys Glu Gln Asp
                485                 490

<210> SEQ ID NO 121
<211> LENGTH: 488
<212> TYPE: PRT
<213> ORGANISM: Neisseria meningitidis

<400> SEQUENCE: 121

```
Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
            20              25                  30

Thr Leu Ser Lys Pro Ala Ala Pro Val Val Ser Glu Lys Glu Thr Glu
            35              40                  45

Ala Lys Glu Asp Ala Pro Gln Ala Gly Ser Gln Gly Gln Gly Ala Pro
50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
            85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
            115                 120                 125

Asn Gln Ala Thr Asp Ala Gly Glu Ser Ser Gln Pro Ala Asn Gln Pro
            130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
            165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
            195                 200                 205

Asn Gly Val Leu Ile Asp Gly Pro Ser Gln Asn Ile Thr Leu Thr His
            210                 215                 220

Cys Lys Gly Asp Ser Cys Ser Gly Asn Asn Phe Leu Asp Glu Glu Val
225                 230                 235                 240

Gln Leu Lys Ser Glu Phe Glu Lys Leu Ser Asp Ala Asp Lys Ile Ser
            245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
            275                 280                 285

Pro Lys Pro Thr Ser Phe Ala Arg Phe Arg Arg Ser Ala Arg Ser Arg
            290                 295                 300

Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
            325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
            370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
            405                 410                 415
```

```
Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Glu Val Ala Gly
            450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
                485

<210> SEQ ID NO 122
<211> LENGTH: 488
<212> TYPE: PRT
<213> ORGANISM: Neisseria meningitidis

<400> SEQUENCE: 122

Met Phe Lys Arg Ser Val Ile Ala Met Ala Cys Ile Phe Ala Leu Ser
1               5                   10                  15

Ala Cys Gly Gly Gly Gly Gly Ser Pro Asp Val Lys Ser Ala Asp
                20                  25                  30

Thr Leu Ser Lys Pro Ala Ala Pro Val Val Ser Glu Lys Glu Thr Glu
            35                  40                  45

Ala Lys Glu Asp Ala Pro Gln Ala Gly Ser Gln Gly Gln Gly Ala Pro
        50                  55                  60

Ser Ala Gln Gly Ser Gln Asp Met Ala Ala Val Ser Glu Glu Asn Thr
65                  70                  75                  80

Gly Asn Gly Gly Ala Val Thr Ala Asp Asn Pro Lys Asn Glu Asp Glu
                85                  90                  95

Val Ala Gln Asn Asp Met Pro Gln Asn Ala Ala Gly Thr Asp Ser Ser
            100                 105                 110

Thr Pro Asn His Thr Pro Asp Pro Asn Met Leu Ala Gly Asn Met Glu
        115                 120                 125

Asn Gln Ala Thr Asp Ala Gly Glu Ser Ser Gln Pro Ala Asn Gln Pro
    130                 135                 140

Asp Met Ala Asn Ala Ala Asp Gly Met Gln Gly Asp Asp Pro Ser Ala
145                 150                 155                 160

Gly Gly Gln Asn Ala Gly Asn Thr Ala Ala Gln Gly Ala Asn Gln Ala
                165                 170                 175

Gly Asn Asn Gln Ala Ala Gly Ser Ser Asp Pro Ile Pro Ala Ser Asn
            180                 185                 190

Pro Ala Pro Ala Asn Gly Gly Ser Asn Phe Gly Arg Val Asp Leu Ala
        195                 200                 205

Asn Gly Val Leu Ile Asp Gly Pro Ser Gln Asn Ile Thr Leu Thr His
    210                 215                 220

Cys Lys Gly Asp Ser Cys Ser Gly Asn Asn Phe Leu Asp Glu Val
225                 230                 235                 240

Gln Leu Lys Ser Glu Phe Glu Lys Leu Ser Asp Ala Asp Lys Ile Ser
                245                 250                 255

Asn Tyr Lys Lys Asp Gly Lys Asn Asp Lys Phe Val Gly Leu Val Ala
            260                 265                 270

Asp Ser Val Gln Met Lys Gly Ile Asn Gln Tyr Ile Ile Phe Tyr Lys
        275                 280                 285

Pro Lys Pro Thr Ser Phe Ala Arg Phe Arg Arg Ser Ala Arg Ser Arg
    290                 295                 300
```

```
Arg Ser Leu Pro Ala Glu Met Pro Leu Ile Pro Val Asn Gln Ala Asp
305                 310                 315                 320

Thr Leu Ile Val Asp Gly Glu Ala Val Ser Leu Thr Gly His Ser Gly
            325                 330                 335

Asn Ile Phe Ala Pro Glu Gly Asn Tyr Arg Tyr Leu Thr Tyr Gly Ala
            340                 345                 350

Glu Lys Leu Pro Gly Gly Ser Tyr Ala Leu Arg Val Gln Gly Glu Pro
            355                 360                 365

Ala Lys Gly Glu Met Leu Ala Gly Ala Ala Val Tyr Asn Gly Glu Val
            370                 375                 380

Leu His Phe His Thr Glu Asn Gly Arg Pro Tyr Pro Thr Arg Gly Arg
385                 390                 395                 400

Phe Ala Ala Lys Val Asp Phe Gly Ser Lys Ser Val Asp Gly Ile Ile
            405                 410                 415

Asp Ser Gly Asp Asp Leu His Met Gly Thr Gln Lys Phe Lys Ala Ala
            420                 425                 430

Ile Asp Gly Asn Gly Phe Lys Gly Thr Trp Thr Glu Asn Gly Ser Gly
            435                 440                 445

Asp Val Ser Gly Lys Phe Tyr Gly Pro Ala Gly Glu Glu Val Ala Gly
            450                 455                 460

Lys Tyr Ser Tyr Arg Pro Thr Asp Ala Glu Lys Gly Gly Phe Gly Val
465                 470                 475                 480

Phe Ala Gly Lys Lys Glu Gln Asp
            485

<210> SEQ ID NO 123
<211> LENGTH: 497
<212> TYPE: PRT
<213> ORGANISM: Neisseria meningitidis

<400> SEQUENCE: 123

Met Phe Lys Arg Ser Val Ile Ala Met Ala Cys Ile Val Ala Leu Ser
1               5                   10                  15

Ala Cys Gly Gly Gly Gly Gly Ser Pro Asp Val Lys Ser Ala Asp
            20                  25                  30

Thr Leu Ser Lys Pro Ala Ala Pro Val Val Thr Glu Asp Val Gly Glu
            35                  40                  45

Glu Val Leu Pro Lys Glu Lys Lys Asp Glu Glu Ala Val Ser Gly Ala
            50                  55                  60

Pro Gln Ala Asp Thr Gln Asp Ala Thr Ala Gly Lys Gly Gly Gln Asp
65                  70                  75                  80

Met Ala Ala Val Ser Ala Glu Asn Thr Gly Asn Gly Gly Ala Ala Thr
            85                  90                  95

Thr Asp Asn Pro Glu Asn Lys Asp Glu Gly Pro Gln Asn Asp Met Pro
            100                 105                 110

Gln Asn Ala Ala Asp Thr Asp Ser Ser Thr Pro Asn His Thr Pro Ala
            115                 120                 125

Pro Asn Met Pro Thr Arg Asp Met Gly Asn Gln Ala Pro Asp Ala Gly
            130                 135                 140

Glu Ser Ala Gln Pro Ala Gln Pro Asp Met Ala Asn Ala Ala Asp
145                 150                 155                 160

Gly Met Gln Gly Asp Asp Pro Ser Ala Gly Glu Asn Ala Gly Asn Thr
            165                 170                 175

Ala Asp Gln Ala Ala Asn Gln Ala Glu Asn Asn Gln Val Gly Gly Ser
```

```
                180                 185                 190
Gln Asn Pro Ala Ser Ser Thr Asn Pro Asn Ala Thr Asn Gly Gly Ser
                195                 200                 205

Asp Phe Gly Arg Ile Asn Val Ala Asn Gly Ile Lys Leu Asp Ser Gly
            210                 215                 220

Ser Glu Asn Val Thr Leu Thr His Cys Lys Asp Lys Val Cys Asp Arg
225                 230                 235                 240

Asp Phe Leu Asp Glu Glu Ala Pro Pro Lys Ser Glu Phe Glu Lys Leu
                245                 250                 255

Ser Asp Glu Glu Lys Ile Asn Lys Tyr Lys Asp Glu Gln Arg Glu
            260                 265                 270

Asn Phe Val Gly Leu Val Ala Asp Arg Val Glu Lys Asn Gly Thr Asn
            275                 280                 285

Lys Tyr Val Ile Ile Tyr Lys Asp Lys Ser Ala Ser Ser Ser Ala
        290                 295                 300

Arg Phe Arg Arg Ser Ala Arg Ser Arg Arg Ser Leu Pro Ala Glu Met
305                 310                 315                 320

Pro Leu Ile Pro Val Asn Gln Ala Asp Thr Leu Ile Val Asp Gly Glu
                325                 330                 335

Ala Val Ser Leu Thr Gly His Ser Gly Asn Ile Phe Ala Pro Glu Gly
                340                 345                 350

Asn Tyr Arg Tyr Leu Thr Tyr Gly Ala Glu Lys Leu Ser Gly Gly Ser
                355                 360                 365

Tyr Ala Leu Ser Val Gln Gly Glu Pro Ala Lys Gly Glu Met Leu Ala
            370                 375                 380

Gly Thr Ala Val Tyr Asn Gly Glu Val Leu His Phe His Met Glu Asn
385                 390                 395                 400

Gly Arg Pro Ser Pro Ser Gly Gly Arg Phe Ala Ala Lys Val Asp Phe
                405                 410                 415

Gly Ser Lys Ser Val Asp Gly Ile Ile Asp Ser Gly Asp Asp Leu His
            420                 425                 430

Met Gly Thr Gln Lys Phe Lys Ala Val Ile Asp Gly Asn Gly Phe Lys
            435                 440                 445

Gly Thr Trp Thr Glu Asn Gly Gly Asp Val Ser Gly Arg Phe Tyr
        450                 455                 460

Gly Pro Ala Gly Glu Glu Val Ala Gly Lys Tyr Ser Tyr Arg Pro Thr
465                 470                 475                 480

Asp Ala Glu Lys Gly Gly Phe Gly Val Phe Ala Gly Lys Lys Glu Gln
                485                 490                 495

Asp

<210> SEQ ID NO 124
<211> LENGTH: 429
<212> TYPE: PRT
<213> ORGANISM: Neisseria gonorrhoeae

<400> SEQUENCE: 124

Met Phe Lys Arg Ser Val Ile Ala Met Ala Cys Ile Phe Pro Leu Ser
1               5                  10                  15

Ala Cys Gly Gly Gly Gly Gly Ser Pro Asp Val Lys Ser Ala Asp
            20                  25                  30

Thr Pro Ser Lys Pro Ala Ala Pro Val Val Ala Glu Asn Ala Gly Glu
        35                  40                  45

Gly Val Leu Pro Lys Glu Lys Lys Asp Glu Glu Ala Ala Gly Gly Ala
```

```
            50                  55                  60
Pro Gln Ala Asp Thr Gln Asp Ala Thr Ala Gly Glu Gly Ser Gln Asp
 65                  70                  75                  80

Met Ala Ala Val Ser Ala Glu Asn Thr Gly Asn Gly Gly Ala Ala Thr
                 85                  90                  95

Thr Asp Asn Pro Lys Asn Glu Asp Ala Gly Ala Gln Asn Asp Met Pro
            100                 105                 110

Gln Asn Ala Ala Glu Ser Ala Asn Gln Thr Gly Asn Asn Gln Pro Ala
        115                 120                 125

Gly Ser Ser Asp Ser Ala Pro Ala Ser Asn Pro Ala Pro Ala Asn Gly
    130                 135                 140

Gly Ser Asp Phe Gly Arg Thr Asn Val Gly Asn Ser Val Val Ile Asp
145                 150                 155                 160

Gly Pro Ser Gln Asn Ile Thr Leu Thr His Cys Lys Gly Asp Ser Cys
                165                 170                 175

Asn Gly Asp Asn Leu Leu Asp Glu Glu Ala Pro Ser Lys Ser Glu Phe
            180                 185                 190

Glu Lys Leu Ser Asp Glu Glu Lys Ile Lys Arg Tyr Lys Lys Asp Glu
        195                 200                 205

Gln Arg Glu Asn Phe Val Gly Leu Val Ala Asp Arg Val Lys Lys Asp
    210                 215                 220

Gly Thr Asn Lys Tyr Ile Ile Phe Tyr Thr Asp Lys Pro Pro Thr Arg
225                 230                 235                 240

Ser Ala Arg Ser Arg Arg Ser Leu Pro Ala Glu Ile Pro Leu Ile Pro
                245                 250                 255

Val Asn Gln Ala Asp Thr Leu Ile Val Asp Gly Glu Ala Val Ser Leu
            260                 265                 270

Thr Gly His Ser Gly Asn Ile Phe Ala Pro Glu Gly Asn Tyr Arg Tyr
        275                 280                 285

Leu Thr Tyr Gly Ala Glu Lys Leu Pro Gly Gly Ser Tyr Ala Leu Arg
    290                 295                 300

Val Gln Gly Glu Pro Ala Lys Gly Glu Met Leu Val Gly Thr Ala Val
305                 310                 315                 320

Tyr Asn Gly Glu Val Leu His Phe His Met Glu Asn Gly Arg Pro Tyr
                325                 330                 335

Pro Ser Gly Gly Arg Phe Ala Ala Lys Val Asp Phe Gly Ser Lys Ser
            340                 345                 350

Val Asp Gly Ile Ile Asp Ser Gly Asp Asp Leu His Met Gly Thr Gln
        355                 360                 365

Lys Phe Lys Ala Ala Ile Asp Gly Asn Gly Phe Lys Gly Thr Trp Thr
    370                 375                 380

Glu Asn Gly Gly Gly Asp Val Ser Gly Arg Phe Tyr Gly Pro Ala Gly
385                 390                 395                 400

Glu Glu Val Ala Gly Lys Tyr Ser Tyr Arg Pro Thr Asp Ala Glu Lys
                405                 410                 415

Gly Gly Phe Gly Val Phe Ala Gly Lys Lys Asp Arg Asp
            420                 425

<210> SEQ ID NO 125
<211> LENGTH: 315
<212> TYPE: PRT
<213> ORGANISM: Neisseria meningitidis

<400> SEQUENCE: 125
```

-continued

```
Met Glu Phe Phe Ile Ile Leu Leu Ala Ala Val Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ser Ala Leu Asp Glu
            130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Ala Val Asn Ala Ser Asn Ala Glu
            210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
            275                 280                 285

Ile Met Pro Ala Asn Val Ala Asp Ile Gly Ser Leu Ile Ser Ala Gly
            290                 295                 300

Met Lys Ile Ile Asp Ser Ser Lys Thr Ala Lys
305                 310                 315

<210> SEQ ID NO 126
<211> LENGTH: 315
<212> TYPE: PRT
<213> ORGANISM: Neisseria meningitidis

<400> SEQUENCE: 126

Met Glu Phe Phe Ile Ile Leu Leu Ala Ala Val Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
50                  55                  60
```

-continued

```
Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315
```

<210> SEQ ID NO 127
<211> LENGTH: 315
<212> TYPE: PRT
<213> ORGANISM: Neisseria meningitidis

<400> SEQUENCE: 127

```
Met Glu Phe Phe Ile Ile Leu Leu Ala Ala Val Val Phe Gly Phe
  1               5                  10                  15

Lys Ser Phe Val Val Ile Pro Gln Gln Glu Val His Val Val Glu Arg
                 20                  25                  30

Leu Gly Arg Phe His Arg Ala Leu Thr Ala Gly Leu Asn Ile Leu Ile
             35                  40                  45

Pro Phe Ile Asp Arg Val Ala Tyr Arg His Ser Leu Lys Glu Ile Pro
     50                  55                  60

Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
```

```
                115                 120                 125
Glu Glu Arg Asp Glu Ile Asn Ser Thr Val Val Ser Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 128
<211> LENGTH: 315
<212> TYPE: PRT
<213> ORGANISM: Neisseria gonorrhoeae

<400> SEQUENCE: 128

Met Glu Phe Phe Ile Ile Leu Leu Ala Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ser Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ala Met Gln Ala Gln Ile Thr
                165                 170                 175
```

```
Ala Glu Arg Glu Lys Arg Ala Arg Ile Ala Glu Ser Glu Gly Arg Lys
                180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Ala Val Asn Ala Ser Asn Ala Glu
        210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
        290                 295                 300

Met Lys Ile Ile Asp Ser Ser Lys Thr Ala Lys
305                 310                 315

<210> SEQ ID NO 129
<211> LENGTH: 315
<212> TYPE: PRT
<213> ORGANISM: Neisseria gonorrhoeae

<400> SEQUENCE: 129

Met Glu Phe Phe Ile Ile Leu Leu Ala Ala Val Ala Val Phe Gly Phe
1               5                   10                  15

Lys Ser Phe Val Val Ile Pro Gln Gln Glu Val His Val Val Glu Arg
                20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
        50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ser Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ala Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240
```

Leu Val Ala Glu Ala Asn Ala Glu Ala Ile Arg Gln Ile Ala Ala
            245                 250                 255

Leu Gln Thr Gln Gly Gly Ala Asp Ala Val Asn Leu Lys Ile Ala Glu
        260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
        290                 295                 300

Met Lys Ile Ile Asp Ser Ser Lys Thr Ala Lys
305                 310                 315

<210> SEQ ID NO 130
<211> LENGTH: 315
<212> TYPE: PRT
<213> ORGANISM: Neisseria meningitidis

<400> SEQUENCE: 130

Met Glu Phe Phe Ile Ile Leu Leu Ala Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly

```
            290                 295                 300
Met Lys Ile Ile Asp Ser Ser Lys Thr Ala Lys
305                 310                 315

<210> SEQ ID NO 131
<211> LENGTH: 315
<212> TYPE: PRT
<213> ORGANISM: Neisseria meningitidis

<400> SEQUENCE: 131

Met Glu Phe Phe Ile Ile Leu Leu Ala Ala Val Ala Val Phe Gly Phe
1               5                   10                  15

Lys Ser Phe Val Val Ile Pro Gln Gln Glu Val His Val Glu Arg
                20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
        50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
        290                 295                 300

Met Lys Ile Ile Asp Ser Ser Lys Thr Ala Lys
305                 310                 315

<210> SEQ ID NO 132
<211> LENGTH: 315
<212> TYPE: PRT
<213> ORGANISM: Neisseria meningitidis
```

<400> SEQUENCE: 132

```
Met Glu Phe Phe Ile Ile Leu Leu Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65              70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315
```

<210> SEQ ID NO 133
<211> LENGTH: 315
<212> TYPE: PRT
<213> ORGANISM: Neisseria meningitidis

<400> SEQUENCE: 133

```
Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
        35                  40                  45
```

Pro Phe Ile Asp Arg Val Ala Tyr Arg His Ser Leu Lys Glu Ile Pro
 50                  55                  60

Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ser Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
290                 295                 300

Met Lys Ile Ile Asp Ser Ser Lys Thr Ala Lys
305                 310                 315

<210> SEQ ID NO 134
<211> LENGTH: 315
<212> TYPE: PRT
<213> ORGANISM: Neisseria meningitidis

<400> SEQUENCE: 134

Met Glu Phe Phe Ile Ile Leu Leu Val Ala Val Ala Val Phe Gly Phe
 1               5                  10                  15

Lys Ser Phe Val Val Ile Pro Gln Gln Glu Val His Val Glu Arg
                 20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
 50                  55                  60

Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ser Ala Leu Asp Glu
        130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 135
<211> LENGTH: 315
<212> TYPE: PRT
<213> ORGANISM: Neisseria meningitidis

<400> SEQUENCE: 135

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ser Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
                260                 265                 270

Gln Tyr Val Ala Ala Phe Asn Asn Leu Ala Lys Glu Ser Asn Thr Leu
            275                 280                 285

Ile Met Pro Ala Asn Val Ala Asp Ile Gly Ser Leu Ile Ser Ala Gly
        290                 295                 300

Met Lys Ile Ile Asp Ser Ser Lys Thr Ala Lys
305                 310                 315

<210> SEQ ID NO 136
<211> LENGTH: 315
<212> TYPE: PRT
<213> ORGANISM: Neisseria meningitidis

<400> SEQUENCE: 136

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ser Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

```
Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
                260                 265                 270

Gln Tyr Val Ala Ala Phe Asn Asn Leu Ala Lys Glu Ser Asn Thr Leu
                275                 280                 285

Ile Met Pro Ala Asn Val Ala Asp Ile Gly Ser Leu Ile Ser Ala Gly
                290                 295                 300

Met Lys Ile Ile Asp Ser Ser Lys Thr Ala Lys
305                 310                 315

<210> SEQ ID NO 137
<211> LENGTH: 315
<212> TYPE: PRT
<213> ORGANISM: Neisseria meningitidis

<400> SEQUENCE: 137

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
                20                  25                  30

Leu Gly Arg Phe His Arg Ala Leu Thr Ala Gly Leu Asn Ile Leu Ile
                35                  40                  45

Pro Phe Ile Asp Arg Val Ala Tyr Arg His Ser Leu Lys Glu Ile Pro
        50                  55                  60

Leu Asp Val Pro Ser Gln Val Cys Ile Thr Arg Asp Asn Thr Gln Leu
65              70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
                100                 105                 110

Thr Thr Leu Arg Ser Val Ile Gly Arg Met Glu Leu Asp Lys Thr Phe
                115                 120                 125

Glu Glu Arg Asp Glu Ile Asn Ser Thr Val Val Ala Ala Leu Asp Glu
        130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
                180                 185                 190

Ile Glu Gln Ile Asn Leu Ala Ser Gly Gln Arg Glu Ala Glu Ile Gln
                195                 200                 205

Gln Ser Glu Gly Glu Ala Gln Ala Ala Val Asn Ala Ser Asn Ala Glu
        210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
                260                 265                 270

Gln Tyr Val Ala Ala Phe Asn Asn Leu Ala Lys Glu Ser Asn Thr Leu
                275                 280                 285
```

```
Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 138
<211> LENGTH: 315
<212> TYPE: PRT
<213> ORGANISM: Neisseria meningitidis

<400> SEQUENCE: 138

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 139
<211> LENGTH: 315
<212> TYPE: PRT
```

<213> ORGANISM: Neisseria meningitidis

<400> SEQUENCE: 139

```
Met Glu Phe Phe Ile Ile Leu Leu Val Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315
```

<210> SEQ ID NO 140
<211> LENGTH: 315
<212> TYPE: PRT
<213> ORGANISM: Neisseria meningitidis

<400> SEQUENCE: 140

```
Met Glu Phe Phe Ile Ile Leu Leu Val Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
```

```
            35                  40                  45
Pro Phe Ile Asp Arg Val Ala Tyr Arg His Ser Leu Lys Glu Ile Pro
 50                  55                  60

Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95

Ser Tyr Gly Ser Ser Asn Tyr Ile Met Ala Ile Thr Gln Leu Ala Gln
                100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ala Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315
```

<210> SEQ ID NO 141
<211> LENGTH: 315
<212> TYPE: PRT
<213> ORGANISM: Neisseria meningitidis

<400> SEQUENCE: 141

```
Met Glu Phe Phe Ile Ile Leu Leu Val Ala Val Ala Val Phe Gly Phe
 1               5                  10                  15

Lys Ser Phe Val Val Ile Pro Gln Gln Glu Val His Val Val Glu Arg
                20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
 50                  55                  60

Leu Asp Val Pro Ser Gln Val Cys Ile Thr Arg Asp Asn Thr Gln Leu
 65                  70                  75                  80

Thr Val Asp Gly Ile Ile Tyr Phe Gln Val Thr Asp Pro Lys Leu Ala
                 85                  90                  95
```

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 142
<211> LENGTH: 315
<212> TYPE: PRT
<213> ORGANISM: Neisseria meningitidis

<400> SEQUENCE: 142

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Thr Val Val Ala Ala Leu Asp Glu
    130                 135                 140

Ala Ala Gly Ala Trp Gly Val Lys Val Leu Arg Tyr Glu Ile Lys Asp
145                 150                 155                 160

```
Leu Val Pro Pro Gln Glu Ile Leu Arg Ser Met Gln Ala Gln Ile Thr
            165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Ala Val Asn Ala Ser Asn Ala Glu
        210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
            275                 280                 285

Ile Met Pro Ala Asn Val Ala Asp Ile Gly Ser Leu Ile Ser Ala Gly
            290                 295                 300

Met Lys Ile Ile Asp Ser Ser Lys Thr Ala Lys
305                 310                 315

<210> SEQ ID NO 143
<211> LENGTH: 315
<212> TYPE: PRT
<213> ORGANISM: Neisseria meningitidis

<400> SEQUENCE: 143

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
        50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ala Ala Leu Asp Glu
        130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Ala Val Asn Ala Ser Asn Ala Glu
```

```
              210                 215                 220
Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
                260                 265                 270

Gln Tyr Val Ala Ala Phe Asn Asn Leu Ala Lys Glu Ser Asn Thr Leu
                275                 280                 285

Ile Met Pro Ala Asn Val Ala Asp Ile Gly Ser Leu Ile Ser Ala Gly
                290                 295                 300

Met Lys Ile Ile Asp Ser Ser Lys Thr Ala Lys
305                 310                 315

<210> SEQ ID NO 144
<211> LENGTH: 315
<212> TYPE: PRT
<213> ORGANISM: Neisseria meningitidis

<400> SEQUENCE: 144

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Val Glu Arg
                20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
                100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ala Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Val Asn Ala Ser Asn Ala Glu
                210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
                260                 265                 270
```

```
Gln Tyr Val Ala Ala Phe Asn Asn Leu Ala Lys Glu Ser Asn Thr Leu
            275                 280                 285

Ile Met Pro Ala Asn Val Ala Asp Ile Gly Ser Leu Ile Ser Ala Gly
            290                 295                 300

Met Lys Ile Ile Asp Ser Ser Lys Thr Ala Lys
305                 310                 315

<210> SEQ ID NO 145
<211> LENGTH: 315
<212> TYPE: PRT
<213> ORGANISM: Neisseria meningitidis

<400> SEQUENCE: 145

Met Glu Phe Phe Ile Ile Leu Leu Val Ala Val Ala Val Phe Gly Phe
1               5                   10                  15

Lys Ser Phe Val Val Ile Pro Gln Gln Glu Val His Val Glu Arg
            20                  25                  30

Leu Gly Arg Phe His Arg Ala Leu Thr Ala Gly Leu Asn Ile Leu Ile
            35                  40                  45

Pro Phe Ile Asp Arg Val Ala Tyr Arg His Ser Leu Lys Glu Ile Pro
        50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
            115                 120                 125

Glu Glu Arg Asp Glu Ile Asn Ser Thr Val Val Ser Ala Leu Asp Glu
130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
            195                 200                 205

Gln Ser Glu Gly Glu Ala Gln Ala Ala Val Asn Ala Ser Asn Ala Glu
        210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
            275                 280                 285

Ile Met Pro Ala Asn Val Ala Asp Ile Gly Ser Leu Ile Ser Ala Gly
            290                 295                 300

Met Lys Ile Ile Asp Ser Ser Lys Thr Ala Lys
305                 310                 315

<210> SEQ ID NO 146
```

<211> LENGTH: 315
<212> TYPE: PRT
<213> ORGANISM: Neisseria meningitidis

<400> SEQUENCE: 146

Met Glu Phe Phe Ile Ile Leu Leu Ala Ala Val Ala Val Phe Gly Phe
1               5                   10                  15

Lys Ser Phe Val Val Ile Pro Gln Gln Glu Val His Val Val Glu Arg
            20                  25                  30

Leu Gly Arg Phe His Arg Ala Leu Thr Ala Gly Leu Asn Ile Leu Ile
        35                  40                  45

Pro Phe Ile Asp Arg Val Ala Tyr Arg His Ser Leu Lys Glu Ile Pro
    50                  55                  60

Leu Asp Val Pro Ser Gln Val Cys Ile Thr Arg Asp Asn Thr Gln Leu
65                  70                  75                  80

Thr Val Asp Gly Ile Ile Tyr Phe Gln Val Thr Asp Pro Lys Leu Ala
                85                  90                  95

Ser Tyr Gly Ser Ser Asn Tyr Ile Met Ala Ile Thr Gln Leu Ala Gln
            100                 105                 110

Thr Thr Leu Arg Ser Val Ile Gly Arg Met Glu Leu Asp Lys Thr Phe
        115                 120                 125

Glu Glu Arg Asp Glu Ile Asn Ser Ile Val Val Ser Ala Leu Asp Glu
    130                 135                 140

Ala Ala Gly Ala Trp Gly Val Lys Val Leu Arg Tyr Glu Ile Lys Asp
145                 150                 155                 160

Leu Val Pro Pro Gln Glu Ile Leu Arg Ser Met Gln Ala Gln Ile Thr
                165                 170                 175

Ala Glu Arg Glu Lys Arg Ala Arg Ile Ala Glu Ser Glu Gly Arg Lys
            180                 185                 190

Ile Glu Gln Ile Asn Leu Ala Ser Gly Gln Arg Glu Ala Glu Ile Gln
        195                 200                 205

Gln Ser Glu Gly Glu Ala Gln Ala Ala Val Asn Ala Ser Asn Ala Glu
    210                 215                 220

Lys Ile Ala Arg Ile Asn Arg Ala Lys Gly Glu Ala Glu Ser Leu Arg
225                 230                 235                 240

Leu Val Ala Glu Ala Asn Ala Glu Ala Ile Arg Gln Ile Ala Ala Ala
                245                 250                 255

Leu Gln Thr Gln Gly Gly Ala Asp Ala Val Asn Leu Lys Ile Ala Glu
            260                 265                 270

Gln Tyr Val Ala Ala Phe Asn Asn Leu Ala Lys Glu Ser Asn Thr Leu
        275                 280                 285

Ile Met Pro Ala Asn Val Ala Asp Ile Gly Ser Leu Ile Ser Ala Gly
    290                 295                 300

Met Lys Ile Ile Asp Ser Ser Lys Thr Ala Lys
305                 310                 315

<210> SEQ ID NO 147
<211> LENGTH: 441
<212> TYPE: PRT
<213> ORGANISM: Neisseria gonorrhoeae

<400> SEQUENCE: 147

Met Lys Lys His Leu Leu Arg Ser Ala Leu Tyr Gly Ile Ala Ala Ala
1               5                   10                  15

Ile Leu Ala Ala Cys Gln Ser Arg Ser Ile Gln Thr Phe Pro Gln Pro
            20                  25                  30

```
Asp Thr Ser Val Ile Asn Gly Pro Asp Arg Pro Ala Gly Ile Pro Asp
            35                  40                  45

Pro Ala Gly Thr Thr Val Ala Gly Gly Ala Val Tyr Thr Val Val
 50                  55                  60

Pro His Leu Ser Met Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
                 85                  90                  95

Trp Gln Asp Val Cys Ala Gln Ala Phe Gln Thr Pro Val His Ser Phe
                100                 105                 110

Gln Ala Lys Arg Phe Phe Glu Arg Tyr Phe Thr Pro Trp Gln Val Ala
                115                 120                 125

Gly Asn Gly Ser Leu Ala Gly Thr Val Thr Gly Tyr Tyr Glu Pro Val
            130                 135                 140

Leu Lys Gly Asp Gly Arg Arg Thr Glu Arg Ala Arg Phe Pro Ile Tyr
145                 150                 155                 160

Gly Ile Pro Asp Asp Phe Ile Ser Val Pro Leu Pro Ala Gly Leu Arg
                165                 170                 175

Gly Gly Lys Asn Leu Val Arg Ile Arg Gln Thr Gly Lys Asn Ser Gly
                180                 185                 190

Thr Ile Asp Asn Ala Gly Gly Thr His Thr Ala Asp Leu Ser Arg Phe
            195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
                260                 265                 270

Lys Tyr Ile Arg Ile Gly Tyr Ala Asp Lys Asn Glu His Pro Tyr Val
            275                 280                 285

Ser Ile Gly Arg Tyr Met Ala Asp Lys Gly Tyr Leu Lys Leu Gly Gln
            290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Gly Asn Glu Gly Pro Val Gly Ala Leu Gly Thr Pro
                340                 345                 350

Leu Met Gly Glu Tyr Ala Gly Ala Ile Asp Arg His Tyr Ile Thr Leu
            355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
            435                 440
```

<210> SEQ ID NO 148
<211> LENGTH: 441
<212> TYPE: PRT
<213> ORGANISM: Neisseria gonorrhoeae

<400> SEQUENCE: 148

```
Met Lys Lys His Leu Leu Arg Ser Ala Leu Tyr Gly Ile Ala Ala Ala
1               5                   10                  15

Ile Leu Ala Ala Cys Gln Ser Arg Ser Ile Gln Thr Phe Pro Gln Pro
            20                  25                  30

Asp Thr Ser Val Ile Asn Gly Pro Asp Arg Pro Ala Gly Ile Pro Asp
        35                  40                  45

Pro Ala Gly Thr Thr Val Ala Gly Gly Ala Val Tyr Thr Val Val
    50                  55                  60

Pro His Leu Ser Met Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Ile His Ser Phe
            100                 105                 110

Gln Ala Lys Arg Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Gly Arg Arg Thr Glu Arg Ala Arg Phe Pro Ile Tyr
145                 150                 155                 160

Gly Ile Pro Asp Asp Phe Ile Ser Val Pro Leu Pro Ala Gly Leu Arg
                165                 170                 175

Gly Gly Lys Asn Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro His Lys
305                 310                 315                 320

Leu Ala Glu Val Leu Gly Gln Asn Pro Ser Tyr Ile Phe Phe Arg Glu
                325                 330                 335

Leu Ala Gly Ser Gly Asn Glu Gly Pro Val Gly Ala Leu Gly Thr Pro
            340                 345                 350

Leu Met Gly Glu Tyr Ala Gly Ala Ile Asp Arg His Tyr Ile Thr Leu
        355                 360                 365

Gly Ala Pro Leu Phe Val Ala Thr Ala His Pro Val Thr Arg Lys Ala
    370                 375                 380
```

```
Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440
```

<210> SEQ ID NO 149
<211> LENGTH: 441
<212> TYPE: PRT
<213> ORGANISM: Neisseria gonorrhoeae

<400> SEQUENCE: 149

```
Met Lys Lys His Leu Leu Arg Ser Ala Leu Tyr Gly Ile Ala Ala Ala
1               5                   10                  15

Ile Leu Ala Ala Cys Gln Ser Arg Ser Ile Gln Thr Phe Pro Gln Pro
            20                  25                  30

Asp Thr Ser Val Ile Asn Gly Pro Asp Arg Pro Ala Gly Ile Pro Asp
        35                  40                  45

Pro Ala Gly Thr Thr Val Ala Gly Gly Ala Val Tyr Thr Val Val
50                  55                  60

Pro His Leu Ser Met Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Arg Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
        130                 135                 140

Leu Lys Gly Asp Gly Arg Arg Thr Glu Arg Ala Arg Phe Pro Ile Tyr
145                 150                 155                 160

Gly Ile Pro Asp Asp Phe Ile Ser Val Pro Leu Pro Ala Gly Leu Arg
                165                 170                 175

Gly Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
290                 295                 300

Thr Ser Met Gln Gly Ile Lys Ala Tyr Met Arg Gln Asn Pro Gln Arg
```

```
            305                 310                 315                 320
Leu Ala Glu Val Leu Gly Gln Asn Pro Ser Tyr Ile Phe Phe Arg Glu
                    325                 330                 335

Leu Ala Gly Ser Gly Gly Asp Gly Pro Val Gly Ala Leu Gly Thr Pro
                    340                 345                 350

Leu Met Gly Gly Tyr Ala Gly Ala Ile Asp Arg His Tyr Ile Thr Leu
                    355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
                435                 440
```

<210> SEQ ID NO 150
<211> LENGTH: 441
<212> TYPE: PRT
<213> ORGANISM: Neisseria meningitidis
<400> SEQUENCE: 150

```
Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
            35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
                100                 105                 110

Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
                180                 185                 190

Thr Ile Asp Asn Ala Gly Gly Thr His Thr Ala Asp Leu Ser Arg Phe
            195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240
```

```
Asp Gly Lys Ala Pro Ile Leu Gly Tyr Ala Glu Asp Pro Val Glu Leu
            245                 250                 255

Phe Phe Met His Ile Gln Gly Ser Gly Arg Leu Lys Thr Pro Ser Gly
        260                 265                 270

Lys Tyr Ile Arg Ile Gly Tyr Ala Asp Lys Asn Glu His Pro Tyr Val
            275                 280                 285

Ser Ile Gly Lys Tyr Met Ala Asp Lys Gly Tyr Leu Lys Leu Gly Gln
        290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Ser Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Thr Ala Gly Lys Met Lys Glu Pro Gly Tyr Val Trp Gln Leu Leu Pro
            420                 425                 430

Asn Gly Met Lys Pro Glu Tyr Arg Pro
        435                 440

<210> SEQ ID NO 151
<211> LENGTH: 441
<212> TYPE: PRT
<213> ORGANISM: Neisseria meningitidis

<400> SEQUENCE: 151

Met Lys Lys Tyr Leu Phe Arg Ala Ala Leu Tyr Gly Ile Ser Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Ala Gly Ile Pro Asp
        35                  40                  45

Pro Ala Gly Thr Thr Val Ala Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175
```

```
Ser Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Thr Ala Gly Lys Met Lys Glu Pro Gly Tyr Val Trp Gln Leu Leu Pro
            420                 425                 430

Asn Gly Met Lys Pro Glu Tyr Arg Pro
            435                 440

<210> SEQ ID NO 152
<211> LENGTH: 441
<212> TYPE: PRT
<213> ORGANISM: Neisseria meningitidis

<400> SEQUENCE: 152

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Ala
        35                  40                  45

Pro Ala Gly Thr Thr Val Ala Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
```

```
                100                 105                 110
Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
130                 135                 140

Leu Lys Gly Asp Asp Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
            165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
            195                 200                 205

Pro Ile Thr Ala Arg Thr Thr Ala Ile Lys Gly Arg Phe Glu Gly Ser
            210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
            245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
            275                 280                 285

Ser Ile Gly Lys Tyr Met Ala Asp Lys Gly Tyr Leu Lys Leu Gly Gln
            290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
            325                 330                 335

Leu Thr Gly Ser Gly Asn Asp Gly Pro Val Gly Ala Leu Gly Thr Pro
            340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
            405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 153
<211> LENGTH: 441
<212> TYPE: PRT
<213> ORGANISM: Neisseria meningitidis

<400> SEQUENCE: 153

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30
```

-continued

```
Asp Thr Ser Val Ile Asn Gly Pro Asp Arg Pro Val Gly Ile Pro Ala
         35                  40                  45

Pro Ala Gly Thr Thr Val Ala Gly Gly Ala Val Tyr Thr Val Val
 50                  55                  60

Pro His Leu Ser Leu Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
             85                  90                  95

Trp Gln Asp Val Cys Ala Gln Ala Phe Gln Thr Pro Val His Ser Phe
                100                 105                 110

Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
            195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
            275                 280                 285

Ser Ile Gly Lys Tyr Met Ala Asp Lys Gly Tyr Leu Lys Leu Gly Gln
290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Gly Asn Asp Gly Pro Val Gly Ala Leu Gly Thr Pro
            340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440
```

<210> SEQ ID NO 154
<211> LENGTH: 441
<212> TYPE: PRT
<213> ORGANISM: Neisseria meningitidis

<400> SEQUENCE: 154

| | | | | | | | | | | | | | | |
|---|---|---|---|---|---|---|---|---|---|---|---|---|---|---|
| Met | Lys | Lys | Tyr | Leu | Phe | Arg | Ala | Ala | Leu | Cys | Gly | Ile | Ala | Ala | Ala |
| 1 | | | | 5 | | | | | 10 | | | | | 15 | |
| Ile | Leu | Ala | Ala | Cys | Gln | Ser | Lys | Ser | Ile | Gln | Thr | Phe | Pro | Gln | Pro |
| | | | 20 | | | | | 25 | | | | | 30 | | |
| Asp | Thr | Ser | Val | Ile | Asn | Gly | Pro | Asp | Arg | Pro | Val | Gly | Ile | Pro | Ala |
| | | | 35 | | | | | 40 | | | | | 45 | | |
| Pro | Ala | Gly | Thr | Thr | Val | Ala | Gly | Gly | Gly | Ala | Val | Tyr | Thr | Val | Val |
| | 50 | | | | | 55 | | | | | 60 | | | | |
| Pro | His | Leu | Ser | Leu | Pro | His | Trp | Ala | Ala | Gln | Asp | Phe | Ala | Lys | Ser |
| 65 | | | | | 70 | | | | | 75 | | | | | 80 |
| Leu | Gln | Ser | Phe | Arg | Leu | Gly | Cys | Ala | Asn | Leu | Lys | Asn | Arg | Gln | Gly |
| | | | | 85 | | | | | 90 | | | | | 95 | |
| Trp | Gln | Asp | Val | Cys | Ala | Gln | Ala | Phe | Gln | Thr | Pro | Val | His | Ser | Phe |
| | | | 100 | | | | | 105 | | | | | 110 | | |
| Gln | Ala | Lys | Gln | Phe | Phe | Glu | Arg | Tyr | Phe | Thr | Pro | Trp | Gln | Val | Ala |
| | | | 115 | | | | | 120 | | | | | 125 | | |
| Gly | Asn | Gly | Ser | Leu | Ala | Gly | Thr | Val | Thr | Gly | Tyr | Tyr | Glu | Pro | Val |
| | 130 | | | | | 135 | | | | | 140 | | | | |
| Leu | Lys | Gly | Asp | Asp | Arg | Arg | Thr | Ala | Gln | Ala | Arg | Phe | Pro | Ile | Tyr |
| 145 | | | | | 150 | | | | | 155 | | | | | 160 |
| Gly | Ile | Pro | Asp | Asp | Phe | Ile | Ser | Val | Pro | Leu | Pro | Ala | Gly | Leu | Arg |
| | | | | 165 | | | | | 170 | | | | | 175 | |
| Ser | Gly | Lys | Ala | Leu | Val | Arg | Ile | Arg | Gln | Thr | Gly | Lys | Asn | Ser | Gly |
| | | | 180 | | | | | 185 | | | | | 190 | | |
| Thr | Ile | Asp | Asn | Thr | Gly | Gly | Thr | His | Thr | Ala | Asp | Leu | Ser | Gln | Phe |
| | | | 195 | | | | | 200 | | | | | 205 | | |
| Pro | Ile | Thr | Ala | Arg | Thr | Thr | Ala | Ile | Lys | Gly | Arg | Phe | Glu | Gly | Ser |
| | 210 | | | | | 215 | | | | | 220 | | | | |
| Arg | Phe | Leu | Pro | Tyr | His | Thr | Arg | Asn | Gln | Ile | Asn | Gly | Gly | Ala | Leu |
| 225 | | | | | 230 | | | | | 235 | | | | | 240 |
| Asp | Gly | Lys | Ala | Pro | Ile | Leu | Gly | Tyr | Ala | Glu | Asp | Pro | Val | Glu | Leu |
| | | | | 245 | | | | | 250 | | | | | 255 | |
| Phe | Phe | Met | His | Ile | Gln | Gly | Ser | Gly | Arg | Leu | Lys | Thr | Pro | Ser | Gly |
| | | | 260 | | | | | 265 | | | | | 270 | | |
| Lys | Tyr | Ile | Arg | Ile | Gly | Tyr | Ala | Asp | Lys | Asn | Glu | His | Pro | Tyr | Val |
| | | | 275 | | | | | 280 | | | | | 285 | | |
| Ser | Ile | Gly | Lys | Tyr | Met | Ala | Asp | Lys | Gly | Tyr | Leu | Lys | Leu | Gly | Gln |
| | 290 | | | | | 295 | | | | | 300 | | | | |
| Thr | Ser | Met | Gln | Gly | Ile | Lys | Ser | Tyr | Met | Arg | Gln | Asn | Pro | Gln | Arg |
| 305 | | | | | 310 | | | | | 315 | | | | | 320 |
| Leu | Ala | Glu | Val | Leu | Gly | Gln | Asn | Pro | Ser | Tyr | Ile | Phe | Phe | Arg | Glu |
| | | | | 325 | | | | | 330 | | | | | 335 | |
| Leu | Thr | Gly | Ser | Gly | Asn | Asp | Gly | Pro | Val | Gly | Ala | Leu | Gly | Thr | Pro |
| | | | 340 | | | | | 345 | | | | | 350 | | |
| Leu | Met | Gly | Glu | Tyr | Ala | Gly | Ala | Val | Asp | Arg | His | Tyr | Ile | Thr | Leu |
| | | | 355 | | | | | 360 | | | | | 365 | | |
| Gly | Ala | Pro | Leu | Phe | Val | Ala | Thr | Ala | His | Pro | Val | Thr | Arg | Lys | Ala |
| | 370 | | | | | 375 | | | | | 380 | | | | |

```
Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
            405                 410                 415

Leu Ala Gly Lys Gln Lys Thr Thr Gly Tyr Val Trp Gln Leu Leu Pro
        420                 425                 430

Asn Gly Met Lys Pro Glu Tyr Arg Pro
        435                 440

<210> SEQ ID NO 155
<211> LENGTH: 441
<212> TYPE: PRT
<213> ORGANISM: Neisseria meningitidis

<400> SEQUENCE: 155

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Ala
        35                  40                  45

Pro Ala Gly Thr Thr Val Ala Gly Gly Ala Val Tyr Thr Val Val
    50                  55                  60

Pro His Leu Ser Leu Pro His Trp Ala Ala Gln Asp Phe Ala Lys Ser
65              70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Lys Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320
```

Leu Ala Glu Val Leu Gly Gln Asn Pro Ser Tyr Ile Phe Arg Glu
            325                 330                 335

Leu Thr Gly Ser Gly Asn Asp Gly Pro Val Gly Ala Leu Gly Thr Pro
        340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 156
<211> LENGTH: 441
<212> TYPE: PRT
<213> ORGANISM: Neisseria meningitidis

<400> SEQUENCE: 156

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Ala
        35                  40                  45

Pro Ala Gly Thr Thr Val Ala Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu

```
                      245                 250                 255
Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
            275                 280                 285

Ser Ile Gly Lys Tyr Met Ala Asp Lys Gly Tyr Leu Lys Leu Gly Gln
            290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Arg Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
                370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gly Leu Leu Pro
                420                 425                 430

Asn Gly Met Lys Pro Glu Tyr Arg Pro
                435                 440

<210> SEQ ID NO 157
<211> LENGTH: 441
<212> TYPE: PRT
<213> ORGANISM: Neisseria meningitidis

<400> SEQUENCE: 157

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Ala
            35                  40                  45

Pro Ala Gly Thr Thr Val Ala Gly Gly Ala Val Tyr Thr Val Val
        50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
        130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175
```

```
Ser Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
            245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
            275                 280                 285

Ser Ile Gly Arg Tyr Met Ala Asp Lys Gly Tyr Leu Lys Leu Gly Gln
            290                 295                 300

Thr Ser Met Gln Gly Ile Lys Ala Tyr Met Gln Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 158
<211> LENGTH: 441
<212> TYPE: PRT
<213> ORGANISM: Neisseria meningitidis

<400> SEQUENCE: 158

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Ala
            35                  40                  45

Pro Ala Gly Thr Thr Val Gly Gly Gly Ala Val Tyr Thr Val Val
        50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Val
            100                 105                 110
```

```
Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Lys Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 159
<211> LENGTH: 441
<212> TYPE: PRT
<213> ORGANISM: Neisseria meningitidis

<400> SEQUENCE: 159

Met Lys Lys Tyr Leu Phe Arg Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
```

```
                  35                  40                  45
Pro Ala Gly Thr Thr Val Gly Gly Gly Ala Val Tyr Thr Val Val
 50                  55                  60
Pro His Leu Ser Leu Pro His Trp Ala Ala Gln Asp Phe Ala Lys Ser
 65                  70                  75                  80
Leu Gln Ser Phe Arg Leu Gly Cys Ala Asn Leu Lys Asn Arg Gln Gly
                 85                  90                  95
Trp Gln Asp Val Cys Ala Gln Ala Phe Gln Thr Pro Val His Ser Phe
                100                 105                 110
Gln Ala Lys Gln Phe Phe Glu Arg Tyr Phe Thr Pro Trp Gln Val Ala
                115                 120                 125
Gly Asn Gly Ser Leu Ala Gly Thr Val Thr Gly Tyr Tyr Glu Pro Val
 130                 135                 140
Leu Lys Gly Asp Asp Arg Arg Thr Ala Gln Ala Arg Phe Pro Ile Tyr
145                  150                 155                 160
Gly Ile Pro Asp Phe Ile Ser Val Pro Leu Pro Ala Gly Leu Arg
                165                 170                 175
Ser Gly Lys Ala Leu Val Arg Ile Arg Gln Thr Gly Lys Asn Ser Gly
                180                 185                 190
Thr Ile Asp Asn Thr Gly Gly Thr His Thr Ala Asp Leu Ser Arg Phe
                195                 200                 205
Pro Ile Thr Ala Arg Thr Thr Ala Ile Lys Gly Arg Phe Glu Gly Ser
 210                 215                 220
Arg Phe Leu Pro Tyr His Thr Arg Asn Gln Ile Asn Gly Gly Ala Leu
225                  230                 235                 240
Asp Gly Lys Ala Pro Ile Leu Gly Tyr Ala Glu Asp Pro Val Glu Leu
                245                 250                 255
Phe Phe Met His Ile Gln Gly Ser Gly Arg Leu Lys Thr Pro Ser Gly
                260                 265                 270
Lys Tyr Ile Arg Ile Gly Tyr Ala Asp Lys Asn Glu His Pro Tyr Val
                275                 280                 285
Ser Ile Gly Arg Tyr Met Ala Asp Lys Gly Tyr Leu Lys Leu Gly Gln
 290                 295                 300
Thr Ser Met Gln Gly Ile Lys Ala Tyr Met Arg Gln Asn Pro Gln Arg
305                  310                 315                 320
Leu Ala Glu Val Leu Gly Gln Asn Pro Ser Tyr Ile Phe Phe Arg Glu
                325                 330                 335
Leu Ala Gly Ser Ser Asn Asp Gly Pro Val Gly Ala Leu Gly Thr Pro
                340                 345                 350
Leu Met Gly Glu Tyr Ala Gly Ala Val Asp Arg His Tyr Ile Thr Leu
                355                 360                 365
Gly Ala Pro Leu Phe Val Ala Thr Ala His Pro Val Thr Arg Lys Ala
                370                 375                 380
Leu Asn Arg Leu Ile Met Ala Gln Asp Thr Gly Ser Ala Ile Lys Gly
385                  390                 395                 400
Ala Val Arg Val Asp Tyr Phe Trp Gly Tyr Gly Asp Glu Ala Gly Glu
                405                 410                 415
Leu Ala Gly Lys Gln Lys Thr Thr Gly Tyr Val Trp Gln Leu Leu Pro
                420                 425                 430
Asn Gly Met Lys Pro Glu Tyr Arg Pro
                435                 440

<210> SEQ ID NO 160
```

```
<211> LENGTH: 441
<212> TYPE: PRT
<213> ORGANISM: Neisseria meningitidis

<400> SEQUENCE: 160

Met Lys Lys Tyr Leu Phe Arg Ala Ala Leu Tyr Gly Ile Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
```

-continued

```
                385                 390                 395                 400
Ala Val Arg Val Asp Tyr Phe Trp Gly Tyr Gly Asp Glu Ala Gly Glu
                            405                 410                 415

Leu Ala Gly Lys Gln Lys Thr Thr Gly Tyr Val Trp Gln Leu Leu Pro
                    420                 425                 430

Asn Gly Met Lys Pro Glu Tyr Arg Pro
                435                 440

<210> SEQ ID NO 161
<211> LENGTH: 441
<212> TYPE: PRT
<213> ORGANISM: Neisseria meningitidis

<400> SEQUENCE: 161

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
            35                  40                  45

Pro Ala Gly Thr Thr Val Gly Gly Gly Ala Val Tyr Thr Val Val
        50                  55                  60

Pro His Leu Ser Leu Pro His Trp Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320
```

-continued

```
Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 162
<211> LENGTH: 441
<212> TYPE: PRT
<213> ORGANISM: Neisseria meningitidis

<400> SEQUENCE: 162

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
            35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255
```

```
Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 163
<211> LENGTH: 441
<212> TYPE: PRT
<213> ORGANISM: Neisseria meningitidis

<400> SEQUENCE: 163

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
```

```
                180                 185                 190
Thr Ile Asp Asn Thr Gly Gly Thr His Thr Ala Asp Leu Ser Arg Phe
            195                 200                 205
Pro Ile Thr Ala Arg Thr Thr Ala Ile Lys Gly Arg Phe Glu Gly Ser
        210                 215                 220
Arg Phe Leu Pro Tyr His Thr Arg Asn Gln Ile Asn Gly Gly Ala Leu
225                 230                 235                 240
Asp Gly Lys Ala Pro Ile Leu Gly Tyr Ala Glu Asp Pro Val Glu Leu
                245                 250                 255
Phe Phe Met His Ile Gln Gly Ser Gly Arg Leu Lys Thr Pro Ser Gly
            260                 265                 270
Lys Tyr Ile Arg Ile Gly Tyr Ala Asp Lys Asn Glu His Pro Tyr Val
        275                 280                 285
Ser Ile Gly Arg Tyr Met Ala Asp Lys Gly Tyr Leu Lys Leu Gly Gln
        290                 295                 300
Thr Ser Met Gln Gly Ile Lys Ser Tyr Met Arg Gln Asn Pro Gln Arg
305                 310                 315                 320
Leu Ala Glu Val Leu Gly Gln Asn Pro Ser Tyr Ile Phe Phe Arg Glu
                325                 330                 335
Leu Ala Gly Ser Ser Asn Asp Gly Pro Val Gly Ala Leu Gly Thr Pro
            340                 345                 350
Leu Met Gly Glu Tyr Ala Gly Ala Val Asp Arg His Tyr Ile Thr Leu
        355                 360                 365
Gly Ala Pro Leu Phe Val Ala Thr Ala His Pro Val Thr Arg Lys Ala
    370                 375                 380
Leu Asn Arg Leu Ile Met Ala Gln Asp Thr Gly Ser Ala Ile Lys Gly
385                 390                 395                 400
Ala Val Arg Val Asp Tyr Phe Trp Gly Tyr Gly Asp Glu Ala Gly Glu
                405                 410                 415
Leu Ala Gly Lys Gln Lys Thr Thr Gly Tyr Val Trp Gln Leu Leu Pro
            420                 425                 430
Asn Gly Met Lys Pro Glu Tyr Arg Pro
            435                 440

<210> SEQ ID NO 164
<211> LENGTH: 441
<212> TYPE: PRT
<213> ORGANISM: Neisseria meningitidis

<400> SEQUENCE: 164

Met Lys Lys Tyr Leu Phe Arg Ala Ala Leu Tyr Gly Ile Ala Ala Ala
1               5                   10                  15
Ile Leu Ala Ala Cys Gln Ser Lys Ser Ile Gln Thr Phe Pro Gln Pro
            20                  25                  30
Asp Thr Ser Val Ile Asn Gly Pro Asp Arg Pro Val Gly Ile Pro Asp
        35                  40                  45
Pro Ala Gly Thr Thr Val Gly Gly Gly Ala Val Tyr Thr Val Val
    50                  55                  60
Pro His Leu Ser Leu Pro His Trp Ala Ala Gln Asp Phe Ala Lys Ser
65                  70                  75                  80
Leu Gln Ser Phe Arg Leu Gly Cys Ala Asn Leu Lys Asn Arg Gln Gly
                85                  90                  95
Trp Gln Asp Val Cys Ala Gln Ala Phe Gln Thr Pro Val His Ser Phe
            100                 105                 110
```

```
Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 165
<211> LENGTH: 441
<212> TYPE: PRT
<213> ORGANISM: Neisseria meningitidis

<400> SEQUENCE: 165

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45
```

```
Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 166
<211> LENGTH: 441
```

<212> TYPE: PRT
<213> ORGANISM: Neisseria meningitidis

<400> SEQUENCE: 166

```
Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400
```

Ala Val Arg Val Asp Tyr Phe Trp Gly Tyr Gly Asp Glu Ala Gly Glu
            405                 410                 415

Leu Ala Gly Lys Gln Lys Thr Thr Gly Tyr Val Trp Gln Leu Leu Pro
        420                 425                 430

Asn Gly Met Lys Pro Glu Tyr Arg Pro
        435                 440

<210> SEQ ID NO 167
<211> LENGTH: 441
<212> TYPE: PRT
<213> ORGANISM: Neisseria meningitidis

<400> SEQUENCE: 167

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu

```
                        325                 330                 335
Leu Ala Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
        370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 168
<211> LENGTH: 441
<212> TYPE: PRT
<213> ORGANISM: Neisseria meningitidis

<400> SEQUENCE: 168

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255
```

```
Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 169
<211> LENGTH: 441
<212> TYPE: PRT
<213> ORGANISM: Neisseria meningitidis

<400> SEQUENCE: 169

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190
```

```
Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
        210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
        245                 250                 255

Phe Phe Met His Ile Gln Gly Ser Gly Arg Leu Lys Thr Pro Ser Gly
        260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
        290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
                435                 440

<210> SEQ ID NO 170
<211> LENGTH: 441
<212> TYPE: PRT
<213> ORGANISM: Neisseria meningitidis

<400> SEQUENCE: 170

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
        50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
                100                 105                 110

Gln Ala Lys Gln Phe Phe Glu Arg Tyr Phe Thr Pro Trp Gln Val Ala
```

```
                115                 120                 125
Gly Asn Gly Ser Leu Ala Gly Thr Val Thr Gly Tyr Tyr Glu Pro Val
        130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
                180                 185                 190

Thr Ile Asp Asn Thr Gly Gly Thr His Thr Ala Asp Leu Ser Arg Phe
                195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
                260                 265                 270

Lys Tyr Ile Arg Ile Gly Tyr Ala Asp Lys Asn Glu His Pro Tyr Val
                275                 280                 285

Ser Ile Gly Lys Tyr Met Ala Asp Lys Gly Tyr Leu Lys Leu Gly Gln
                290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
                370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
            435                 440

<210> SEQ ID NO 171
<211> LENGTH: 441
<212> TYPE: PRT
<213> ORGANISM: Neisseria meningitidis

<400> SEQUENCE: 171

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
                35                  40                  45
```

```
Pro Ala Gly Thr Thr Val Gly Gly Gly Ala Val Tyr Thr Val Val
 50                  55                  60

Pro His Leu Ser Leu Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
                 85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Lys Tyr Met Ala Asp Lys Gly Tyr Leu Lys Leu Gly Gln
290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 172
<211> LENGTH: 441
<212> TYPE: PRT
```

<213> ORGANISM: Neisseria meningitidis

<400> SEQUENCE: 172

| | | | | | | | | | | | | | | |
|---|---|---|---|---|---|---|---|---|---|---|---|---|---|---|
| Met | Lys | Lys | Tyr | Leu | Phe | Arg | Ala | Ala | Leu | Tyr | Gly | Ile | Ala | Ala |
| 1 | | | | 5 | | | | | 10 | | | | | 15 |
| Ala | | | | | | | | | | | | | | |
| Ile | Leu | Ala | Ala | Cys | Gln | Ser | Lys | Ser | Ile | Gln | Thr | Phe | Pro | Gln |
| | | | 20 | | | | | 25 | | | | | 30 | |
| Pro | | | | | | | | | | | | | | |
| Asp | Thr | Ser | Val | Ile | Asn | Gly | Pro | Asp | Arg | Pro | Val | Gly | Ile | Pro |
| | | 35 | | | | | 40 | | | | | 45 | | |
| Asp | | | | | | | | | | | | | | |
| Pro | Ala | Gly | Thr | Thr | Val | Gly | Gly | Gly | Ala | Val | Tyr | Thr | Val | Val |
| | 50 | | | | | 55 | | | | | 60 | | | |
| Pro | His | Leu | Ser | Leu | Pro | His | Trp | Ala | Glu | Gln | Asp | Phe | Ala | Lys |
| 65 | | | | | 70 | | | | | 75 | | | | |
| Ser | | | | | | | | | | | | | | 80 |
| Leu | Gln | Ser | Phe | Arg | Leu | Gly | Cys | Ala | Asn | Leu | Lys | Asn | Arg | Gln |
| | | | | 85 | | | | | 90 | | | | | 95 |
| Gly | | | | | | | | | | | | | | |
| Trp | Gln | Asp | Val | Cys | Ala | Gln | Ala | Phe | Gln | Thr | Pro | Val | His | Ser |
| | | | | 100 | | | | | 105 | | | | | 110 |
| Phe | | | | | | | | | | | | | | |
| Gln | Ala | Lys | Gln | Phe | Phe | Glu | Arg | Tyr | Phe | Thr | Pro | Trp | Gln | Val |
| | | | 115 | | | | | 120 | | | | | 125 | |
| Ala | | | | | | | | | | | | | | |
| Gly | Asn | Gly | Ser | Leu | Ala | Gly | Thr | Val | Thr | Gly | Tyr | Tyr | Glu | Pro |
| | 130 | | | | | 135 | | | | | 140 | | | |
| Val | | | | | | | | | | | | | | |
| Leu | Lys | Gly | Asp | Asp | Arg | Arg | Thr | Ala | Gln | Ala | Arg | Phe | Pro | Ile |
| 145 | | | | | 150 | | | | | 155 | | | | |
| Tyr | | | | | | | | | | | | | | 160 |
| Gly | Ile | Pro | Asp | Asp | Phe | Ile | Ser | Val | Pro | Leu | Pro | Ala | Gly | Leu |
| | | | | 165 | | | | | 170 | | | | | 175 |
| Arg | | | | | | | | | | | | | | |
| Ser | Gly | Lys | Ala | Leu | Val | Arg | Ile | Arg | Gln | Thr | Gly | Lys | Asn | Ser |
| | | | 180 | | | | | 185 | | | | | 190 | |
| Gly | | | | | | | | | | | | | | |
| Thr | Ile | Asp | Asn | Thr | Gly | Gly | Thr | His | Thr | Ala | Asp | Leu | Ser | Arg |
| | | 195 | | | | | 200 | | | | | 205 | | |
| Phe | | | | | | | | | | | | | | |
| Pro | Ile | Thr | Ala | Arg | Thr | Thr | Ala | Ile | Lys | Gly | Arg | Phe | Glu | Gly |
| | 210 | | | | | 215 | | | | | 220 | | | |
| Ser | | | | | | | | | | | | | | |
| Arg | Phe | Leu | Pro | Tyr | His | Thr | Arg | Asn | Gln | Ile | Asn | Gly | Gly | Ala |
| 225 | | | | | 230 | | | | | 235 | | | | |
| Leu | | | | | | | | | | | | | | 240 |
| Asp | Gly | Lys | Ala | Pro | Ile | Leu | Gly | Tyr | Ala | Glu | Asp | Pro | Val | Glu |
| | | | | 245 | | | | | 250 | | | | | 255 |
| Leu | | | | | | | | | | | | | | |
| Phe | Phe | Met | His | Ile | Gln | Gly | Ser | Gly | Arg | Leu | Lys | Thr | Pro | Ser |
| | | | 260 | | | | | 265 | | | | | 270 | |
| Gly | | | | | | | | | | | | | | |
| Lys | Tyr | Ile | Arg | Ile | Gly | Tyr | Ala | Asp | Lys | Asn | Glu | His | Pro | Tyr |
| | | 275 | | | | | 280 | | | | | 285 | | |
| Val | | | | | | | | | | | | | | |
| Ser | Ile | Gly | Arg | Tyr | Met | Ala | Asp | Lys | Gly | Tyr | Leu | Lys | Leu | Gly |
| | 290 | | | | | 295 | | | | | 300 | | | |
| Gln | | | | | | | | | | | | | | |
| Thr | Ser | Met | Gln | Gly | Ile | Lys | Ala | Tyr | Met | Arg | Gln | Asn | Pro | Gln |
| 305 | | | | | 310 | | | | | 315 | | | | |
| Arg | | | | | | | | | | | | | | 320 |
| Leu | Ala | Glu | Val | Leu | Gly | Gln | Asn | Pro | Ser | Tyr | Ile | Phe | Phe | Arg |
| | | | | 325 | | | | | 330 | | | | | 335 |
| Glu | | | | | | | | | | | | | | |
| Leu | Ala | Gly | Ser | Ser | Asn | Asp | Gly | Pro | Val | Gly | Ala | Leu | Gly | Thr |
| | | | 340 | | | | | 345 | | | | | 350 | |
| Pro | | | | | | | | | | | | | | |
| Leu | Met | Gly | Glu | Tyr | Ala | Gly | Ala | Val | Asp | Arg | His | Tyr | Ile | Thr |
| | | | 355 | | | | | 360 | | | | | 365 | |
| Leu | | | | | | | | | | | | | | |
| Gly | Ala | Pro | Leu | Phe | Val | Ala | Thr | Ala | His | Pro | Val | Thr | Arg | Lys |
| | 370 | | | | | 375 | | | | | 380 | | | |
| Ala | | | | | | | | | | | | | | |
| Leu | Asn | Arg | Leu | Ile | Met | Ala | Gln | Asp | Thr | Gly | Ser | Ala | Ile | Lys |
| 385 | | | | | 390 | | | | | 395 | | | | |
| Gly | | | | | | | | | | | | | | 400 |

```
Ala Val Arg Val Asp Tyr Phe Trp Gly Tyr Gly Asp Glu Ala Gly Glu
            405                 410                 415

Leu Ala Gly Lys Gln Lys Thr Thr Gly Tyr Val Trp Gln Leu Leu Pro
        420                 425                 430

Asn Gly Met Lys Pro Glu Tyr Arg Pro
        435                 440

<210> SEQ ID NO 173
<211> LENGTH: 441
<212> TYPE: PRT
<213> ORGANISM: Neisseria meningitidis

<400> SEQUENCE: 173

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Ser Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335
```

```
Leu Ala Gly Ser Ser Asn Asp Gly Pro Val Gly Ala Leu Gly Thr Pro
            340                 345                 350

Leu Met Gly Glu Tyr Ala Gly Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 174
<211> LENGTH: 441
<212> TYPE: PRT
<213> ORGANISM: Neisseria meningitidis

<400> SEQUENCE: 174

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Val
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
```

```
                   260                 265                 270
Lys Tyr Ile Arg Ile Gly Tyr Ala Asp Lys Asn Glu His Pro Tyr Val
            275                 280                 285

Ser Ile Gly Arg Tyr Met Ala Asp Lys Gly Tyr Leu Lys Leu Gly Gln
        290                 295                 300

Thr Ser Met Gln Gly Ile Lys Ala Tyr Met Gln Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 175
<211> LENGTH: 441
<212> TYPE: PRT
<213> ORGANISM: Neisseria meningitidis

<400> SEQUENCE: 175

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Val
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190
```

```
Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Arg Leu Lys Thr Pro Ser Gly
                260                 265                 270

Lys Tyr Ile Arg Ile Gly Tyr Ala Asp Lys Asn Glu His Pro Tyr Val
                275                 280                 285

Ser Ile Gly Arg Tyr Met Ala Asp Lys Gly Tyr Leu Lys Leu Gly Gln
290                 295                 300

Thr Ser Met Gln Gly Ile Lys Ala Tyr Met Gln Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
                355                 360                 365

Gly Ala Pro Leu Phe Val Ala Thr Ala His Pro Val Thr Arg Lys Ala
                370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
                420                 425                 430

Asn Gly Met Lys Pro Glu Tyr Arg Pro
                435                 440

<210> SEQ ID NO 176
<211> LENGTH: 441
<212> TYPE: PRT
<213> ORGANISM: Neisseria meningitidis

<400> SEQUENCE: 176

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
                35                  40                  45

Pro Ala Gly Thr Thr Val Gly Gly Gly Ala Val Tyr Thr Val Val
            50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Val
                100                 105                 110

Gln Ala Lys Gln Phe Phe Glu Arg Tyr Phe Thr Pro Trp Gln Val Ala
                115                 120                 125
```

Gly Asn Gly Ser Leu Ala Gly Thr Val Thr Gly Tyr Tyr Glu Pro Val
        130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
        180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
        290                 295                 300

Thr Ser Met Gln Gly Ile Lys Ala Tyr Met Gln Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
        370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 177
<211> LENGTH: 441
<212> TYPE: PRT
<213> ORGANISM: Neisseria meningitidis

<400> SEQUENCE: 177

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
                20                  25                  30

Asp Thr Ser Val Ile Asn Gly Pro Asp Arg Pro Val Gly Ile Pro Asp
            35                  40                  45

Pro Ala Gly Thr Thr Val Gly Gly Gly Gly Ala Val Tyr Thr Val Val

```
                50                  55                  60
Pro His Leu Ser Leu Pro His Trp Ala Ala Gln Asp Phe Ala Lys Ser
 65                  70                  75                  80

Leu Gln Ser Phe Arg Leu Gly Cys Ala Asn Leu Lys Asn Arg Gln Gly
                 85                  90                  95

Trp Gln Asp Val Cys Ala Gln Ala Phe Gln Thr Pro Val His Ser Phe
                100                 105                 110

Gln Ala Lys Gln Phe Phe Glu Arg Tyr Phe Thr Pro Trp Gln Val Ala
            115                 120                 125

Gly Asn Gly Ser Leu Ala Gly Thr Val Thr Gly Tyr Tyr Glu Pro Val
        130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Ala Gly Ser Ser Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 178
<211> LENGTH: 441
<212> TYPE: PRT
<213> ORGANISM: Neisseria meningitidis
```

<400> SEQUENCE: 178

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65              70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Gly Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Thr His Pro Ile Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu

```
                    405                 410                 415
Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 179
<211> LENGTH: 441
<212> TYPE: PRT
<213> ORGANISM: Neisseria meningitidis

<400> SEQUENCE: 179

Met Lys Lys Tyr Leu Phe Arg Ala Ala Leu Cys Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Gly Arg Pro Val Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Gln Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Lys Tyr Met Ala Asp Lys Gly Tyr Leu Lys Leu Gly Gln
    290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335
```

Leu Thr Gly Ser Ser Asn Asp Gly Pro Val Gly Ala Leu Gly Thr Pro
                340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
        370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 180
<211> LENGTH: 441
<212> TYPE: PRT
<213> ORGANISM: Neisseria meningitidis

<400> SEQUENCE: 180

Met Lys Lys Tyr Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Val Ile Asn Gly Pro Asp Arg Pro Val Gly Ile Pro Asp
        35                  40                  45

Leu Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn His Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Thr Gly Gly Thr His Thr Ala Asp Leu Ser Arg Phe
        195                 200                 205

Pro Ile Thr Ala Arg Thr Thr Ala Ile Lys Gly Arg Phe Glu Gly Ser
    210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
            275                 280                 285

Ser Ile Gly Lys Tyr Met Ala Asp Lys Gly Tyr Leu Lys Leu Gly Gln
290                 295                 300

Thr Ser Met Gln Gly Ile Lys Ser Tyr Met Arg Gln Asn Pro Gln Arg
305                 310                 315                 320

Leu Ala Glu Val Leu Gly Gln Asn Pro Ser Tyr Ile Phe Phe Arg Glu
                325                 330                 335

Leu Thr Gly Ser Gly Asn Asp Gly Pro Val Gly Ala Leu Gly Thr Pro
            340                 345                 350

Leu Met Gly Glu Tyr Ala Gly Ala Val Asp Arg His Tyr Ile Thr Leu
            355                 360                 365

Gly Ala Pro Leu Phe Val Ala Thr Ala His Pro Val Thr Arg Lys Ala
370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
            435                 440

<210> SEQ ID NO 181
<211> LENGTH: 441
<212> TYPE: PRT
<213> ORGANISM: Neisseria meningitidis

<400> SEQUENCE: 181

Met Lys Lys His Leu Phe Arg Ala Ala Leu Tyr Gly Ile Ala Ala Ala
1               5                   10                  15

Ile Leu Ala Ala Cys Gln Ser Lys Ser Ile Gln Thr Phe Pro Gln Pro
            20                  25                  30

Asp Thr Ser Ile Ile Lys Gly Pro Asp Arg Pro Ala Gly Ile Pro Asp
        35                  40                  45

Pro Ala Gly Thr Thr Val Gly Gly Gly Ala Val Tyr Thr Val Val
    50                  55                  60

Pro His Leu Ser Leu Pro His Trp Ala Ala Gln Asp Phe Ala Lys Ser
65                  70                  75                  80

Leu Gln Ser Phe Arg Leu Gly Cys Ala Asn Leu Lys Asn Arg Gln Gly
                85                  90                  95

Trp Gln Asp Val Cys Ala Gln Ala Phe Gln Thr Pro Val His Ser Phe
            100                 105                 110

Gln Ala Lys Gln Phe Phe Glu Arg Tyr Phe Thr Pro Trp Gln Val Ala
        115                 120                 125

Gly Asn Gly Ser Leu Ala Gly Thr Val Thr Gly Tyr Tyr Glu Pro Val
    130                 135                 140

Leu Lys Gly Asp Asp Arg Arg Thr Ala Gln Ala Arg Phe Pro Ile Tyr
145                 150                 155                 160

Gly Ile Pro Asp Asp Phe Ile Ser Val Pro Leu Pro Ala Gly Leu Arg
                165                 170                 175

Ser Gly Lys Ala Leu Val Arg Ile Arg Gln Thr Gly Lys Asn Ser Gly
            180                 185                 190

Thr Ile Asp Asn Ala Gly Gly Thr His Thr Ala Asp Leu Ser Arg Phe

```
                195                 200                 205
Pro Ile Thr Ala Arg Thr Thr Ala Ile Lys Gly Arg Phe Glu Gly Ser
210                 215                 220

Arg Phe Leu Pro Tyr His Thr Arg Asn Gln Ile Asn Gly Gly Ala Leu
225                 230                 235                 240

Asp Gly Lys Ala Pro Ile Leu Gly Tyr Ala Glu Asp Pro Val Glu Leu
                245                 250                 255

Phe Phe Met His Ile Gln Gly Ser Gly Arg Leu Lys Thr Pro Ser Gly
            260                 265                 270

Lys Tyr Ile Arg Ile Gly Tyr Ala Asp Lys Asn Glu His Pro Tyr Val
        275                 280                 285

Ser Ile Gly Arg Tyr Met Ala Asp Lys Gly Tyr Leu Lys Leu Gly Gln
    290                 295                 300

Thr Ser Met Gln Gly Ile Lys Ala Tyr Met Arg Gln Asn Pro Gln Arg
305                 310                 315                 320

Leu Ala Glu Val Leu Gly Gln Asn Pro Ser Tyr Val Phe Phe Arg Glu
                325                 330                 335

Leu Ala Gly Ser Gly Asn Asp Gly Pro Val Gly Ala Leu Gly Thr Pro
            340                 345                 350

Leu Met Gly Glu Tyr Ala Gly Ala Val Asp Arg His Tyr Ile Thr Leu
        355                 360                 365

Gly Ala Pro Leu Phe Val Ala Thr Ala His Pro Val Thr Arg Lys Ala
    370                 375                 380

Leu Asn Arg Leu Ile Met Ala Gln Asp Thr Gly Ser Ala Ile Lys Gly
385                 390                 395                 400

Ala Val Arg Val Asp Tyr Phe Trp Gly Tyr Gly Asp Glu Ala Gly Glu
                405                 410                 415

Leu Ala Gly Lys Gln Lys Thr Thr Gly Tyr Val Trp Gln Leu Leu Pro
            420                 425                 430

Asn Gly Met Lys Pro Glu Tyr Arg Pro
        435                 440

<210> SEQ ID NO 182
<211> LENGTH: 608
<212> TYPE: PRT
<213> ORGANISM: Neisseria meningitidis

<400> SEQUENCE: 182

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser Gly His Ile
    50                  55                  60

Gly Leu Gly Asn Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125
```

```
Ile His Trp Asp Gly Tyr Glu His His Pro Ala Asp Gly Tyr Asp Gly
        130                 135                 140

Pro Gln Gly Gly Gly Tyr Pro Val Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ala Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
210                 215                 220

Asn Gly Thr Ala Asp Ile Val Lys Asn Ile Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
290                 295                 300

Gly Ile Glu Ala Val Ser Asn Ile Phe Thr Ala Val Ile Pro Ile Lys
305                 310                 315                 320

Gly Ile Gly Ala Val Arg Gly Lys Tyr Gly Leu Gly Gly Ile Thr Ala
                325                 330                 335

His Pro Val Lys Arg Ser Gln Met Gly Ala Ile Ala Leu Pro Lys Gly
            340                 345                 350

Lys Ser Ala Val Ser Asn Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Ile Pro Lys Ala
        435                 440                 445

Lys Pro Val Phe Asp Ala Lys Pro Arg Trp Glu Val Asp Arg Lys Leu
450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
            500                 505                 510

Gly Met Gly Lys Phe Thr Asp Ser Met Asn Asp Lys Ala Phe Ser Arg
        515                 520                 525

Leu Val Lys Ser Val Lys Glu Asn Gly Phe Thr Asn Pro Val Val Glu
530                 535                 540

Tyr Val Glu Ile Asn Gly Lys Ala Tyr Ile Val Arg Gly Asn Asn Arg
```

```
                545                 550                 555                 560
Val Phe Ala Ala Glu Tyr Leu Gly Arg Ile His Glu Leu Lys Phe Lys
                565                 570                 575
Lys Val Asp Phe Pro Val Pro Asn Thr Ser Trp Lys Asn Pro Thr Asp
                580                 585                 590
Val Leu Asn Glu Ser Gly Asn Val Lys Arg Pro Arg Tyr Arg Ser Lys
                595                 600                 605

<210> SEQ ID NO 183
<211> LENGTH: 427
<212> TYPE: PRT
<213> ORGANISM: Neisseria meningitidis

<400> SEQUENCE: 183

Arg Lys Ile Ser Leu Ile Leu Ser Ile Leu Ala Val Cys Leu Pro Met
1               5                   10                  15

His Ala His Ala Ser Asp Leu Ala Asn Asp Ser Phe Ile Arg Gln Val
                20                  25                  30

Leu Asp Arg Gln His Phe Glu Pro Asp Gly Lys Tyr His Leu Phe Gly
            35                  40                  45

Ser Arg Gly Glu Leu Ala Glu Arg Ser Gly His Ile Gly Leu Gly Lys
        50                  55                  60

Ile Gln Ser His Gln Leu Gly Asn Leu Phe Ile Gln Gln Ala Ala Ile
65                  70                  75                  80

Lys Gly Asn Ile Gly Tyr Ile Val Arg Phe Ser Asp His Gly His Glu
                85                  90                  95

Val His Ser Pro Phe Asp Asn His Ala Ser His Ser Asp Ser Asp Glu
                100                 105                 110

Ala Gly Ser Pro Val Asp Gly Phe Ser Leu Tyr Arg Ile His Trp Asp
            115                 120                 125

Gly Tyr Glu His His Pro Ala Asp Gly Tyr Asp Gly Pro Gln Gly Gly
        130                 135                 140

Gly Tyr Pro Ala Pro Lys Gly Ala Arg Asp Ile Tyr Ser Tyr Asp Ile
145                 150                 155                 160

Lys Gly Val Ala Gln Asn Ile Arg Leu Asn Leu Thr Asp Asn Arg Ser
                165                 170                 175

Thr Gly Gln Arg Leu Ala Asp Arg Phe His Asn Ala Gly Ala Met Leu
            180                 185                 190

Thr Gln Gly Val Gly Asp Gly Phe Lys Arg Ala Thr Arg Tyr Ser Pro
        195                 200                 205

Glu Leu Asp Arg Ser Gly Asn Ala Ala Glu Ala Phe Asn Gly Thr Ala
    210                 215                 220

Asp Ile Val Lys Asn Ile Ile Gly Ala Ala Gly Glu Ile Val Gly Ala
225                 230                 235                 240

Gly Asp Ala Val Gln Gly Ile Ser Glu Gly Ser Asn Ile Ala Val Met
                245                 250                 255

His Gly Leu Gly Leu Leu Ser Thr Glu Asn Lys Met Ala Arg Ile Asn
            260                 265                 270

Asp Leu Ala Asp Met Ala Gln Leu Lys Asp Tyr Ala Ala Ala Ala Ile
        275                 280                 285

Arg Asp Trp Ala Val Gln Asn Pro Asn Ala Ala Gln Gly Ile Glu Ala
    290                 295                 300

Val Ser Asn Ile Phe Thr Ala Val Ile Pro Val Lys Gly Ile Gly Ala
305                 310                 315                 320
```

Val Arg Gly Lys Tyr Gly Leu Gly Gly Ile Thr Ala His Pro Val Lys
            325                 330                 335

Arg Ser Gln Met Gly Ala Ile Ala Leu Pro Lys Gly Lys Ser Ala Val
            340                 345                 350

Ser Asn Asn Phe Ala Asp Ala Ala Tyr Ala Lys Tyr Pro Ser Pro Tyr
            355                 360                 365

His Ser Arg Asn Ile Arg Ser Asn Leu Glu Gln Arg Tyr Gly Lys Glu
        370                 375                 380

Asn Ile Thr Ser Ser Thr Val Pro Pro Ser Asn Gly Lys Asn Val Lys
385                 390                 395                 400

Leu Ala Asp Gln Arg His Pro Lys Thr Gly Val Pro Phe Asp Gly Lys
                405                 410                 415

Gly Phe Pro Asn Phe Glu Lys His Val Lys Tyr
            420                 425

<210> SEQ ID NO 184
<211> LENGTH: 423
<212> TYPE: PRT
<213> ORGANISM: Neisseria meningitidis

<400> SEQUENCE: 184

Lys Ile Ser Leu Ile Leu Ser Ile Leu Ala Val Cys Leu Pro Met His
1               5                   10                  15

Ala His Ala Ser Asp Leu Ala Asn Asp Ser Phe Ile Arg Gln Val Leu
            20                  25                  30

Asp Arg Gln His Phe Glu Pro Asp Gly Lys Tyr His Leu Phe Gly Ser
        35                  40                  45

Arg Gly Glu Leu Ala Glu Arg Ser Gly His Ile Gly Leu Gly Asn Ile
    50                  55                  60

Gln Ser His Gln Leu Gly Asn Leu Met Ile Gln Ala Ala Ile Lys
65                  70                  75                  80

Gly Asn Ile Gly Tyr Ile Val Arg Phe Ser Asp His Gly His Glu Val
                85                  90                  95

His Ser Pro Phe Asp Asn His Ala Ser His Ser Asp Ser Asp Glu Ala
            100                 105                 110

Gly Ser Pro Val Asp Gly Phe Ser Leu Tyr Arg Ile His Trp Asp Gly
        115                 120                 125

Tyr Glu His His Pro Ala Asp Gly Tyr Asp Gly Pro Gln Gly Gly Gly
    130                 135                 140

Tyr Pro Ala Pro Lys Gly Ala Arg Asp Ile Tyr Ser Tyr Asp Ile Lys
145                 150                 155                 160

Gly Val Ala Gln Asn Ile Arg Leu Asn Leu Thr Asp Asn Arg Ser Thr
                165                 170                 175

Gly Gln Arg Leu Ala Asp Arg Phe His Asn Ala Gly Ala Met Leu Thr
            180                 185                 190

Gln Gly Val Gly Asp Gly Phe Lys Arg Ala Thr Arg Tyr Ser Pro Glu
        195                 200                 205

Leu Asp Arg Ser Gly Asn Ala Ala Glu Ala Phe Asn Gly Thr Ala Asp
    210                 215                 220

Ile Val Lys Asn Ile Ile Gly Ala Ala Gly Glu Ile Val Gly Ala Gly
225                 230                 235                 240

Asp Ala Val Gln Gly Ile Ser Glu Gly Ser Asn Ile Ala Val Met His
                245                 250                 255

Gly Leu Gly Leu Leu Ser Thr Glu Asn Lys Met Ala Arg Ile Asn Asp
            260                 265                 270

```
Leu Ala Asp Met Ala Gln Leu Lys Asp Tyr Ala Ala Ala Ile Arg
        275                 280                 285

Asp Trp Ala Val Gln Asn Pro Asn Ala Ala Gln Gly Ile Glu Ala Val
        290                 295                 300

Ser Asn Ile Phe Met Ala Ala Ile Pro Ile Lys Gly Ile Gly Ala Val
305                 310                 315                 320

Arg Gly Lys Tyr Gly Leu Gly Gly Ile Thr Ala His Pro Ile Lys Arg
                325                 330                 335

Ser Gln Met Gly Ala Ile Ala Leu Pro Lys Gly Lys Ser Ala Val Ser
                340                 345                 350

Asp Asn Phe Ala Asp Ala Ala Tyr Ala Lys Tyr Pro Ser Pro Tyr His
            355                 360                 365

Ser Arg Asn Ile Arg Ser Asn Leu Glu Gln Arg Tyr Gly Lys Glu Asn
        370                 375                 380

Ile Thr Ser Ser Thr Val Pro Pro Ser Asn Gly Lys Asn Val Lys Leu
385                 390                 395                 400

Ala Asp Gln Arg His Pro Lys Thr Gly Val Pro Phe Asp Gly Lys Gly
                405                 410                 415

Phe Pro Asn Phe Glu Lys His
            420

<210> SEQ ID NO 185
<211> LENGTH: 608
<212> TYPE: PRT
<213> ORGANISM: Neisseria meningitidis

<400> SEQUENCE: 185

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser Gly His Ile
    50                  55                  60

Gly Leu Gly Asn Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
    130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ala Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
```

```
        210                 215                 220
Asn Gly Thr Ala Asp Ile Val Lys Asn Ile Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
                260                 265                 270

Ala Arg Ile Asn Asp Leu Ala Asp Met Ala Gln Leu Lys Asp Tyr Ala
                275                 280                 285

Ala Ala Ala Ile Arg Asp Trp Ala Val Gln Asn Pro Asn Ala Ala Gln
            290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Gly Ile Thr Ala
                325                 330                 335

His Pro Ile Lys Arg Ser Gln Met Gly Ala Ile Ala Leu Pro Lys Gly
                340                 345                 350

Lys Ser Ala Val Ser Asp Asn Phe Ala Asp Ala Ala Tyr Ala Lys Tyr
            355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
                420                 425                 430

Thr Lys Leu Asp Ile Gln Glu Leu Ser Gly Gly Ile Pro Lys Ala
            435                 440                 445

Lys Pro Val Ser Asp Ala Lys Pro Arg Trp Glu Val Asp Arg Lys Leu
    450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Asn Gln His Ala Gln Leu Glu
                485                 490                 495

Arg Glu Ile Asn Lys Leu Lys Ser Ala Asp Glu Ile Asn Phe Ala Asp
                500                 505                 510

Gly Met Gly Lys Phe Thr Asp Ser Met Asp Asp Lys Ala Phe Ser Arg
            515                 520                 525

Leu Val Lys Ser Val Lys Glu Asn Gly Phe Thr Asn Pro Val Val Glu
    530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
                580                 585                 590

Val Leu Asn Glu Ser Gly Asn Val Lys Arg Pro Arg Tyr Arg Ser Lys
            595                 600                 605

<210> SEQ ID NO 186
<211> LENGTH: 608
<212> TYPE: PRT
<213> ORGANISM: Neisseria meningitidis
```

<400> SEQUENCE: 186

```
Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser Gly His Ile
    50                  55                  60

Gly Leu Gly Lys Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
    130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175

Asp Asn Arg Ser Thr Gly Gln Arg Leu Ala Asp Arg Phe His Asn Ala
            180                 185                 190

Gly Ser Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
    210                 215                 220

Asn Gly Thr Ala Asp Ile Val Lys Asn Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
    290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Ile Thr Ala
                325                 330                 335

His Pro Ile Lys Arg Ser Gln Met Gly Ala Ile Ala Leu Pro Lys Gly
            340                 345                 350

Lys Ser Ala Val Ser Asp Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
```

```
                         405                 410                 415
Phe Asp Gly Lys Gly Phe Pro Asn Phe Glu Lys His Val Lys Tyr Asp
                420                 425                 430

Thr Lys Leu Asp Ile Gln Glu Leu Ser Gly Gly Ile Pro Lys Ala
            435                 440                 445

Lys Pro Val Ser Asp Ala Lys Pro Arg Trp Glu Val Asp Arg Lys Leu
        450                 455                 460

Asn Lys Leu Thr Thr Arg Glu Gln Val Glu Lys Asn Val Gln Glu Ile
465                 470                 475                 480

Arg Asn Gly Asn Lys Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
                500                 505                 510

Gly Met Gly Lys Phe Thr Asp Ser Met Asn Asp Lys Ala Phe Ser Arg
            515                 520                 525

Leu Val Lys Ser Val Lys Glu Asn Gly Phe Thr Asn Pro Val Val Glu
        530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
                580                 585                 590

Val Leu Asn Glu Ser Gly Asn Val Lys Arg Pro Arg Tyr Arg Ser Lys
            595                 600                 605

<210> SEQ ID NO 187
<211> LENGTH: 608
<212> TYPE: PRT
<213> ORGANISM: Neisseria meningitidis

<400> SEQUENCE: 187

Leu Gly Ile Ser Arg Lys Ile Ser Leu Ile Leu Ser Ile Leu Ala Val
1               5                   10                  15

Cys Leu Pro Met His Ala His Ala Ser Asp Leu Ala Asn Asp Ser Phe
            20                  25                  30

Ile Arg Gln Val Leu Asp Arg Gln His Phe Glu Pro Asp Gly Lys Tyr
        35                  40                  45

His Leu Phe Gly Ser Arg Gly Glu Leu Ala Glu Arg Ser Gly His Ile
    50                  55                  60

Gly Leu Gly Lys Ile Gln Ser His Gln Leu Gly Asn Leu Met Ile Gln
65                  70                  75                  80

Gln Ala Ala Ile Lys Gly Asn Ile Gly Tyr Ile Val Arg Phe Ser Asp
                85                  90                  95

His Gly His Glu Val His Ser Pro Phe Asp Asn His Ala Ser His Ser
            100                 105                 110

Asp Ser Asp Glu Ala Gly Ser Pro Val Asp Gly Phe Ser Leu Tyr Arg
        115                 120                 125

Ile His Trp Asp Gly Tyr Glu His His Pro Ala Asp Gly Tyr Asp Gly
    130                 135                 140

Pro Gln Gly Gly Gly Tyr Pro Ala Pro Lys Gly Ala Arg Asp Ile Tyr
145                 150                 155                 160

Ser Tyr Asp Ile Lys Gly Val Ala Gln Asn Ile Arg Leu Asn Leu Thr
                165                 170                 175
```

```
Asp Asn Arg Ser Thr Gly Gln Arg Leu Ala Asp Arg Phe His Asn Ala
            180                 185                 190

Gly Ser Met Leu Thr Gln Gly Val Gly Asp Gly Phe Lys Arg Ala Thr
        195                 200                 205

Arg Tyr Ser Pro Glu Leu Asp Arg Ser Gly Asn Ala Ala Glu Ala Phe
    210                 215                 220

Asn Gly Thr Ala Asp Ile Val Lys Asn Ile Ile Gly Ala Ala Gly Glu
225                 230                 235                 240

Ile Val Gly Ala Gly Asp Ala Val Gln Gly Ile Ser Glu Gly Ser Asn
                245                 250                 255

Ile Ala Val Met His Gly Leu Gly Leu Leu Ser Thr Glu Asn Lys Met
            260                 265                 270

Ala Arg Ile Asn Asp Leu Ala Asp Met Ala Gln Leu Lys Asp Tyr Ala
        275                 280                 285

Ala Ala Ala Ile Arg Asp Trp Ala Val Gln Asn Pro Asn Ala Ala Gln
    290                 295                 300

Gly Ile Glu Ala Val Ser Asn Ile Phe Met Ala Ala Ile Pro Ile Lys
305                 310                 315                 320

Gly Ile Gly Ala Val Arg Gly Lys Tyr Gly Leu Gly Gly Ile Thr Ala
                325                 330                 335

His Pro Ile Lys Arg Ser Gln Met Gly Ala Ile Ala Leu Pro Lys Gly
            340                 345                 350

Lys Ser Ala Val Ser Asp Asn Phe Ala Asp Ala Ala Tyr Ala Lys Tyr
        355                 360                 365

Pro Ser Pro Tyr His Ser Arg Asn Ile Arg Ser Asn Leu Glu Gln Arg
    370                 375                 380

Tyr Gly Lys Glu Asn Ile Thr Ser Ser Thr Val Pro Pro Ser Asn Gly
385                 390                 395                 400

Lys Asn Val Lys Leu Ala Asp Gln Arg His Pro Lys Thr Gly Val Pro
                405                 410                 415

Phe Asp Gly Lys Gly Phe Pro Asn Phe Glu Lys His Val Lys Tyr Asp
            420                 425                 430

Thr Lys Leu Asp Ile Gln Glu Leu Ser Gly Gly Gly Ile Pro Lys Ala
        435                 440                 445

Lys Pro Val Phe Asp Ala Lys Pro Arg Trp Glu Val Asp Arg Lys Leu
    450                 455                 460

Asn Lys Leu Thr Thr Arg Glu Gln Val Glu Lys Asn Val Gln Glu Ile
465                 470                 475                 480

Arg Asn Gly Asn Ile Asn Ser Asn Phe Ser Gln His Ala Gln Leu Glu
                485                 490                 495

Arg Glu Ile Asn Lys Leu Lys Ser Ala Asp Glu Ile Asn Phe Ala Asp
            500                 505                 510

Gly Met Gly Lys Phe Thr Asp Ser Met Asn Asp Lys Ala Phe Ser Arg
        515                 520                 525

Leu Val Lys Ser Val Lys Glu Asn Gly Phe Thr Asn Pro Val Val Glu
    530                 535                 540

Tyr Val Glu Ile Asn Gly Lys Ala Tyr Ile Val Arg Gly Asn Asn Arg
545                 550                 555                 560

Val Phe Ala Ala Glu Tyr Leu Gly Arg Ile His Glu Leu Lys Phe Lys
                565                 570                 575

Lys Val Asp Phe Pro Val Pro Asn Thr Ser Trp Lys Asn Pro Thr Asp
            580                 585                 590

Val Leu Asn Glu Ser Gly Asn Val Lys Arg Pro Arg Tyr Arg Ser Lys
```

<210> SEQ ID NO 188
<211> LENGTH: 201
<212> TYPE: PRT
<213> ORGANISM: Neisseria meningitidis

<400> SEQUENCE: 188

Met Thr Ile Tyr Phe Lys Asn Gly Phe Tyr Asp Asp Thr Leu Gly Gly
1               5                   10                  15

Ile Pro Glu Gly Ala Val Ala Val Arg Ala Glu Glu Tyr Ala Ala Leu
            20                  25                  30

Leu Ala Gly Gln Ala Gln Gly Gly Gln Ile Ala Ala Asp Ser Asp Gly
        35                  40                  45

Arg Pro Val Leu Thr Pro Pro Arg Pro Ser Glu Tyr His Glu Trp Asp
    50                  55                  60

Gly Lys Lys Trp Glu Ile Gly Glu Ala Ala Ala Ala Arg Phe Ala
65                  70                  75                  80

Glu Gln Lys Thr Ala Thr Ala Phe Arg Leu Ala Ala Lys Ala Asp Glu
                85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn
        115                 120                 125

Ala Pro Thr Pro Met Leu Ala Gln Ile Ala Ala Thr Arg Gly Val Glu
    130                 135                 140

Leu Asp Val Leu Ile Glu Lys Val Ile Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Thr Ile Glu Thr Ala Pro Gly Leu Asp Ala Leu Glu Lys Glu
            180                 185                 190

Ile Glu Glu Trp Thr Leu Asn Ile Gly
        195                 200

<210> SEQ ID NO 189
<211> LENGTH: 201
<212> TYPE: PRT
<213> ORGANISM: Neisseria meningitidis

<400> SEQUENCE: 189

Met Thr Ile Tyr Phe Lys Asn Gly Phe Tyr Asp Asp Thr Leu Gly Gly
1               5                   10                  15

Ile Pro Glu Gly Ala Val Ala Val Arg Ala Glu Glu Tyr Ala Ala Leu
            20                  25                  30

Leu Ala Gly Gln Ala Gln Gly Gly Gln Ile Ala Ala Asp Ser Asp Gly
        35                  40                  45

Arg Pro Val Leu Thr Pro Pro Arg Pro Ser Glu Tyr His Glu Trp Asp
    50                  55                  60

Gly Lys Lys Trp Glu Ile Gly Glu Ala Ala Ala Ala Arg Phe Ala
65                  70                  75                  80

Glu Gln Lys Thr Ala Thr Ala Phe Arg Leu Ala Ala Lys Ala Asp Glu
                85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn

```
                115                 120                 125
Ala Pro Thr Pro Met Leu Ala Gln Ile Ala Ala Thr Arg Gly Val Glu
            130                 135                 140

Leu Asp Val Leu Ile Glu Lys Val Ile Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Thr Ile Glu Thr Ala Pro Gly Leu Asp Ala Leu Glu Lys Glu
            180                 185                 190

Ile Glu Glu Trp Thr Leu Asn Ile Gly
        195                 200

<210> SEQ ID NO 190
<211> LENGTH: 201
<212> TYPE: PRT
<213> ORGANISM: Neisseria meningitidis

<400> SEQUENCE: 190

Met Thr Ile Tyr Phe Lys Asn Gly Phe Tyr Asp Asp Thr Leu Gly Ser
1               5                   10                  15

Ile Pro Glu Gly Ala Val Ala Val Arg Ala Glu Glu Tyr Ala Ala Leu
            20                  25                  30

Leu Ala Gly Gln Ala Gln Gly Gly Gln Ile Ala Ala Asp Ser Asp Gly
        35                  40                  45

Arg Pro Val Leu Thr Pro Pro Arg Pro Ser Glu Tyr His Glu Trp Asp
    50                  55                  60

Gly Lys Lys Trp Glu Ile Gly Glu Ala Ala Ala Ala Arg Phe Ala
65                  70                  75                  80

Glu Gln Lys Thr Ala Thr Ala Phe Arg Leu Ala Ala Lys Ala Asp Glu
                85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn
        115                 120                 125

Ala Pro Thr Pro Met Leu Ala Gln Ile Ala Ala Ala Arg Gly Val Glu
    130                 135                 140

Leu Asp Val Leu Ile Glu Lys Val Val Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Thr Ile Glu Thr Ala Pro Gly Leu Asp Ala Leu Glu Lys Glu
            180                 185                 190

Ile Glu Glu Trp Thr Leu Asn Ile Gly
        195                 200

<210> SEQ ID NO 191
<211> LENGTH: 188
<212> TYPE: PRT
<213> ORGANISM: Neisseria meningitidis

<400> SEQUENCE: 191

Asn Gly Phe Tyr Asp Asp Thr Leu Gly Ser Ile Pro Glu Gly Ala Val
1               5                   10                  15

Ala Val Arg Ala Glu Glu Tyr Ala Ala Leu Leu Ala Gly Gln Ala Gln
            20                  25                  30

Gly Gly Gln Ile Ala Ala Asp Ser Asp Gly Arg Pro Val Leu Thr Pro
```

```
                        35                  40                  45
Pro Arg Pro Ser Asp Tyr His Glu Trp Asp Gly Lys Lys Trp Lys Ile
 50                  55                  60

Ser Lys Ala Ala Ala Ala Ala Arg Phe Ala Glu Gln Lys Thr Ala Thr
 65                  70                  75                  80

Ala Phe Arg Leu Ala Glu Lys Ala Asp Glu Leu Lys Asn Ser Leu Leu
                 85                  90                  95

Ala Gly Tyr Pro Gln Val Glu Ile Asp Ser Phe Tyr Arg Gln Glu Lys
            100                 105                 110

Glu Ala Leu Ala Arg Gln Ala Asp Asn Asn Ala Pro Thr Pro Met Leu
        115                 120                 125

Ala Gln Ile Ala Ala Ala Arg Gly Val Glu Leu Asp Val Leu Ile Glu
    130                 135                 140

Lys Val Val Glu Lys Ser Ala Arg Leu Ala Val Ala Ala Gly Ala Ile
145                 150                 155                 160

Ile Gly Lys Arg Gln Gln Leu Glu Asp Lys Leu Asn Ala Ile Glu Thr
                165                 170                 175

Ala Pro Gly Leu Asp Ala Leu Glu Lys Glu Ile Glu
            180                 185

<210> SEQ ID NO 192
<211> LENGTH: 201
<212> TYPE: PRT
<213> ORGANISM: Neisseria meningitidis

<400> SEQUENCE: 192

Met Thr Ile Tyr Phe Lys Asn Gly Phe Tyr Asp Asp Thr Leu Gly Ser
 1               5                  10                  15

Ile Pro Glu Gly Ala Val Ala Val Arg Ala Glu Glu Tyr Ala Ala Leu
                20                  25                  30

Leu Ala Gly Gln Ala Gln Gly Gly Gln Ile Ala Ala Asp Ser Asp Gly
            35                  40                  45

Arg Pro Val Leu Thr Pro Pro Arg Pro Ser Asp Tyr His Glu Trp Asp
 50                  55                  60

Gly Lys Lys Trp Lys Ile Gly Lys Ala Ala Ala Ala Arg Phe Ala
 65                  70                  75                  80

Glu Gln Lys Thr Ala Thr Ala Phe Arg Leu Ala Glu Lys Ala Asp Glu
                 85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn
        115                 120                 125

Ala Pro Thr Pro Met Leu Ala Gln Ile Ala Ala Ala Arg Gly Val Glu
    130                 135                 140

Leu Asp Val Leu Ile Glu Lys Val Val Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Ala Ile Glu Thr Ala Pro Gly Leu Asp Ala Leu Glu Lys Glu
            180                 185                 190

Ile Glu Glu Trp Thr Leu Asn Ile Gly
        195                 200

<210> SEQ ID NO 193
<211> LENGTH: 201
```

<212> TYPE: PRT
<213> ORGANISM: Neisseria meningitidis

<400> SEQUENCE: 193

```
Met Thr Ile Tyr Phe Lys Asn Gly Phe Tyr Asp Asp Thr Leu Gly Gly
1               5                   10                  15

Ile Pro Glu Gly Ala Val Ala Val Arg Ala Glu Glu Tyr Ala Ala Leu
            20                  25                  30

Leu Ala Gly Gln Ala Gln Gly Gly Gln Ile Ala Ala Asp Ser Asp Gly
        35                  40                  45

Arg Pro Val Leu Thr Pro Pro Arg Pro Ser Asp Tyr His Glu Trp Asp
    50                  55                  60

Gly Lys Lys Trp Lys Ile Ser Lys Ala Ala Ala Ala Arg Phe Ala
65                  70                  75                  80

Lys Gln Lys Thr Ala Leu Ala Phe Arg Leu Ala Glu Lys Ala Asp Glu
                85                  90                  95

Leu Lys Asn Ser Leu Leu Ala Gly Tyr Pro Gln Val Glu Ile Asp Ser
            100                 105                 110

Phe Tyr Arg Gln Glu Lys Glu Ala Leu Ala Arg Gln Ala Asp Asn Asn
        115                 120                 125

Ala Pro Thr Pro Met Leu Ala Gln Ile Ala Ala Arg Gly Val Glu
    130                 135                 140

Leu Asp Val Leu Ile Glu Lys Val Ile Glu Lys Ser Ala Arg Leu Ala
145                 150                 155                 160

Val Ala Ala Gly Ala Ile Ile Gly Lys Arg Gln Gln Leu Glu Asp Lys
                165                 170                 175

Leu Asn Thr Ile Glu Thr Ala Pro Gly Leu Asp Ala Leu Glu Lys Glu
            180                 185                 190

Ile Glu Glu Trp Thr Leu Asn Ile Gly
        195                 200
```

<210> SEQ ID NO 194
<211> LENGTH: 191
<212> TYPE: PRT
<213> ORGANISM: Neisseria meningitidis

<400> SEQUENCE: 194

```
Ile Ser Lys Thr Gly Phe Tyr Asp Asp Thr Leu Gly Ser Ile Pro Glu
1               5                   10                  15

Gly Ala Val Ala Val Arg Ala Glu Glu Tyr Ala Ala Leu Leu Ala Gly
            20                  25                  30

Gln Thr Gln Gly Gly Gln Ile Ala Ala Asp Ser Asp Gly Arg Pro Val
        35                  40                  45

Leu Thr Pro Pro Arg Pro Ser Glu Tyr His Glu Trp Asp Gly Lys Lys
    50                  55                  60

Trp Glu Ile Gly Glu Ala Ala Ala Ala Arg Phe Ala Glu Gln Lys
65                  70                  75                  80

Thr Ala Thr Ala Phe Arg Leu Ala Ala Lys Ala Asp Glu Leu Lys Asn
                85                  90                  95

Ser Leu Leu Ala Gly Tyr Pro Gln Val Glu Ile Asp Ser Phe Tyr Arg
            100                 105                 110

Gln Glu Lys Glu Ala Leu Ala Arg Gln Ala Asp Asn Asn Ala Pro Thr
        115                 120                 125

Pro Met Leu Ala Gln Ile Ala Ala Arg Gly Val Glu Leu Asp Val
    130                 135                 140
```

```
Leu Ile Glu Lys Val Val Glu Lys Ser Ala Arg Leu Ala Val Ala Ala
145                 150                 155                 160

Gly Ala Ile Ile Gly Lys Arg Gln Gln Leu Glu Asp Lys Leu Asn Ala
            165                 170                 175

Ile Glu Thr Ala Pro Gly Leu Asp Ala Leu Glu Lys Glu Ile Glu
        180                 185                 190

<210> SEQ ID NO 195
<211> LENGTH: 197
<212> TYPE: PRT
<213> ORGANISM: Neisseria meningitidis

<400> SEQUENCE: 195

Ile Tyr Phe Lys Asn Gly Phe Tyr Asp Asp Thr Leu Gly Ser Ile Pro
1               5                   10                  15

Glu Gly Ala Val Ala Val Arg Ala Glu Glu Tyr Ala Ala Leu Leu Ala
            20                  25                  30

Gly Gln Thr Gln Gly Gly Gln Ile Ala Ala Asp Ser Asp Gly Arg Pro
        35                  40                  45

Val Leu Thr Pro Pro Arg Pro Ser Glu Tyr His Glu Trp Asp Gly Lys
    50                  55                  60

Lys Trp Glu Ile Gly Glu Ala Ala Ala Ala Arg Phe Ala Glu Gln
65                  70                  75                  80

Lys Thr Ala Thr Ala Phe Arg Leu Ala Lys Ala Asp Glu Leu Lys
            85                  90                  95

Asn Ser Leu Leu Ala Gly Tyr Pro Gln Val Glu Ile Asp Ser Phe Tyr
            100                 105                 110

Arg Gln Glu Lys Glu Ala Leu Ala Arg Gln Ala Asp Asn Asn Ala Pro
        115                 120                 125

Thr Pro Met Leu Ala Gln Ile Ala Ala Arg Gly Val Glu Leu Asp
    130                 135                 140

Val Leu Ile Glu Lys Val Val Glu Lys Ser Ala Arg Leu Ala Val Ala
145                 150                 155                 160

Ala Gly Ala Ile Ile Gly Lys Pro Ala Ala Arg Arg Gln Ile Glu
            165                 170                 175

His His Arg Asn Pro Arg Pro Gly Leu Asp Ala Leu Glu Lys Glu Ile
        180                 185                 190

Glu Glu Trp Thr Ala
        195

<210> SEQ ID NO 196
<211> LENGTH: 187
<212> TYPE: PRT
<213> ORGANISM: Neisseria meningitidis

<400> SEQUENCE: 196

Met Lys Lys Ile Ile Ile Ala Ala Leu Ala Ala Ala Ala Val Gly Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Val Ala Asn Leu Gln Ser Gly Ser Gln His
65                  70                  75                  80
```

```
Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Glu
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 197
<211> LENGTH: 187
<212> TYPE: PRT
<213> ORGANISM: Neisseria meningitidis

<400> SEQUENCE: 197

Met Lys Lys Ile Ile Phe Ala Ala Leu Ala Ala Ala Val Gly Thr
1               5                   10                  15

Ala Ser Ala Ala Thr Tyr Lys Val Asp Glu Tyr His Ala Asn Ala Arg
                20                  25                  30

Phe Ala Ile Asp His Phe Asn Thr Ser Thr Asn Val Gly Gly Phe Tyr
            35                  40                  45

Gly Leu Thr Gly Ser Val Glu Phe Asp Gln Ala Lys Arg Asp Gly Lys
        50                  55                  60

Ile Asp Ile Thr Ile Pro Val Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Glu
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 198
<211> LENGTH: 187
<212> TYPE: PRT
<213> ORGANISM: Neisseria meningitidis

<400> SEQUENCE: 198

Met Lys Lys Ile Ile Phe Ala Ala Leu Ala Ala Ala Val Gly Thr
1               5                   10                  15

Ala Ser Ala Ala Thr Tyr Lys Val Asp Glu Tyr His Ala Asn Ala Arg
                20                  25                  30
```

Phe Ala Ile Asp His Phe Asn Thr Ser Thr Asn Val Gly Gly Phe Tyr
             35                  40                  45

Gly Leu Thr Gly Ser Val Glu Phe Asp Gln Ala Lys Arg Asp Gly Lys
 50                  55                  60

Ile Asp Ile Thr Ile Pro Val Ala Asn Leu Gln Ser Gly Ser Gln His
 65                  70                  75                  80

Phe Thr Asp His Leu Lys Ser Ala Asp Ile Phe Asp Ala Ala Gln Tyr
                 85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Ala
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 199
<211> LENGTH: 187
<212> TYPE: PRT
<213> ORGANISM: Neisseria meningitidis

<400> SEQUENCE: 199

Met Lys Lys Ile Ile Phe Ala Ala Leu Ala Ala Ala Ala Val Gly Thr
 1                5                  10                  15

Ala Ser Ala Ala Thr Tyr Lys Val Asp Glu Tyr His Ala Asn Ala Arg
                 20                  25                  30

Phe Ala Ile Asp His Phe Asn Thr Ser Thr Asn Val Gly Gly Phe Tyr
             35                  40                  45

Gly Leu Thr Gly Ser Val Glu Phe Asp Gln Ala Lys Arg Asp Gly Lys
 50                  55                  60

Ile Asp Ile Thr Ile Pro Val Ala Asn Leu Gln Ser Gly Ser Gln His
 65                  70                  75                  80

Phe Thr Asp His Leu Lys Ser Ala Asp Ile Phe Asp Ala Ala Gln Tyr
                 85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Ala
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 200
<211> LENGTH: 187
<212> TYPE: PRT
<213> ORGANISM: Neisseria meningitidis

<400> SEQUENCE: 200

Met Lys Lys Ile Ile Phe Ala Ala Leu Ala Ala Ala Val Gly Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Val Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Ala
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 201
<211> LENGTH: 187
<212> TYPE: PRT
<213> ORGANISM: Neisseria meningitidis

<400> SEQUENCE: 201

Met Lys Lys Ile Ile Phe Ala Ala Leu Glu Ala Ala Val Gly Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Val Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Ala
    130                 135                 140

Lys Thr Glu Val Cys Gly Gly Asp Phe Ser Thr Thr Ile Asp Arg Thr
145                 150                 155                 160

Lys Trp Gly Val Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 202
<211> LENGTH: 187
<212> TYPE: PRT
<213> ORGANISM: Neisseria meningitidis

<400> SEQUENCE: 202

Met Lys Lys Ile Ile Phe Ala Ala Leu Ala Ala Ala Ala Ile Ser Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Ile Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Glu
    130                 135                 140

Lys Thr Glu Val Cys Gly Gly Asp Phe Ser Thr Thr Ile Asp Arg Thr
145                 150                 155                 160

Lys Trp Gly Met Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 203
<211> LENGTH: 187
<212> TYPE: PRT
<213> ORGANISM: Neisseria meningitidis

<400> SEQUENCE: 203

Met Lys Lys Ile Ile Ala Ala Leu Ala Ala Ala Ala Ile Gly Thr
1               5                   10                  15

Ala Ser Ala Ala Thr Tyr Lys Val Asp Glu Tyr His Ala Asn Ala Arg
            20                  25                  30

Phe Ser Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Val Ala Asn Leu Gln Ser Gly Ser Gln His
65                  70                  75                  80

Phe Thr Asp His Leu Lys Ser Ala Asp Ile Phe Asp Ala Ala Gln Tyr
                85                  90                  95

Pro Asp Ile Arg Phe Val Ser Thr Lys Phe Asn Phe Asn Gly Lys Lys
            100                 105                 110

Leu Val Ser Val Asp Gly Asn Leu Thr Met His Gly Lys Thr Ala Pro
        115                 120                 125

Val Lys Leu Lys Ala Glu Lys Phe Asn Cys Tyr Gln Ser Pro Met Leu
    130                 135                 140

Lys Thr Glu Val Cys Gly Gly Asp Phe Ser Thr Thr Ile Asp Arg Thr
145                 150                 155                 160

Lys Trp Gly Met Asp Tyr Leu Val Asn Val Gly Met Thr Lys Ser Val
                165                 170                 175

Arg Ile Asp Ile Gln Ile Glu Ala Ala Lys Gln
            180                 185

<210> SEQ ID NO 204
<211> LENGTH: 17
<212> TYPE: PRT
<213> ORGANISM: Neisseria meningitidis

<400> SEQUENCE: 204

Met Asn Lys Ile Tyr Arg Ile Ile Trp Asn Ser Ala Leu Asn Ala Trp
1               5                   10                  15

Val

<210> SEQ ID NO 205
<211> LENGTH: 16
<212> TYPE: PRT
<213> ORGANISM: Neisseria meningitidis

<400> SEQUENCE: 205

Val Ser Glu Leu Thr Arg Asn His Thr Lys Arg Ala Ser Ala Thr Val
1               5                   10                  15

<210> SEQ ID NO 206
<211> LENGTH: 8
<212> TYPE: PRT
<213> ORGANISM: Neisseria meningitidis

<400> SEQUENCE: 206

Thr Ala Val Leu Ala Thr Leu Leu
1               5

<210> SEQ ID NO 207
<211> LENGTH: 12
<212> TYPE: PRT
<213> ORGANISM: Neisseria meningitidis

<400> SEQUENCE: 207

Thr Leu Lys Ala Gly Asp Asn Leu Lys Ile Lys Gln
1               5                   10

<210> SEQ ID NO 208
<211> LENGTH: 15
<212> TYPE: PRT
<213> ORGANISM: Neisseria meningitidis

<400> SEQUENCE: 208

Phe Thr Tyr Ser Leu Lys Lys Asp Leu Thr Asp Leu Thr Ser Val
1               5                   10                  15

<210> SEQ ID NO 209
<211> LENGTH: 10
<212> TYPE: PRT
<213> ORGANISM: Neisseria meningitidis

<400> SEQUENCE: 209

Thr Glu Lys Leu Ser Phe Gly Ala Asn Gly

```
<210> SEQ ID NO 210
<211> LENGTH: 23
<212> TYPE: PRT
<213> ORGANISM: Neisseria meningitidis

<400> SEQUENCE: 210

Lys Val Asn Ile Thr Ser Asp Thr Lys Gly Leu Asn Phe Ala Lys Glu
1               5                   10                  15

Thr Ala Gly Thr Asn Gly Asp
            20

<210> SEQ ID NO 211
<211> LENGTH: 15
<212> TYPE: PRT
<213> ORGANISM: Neisseria meningitidis

<400> SEQUENCE: 211

Thr Val His Leu Asn Gly Ile Gly Ser Thr Leu Thr Asp Thr Leu
1               5                   10                  15

<210> SEQ ID NO 212
<211> LENGTH: 19
<212> TYPE: PRT
<213> ORGANISM: Neisseria meningitidis
<220> FEATURE:
<221> NAME/KEY: VARIANT
<222> LOCATION: (5)..(5)
<223> OTHER INFORMATION: Xaa= Val or Ile

<400> SEQUENCE: 212

Arg Ala Ala Ser Xaa Lys Asp Val Leu Asn Ala Gly Trp Asn Ile Lys
1               5                   10                  15

Gly Val Lys

<210> SEQ ID NO 213
<211> LENGTH: 56
<212> TYPE: PRT
<213> ORGANISM: Neisseria meningitidis

<400> SEQUENCE: 213

Asn Val Asp Phe Val Arg Thr Tyr Asp Thr Val Glu Phe Leu Ser Ala
1               5                   10                  15

Asp Thr Lys Thr Thr Thr Val Asn Val Glu Ser Lys Asp Asn Gly Lys
            20                  25                  30

Lys Thr Glu Val Lys Ile Gly Ala Lys Thr Ser Val Ile Lys Glu Lys
        35                  40                  45

Asp Gly Lys Leu Val Thr Gly Lys
    50                  55

<210> SEQ ID NO 214
<211> LENGTH: 53
<212> TYPE: PRT
<213> ORGANISM: Neisseria meningitidis

<400> SEQUENCE: 214

Lys Gly Glu Asn Gly Ser Ser Thr Asp Glu Gly Glu Gly Leu Val Thr
1               5                   10                  15

Ala Lys Glu Val Ile Asp Ala Val Asn Lys Ala Gly Trp Arg Met Lys
            20                  25                  30

Thr Thr Thr Ala Asn Gly Gln Thr Gly Gln Ala Asp Lys Phe Glu Thr
```

35                  40                  45

Val Thr Ser Gly Thr
    50

<210> SEQ ID NO 215
<211> LENGTH: 16
<212> TYPE: PRT
<213> ORGANISM: Neisseria meningitidis

<400> SEQUENCE: 215

Gly Thr Thr Ala Thr Val Ser Lys Asp Asp Gln Gly Asn Ile Thr Val
1               5                   10                  15

<210> SEQ ID NO 216
<211> LENGTH: 72
<212> TYPE: PRT
<213> ORGANISM: Neisseria meningitidis

<400> SEQUENCE: 216

Tyr Asp Val Asn Val Gly Asp Ala Leu Asn Val Asn Gln Leu Gln Asn
1               5                   10                  15

Ser Gly Trp Asn Leu Asp Ser Lys Ala Val Ala Gly Ser Ser Gly Lys
            20                  25                  30

Val Ile Ser Gly Asn Val Ser Pro Ser Lys Gly Lys Met Asp Glu Thr
        35                  40                  45

Val Asn Ile Asn Ala Gly Asn Asn Ile Glu Ile Thr Arg Asn Gly Lys
    50                  55                  60

Asn Ile Asp Ile Ala Thr Ser Met
65                  70

<210> SEQ ID NO 217
<211> LENGTH: 20
<212> TYPE: PRT
<213> ORGANISM: Neisseria meningitidis

<400> SEQUENCE: 217

Pro Gln Phe Ser Ser Val Ser Leu Gly Ala Gly Ala Asp Ala Pro Thr
1               5                   10                  15

Leu Ser Val Asp
            20

<210> SEQ ID NO 218
<211> LENGTH: 116
<212> TYPE: PRT
<213> ORGANISM: Neisseria meningitidis

<400> SEQUENCE: 218

Asn Lys Pro Val Arg Ile Thr Asn Val Ala Pro Gly Val Lys Glu Gly
1               5                   10                  15

Asp Val Thr Asn Val Ala Gln Leu Lys Gly Val Ala Gln Asn Leu Asn
            20                  25                  30

Asn Arg Ile Asp Asn Val Asp Gly Asn Ala Arg Ala Gly Ile Ala Gln
        35                  40                  45

Ala Ile Ala Thr Ala Gly Leu Val Gln Ala Tyr Leu Pro Gly Lys Ser
    50                  55                  60

Met Met Ala Ile Gly Gly Gly Thr Tyr Arg Gly Glu Ala Gly Tyr Ala
65                  70                  75                  80

Ile Gly Tyr Ser Ser Ile Ser Asp Gly Gly Asn Trp Ile Ile Lys Gly
                85                  90                  95

```
Thr Ala Ser Gly Asn Ser Arg Gly His Phe Gly Ala Ser Ala Ser Val
            100                 105                 110

Gly Tyr Gln Trp
        115

<210> SEQ ID NO 219
<211> LENGTH: 40
<212> TYPE: PRT
<213> ORGANISM: Neisseria meningitidis

<400> SEQUENCE: 219

Met Lys Thr Phe Phe Lys Thr Leu Ser Ala Ala Leu Ala Leu Ile
1               5                   10                  15

Leu Ala Ala Cys Gly Gly Gln Lys Asp Ser Ala Pro Ala Ala Ser Ala
            20                  25                  30

Ser Ala Ala Ala Asp Asn Gly Ala
        35                  40

<210> SEQ ID NO 220
<211> LENGTH: 19
<212> TYPE: PRT
<213> ORGANISM: Neisseria meningitidis

<400> SEQUENCE: 220

Lys Lys Glu Ile Val Phe Gly Thr Thr Val Gly Asp Phe Gly Asp Met
1               5                   10                  15

Val Lys Glu

<210> SEQ ID NO 221
<211> LENGTH: 223
<212> TYPE: PRT
<213> ORGANISM: Neisseria meningitidis

<400> SEQUENCE: 221

Glu Leu Glu Lys Lys Gly Tyr Thr Val Lys Leu Val Glu Phe Thr Asp
1               5                   10                  15

Tyr Val Arg Pro Asn Leu Ala Leu Ala Glu Gly Glu Leu Asp Ile Asn
            20                  25                  30

Val Phe Gln His Lys Pro Tyr Leu Asp Asp Phe Lys Lys Glu His Asn
        35                  40                  45

Leu Asp Ile Thr Glu Val Phe Gln Val Pro Thr Ala Pro Leu Gly Leu
    50                  55                  60

Tyr Pro Gly Lys Leu Lys Ser Leu Glu Glu Val Lys Asp Gly Ser Thr
65                  70                  75                  80

Val Ser Ala Pro Asn Asp Pro Ser Asn Phe Ala Arg Val Leu Val Met
                85                  90                  95

Leu Asp Glu Leu Gly Trp Ile Lys Leu Lys Asp Gly Ile Asn Pro Leu
            100                 105                 110

Thr Ala Ser Lys Ala Asp Ile Ala Glu Asn Leu Lys Asn Ile Lys Ile
        115                 120                 125

Val Glu Leu Glu Ala Ala Gln Leu Pro Arg Ser Arg Ala Asp Val Asp
    130                 135                 140

Phe Ala Val Val Asn Gly Asn Tyr Ala Ile Ser Ser Gly Met Lys Leu
145                 150                 155                 160

Thr Glu Ala Leu Phe Gln Glu Pro Ser Phe Ala Tyr Val Asn Trp Ser
                165                 170                 175

Ala Val Lys Thr Ala Asp Lys Asp Ser Gln Trp Leu Lys Asp Val Thr
            180                 185                 190
```

Glu Ala Tyr Asn Ser Asp Ala Phe Lys Ala Tyr Ala His Lys Arg Phe
        195                 200                 205

Glu Gly Tyr Lys Ser Pro Ala Trp Asn Glu Gly Ala Ala Lys
    210                 215                 220

<210> SEQ ID NO 222
<211> LENGTH: 12
<212> TYPE: PRT
<213> ORGANISM: Neisseria meningitidis

<400> SEQUENCE: 222

Met Phe Lys Arg Ser Val Ile Ala Met Ala Cys Ile
1               5                   10

<210> SEQ ID NO 223
<211> LENGTH: 20
<212> TYPE: PRT
<213> ORGANISM: Neisseria meningitidis

<400> SEQUENCE: 223

Ala Leu Ser Ala Cys Gly Gly Gly Gly Gly Ser Pro Asp Val Lys
1               5                   10                  15

Ser Ala Asp Thr
            20

<210> SEQ ID NO 224
<211> LENGTH: 8
<212> TYPE: PRT
<213> ORGANISM: Neisseria meningitidis

<400> SEQUENCE: 224

Ser Lys Pro Ala Ala Pro Val Val
1               5

<210> SEQ ID NO 225
<211> LENGTH: 7
<212> TYPE: PRT
<213> ORGANISM: Neisseria meningitidis

<400> SEQUENCE: 225

Gln Asp Met Ala Ala Val Ser
1               5

<210> SEQ ID NO 226
<211> LENGTH: 12
<212> TYPE: PRT
<213> ORGANISM: Neisseria meningitidis

<400> SEQUENCE: 226

Glu Asn Thr Gly Asn Gly Gly Ala Ala Thr Thr Asp
1               5                   10

<210> SEQ ID NO 227
<211> LENGTH: 13
<212> TYPE: PRT
<213> ORGANISM: Neisseria meningitidis

<400> SEQUENCE: 227

Asp Gly Pro Ser Gln Asn Ile Thr Leu Thr His Cys Lys
1               5                   10

<210> SEQ ID NO 228
<211> LENGTH: 58

-continued

<212> TYPE: PRT
<213> ORGANISM: Neisseria meningitidis

<400> SEQUENCE: 228

Arg Arg Ser Ala Arg Ser Arg Arg Ser Leu Pro Ala Glu Met Pro Leu
1               5                   10                  15

Ile Pro Val Asn Gln Ala Asp Thr Leu Ile Val Asp Gly Glu Ala Val
            20                  25                  30

Ser Leu Thr Gly His Ser Gly Asn Ile Phe Ala Pro Gly Gly Asn Tyr
        35                  40                  45

Arg Tyr Leu Thr Tyr Gly Ala Glu Lys Leu
    50                  55

<210> SEQ ID NO 229
<211> LENGTH: 25
<212> TYPE: PRT
<213> ORGANISM: Neisseria meningitidis

<400> SEQUENCE: 229

Val Gln Gly Glu Pro Ala Lys Gly Glu Met Leu Ala Gly Thr Ala Val
1               5                   10                  15

Tyr Asn Gly Glu Val Leu His Phe His
            20                  25

<210> SEQ ID NO 230
<211> LENGTH: 27
<212> TYPE: PRT
<213> ORGANISM: Neisseria meningitidis

<400> SEQUENCE: 230

Gly Arg Phe Ala Ala Lys Val Asp Phe Gly Ser Lys Ser Val Asp Gly
1               5                   10                  15

Ile Ile Asp Ser Gly Asp Asp Leu His Met Gly
            20                  25

<210> SEQ ID NO 231
<211> LENGTH: 62
<212> TYPE: PRT
<213> ORGANISM: Neisseria meningitidis
<220> FEATURE:
<221> NAME/KEY: VARIANT
<222> LOCATION: (27)..(27)
<223> OTHER INFORMATION: Xaa = Arg or Lys

<400> SEQUENCE: 231

Gln Lys Phe Lys Ala Ala Ile Asp Gly Asn Gly Phe Lys Gly Thr Trp
1               5                   10                  15

Thr Glu Asn Gly Gly Asp Val Ser Gly Xaa Phe Tyr Gly Pro Ala
            20                  25                  30

Gly Glu Glu Val Ala Gly Lys Tyr Ser Tyr Arg Pro Thr Asp Ala Glu
        35                  40                  45

Lys Gly Gly Phe Gly Val Phe Ala Gly Lys Lys Asp Arg Asp
    50                  55                  60

<210> SEQ ID NO 232
<211> LENGTH: 8
<212> TYPE: PRT
<213> ORGANISM: Neisseria meningitidis

<400> SEQUENCE: 232

Met Glu Phe Phe Ile Ile Leu Leu
1               5

<210> SEQ ID NO 233
<211> LENGTH: 130
<212> TYPE: PRT
<213> ORGANISM: Neisseria meningitidis

<400> SEQUENCE: 233

Ala Val Ala Val Phe Gly Phe Lys Ser Phe Val Ile Pro Gln Gln
1               5                   10                  15

Glu Val His Val Val Glu Arg Leu Gly Arg Phe His Arg Ala Leu Thr
            20                  25                  30

Ala Gly Leu Asn Ile Leu Ile Pro Phe Ile Asp Arg Val Ala Tyr Arg
        35                  40                  45

His Ser Leu Lys Glu Ile Pro Leu Asp Val Pro Ser Gln Val Cys Ile
    50                  55                  60

Thr Arg Asp Asn Thr Gln Leu Thr Val Asp Gly Ile Ile Tyr Phe Gln
65                  70                  75                  80

Val Thr Asp Pro Lys Leu Ala Ser Tyr Gly Ser Ser Asn Tyr Ile Met
                85                  90                  95

Ala Ile Thr Gln Leu Ala Gln Thr Thr Leu Arg Ser Val Ile Gly Arg
            100                 105                 110

Met Glu Leu Asp Lys Thr Phe Glu Glu Arg Asp Glu Ile Asn Ser Thr
        115                 120                 125

Val Val
    130

<210> SEQ ID NO 234
<211> LENGTH: 176
<212> TYPE: PRT
<213> ORGANISM: Neisseria meningitidis

<400> SEQUENCE: 234

Ala Leu Asp Glu Ala Ala Gly Ala Trp Gly Val Lys Val Leu Arg Tyr
1               5                   10                  15

Glu Ile Lys Asp Leu Val Pro Pro Gln Glu Ile Leu Arg Ser Met Gln
            20                  25                  30

Ala Gln Ile Thr Ala Glu Arg Glu Lys Arg Ala Arg Ile Ala Glu Ser
        35                  40                  45

Glu Gly Arg Lys Ile Glu Gln Ile Asn Leu Ala Ser Gly Gln Arg Glu
    50                  55                  60

Ala Glu Ile Gln Gln Ser Glu Gly Glu Ala Gln Ala Val Asn Ala
65                  70                  75                  80

Ser Asn Ala Glu Lys Ile Ala Arg Ile Asn Arg Ala Lys Gly Glu Ala
                85                  90                  95

Glu Ser Leu Arg Leu Val Ala Glu Ala Asn Ala Glu Ala Asn Arg Gln
            100                 105                 110

Ile Ala Ala Ala Leu Gln Thr Gln Ser Gly Ala Asp Ala Val Asn Leu
        115                 120                 125

Lys Ile Ala Gly Gln Tyr Val Thr Ala Phe Lys Asn Leu Ala Lys Glu
    130                 135                 140

Asp Asn Thr Arg Ile Lys Pro Ala Lys Val Ala Glu Ile Gly Asn Pro
145                 150                 155                 160

Asn Phe Arg Arg His Glu Lys Phe Ser Pro Glu Ala Lys Thr Ala Lys
                165                 170                 175

<210> SEQ ID NO 235

<211> LENGTH: 10
<212> TYPE: PRT
<213> ORGANISM: Neisseria meningitidis

<400> SEQUENCE: 235

Met Lys Lys Tyr Leu Phe Arg Ala Ala Leu
1               5                   10

<210> SEQ ID NO 236
<211> LENGTH: 185
<212> TYPE: PRT
<213> ORGANISM: Neisseria meningitidis
<220> FEATURE:
<221> NAME/KEY: VARIANT
<222> LOCATION: (44)..(44)
<223> OTHER INFORMATION: Xaa = Gly or Ala

<400> SEQUENCE: 236

Gly Ile Ala Ala Ala Ile Leu Ala Ala Cys Gln Ser Lys Ser Ile Gln
1               5                   10                  15

Thr Phe Pro Gln Pro Asp Thr Ser Val Ile Asn Gly Pro Asp Arg Pro
            20                  25                  30

Val Gly Ile Pro Asp Pro Ala Gly Thr Thr Val Xaa Gly Gly Gly Ala
        35                  40                  45

Val Tyr Thr Val Val Pro His Leu Ser Leu Pro His Trp Ala Ala Gln
    50                  55                  60

Asp Phe Ala Lys Ser Leu Gln Ser Phe Arg Leu Gly Cys Ala Asn Leu
65                  70                  75                  80

Lys Asn Arg Gln Gly Trp Gln Asp Val Cys Ala Gln Ala Phe Gln Thr
                85                  90                  95

Pro Val His Ser Phe Gln Ala Lys Gln Phe Phe Glu Arg Tyr Phe Thr
            100                 105                 110

Pro Trp Gln Val Ala Gly Asn Gly Ser Leu Ala Gly Thr Val Thr Gly
        115                 120                 125

Tyr Tyr Glu Pro Val Leu Lys Gly Asp Asp Arg Arg Thr Ala Gln Ala
    130                 135                 140

Arg Phe Pro Ile Tyr Gly Ile Pro Asp Phe Ile Ser Val Pro Leu
145                 150                 155                 160

Pro Ala Gly Leu Arg Ser Gly Lys Ala Leu Val Arg Ile Arg Gln Thr
                165                 170                 175

Gly Lys Asn Ser Gly Thr Ile Asp Asn
            180                 185

<210> SEQ ID NO 237
<211> LENGTH: 9
<212> TYPE: PRT
<213> ORGANISM: Neisseria meningitidis

<400> SEQUENCE: 237

Gly Gly Thr His Thr Ala Asp Leu Ser
1               5

<210> SEQ ID NO 238
<211> LENGTH: 104
<212> TYPE: PRT
<213> ORGANISM: Neisseria meningitidis
<220> FEATURE:
<221> NAME/KEY: VARIANT
<222> LOCATION: (85)..(85)
<223> OTHER INFORMATION: Xaa = Arg or Lys

<400> SEQUENCE: 238

-continued

Phe Pro Ile Thr Ala Arg Thr Thr Ala Ile Lys Gly Arg Phe Glu Gly
1               5                   10                  15

Ser Arg Phe Leu Pro Tyr His Thr Arg Asn Gln Ile Asn Gly Gly Ala
            20                  25                  30

Leu Asp Gly Lys Ala Pro Ile Leu Gly Tyr Ala Glu Asp Pro Val Glu
        35                  40                  45

Leu Phe Phe Met His Ile Gln Gly Ser Gly Arg Leu Lys Thr Pro Ser
    50                  55                  60

Gly Lys Tyr Ile Arg Ile Gly Tyr Ala Asp Lys Asn Glu His Pro Tyr
65                  70                  75                  80

Val Ser Ile Gly Xaa Tyr Met Ala Asp Lys Gly Tyr Leu Lys Leu Gly
                85                  90                  95

Gln Thr Ser Met Gln Gly Ile Lys
            100

<210> SEQ ID NO 239
<211> LENGTH: 25
<212> TYPE: PRT
<213> ORGANISM: Neisseria meningitidis

<400> SEQUENCE: 239

Tyr Met Arg Gln Asn Pro Gln Arg Leu Ala Glu Val Leu Gly Gln Asn
1               5                   10                  15

Pro Ser Tyr Ile Phe Phe Arg Glu Leu
            20                  25

<210> SEQ ID NO 240
<211> LENGTH: 100
<212> TYPE: PRT
<213> ORGANISM: Neisseria meningitidis

<400> SEQUENCE: 240

Asn Asp Gly Pro Val Gly Ala Leu Gly Thr Pro Leu Met Gly Glu Tyr
1               5                   10                  15

Ala Gly Ala Val Asp Arg His Tyr Ile Thr Leu Gly Ala Pro Leu Phe
            20                  25                  30

Val Ala Thr Ala His Pro Val Thr Arg Lys Ala Leu Asn Arg Leu Ile
        35                  40                  45

Met Ala Gln Asp Thr Gly Ser Ala Ile Lys Gly Ala Val Arg Val Asp
    50                  55                  60

Tyr Phe Trp Gly Tyr Gly Asp Glu Ala Gly Glu Leu Ala Gly Lys Gln
65                  70                  75                  80

Lys Thr Thr Gly Tyr Val Trp Gln Leu Leu Pro Asn Gly Met Lys Pro
                85                  90                  95

Glu Tyr Arg Pro
            100

<210> SEQ ID NO 241
<211> LENGTH: 63
<212> TYPE: PRT
<213> ORGANISM: Neisseria meningitidis

<400> SEQUENCE: 241

Arg Lys Ile Ser Leu Ile Leu Ser Ile Leu Ala Val Cys Leu Pro Met
1               5                   10                  15

His Ala His Ala Ser Asp Leu Ala Asn Asp Ser Phe Ile Arg Gln Val
            20                  25                  30

```
Leu Asp Arg Gln His Phe Glu Pro Asp Gly Lys Tyr His Leu Phe Gly
         35                  40                  45

Ser Arg Gly Glu Leu Ala Glu Arg Ser Gly His Ile Gly Leu Gly
     50                  55                  60

<210> SEQ ID NO 242
<211> LENGTH: 125
<212> TYPE: PRT
<213> ORGANISM: Neisseria meningitidis

<400> SEQUENCE: 242

Ile Gln Ser His Gln Leu Gly Asn Leu Met Ile Gln Gln Ala Ala Ile
1               5                   10                  15

Lys Gly Asn Ile Gly Tyr Ile Val Arg Phe Ser Asp His Gly His Glu
            20                  25                  30

Val His Ser Pro Phe Asp Asn His Ala Ser His Ser Asp Ser Asp Glu
        35                  40                  45

Ala Gly Ser Pro Val Asp Gly Phe Ser Leu Tyr Arg Ile His Trp Asp
    50                  55                  60

Gly Tyr Glu His His Pro Ala Asp Gly Tyr Asp Gly Pro Gln Gly Gly
65                  70                  75                  80

Gly Tyr Pro Ala Pro Lys Gly Ala Arg Asp Ile Tyr Ser Tyr Asp Ile
                85                  90                  95

Lys Gly Val Ala Gln Asn Ile Arg Leu Asn Leu Thr Asp Asn Arg Ser
            100                 105                 110

Thr Gly Gln Arg Leu Ala Asp Arg Phe His Asn Ala Gly
        115                 120                 125

<210> SEQ ID NO 243
<211> LENGTH: 119
<212> TYPE: PRT
<213> ORGANISM: Neisseria meningitidis

<400> SEQUENCE: 243

Met Leu Thr Gln Gly Val Gly Asp Gly Phe Lys Arg Ala Thr Arg Tyr
1               5                   10                  15

Ser Pro Glu Leu Asp Arg Ser Gly Asn Ala Ala Glu Ala Phe Asn Gly
            20                  25                  30

Thr Ala Asp Ile Val Lys Asn Ile Ile Gly Ala Ala Gly Glu Ile Val
        35                  40                  45

Gly Ala Gly Asp Ala Val Gln Gly Ile Ser Glu Gly Ser Asn Ile Ala
    50                  55                  60

Val Met His Gly Leu Gly Leu Leu Ser Thr Glu Asn Lys Met Ala Arg
65                  70                  75                  80

Ile Asn Asp Leu Ala Asp Met Ala Gln Leu Lys Asp Tyr Ala Ala Ala
                85                  90                  95

Ala Ile Arg Asp Trp Ala Val Gln Asn Pro Asn Ala Gln Gly Ile
            100                 105                 110

Glu Ala Val Ser Asn Ile Phe
        115

<210> SEQ ID NO 244
<211> LENGTH: 41
<212> TYPE: PRT
<213> ORGANISM: Neisseria meningitidis
<220> FEATURE:
<221> NAME/KEY: VARIANT
<222> LOCATION: (23)..(23)
<223> OTHER INFORMATION: Xaa = Val or Ile
```

```
<400> SEQUENCE: 244

Ile Pro Ile Lys Gly Ile Gly Ala Val Arg Gly Lys Tyr Gly Leu Gly
1               5                   10                  15

Gly Ile Thr Ala His Pro Xaa Lys Arg Ser Gln Met Gly Glu Ile Ala
            20                  25                  30

Leu Pro Lys Gly Lys Ser Ala Val Ser
        35                  40

<210> SEQ ID NO 245
<211> LENGTH: 73
<212> TYPE: PRT
<213> ORGANISM: Neisseria meningitidis

<400> SEQUENCE: 245

Asn Phe Ala Asp Ala Ala Tyr Ala Lys Tyr Pro Ser Pro Tyr His Ser
1               5                   10                  15

Arg Asn Ile Arg Ser Asn Leu Glu Gln Arg Tyr Gly Lys Glu Asn Ile
            20                  25                  30

Thr Ser Ser Thr Val Pro Pro Ser Asn Gly Lys Asn Val Lys Leu Ala
        35                  40                  45

Asn Lys Arg His Pro Lys Thr Lys Val Pro Phe Asp Gly Lys Gly Phe
    50                  55                  60

Pro Asn Phe Glu Lys Asp Val Lys Tyr
65                  70

<210> SEQ ID NO 246
<211> LENGTH: 13
<212> TYPE: PRT
<213> ORGANISM: Neisseria meningitidis

<400> SEQUENCE: 246

Ile Tyr Phe Lys Asn Gly Phe Tyr Asp Asp Thr Leu Gly
1               5                   10

<210> SEQ ID NO 247
<211> LENGTH: 52
<212> TYPE: PRT
<213> ORGANISM: Neisseria meningitidis

<400> SEQUENCE: 247

Ile Pro Glu Gly Ala Val Ala Val Arg Ala Glu Tyr Ala Ala Leu
1               5                   10                  15

Leu Ala Gly Gln Ala Gln Gly Gly Gln Ile Ala Ala Asp Ser Asp Gly
            20                  25                  30

Arg Pro Val Leu Thr Pro Pro Arg Pro Ser Ser Tyr His Glu Trp Asp
        35                  40                  45

Gly Lys Lys Trp
    50

<210> SEQ ID NO 248
<211> LENGTH: 19
<212> TYPE: PRT
<213> ORGANISM: Neisseria meningitidis

<400> SEQUENCE: 248

Ala Ala Ala Ala Ala Arg Phe Ala Glu Gln Lys Thr Ala Thr Ala Phe
1               5                   10                  15

Arg Leu Ala
```

<210> SEQ ID NO 249
<211> LENGTH: 86
<212> TYPE: PRT
<213> ORGANISM: Neisseria meningitidis
<220> FEATURE:
<221> NAME/KEY: VARIANT
<222> LOCATION: (61)..(61)
<223> OTHER INFORMATION: Xaa = Ile or Val

<400> SEQUENCE: 249

Lys Ala Asp Glu Leu Lys Asn Ser Leu Leu Ala Gly Tyr Pro Gln Val
1               5                   10                  15

Glu Ile Asp Ser Phe Tyr Arg Gln Lys Glu Ala Leu Ala Arg Gln
            20                  25                  30

Ala Asp Asn Asn Ala Pro Thr Pro Met Leu Ala Gln Ile Ala Ala Ala
        35                  40                  45

Arg Gly Val Glu Leu Asp Val Leu Ile Glu Lys Val Xaa Glu Lys Ser
    50                  55                  60

Ala Arg Leu Ala Val Ala Ala Gly Ala Ile Ile Gly Lys Arg Gln Gln
65                  70                  75                  80

Leu Glu Asp Lys Leu Asn
                85

<210> SEQ ID NO 250
<211> LENGTH: 18
<212> TYPE: PRT
<213> ORGANISM: Neisseria meningitidis

<400> SEQUENCE: 250

Ile Glu Thr Ala Pro Gly Leu Asp Ala Leu Glu Lys Glu Ile Glu Glu
1               5                   10                  15

Trp Thr

<210> SEQ ID NO 251
<211> LENGTH: 143
<212> TYPE: PRT
<213> ORGANISM: Neisseria meningitidis
<220> FEATURE:
<221> NAME/KEY: VARIANT
<222> LOCATION: (71)..(71)
<223> OTHER INFORMATION: Xaa = Ile or Val

<400> SEQUENCE: 251

Met Lys Lys Ile Ile Phe Ala Ala Leu Ala Ala Ala Val Gly Thr
1               5                   10                  15

Ala Ser Ala Ala Thr Tyr Lys Val Asp Glu Tyr His Ala Asn Ala Arg
            20                  25                  30

Phe Ala Ile Asp His Phe Asn Thr Ser Thr Asn Val Gly Gly Phe Tyr
        35                  40                  45

Gly Leu Thr Gly Ser Val Glu Phe Asp Gln Ala Lys Arg Asp Gly Lys
    50                  55                  60

Ile Asp Ile Thr Ile Pro Xaa Ala Asn Leu Gln Ser Gly Ser Gln His
65                  70                  75                  80

Phe Thr Asp His Leu Lys Ser Ala Asp Ile Phe Asp Ala Ala Gln Tyr
            85                  90                  95

Pro Asp Ile Arg Phe Val Ser Thr Lys Phe Asn Phe Asn Gly Lys Lys
        100                 105                 110

Leu Val Ser Val Asp Gly Asn Leu Thr Met His Gly Lys Thr Ala Pro
    115                 120                 125

```
Val Lys Leu Lys Ala Glu Lys Phe Asn Cys Tyr Gln Ser Pro Met
    130                 135                 140
```

```
<210> SEQ ID NO 252
<211> LENGTH: 127
<212> TYPE: PRT
<213> ORGANISM: Neisseria meningitidis
<220> FEATURE:
<221> NAME/KEY: VARIANT
<222> LOCATION: (52)..(52)
<223> OTHER INFORMATION: Xaa = Ile or Val

<400> SEQUENCE: 252
```

```
Ala Thr Tyr Lys Val Asp Glu Tyr His Ala Asn Ala Arg Phe Ala Ile
1               5                   10                  15

Asp His Phe Asn Thr Ser Thr Asn Val Gly Gly Phe Tyr Gly Leu Thr
            20                  25                  30

Gly Ser Val Glu Phe Asp Gln Ala Lys Arg Asp Gly Lys Ile Asp Ile
        35                  40                  45

Thr Ile Pro Xaa Ala Asn Leu Gln Ser Gly Ser Gln His Phe Thr Asp
    50                  55                  60

His Leu Lys Ser Ala Asp Ile Phe Asp Ala Ala Gln Tyr Pro Asp Ile
65                  70                  75                  80

Arg Phe Val Ser Thr Lys Phe Asn Phe Asn Gly Lys Lys Leu Val Ser
                85                  90                  95

Val Asp Gly Asn Leu Thr Met His Gly Lys Thr Ala Pro Val Lys Leu
            100                 105                 110

Lys Ala Glu Lys Phe Asn Cys Tyr Gln Ser Pro Met Ala Asn Asp
        115                 120                 125
```

```
<210> SEQ ID NO 253
<211> LENGTH: 43
<212> TYPE: PRT
<213> ORGANISM: Neisseria meningitidis
<220> FEATURE:
<221> NAME/KEY: VARIANT
<222> LOCATION: (20)...(20)
<223> OTHER INFORMATION: Xaa = Met or Val

<400> SEQUENCE: 253
```

```
Lys Thr Glu Val Cys Gly Gly Asp Phe Ser Thr Thr Ile Asp Arg Thr
1               5                   10                  15

Lys Trp Gly Xaa Asp Tyr Leu Val Asn Val Gly Met Thr Lys Ser Val
            20                  25                  30

Arg Ile Asp Ile Gln Ile Glu Ala Ala Lys Gln
        35                  40
```

```
<210> SEQ ID NO 254
<211> LENGTH: 6
<212> TYPE: PRT
<213> ORGANISM: Neisseria meningitidis

<400> SEQUENCE: 254
```

```
Gln Asn Asp Met Pro Gln
1               5
```

```
<210> SEQ ID NO 255
<211> LENGTH: 5
<212> TYPE: PRT
<213> ORGANISM: Neisseria meningitidis

<400> SEQUENCE: 255
```

```
Lys Ser Glu Phe Glu
1               5

<210> SEQ ID NO 256
<211> LENGTH: 6
<212> TYPE: PRT
<213> ORGANISM: Neisseria meningitidis

<400> SEQUENCE: 256

Gly Gly Ser Tyr Ala Leu
1               5
```